United States Patent
Castro et al.

(10) Patent No.: US 10,696,650 B2
(45) Date of Patent: Jun. 30, 2020

(54) AHR INHIBITORS AND USES THEREOF

(71) Applicant: Kyn Therapeutics, Cambridge, MA (US)

(72) Inventors: Alfredo C. Castro, Woburn, MA (US); Catherine Anne Evans, Somerville, MA (US)

(73) Assignee: Ikena Oncology, Inc., Boston, MA (US)

( * ) Notice: Subject to any disclaimer, the term of this patent is extended or adjusted under 35 U.S.C. 154(b) by 0 days.

(21) Appl. No.: 16/104,747

(22) Filed: Aug. 17, 2018

(65) Prior Publication Data

US 2019/0055218 A1   Feb. 21, 2019

Related U.S. Application Data

(60) Provisional application No. 62/546,757, filed on Aug. 17, 2017, provisional application No. 62/613,141, filed on Jan. 3, 2018.

(51) Int. Cl.

| | | |
|---|---|---|
| *C07D 401/12* | (2006.01) |
| *C07D 403/12* | (2006.01) |
| *C07D 405/12* | (2006.01) |
| *C07D 409/14* | (2006.01) |
| *C07D 417/14* | (2006.01) |
| *C07D 417/12* | (2006.01) |
| *C07D 413/14* | (2006.01) |
| *C07D 231/14* | (2006.01) |
| *C07D 215/38* | (2006.01) |
| *C07D 207/34* | (2006.01) |
| *A61P 35/00* | (2006.01) |
| *A61P 29/00* | (2006.01) |
| *C07D 413/12* | (2006.01) |
| *A61K 9/00* | (2006.01) |

(52) U.S. Cl.
CPC ............ *C07D 401/12* (2013.01); *A61P 29/00* (2018.01); *A61P 35/00* (2018.01); *C07D 207/34* (2013.01); *C07D 215/38* (2013.01); *C07D 231/14* (2013.01); *C07D 403/12* (2013.01); *C07D 405/12* (2013.01); *C07D 409/14* (2013.01); *C07D 413/12* (2013.01); *C07D 413/14* (2013.01); *C07D 417/12* (2013.01); *C07D 417/14* (2013.01); *A61K 9/0053* (2013.01)

(58) Field of Classification Search
CPC .. A61K 9/0053; C07D 207/34; C07D 215/38; C07D 231/14; C07D 401/12; C07D 403/12; C07D 405/12; C07D 409/14; C07D 413/12; C07D 413/14; C07D 417/12; C07D 417/14
See application file for complete search history.

(56) References Cited

U.S. PATENT DOCUMENTS

| | | |
|---|---|---|
| 8,906,682 B2 | 12/2014 | June et al. |
| 2004/0009978 A1 | 1/2004 | Hayakawa et al. |
| 2004/0235877 A1 | 11/2004 | Ishizuka et al. |
| 2006/0128729 A1 | 6/2006 | Pal et al. |
| 2011/0281863 A1 | 11/2011 | Bearss et al. |
| 2014/0294860 A1 | 10/2014 | Platten et al. |
| 2018/0298013 A1 | 10/2018 | Romero et al. |

FOREIGN PATENT DOCUMENTS

| | | |
|---|---|---|
| WO | 2006029879 | 3/2006 |
| WO | 2006105021 | 10/2006 |
| WO | 2006122150 | 11/2006 |
| WO | 2007005874 | 1/2007 |
| WO | 2007075598 | 7/2007 |
| WO | 2008036642 | 3/2008 |
| WO | 2008036653 | 3/2008 |
| WO | 2008132601 | 11/2008 |
| WO | 2009009116 | 1/2009 |
| WO | 2009044273 | 4/2009 |
| WO | 2009073620 | 6/2009 |
| WO | 2010019570 | 2/2010 |
| WO | 2010077634 | 7/2010 |
| WO | 2011028683 | 3/2011 |
| WO | 2011056652 | 5/2011 |
| WO | 2011070024 | 6/2011 |
| WO | 2011107553 | 9/2011 |
| WO | 2011109400 | 9/2011 |
| WO | 2011131407 | 10/2011 |
| WO | 2011140249 | 11/2011 |
| WO | 2012032433 | 3/2012 |
| WO | 2012142237 | 10/2012 |
| WO | 2012145493 | 10/2012 |
| WO | 2013079174 | 6/2013 |
| WO | 2013087699 | 6/2013 |
| WO | 2013119716 | 8/2013 |
| WO | 2013132044 | 9/2013 |
| WO | 2013169264 | 11/2013 |
| WO | 2014008218 | 1/2014 |
| WO | 2014036357 | 3/2014 |

(Continued)

OTHER PUBLICATIONS

Choi et al. The American Society for Pharmacology and Experimental Therapeutics, vol. 81, No. 1, pp. 3-11, 2012. (Year: 2012).*
Choi et al., "Development of novel CH223191-based antagonists of the aryl hydrocarbon receptor," Mol Pharmacol, 81(1):3-11 (Jan. 2012).
International Search Report and Written Opinion for International Application No. PCT/US2018/046957, dated Nov. 1, 2018 (9 pages).
Pubmed Compound Summary for CID 19475600, 'LCWK-KZMUKFZXDDUHFFFAOYSA-N', U.S. National Library of Medicine, Dec. 5, 2007 (pp. 1-9); p. 3 (https://pubchem.ncbi.nlm.nih.gov/compound/19475600).
Pubmed Compound Summary for CID 110473910, 'YOJC-CGORNWLKMVUHFFFAOYSA-N', U.S. National Library of Medicine, Jan. 18, 2016 (pp. 1-10); p. 3 (https://pubchem.ncbi.nlm.nih.gov/compound/110473910).

(Continued)

*Primary Examiner* — Jean P Cornet
(74) *Attorney, Agent, or Firm* — Andrea L.C. Reid

(57) ABSTRACT

The present invention provides compounds useful as inhibitors of AHR, compositions thereof, and methods of using the same.

20 Claims, No Drawings

(56) References Cited

FOREIGN PATENT DOCUMENTS

| WO | 2014138485 A1 | 9/2014 |
|---|---|---|
| WO | 2019018562 | 1/2019 |
| WO | 2019087129 | 5/2019 |
| WO | 2019089826 | 5/2019 |
| WO | 2019101641 | 5/2019 |
| WO | 2019101642 | 5/2019 |
| WO | 2019101643 | 5/2019 |
| WO | 2019101647 | 5/2019 |

OTHER PUBLICATIONS

Adams et al., "Big opportunities for small molecules in immuno-oncology," Nature Reviews Drug Discovery, vol. 14, No. 9, Sep. 2015 (pp. 603-622).

Berge et al., "Pharmaceutical Salts," Journal of Pharmaceutical Sciences, vol. 66, No. 1, Jan. 1977 (pp. 1-19).

Esser et al., "The aryl hydrocarbon receptor in immunity," Trends in Immunology, vol. 30, No. 9, Sep. 2009 (pp. 447-454).

Funatake et al., "Cutting edge: activation of the aryl hydrocarbon receptor by 2,3,7,8-tetrachlorodibenzo-p-dioxin generates a population of CD4+ CD25+ cells with characteristics of regulatory T cells," Journal of Immunology, vol. 175, No. 7, Oct. 2005 (pp. 4184-4188).

Gandhi et al., "Activation of the aryl hydrocarbon receptor induces human type 1 regulatory T cell-like and Foxp3(+) regulatory T cells," Nature Immunology, vol. 11, No. 9, Sep. 2010 (pp. 846-853).

Head et al., "The aryl hydrocarbon receptor is a modulator of anti-viral immunity," Biochemical Pharmacology, vol. 77, No. 4, Feb. 2009 (pp. 642-653).

International Search Report and Written Opinion for International Application No. PCT/US2018/028532, dated Oct. 30, 2018 (10 pages).

Ishida et al., "Activation of aryl hydrocarbon receptor promotes invasion of clear cell renal cell carcinoma and is associated with poor prognosis and cigarette smoke," International Journal of Cancer, vol. 137, No. 2, Jul. 2015 (pp. 299-310).

Ishida et al., "Activation of the aryl hydrocarbon receptor pathway enhances cancer cell invasion by upregulating the MMP expression and is associated with poor prognosis in upper urinary tract urothelial cancer," Carcinogenesis, vol. 31, No. 2, Feb. 2010 (pp. 287-295).

Jin et al., "Aryl hydrocarbon receptor activation reduces dendritic cell function during influenza virus infection," Toxicological Sciences, vol. 116, No. 2, Aug. 2010 (pp. 512-522).

Jin et al., "New insights into the role of the aryl hydrocarbon receptor in the function of CD11c+ cells during respiratory viral infection," European Journal of Immunology, vol. 44, No. 6, Jun. 2014 (pp. 1685-1698).

Mezrich et al., "An interaction between kynurenine and the aryl hydrocarbon receptor can generate regulatory T cells," Journal of Immunology, vol. 185, No. 6, Sep. 2010 (pp. 3190-3198).

Moon et al., "Targeting the indoleamine 2,3-dioxygenase pathway in cancer," Journal for Immunotherapy of Cancer, vol. 3, No. 51, Dec. 2015 (10 pages).

Murray et al., "AH Receptor Ligands in Cancer: Friend of Foe," Nature Reviews Cancer, vol. 14, No. 12, Dec. 2014 (pp. 801-814).

Nguyen et al., "The roles of aryl hydrocarbon receptor in immune responses," International Immunology, vol. 25, No. 6, Jun. 2013 (pp. 335-343).

Nguyen et al., "Aryl hydrocarbon receptor and kynurenine: recent advances in autoimmune disease research," Frontiers in Immunology, vol. 5, No. 551, Oct. 2014 (6 pages).

Okazaki et al., "A rheostat for immune responses: the unique properties of PD-1 and their advantages for clinical application," Nature Immunology, vol. 14, No. 12, Dec. 2013 (pp. 1212-1218).

Opitz et al., "An endogenous tumour-promoting ligand of the human aryl hydrocarbon receptor," Nature, vol. 478, No. 7368, Oct. 2011 (pp. 197-203).

Peng et al., "Aryl hydrocarbon receptor pathway activation enhances gastric cancer cell invasiveness likely through a c-Jun-dependent induction of matrix metalloproteinase-9," BMC Cell Biology, vol. 10, No. 27, Apr. 2009 (7 pages).

Pubmed Compound Summary for CID 56889663, 'FEUZRBLRM-MOWLUUHFFFAOYSA-N', U.S. National Library of Medicine, Mar. 30, 2012 (pp. 1-11); p. 3 (https://pubchem.ncbi.nlm.nih.gov/compound/56889663).

Pubmed Compound Summary for CID 56913247, 'BIPWCZYHWSCQMCUHFFFAOYSA-N', U.S. National Library of Medicine, Mar. 30, 2012 (pp. 1-11); p. 3 (https://pubchem.ncbi.nlm.nih.gov/compound/56913247).

Pubmed Compound Summary for CID 71138224, 'HFJKTM-MVPWAAQQUHFFFAOYSA-N', U.S. National Library of Medicine, Mar. 21, 2013 (pp. 1-8); p. 3 (https://pubchem.ncbi.nlm.nih.gov/compound/71138224).

Ross et al., "Bispecific T cell engager (BiTE®) antibody constructs can mediate bystander tumor cell killing," PLoS ONE, vol. 12, No. 8, Aug. 2017 (24 pages).

Su et al., "Prognostic value of nuclear translocation of aryl hydrocarbon receptor for non-small cell lung cancer," Anticancer Research, vol. 33, No. 9, Sep. 2013 (pp. 3953-3961).

Toogood, "Small molecule immuno-oncology therapeutic agents," Bioorganic and Medicinal Chemistry Letters, vol. 28, No. 3, Feb. 2018 (pp. 319-329).

Uyttenhove et al., "Evidence for a tumoral immune resistance mechanism based on tryptophan degradation by indoleamine 2,3-dioxygenase," Nature Medicine, vol. 9, No. 10, Oct. 2003 (pp. 1269-1274).

Vogel et al., "Cross-talk between Aryl Hydrocarbon Receptor and the Inflammatory Response: A Role for Nuclear Factor-κB," Journal of Biological Chemistry, vol. 289, No. 3, Jan. 2014 (pp. 1866-1875).

Wagage et al., "The aryl hydrocarbon receptor promotes IL-10 production by NK cells," Journal of Immunology, vol. 192, No. 4, Feb. 2014 (pp. 1661-1670).

Zou et al., "PD-L1 (B7-H1) and PD-1 Pathway Blockade for Cancer Therapy: Mechanisms, Response Biomarkers, and Combinations," Science Translational Medicine, vol. 8, No. 328, Mar. 2016 (34 pages).

* cited by examiner

AHR INHIBITORS AND USES THEREOF

BACKGROUND OF THE INVENTION

The aryl hydrocarbon receptor (AHR) is a transcription factor that without ligand exists in the inactive state in the cytoplasm bound to HSP90. Upon ligand binding, AHR translocates to the nucleus where it dimerizes with ARNT forming a functional transcription factor. AHR/ARNT binds dioxin response elements (DRE) in the promotor of many genes where it modulates gene transcription. The most well documented genes regulated by AHR are the cytochrome P450 genes Cyp1b1 and Cyp1a1, where activation of AHR greatly increases expression of these genes. Therefore, Cyp1b1 and Cyp1a1 mRNA levels are a selective readout of AHR activation (reviewed in Murray et al., 2014).

Many exogenous and endogenous agonists of AHR exist that activate the receptor. The best characterized exogenous ligand class are the dioxins. One of the first endogenous ligands to be characterized is kynurenine, generated by TDO (Opitz 2011) or IDO (Mezrich 2010). Kynurenine is a stable metabolite in the IDO/TDO pathway and is the product of tryptophan degradation. Kynurenine has been shown to activate AHR as measured by an increase in Cyp1a1 and/or Cyp1b1 mRNA levels in multiple cell types, along with other DRE-driven genes.

AHR activation has pro-tumor effects by acting directly on the tumor cells and indirectly by causing immunosuppression, therefore not allowing the body's own immune system to attack the tumor. For example, AHR activation through multiple ligands leads to increased expression of FoxP3 and results in a polarization of CD4+ T-cells toward a suppressive subset called Foxp3+ T-regulatory cells (Tregs). These T-reg cells inhibit the proliferation of activated T cells (Funatake 2005, other refs). Interestingly, kynurenine has been shown to induce immunosuppressive Tregs through AHR. Kynurenine does not affect T-reg generation in AHR-null T cells or when an AHR antagonist is added (Mezrich). In addition to T-regs, AHR activation also leads to expansion of suppressive Tr1 T cells (Gandhi 2010). It has also been shown that expression of IDO is regulated by AHR activation in both tumor cells and T cells, leading to increased immune suppression (Vogel). It is likely there is also a role for AHR in immune suppressive myeloid cells (Nguyen 2013). Immune suppression is often associated with high levels of anti-inflammatory cytokines and there is evidence that AHR is involved in activation of many of these cytokines, such as IL-10 (Gandhi 2010, Wagage 2014).

There remains an unmet need to develop inhibitors of AHR for treating diseases, disorders and conditions associated therewith.

SUMMARY OF THE INVENTION

It has now been found that compounds of this invention, and pharmaceutically acceptable compositions thereof, are effective as inhibitors of AHR. Such compounds have the general formula I:

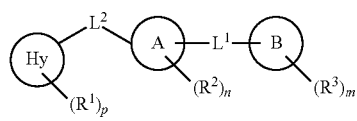

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with AHR. Such diseases, disorders, or conditions include those described herein.

Compounds provided by this invention are also useful for the study of AHR in biological and pathological phenomena; the study of intracellular signal transduction pathways; and the comparative evaluation of new AHR inhibitors in vitro or in vivo.

DETAILED DESCRIPTION OF CERTAIN EMBODIMENTS

1. General Description of Compounds of the Invention

In certain embodiments, the present invention provides inhibitors of AHR. In some embodiments, such compounds include those of formula I:

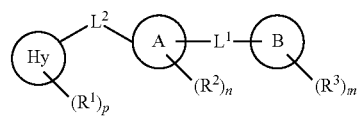

or a pharmaceutically acceptable salt thereof, wherein:
Hy is a 5-6 membered heteroaryl ring having 1-2 nitrogens;
Ring A is selected from phenyl, pyridyl, or pyrimdinyl;
$L^2$ is

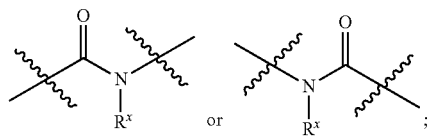

each $R^x$ is independently hydrogen or $C_{1-4}$ alkyl;
Ring B is phenyl, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;
each $R^1$ is independently selected from R, —C(O)R, —C(O)OR, —SO$_2$R, —C(O)N(R)$_2$, or —SO$_2$RN(R)$_2$;
each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$L^1$ is a covalent bond or an optionally substituted $C_{1-6}$ membered straight or branched saturated or unsaturated bivalent hydrocarbon chain wherein one methylene unit of $L^1$ is optionally replaced with -Cy-, —O—, —S—, —NR—, —N=N—, —C(O)—, —C(=NR)—, —C(O)
O—, —OC(O)—, —C(O)N(R)—, —N(R)C(O)—,
—SO₂—, —N(R)SO₂—, or —SO₂N(R)—; and -Cy- is a 3-8 membered bivalent saturated, partially unsaturated, or aromatic monocyclic ring having 0-2 heteroatoms independently selected from nitrogen, oxygen, or sulfur.

each of R² and R³ is independently selected from R, halogen, cyano, nitro, —OR, —SR, —N(R)₂, —N(R)C(O)R, —C(O)N(R)₂, —N(R)C(O)N(R)₂, —N(R)C(O)OR, —OC(O)N(R)₂, —N(R)SO₂R, —SO₂RN(R)₂, —C(O)R, —C(O)OR, —OC(O)R, —C(O)OR, —S(O)R, or —SO₂R, or:

R² and R^x are taken together to form an optionally substituted 4-7 membered partially unsaturated ring having 0-2 heteroatoms, in addition to the nitrogen to which R^x is attached, independently selected from nitrogen, oxygen, or sulfur; or R² and L¹ are taken together to form an optionally substituted 4-7 membered partially unsaturated or aromatic ring having 0-2 heteroatoms independently selected from nitrogen, oxygen, or sulfur;

each of m and n is independently 1, 2, 3, 4, or 5; and
p is 0, 1, 2, or 3.

In some embodiments, the present invention provides inhibitors of AHR, such compounds include those of formula I':

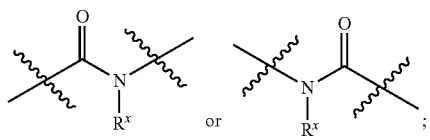

I' or a pharmaceutically acceptable salt thereof, wherein:

Hy is absent or a 5-6 membered heteroaryl ring having 1-2 nitrogens;

Ring A is selected from phenyl, pyridyl, pyrimdinyl, quinolinyl, naphthalenyl, benzo[1,3]dioxolyl, indolinyl, quinoxalinyl or chromenonyl;

L² is

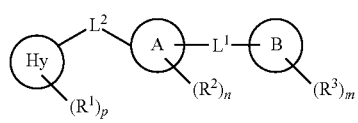

each R^x is independently hydrogen or $C_{1-4}$ alkyl;

Ring B is absent, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

each R¹ is independently selected from R, —C(O)R, —C(O)OR, —SO₂R, —C(O)N(R)₂, or —SO₂RN(R)₂;

each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

L¹ is a covalent bond or an optionally substituted $C_{1-6}$ membered straight or branched saturated or unsaturated bivalent hydrocarbon chain wherein one methylene unit of L¹ is optionally replaced with -Cy-, —O—, —S—, —NR—, —N=N—, —C(O)—, —C(=NR)—, —C(O)O—, —OC(O)—, —C(O)N(R)—, —N(R)C(O)—, —SO₂—, —N(R)SO₂—, or —SO₂N(R)—; and -Cy- is a 3-8 membered bivalent saturated, partially unsaturated, or aromatic monocyclic ring having 0-2 heteroatoms independently selected from nitrogen, oxygen, or sulfur.

each of R² and R³ is independently selected from R, halogen, cyano, nitro, —OR, —SR, —N(R)₂, —N(R)C(O)R, —C(O)N(R)₂, —N(R)C(O)N(R)₂, —N(R)C(O)OR, —OC(O)N(R)₂, —N(R)SO₂R, —SO₂RN(R)₂, —C(O)R, —C(O)OR, —OC(O)R, —C(O)OR, —S(O)R, or —SO₂R, or:

R² and R^x are taken together to form an optionally substituted 4-7 membered partially unsaturated ring having 0-2 heteroatoms, in addition to the nitrogen to which R^x is attached, independently selected from nitrogen, oxygen, or sulfur; or R² and L¹ are taken together to form an optionally substituted 4-7 membered partially unsaturated or aromatic ring having 0-2 heteroatoms independently selected from nitrogen, oxygen, or sulfur;

each of m and n is independently 1, 2, 3, 4, or 5; and
p is 0, 1, 2, or 3.

In some embodiments, the present invention provides a compound of formula I or formula I', with the proviso that said compound is other than:

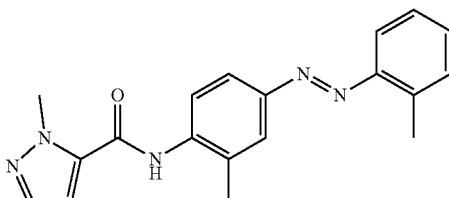

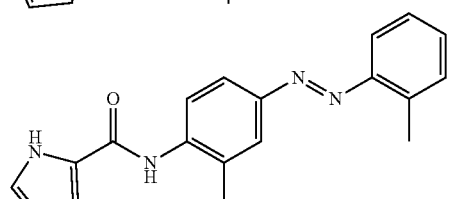

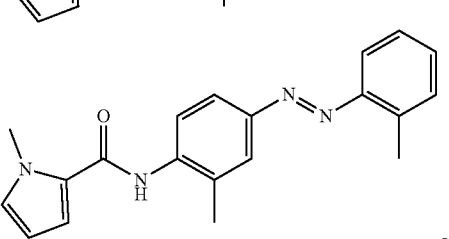

or

-continued

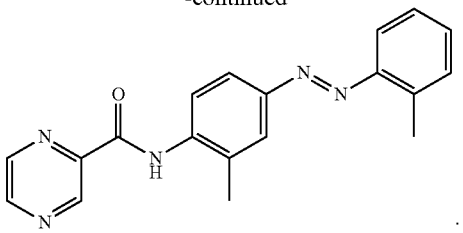

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

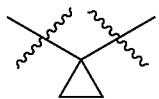

As used herein, the term "cyclobutylenyl" refers to a bivalent cyclobutyl group of the following structure:

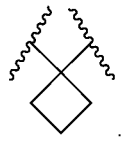

As used herein, the term "oxetanyl" refers to a bivalent oxetanyl group of the following structure:

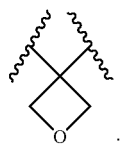 [SMILES: *C1(*)COC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}R^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\bullet$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

3. Description of Exemplary Embodiments

In certain embodiments, the present invention provides inhibitors of AHR. In some embodiments, such compounds include those of formula I:

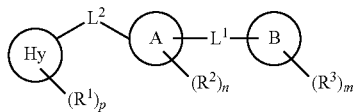

or a pharmaceutically acceptable salt thereof, wherein:
Hy is a 5-6 membered heteroaryl ring having 1-2 nitrogens;
Ring A is selected from phenyl, pyridyl, or pyrimdinyl;
$L^2$ is

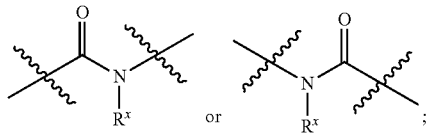

each $R^x$ is independently hydrogen or $C_{1-4}$ alkyl;
Ring B is phenyl, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;
each $R^1$ is independently selected from R, —C(O)R, —C(O)OR, —SO$_2$R, —C(O)N(R)$_2$, or —SO$_2$RN(R)$_2$;
each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$L^1$ is a covalent bond or an optionally substituted $C_{1-6}$ membered straight or branched saturated or unsaturated bivalent hydrocarbon chain wherein one methylene unit of $L^1$ is optionally replaced with -Cy-, —O—, —S—, —NR—, —N=N—, —C(O)—, —C(=NR)—, —C(O)O—, —OC(O)—, —C(O)N(R)—, —N(R)C(O)—, —SO$_2$—, —N(R)SO$_2$—, or —SO$_2$N(R)—; and
-Cy- is a 3-8 membered bivalent saturated, partially unsaturated, or aromatic monocyclic ring having 0-2 heteroatoms independently selected from nitrogen, oxygen, or sulfur.
each of $R^2$ and $R^3$ is independently selected from R, halogen, cyano, nitro, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$RN(R)$_2$, —C(O)R, —C(O)OR, —OC(O)R, —C(O)OR, —S(O)R, or —SO$_2$R, or:
  $R^2$ and $R^x$ are taken together to form an optionally substituted 4-7 membered partially unsaturated ring having 0-2 heteroatoms, in addition to the nitrogen to which $R^x$ is attached, independently selected from nitrogen, oxygen, or sulfur; or
  $R^2$ and $L^1$ are taken together to form an optionally substituted 4-7 membered partially unsaturated or aromatic ring having 0-2 heteroatoms independently selected from nitrogen, oxygen, or sulfur;

each of m and n is independently 1, 2, 3, 4, or 5; and
p is 0, 1, 2, or 3.
In certain embodiments, the present invention provides inhibitors of AHR. In some embodiments, such compounds include those of formula I':

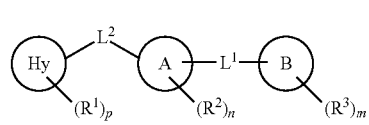

or a pharmaceutically acceptable salt thereof, wherein:
Hy is absent or a 5-6 membered heteroaryl ring having 1-2 nitrogens;
Ring A is selected from phenyl, pyridyl, pyrimdinyl, quinolinyl, naphthalenyl, benzo[1,3]dioxolyl, indolinyl, quinoxalinyl or chromenonyl;
$L^2$ is

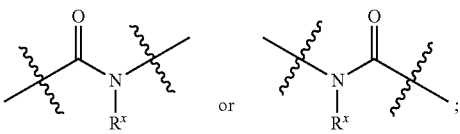

each $R^x$ is independently hydrogen or $C_{1-4}$ alkyl;
Ring B is absent, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;
each $R^1$ is independently selected from R, —C(O)R, —C(O)OR, —SO$_2$R, —C(O)N(R)$_2$, or —SO$_2$RN(R)$_2$;
each R is independently hydrogen, deuterium, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$L^1$ is a covalent bond or an optionally substituted $C_{1-6}$ membered straight or branched saturated or unsaturated bivalent hydrocarbon chain wherein one methylene unit of $L^1$ is optionally replaced with -Cy-, —O—, —S—, —NR—, —N=N—, —C(O)—, —C(=NR)—, —C(O)O—, —OC(O)—, —C(O)N(R)—, —N(R)C(O)—, —SO$_2$—, —N(R)SO$_2$—, or —SO$_2$N(R)—; and
-Cy- is a 3-8 membered bivalent saturated, partially unsaturated, or aromatic monocyclic ring having 0-2 heteroatoms independently selected from nitrogen, oxygen, or sulfur.
each of $R^2$ and $R^3$ is independently selected from R, halogen, cyano, nitro, —OR, —SR, —N(R)$_2$, —N(R)C(O)R, —C(O)N(R)₂, —N(R)C(O)N(R)₂, —N(R)C(O)OR, —OC(O)N(R)₂, —N(R)SO₂R, —SO₂RN(R)₂, —C(O)R, —C(O)OR, —OC(O)R, —C(O)OR, —S(O)R, or —SO₂R, or:

R² and R$^x$ are taken together to form an optionally substituted 4-7 membered partially unsaturated ring having 0-2 heteroatoms, in addition to the nitrogen to which R$^x$ is attached, independently selected from nitrogen, oxygen, or sulfur; or R² and L¹ are taken together to form an optionally substituted 4-7 membered partially unsaturated or aromatic ring having 0-2 heteroatoms independently selected from nitrogen, oxygen, or sulfur;

each of m and n is independently 1, 2, 3, 4, or 5; and p is 0, 1, 2, or 3.

In some embodiments, the present invention provides a compound of formula I or formula I', with the proviso that said compound is other than:

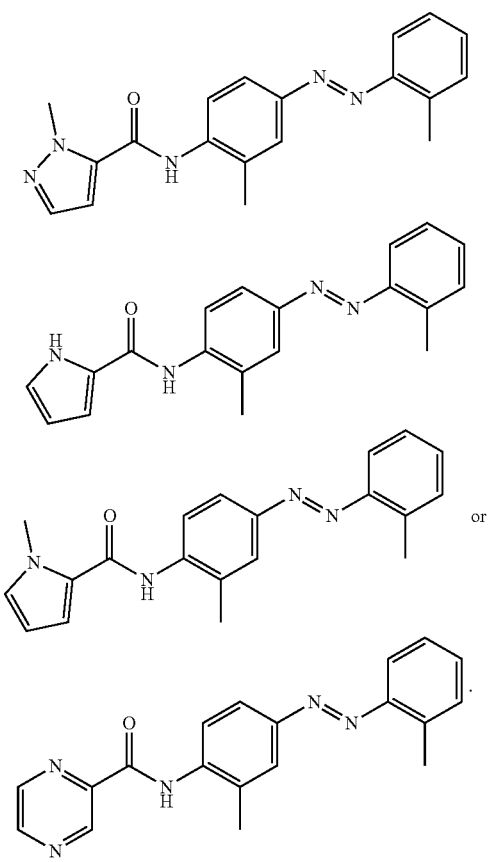

As defined generally above, Hy is absent or a 5-6 membered heteroaryl ring having 1-2 nitrogens. In some embodiments, Hy is absent. In some embodiments, Hy is pyrazolyl. In some embodiments, Hy is pyrolyl. In other embodiments, Hy is pyridyl. In some embodiments, Hy is selected from those depicted in Table 1, below.

As defined generally above, R$^x$ is hydrogen or $C_{1-4}$ alkyl. In some embodiments, R$^x$ is hydrogen. In other embodiments, R$^x$ is $C_{1-4}$ alkyl. In some embodiments, R$^x$ is methyl. In some embodiments, R$^x$ is selected from those depicted in Table 1, below.

As defined generally above, Ring A is phenyl, pyridyl, pyrimdinyl, quinolinyl, naphthalenyl, benzo[1,3]dioxolyl, indolinyl, quinoxalinyl or chromenonyl. In some embodiments, Ring A is phenyl. In some embodiments, Ring A is pyridyl. In some embodiments, Ring A is pyrimdinyl. In some embodiments, Ring A is quinolinyl. In some embodiments, Ring A is naphthalenyl. In some embodiments, Ring A is benzo[1,3]dioxolyl. In other embodiments, Ring A is indolinyl. In other embodiments, Ring A is quinoxalinyl. In other embodiments, Ring A is chromenonyl. In some embodiments, Ring A is selected from those depicted in Table 1, below.

As defined generally above, Ring B is absent, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, Ring B is absent. In some embodiments, Ring B is a 3-8 membered saturated or partially unsaturated monocyclic carbocyclic ring. In some embodiments, Ring B is phenyl. In some embodiments, Ring B is an 8-10 membered bicyclic aromatic carbocyclic ring. In some embodiments, Ring B is a 4-8 membered saturated or partially unsaturated monocyclic heterocyclic ring having 1-2 heteroatoms independently selected from nitrogen, oxygen, or sulfur. In some embodiments, Ring B is a 5-6 membered monocyclic heteroaromatic ring having 1-4 heteroatoms independently selected from nitrogen, oxygen, or sulfur. In other embodiments, Ring B is an 8-10 membered bicyclic heteroaryl ring having 1-4 heteroatoms independently selected from nitrogen, oxygen, or sulfur.

In some embodiments, Ring B is absent. In some embodiments, Ring B is phenyl. In some embodiments, Ring B is naphthalenyl. In some embodiments, Ring B is quinolinyl. In some embodiments, Ring B is dihydroquinolinyl. In some embodiments, Ring B is pyrazolyl. In some embodiments, Ring B is pyridyl. In some embodiments, Ring B is benzo[1,3]dioxolyl. In some embodiments, Ring B is indolinyl. In some embodiments, Ring B is indolyl. In some embodiments, Ring B is thiazolyl. In some embodiments, Ring B is oxazolyl. In some embodiments, Ring B is thiophenyl. In some embodiments, Ring B is cyclohexyl. In some embodiments, Ring B is piperidinyl. In some embodiments, Ring B is selected from those depicted in Table 1, below.

As defined generally above, each of R² and R³ is independently selected from R, halogen, cyano, nitro, —OR, —SR, —N(R)₂, —N(R)C(O)R, —C(O)N(R)₂, —N(R)C(O)N(R)₂, —N(R)C(O)OR, —OC(O)N(R)₂, —N(R)SO₂R, —SO₂RN(R)₂, —C(O)R, —C(O)OR, —OC(O)R, —C(O)OR, —S(O)R, or —SO₂R, or:

R² and R$^x$ are taken together to form an optionally substituted 4-7 membered partially unsaturated ring having 0-2 heteroatoms, in addition to the nitrogen to which R$^x$ is attached, independently selected from nitrogen, oxygen, or sulfur; or R² and L¹ are taken together to form an optionally substituted 4-7 membered partially unsaturated or aromatic ring having 0-2 heteroatoms independently selected from nitrogen, oxygen, or sulfur.

In some embodiments, R² is hydrogen. In some embodiments, R² is deuterium. In other embodiments, R² is halogen, cyano, nitro, —OR, —SR, —N(R)₂, —N(R)C(O)R, —C(O)N(R)₂, —N(R)C(O)N(R)₂, —N(R)C(O)OR, —OC (O)N(R)$_2$, —N(R)SO$_2$R, —SO$_2$RN(R)$_2$, —C(O)R, —C(O) OR, —OC(O)R, —C(O)OR, —S(O)R, —SO$_2$R, or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In certain embodiments, R$^2$ is optionally substituted C$_{1-6}$ aliphatic. In some embodiments, R$^2$ is methyl. In some embodiments, R$^2$ is selected from those depicted in Table 1, below.

In certain embodiments, R$^2$ and R$^x$ are taken together to form an optionally substituted 4-7 membered partially unsaturated ring having 0-2 heteroatoms, in addition to the nitrogen to which R$^x$ is attached, independently selected from nitrogen, oxygen, or sulfur. In certain embodiments, the ring formed thereby is as depicted in Table 1.

In some embodiments, R$^2$ and L$^1$ are taken together to form an optionally substituted 4-7 membered partially unsaturated or aromatic ring having 0-2 heteroatoms independently selected from nitrogen, oxygen, or sulfur. In certain embodiments, the ring formed thereby is as depicted in Table 1.

In some embodiments, R$^3$ is hydrogen. In some embodiments, R$^3$ is deuterium. In other embodiments, R$^3$ is halogen, cyano, nitro, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)SO$_2$R, —SO$_2$RN(R)$_2$, —C(O)R, —C(O)OR, —OC(O)R, —C(O)OR, —S(O)R, —SO$_2$R, or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring; a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, R$^3$ is selected from those depicted in Table 1, below.

In certain embodiments, R$^3$ is optionally substituted C$_{1-6}$ aliphatic. In some embodiments, R$^3$ is methyl.

As defined generally above, R$^1$ is R, —C(O)R, —C(O) OR, —SO$_2$R, —C(O)N(R)$_2$, or —SO$_2$RN(R)$_2$. In some embodiments, R$^1$ is hydrogen. In some embodiments, R$^1$ is R. In some embodiments, R$^1$ is —C(O)R. In some embodiments, R$^1$ is —C(O)OR. In some embodiments, R$^1$ is —SO$_2$R. In some embodiments, R$^1$ is —C(O)N(R)$_2$. In some embodiments, R$^1$ is —SO$_2$RN(R)$_2$. In some embodiments, R$^1$ is hydrogen. In some embodiments, R$^1$ is deuterium. In some embodiments, R$^1$ is an optionally substituted group selected from C$_{1-6}$ aliphatic. In some embodiments, R$^1$ is selected from those depicted in Table 1, below.

As defined generally above, n is 1, 2, 3, 4 or 5. In some embodiments, n is 1. In some embodiments, n is 2. In some embodiments, n is 3. In some embodiments, n is 4. In some embodiments, n is 5. In some embodiments, n is selected from those depicted in Table 1, below.

As defined generally above, m is 1, 2, 3, 4 or 5. In some embodiments, m is 1. In some embodiments, m is 2. In some embodiments, m is 3. In some embodiments, m is 4. In some embodiments, m is 5. In some embodiments, m is selected from those depicted in Table 1, below.

As defined generally above, L$^1$ is a covalent bond or an optionally substituted C$_{1-6}$ membered straight or branched saturated or unsaturated bivalent hydrocarbon chain wherein a methylene unit of L$^1$ is optionally replaced with -Cy-, —O—, —S—, —NR—, —N=N—, —C(O)—, —C(=NR)—, —C(O)O—, —OC(O)—, —C(O)N(R)—, —N(R)C(O)—, —SO$_2$—, —N(R)SO$_2$—, or —SO$_2$N(R)—S. In some embodiments, L$^1$ is a covalent bond. In some embodiments, L$^1$ is an optionally substituted C$_{1-6}$ membered straight or branched bivalent saturated hydrocarbon chain. In some embodiments, L$^1$ is an optionally substituted C$_{1-6}$ membered straight or branched bivalent unsaturated hydrocarbon chain. In some embodiments, L$^1$ is —CH=CH—, —C(O)NH—, —NHCH$_2$—, —N=N—, —CH$_2$O—, or

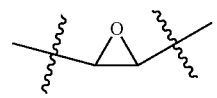

In some embodiments, L$^1$ is selected from those depicted in Table 1, below.

In some embodiments, the present invention provides a compound selected from any of formulae I-a, I-b, I-c, I-d, I-e, and I-f:

I-a
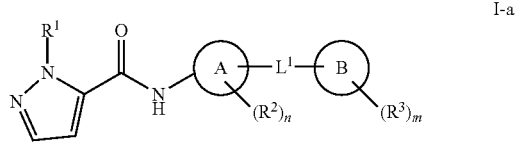

I-b
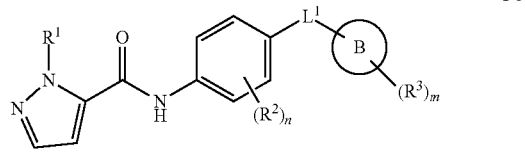

I-c
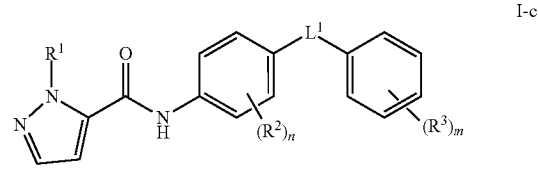

I-d
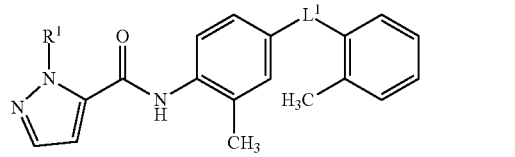

I-e
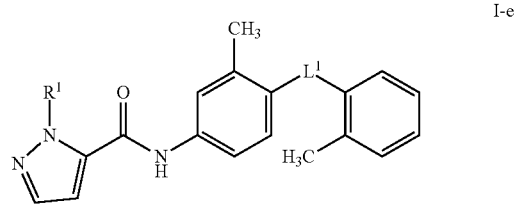

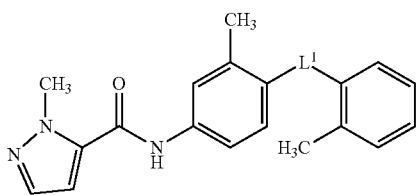

I-f or a pharmaceutically acceptable salt thereof; wherein each variable is as described in embodiments for formula I and formula I', supra, or described in embodiments herein, both singly and in combination.

In some embodiments, the present invention provides a compound selected from any of formulae II-a, II-b, II-c, II-d, II-e, and II-f:

II-a
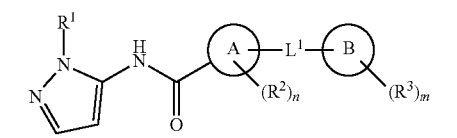

II-b
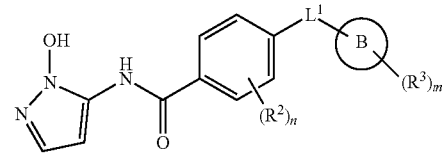

II-c
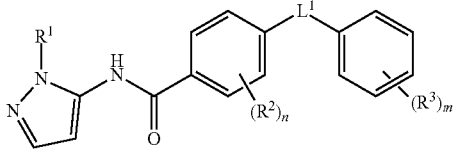

II-d
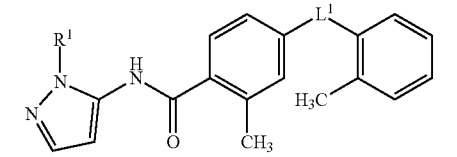

II-e
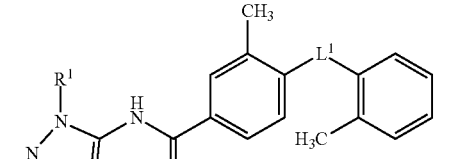

II-f
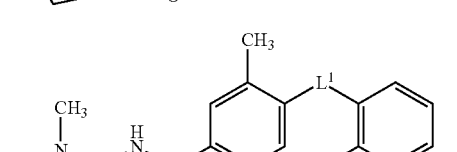

or a pharmaceutically acceptable salt thereof; wherein each variable is as described in embodiments for formula I and formula I', supra, or described in embodiments herein, both singly and in combination.

In some embodiments, the present invention provides a compound selected from any of formulae III-a, III-b, III-c, III-d, III-e, III-f, III-g, III-h, III-i, III-j, III-k, III-l, III-m, III-n, III-o, III-p, III-q, III-r, III-s, III-t and III-u:

III-a
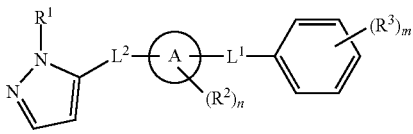

III-b
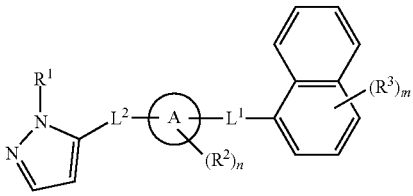

III-c
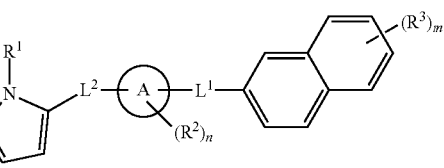

III-d
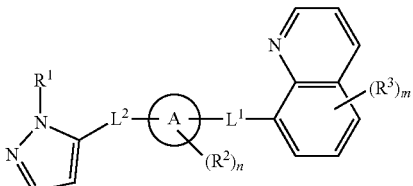

III-e

III-f
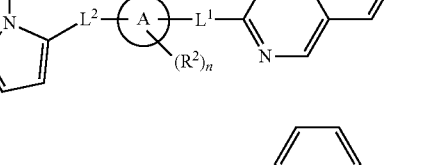

III-g
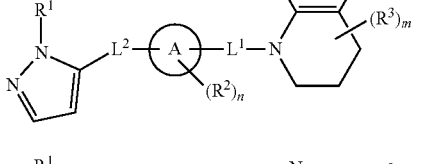

III-h
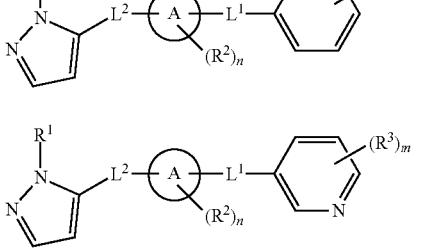

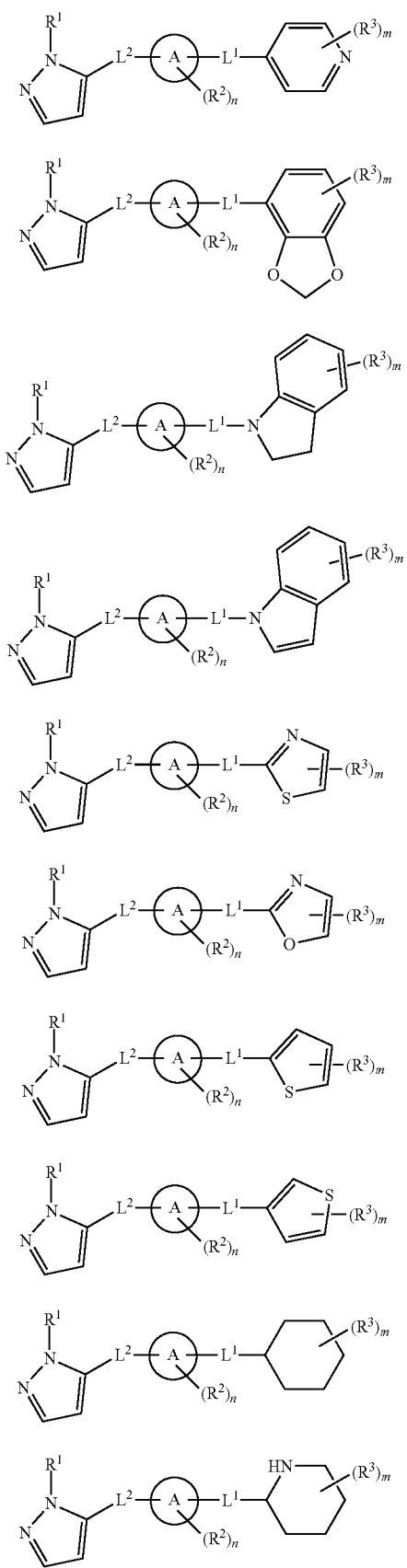
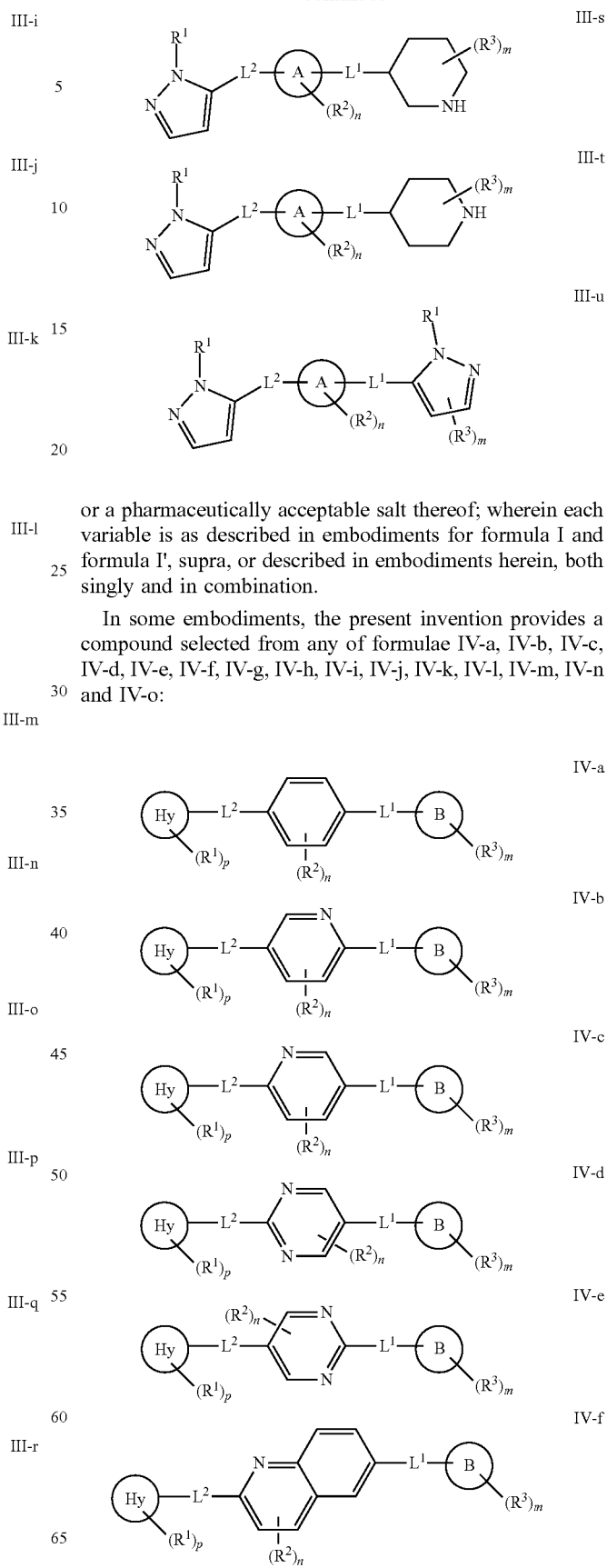
or a pharmaceutically acceptable salt thereof; wherein each variable is as described in embodiments for formula I and formula I', supra, or described in embodiments herein, both singly and in combination.
In some embodiments, the present invention provides a compound selected from any of formulae IV-a, IV-b, IV-c, IV-d, IV-e, IV-f, IV-g, IV-h, IV-i, IV-j, IV-k, IV-l, IV-m, IV-n and IV-o:

IV-g
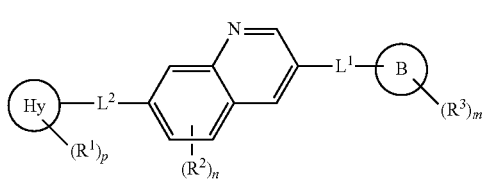

IV-h
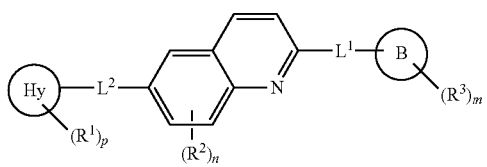

IV-i
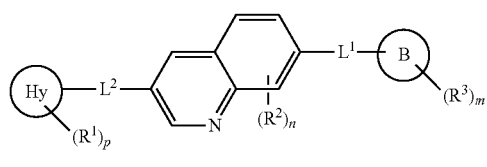

IV-j
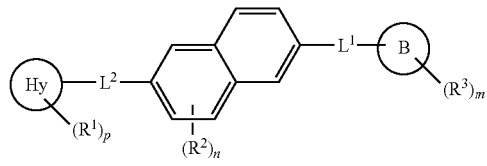

IV-k
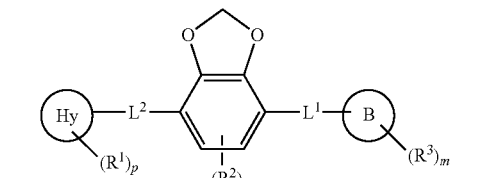

IV-l
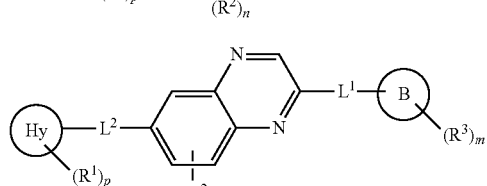

IV-m
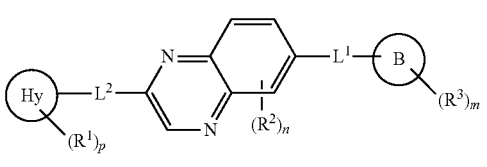

IV-n
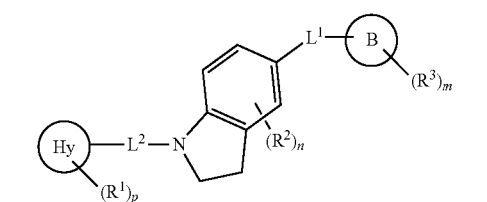

IV-o
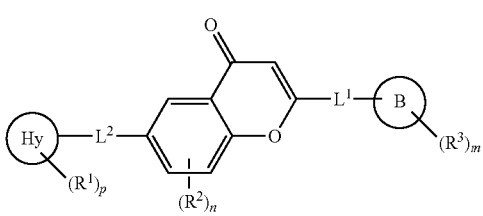

or a pharmaceutically acceptable salt thereof; wherein each variable is as described in embodiments for formula I and formula I', supra, or described in embodiments herein, both singly and in combination.

In some embodiments, the present invention provides a compound selected from any of formulae V-a, V-b, V-c, V-d, V-e, V-f, V-g, V-h, V-i, V-j, V-k, V-l, V-m and V-n:

V-a
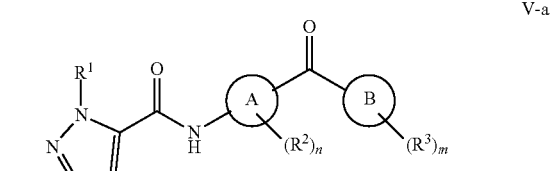

V-b
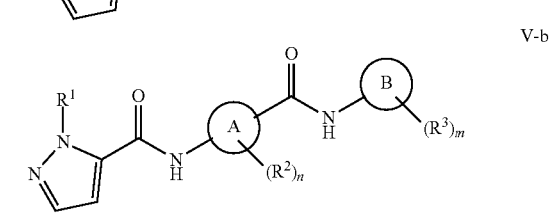

V-c
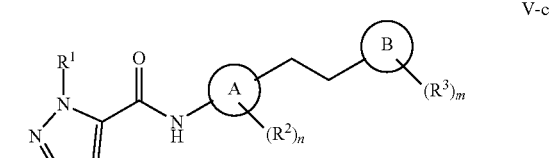

V-d
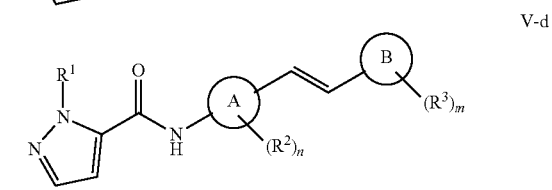

V-e
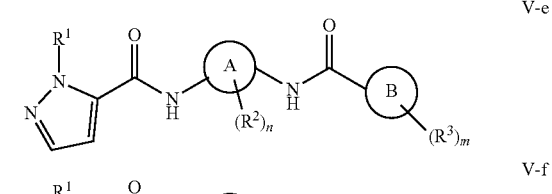

V-f
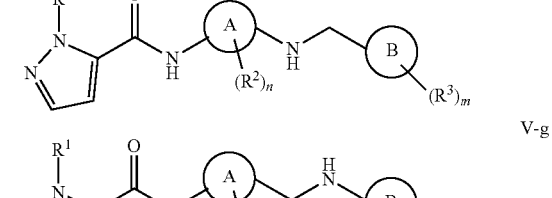

V-g
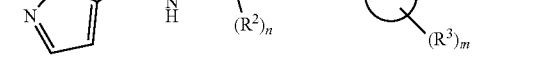

-continued

V-h
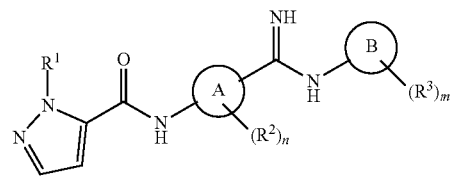

V-i
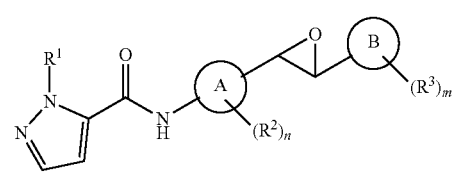

V-j
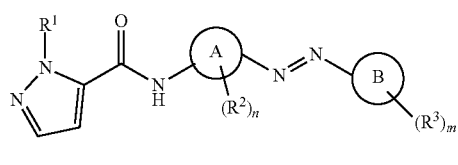

V-k
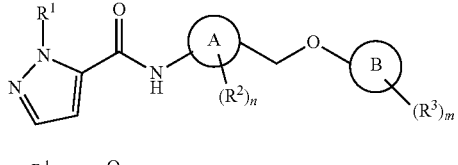

V-l
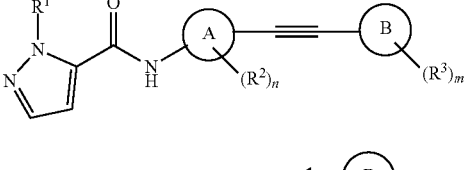

V-m
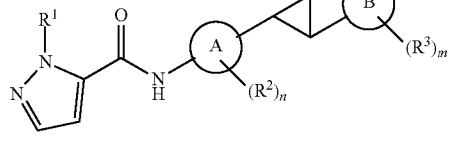

V-n
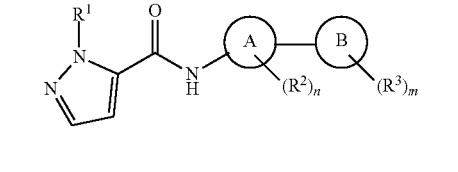

or a pharmaceutically acceptable salt thereof; wherein each variable is as described in embodiments for formula I and formula I', supra, or described in embodiments herein, both singly and in combination.

In some embodiments, the present invention provides a compound selected from any of formulae VI-a, VI-b, VI-c, VI-d, VI-e, VI-f, VI-g, VI-h, VI-i, VI-j, VI-k, VI-l, VI-m and VI-n:

VI-a
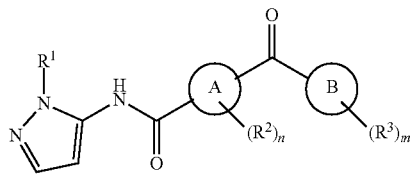

-continued

VI-b
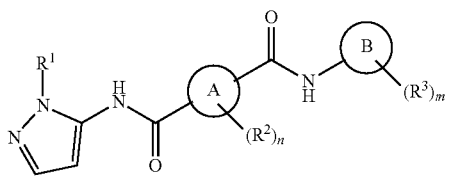

VI-c
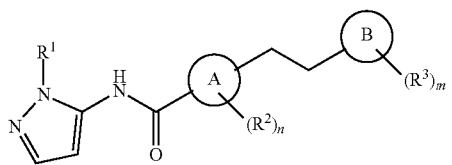

VI-d
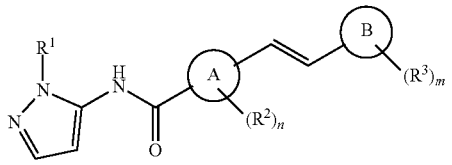

VI-e
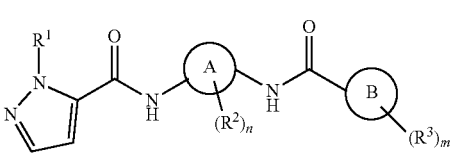

VI-f
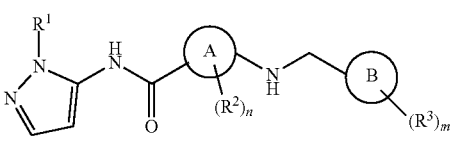

VI-g
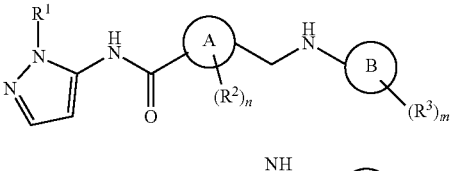

VI-h
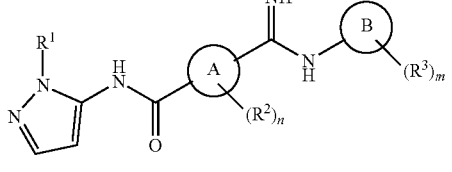

VI-i
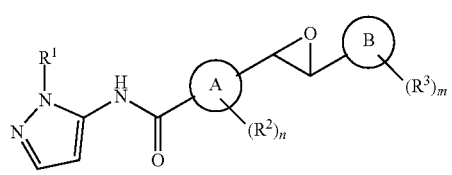

VI-j
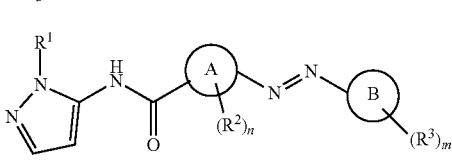

VI-k

-continued

VI-l

VI-m

VI-n or a pharmaceutically acceptable salt thereof; wherein each variable is as described in embodiments for formula I and formula I', supra, or described in embodiments herein, both singly and in combination.

Exemplary compounds of formula I are set forth in Table 1, below:

TABLE 1

Exemplary Compounds of Formula I

I-1

I-2

I-3

I-4

TABLE 1-continued

Exemplary Compounds of Formula I

I-5

I-6

I-7

I-8

I-9

I-10

I-11

TABLE 1-continued

Exemplary Compounds of Formula I

I-12

I-13

I-14

I-15

I-16

I-17

I-18

I-19

I-20

I-21

I-22

I-23

I-24

I-25

TABLE 1-continued
Exemplary Compounds of Formula I
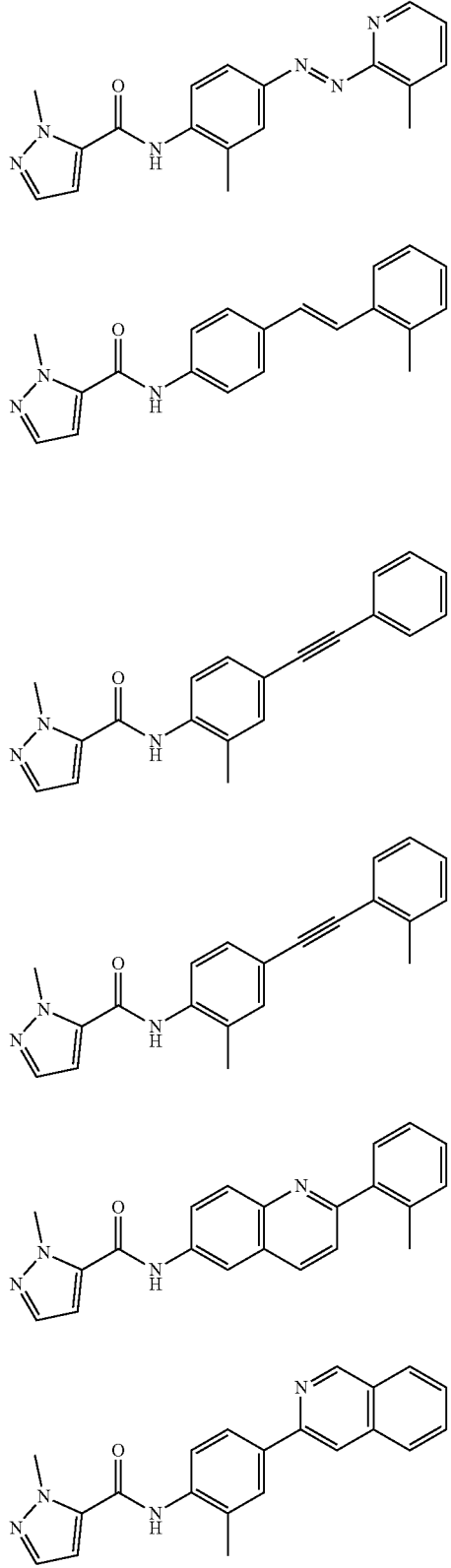
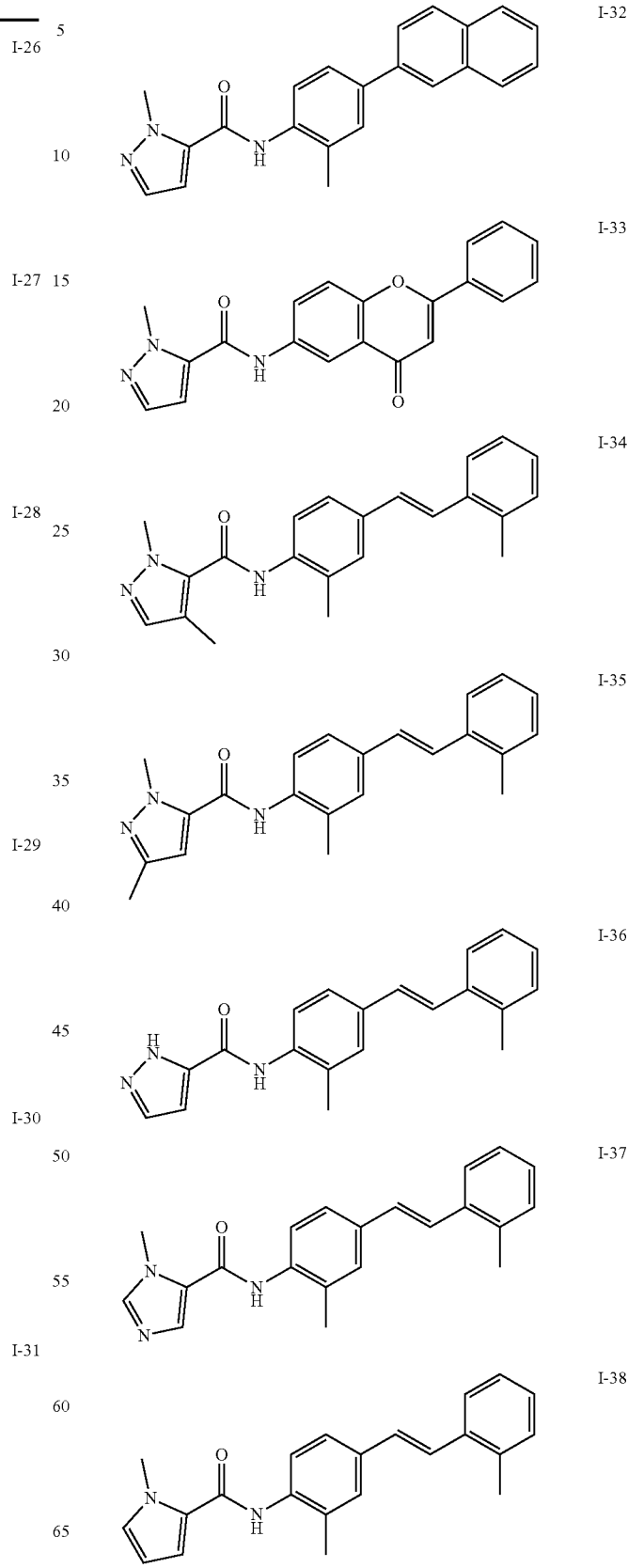

TABLE 1-continued
Exemplary Compounds of Formula I
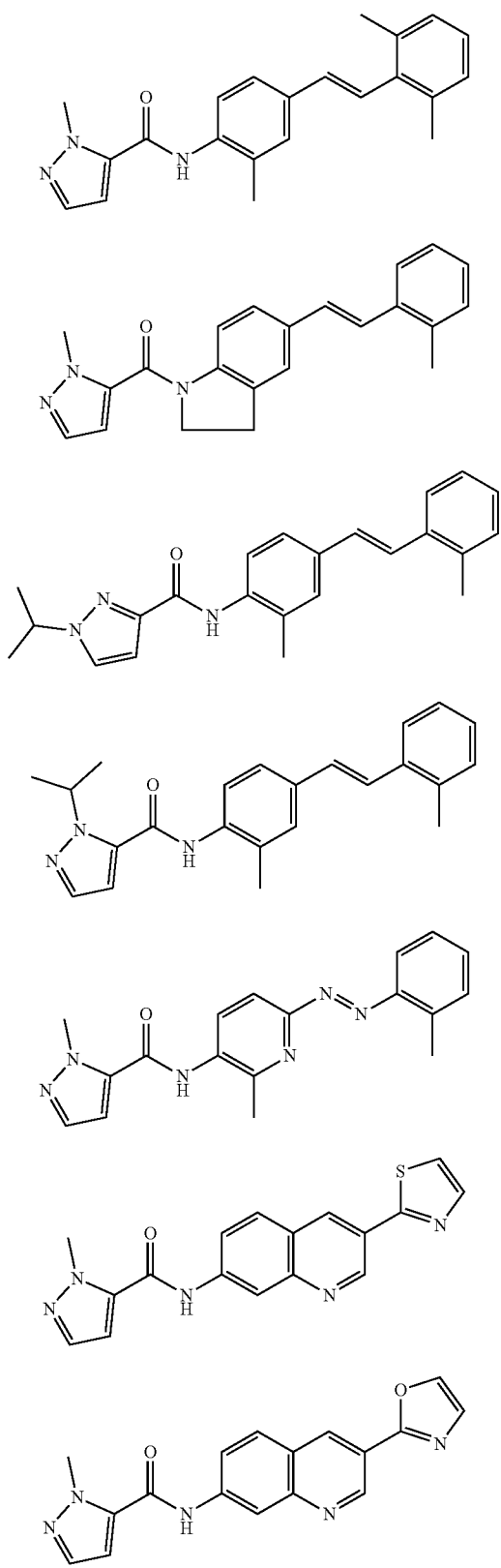
I-39
I-40
I-41
I-42
I-43
I-44
I-45
TABLE 1-continued
Exemplary Compounds of Formula I
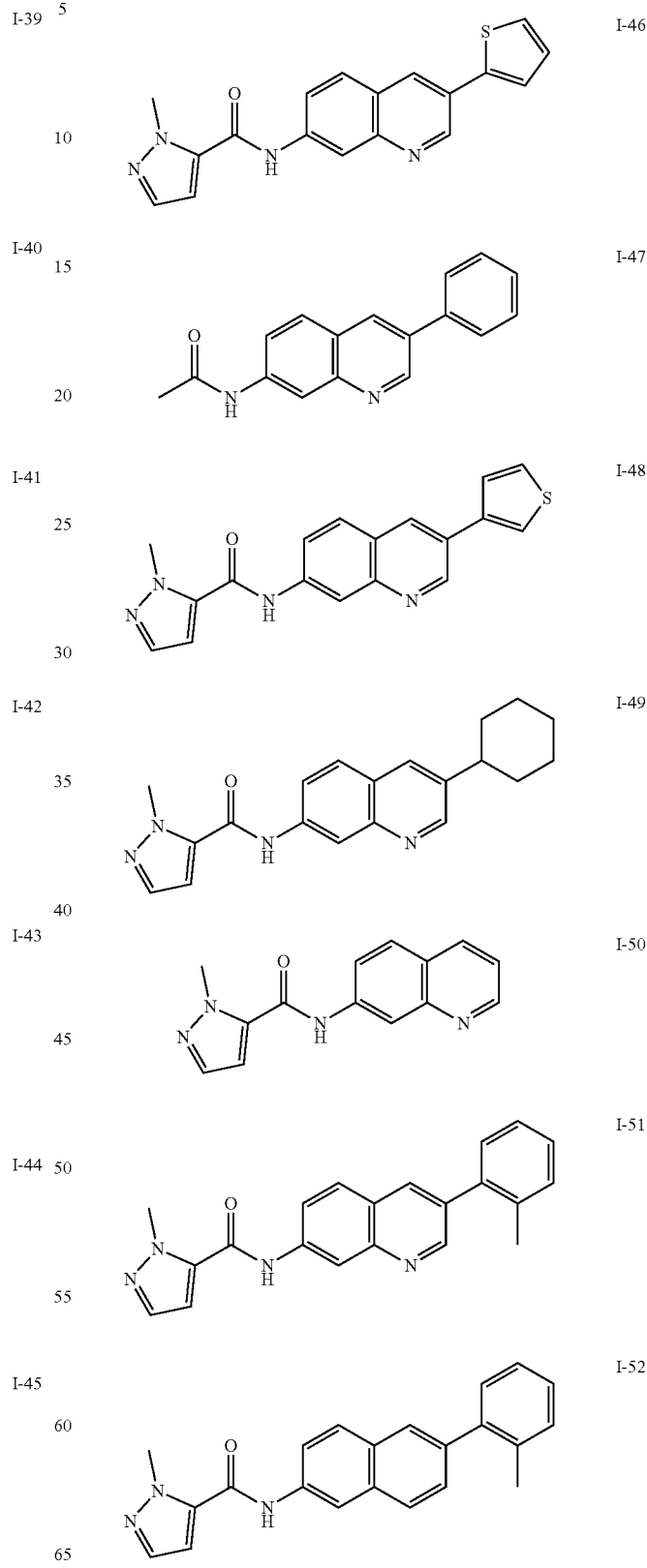
I-46
I-47
I-48
I-49
I-50
I-51
I-52

TABLE 1-continued
Exemplary Compounds of Formula I
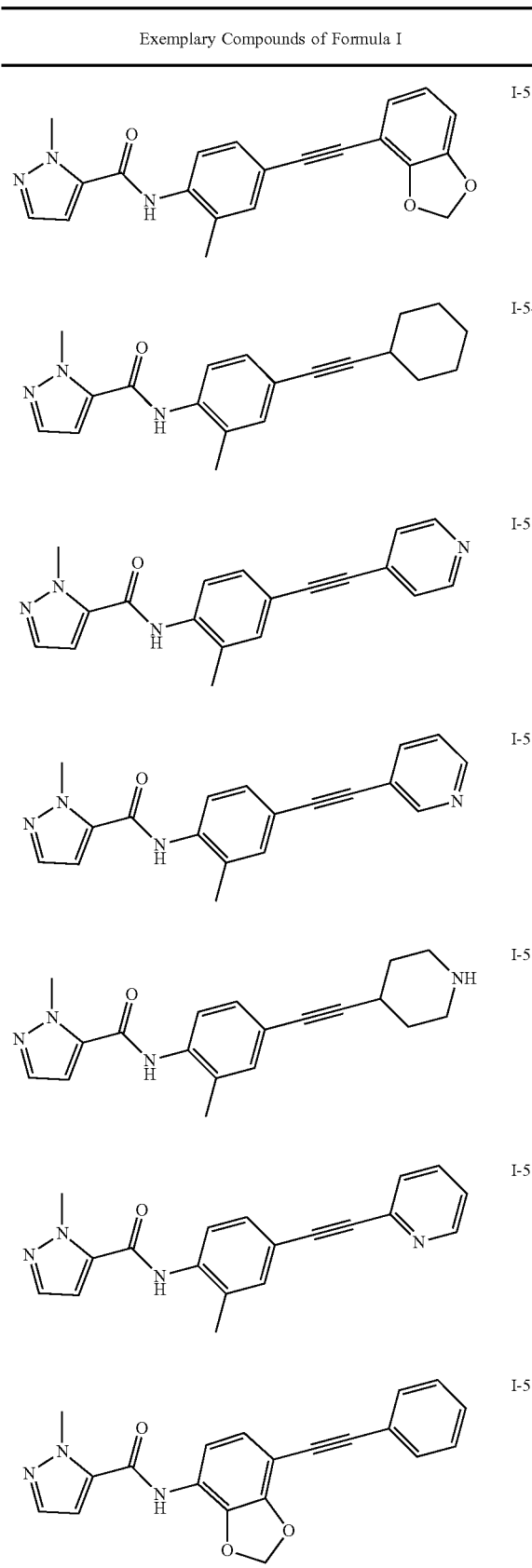
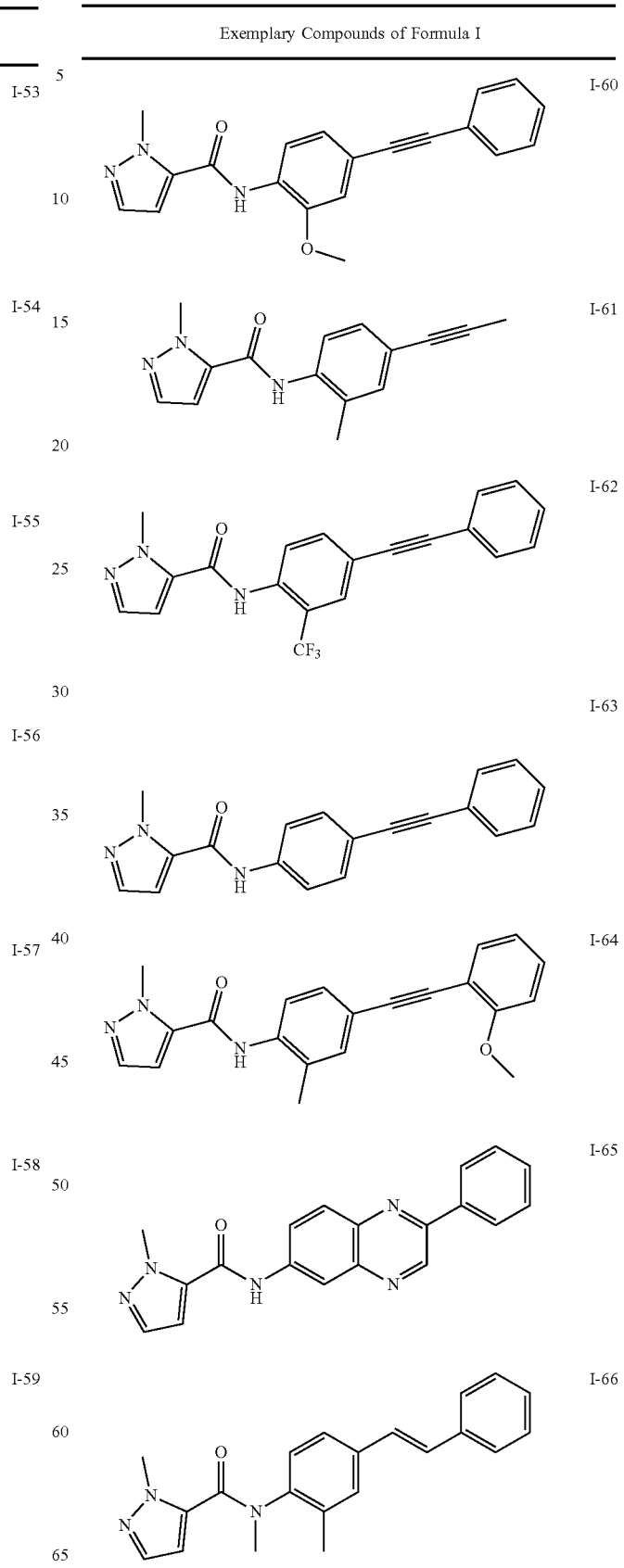

TABLE 1-continued
Exemplary Compounds of Formula I
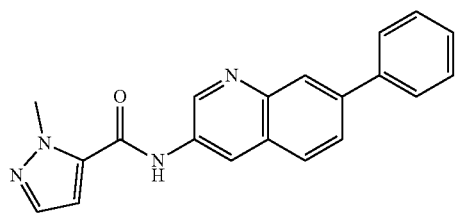 [SMILES: Cn1nccc1C(=O)Nc1cnc2cc(-c3ccccc3)ccc2c1]
I-67
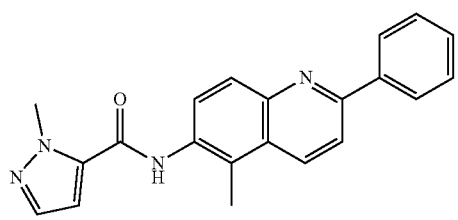 [SMILES: Cc1c(NC(=O)c2ccnn2C)ccc2nc(-c3ccccc3)ccc12]
I-68
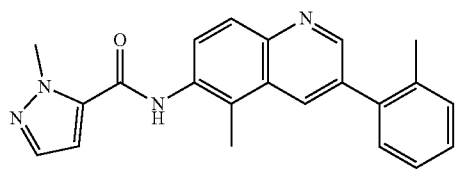 [SMILES: Cc1ccccc1-c1cnc2ccc(NC(=O)c3ccnn3C)c(C)c2c1]
I-69
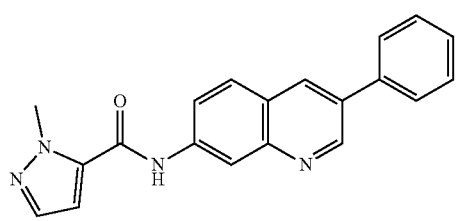 [SMILES: Cn1nccc1C(=O)Nc1ccc2cc(-c3ccccc3)cnc2c1]
I-70
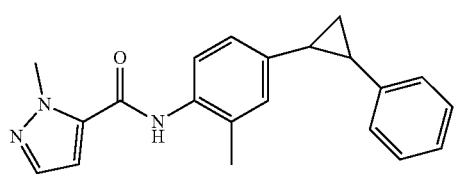 [SMILES: Cc1cc(C2CC2c2ccccc2)ccc1NC(=O)c1ccnn1C]
I-71
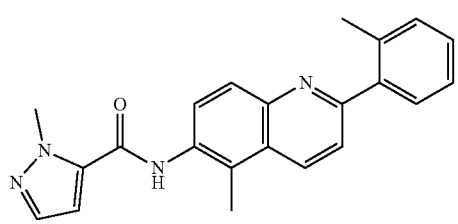 [SMILES: Cc1ccccc1-c1ccc2c(C)c(NC(=O)c3ccnn3C)ccc2n1]
I-72
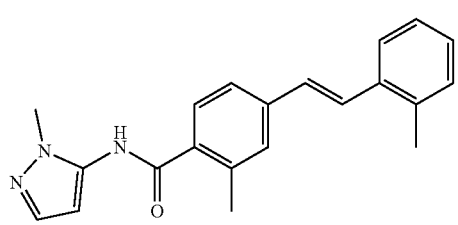 [SMILES: Cc1ccccc1/C=C/c1ccc(C(=O)Nc2ccnn2C)c(C)c1]
I-73
TABLE 1-continued
Exemplary Compounds of Formula I
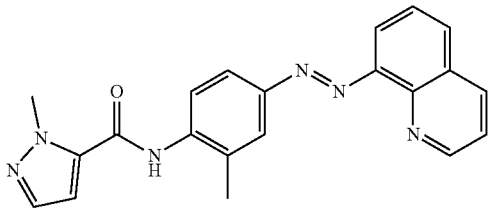 [SMILES: Cc1cc(/N=N/c2cccc3cccnc23)ccc1NC(=O)c1ccnn1C]
I-74
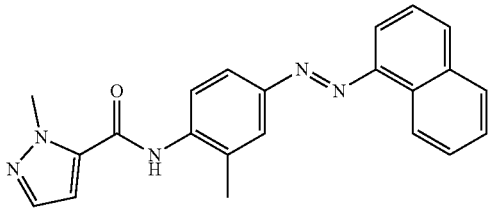 [SMILES: Cc1cc(/N=N/c2cccc3ccccc23)ccc1NC(=O)c1ccnn1C]
I-75
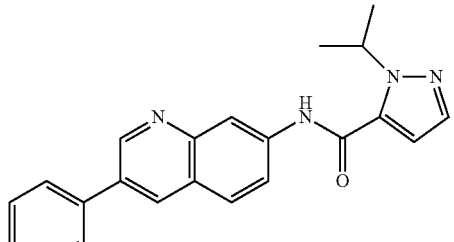
I-76
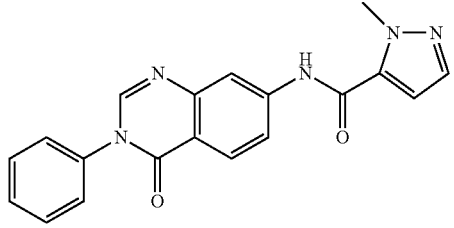 [SMILES: Cn1nccc1C(=O)Nc1ccc2c(=O)n(-c3ccccc3)cnc2c1]
I-77
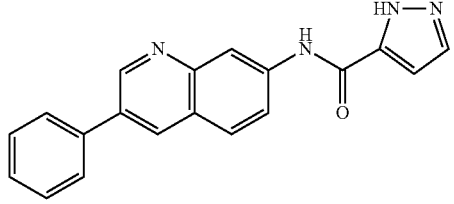 [SMILES: O=C(Nc1ccc2cc(-c3ccccc3)cnc2c1)c1ccn[nH]1]
I-78
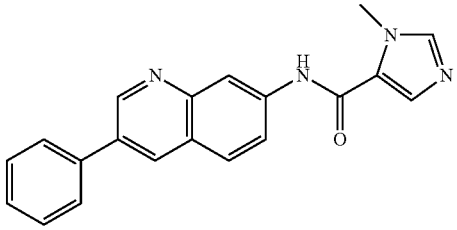 [SMILES: Cn1cncc1C(=O)Nc1ccc2cc(-c3ccccc3)cnc2c1]
I-79

TABLE 1-continued
Exemplary Compounds of Formula I
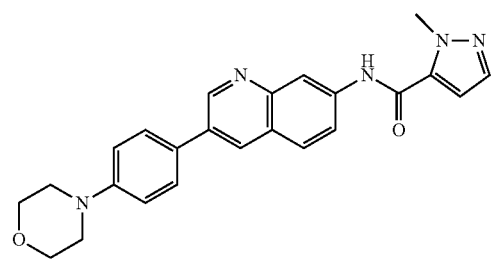 [SMILES: Cn1nccc1C(=O)Nc1ccc2cc(-c3ccc(N4CCOCC4)cc3)cnc2c1]
I-80
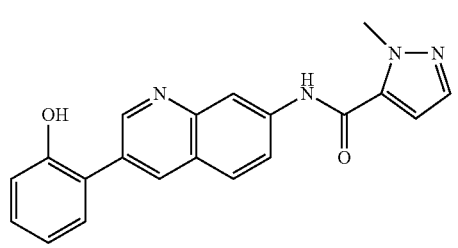 [SMILES: Cn1nccc1C(=O)Nc1ccc2cc(-c3ccccc3O)cnc2c1]
I-81
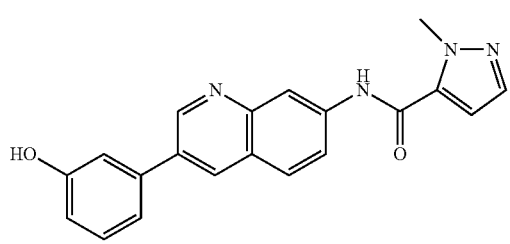 [SMILES: Cn1nccc1C(=O)Nc1ccc2cc(-c3cccc(O)c3)cnc2c1]
I-82
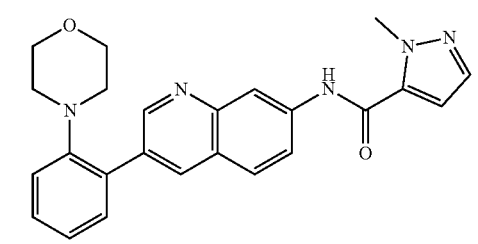 [SMILES: Cn1nccc1C(=O)Nc1ccc2cc(-c3ccccc3N3CCOCC3)cnc2c1]
I-83
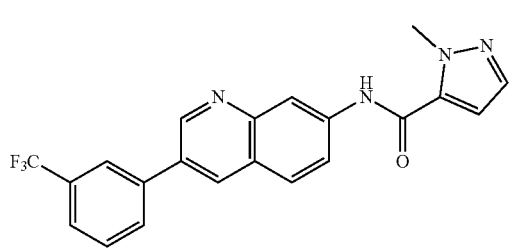 [SMILES: Cn1nccc1C(=O)Nc1ccc2cc(-c3cccc(C(F)(F)F)c3)cnc2c1]
I-84
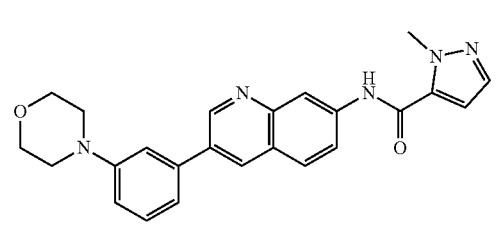 [SMILES: Cn1nccc1C(=O)Nc1ccc2cc(-c3cccc(N4CCOCC4)c3)cnc2c1]
I-85
TABLE 1-continued
Exemplary Compounds of Formula I
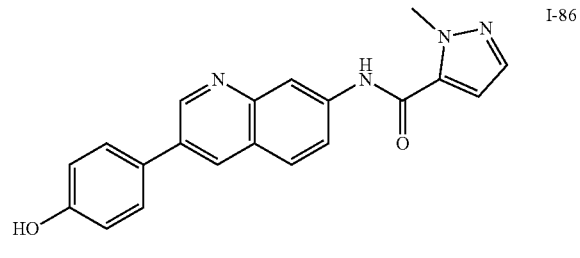
I-86
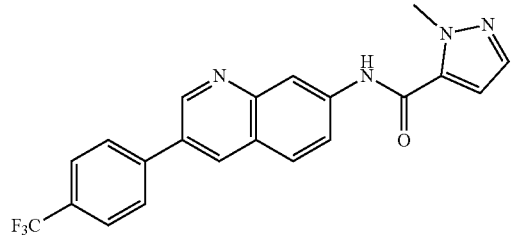 [SMILES: Cn1nccc1C(=O)Nc1ccc2cc(-c3ccc(C(F)(F)F)cc3)cnc2c1]
I-87
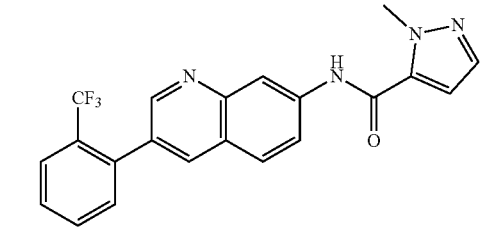 [SMILES: Cn1nccc1C(=O)Nc1ccc2cc(-c3ccccc3C(F)(F)F)cnc2c1]
I-88
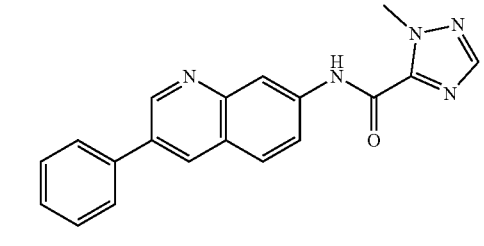 [SMILES: Cn1ncnc1C(=O)Nc1ccc2cc(-c3ccccc3)cnc2c1]
I-89
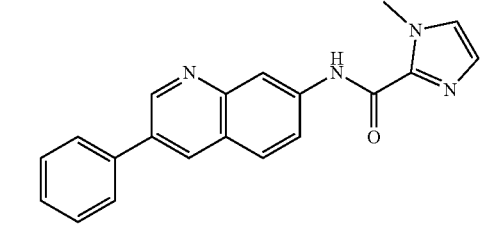 [SMILES: Cn1ccnc1C(=O)Nc1ccc2cc(-c3ccccc3)cnc2c1]
I-90
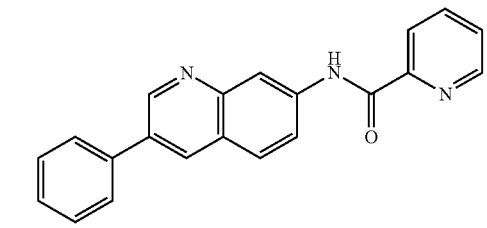 [SMILES: O=C(Nc1ccc2cc(-c3ccccc3)cnc2c1)c1ccccn1]
I-91

TABLE 1-continued

Exemplary Compounds of Formula I

I-92
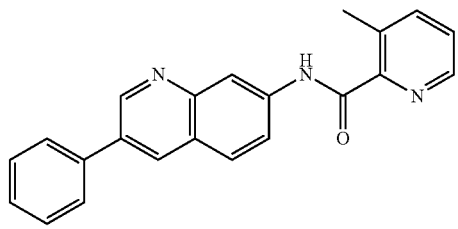 [SMILES: Cc1cccnc1C(=O)Nc1ccc2cc(-c3ccccc3)cnc2c1]

I-93
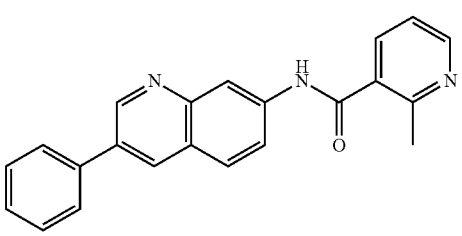 [SMILES: Cc1ncccc1C(=O)Nc1ccc2cc(-c3ccccc3)cnc2c1]

I-94
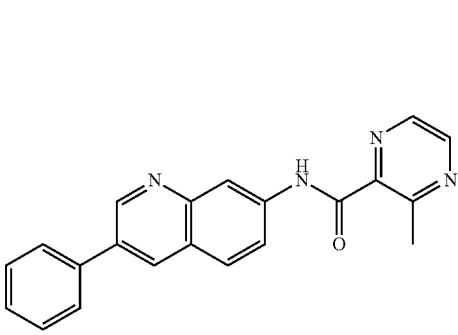 [SMILES: Cc1nccnc1C(=O)Nc1ccc2cc(-c3ccccc3)cnc2c1]

I-95
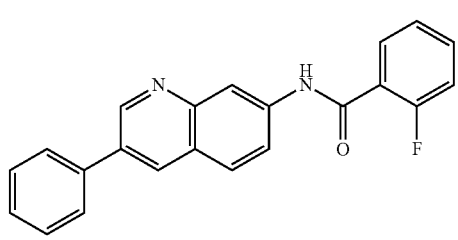 [SMILES: O=C(Nc1ccc2cc(-c3ccccc3)cnc2c1)c1ccccc1F]

I-96
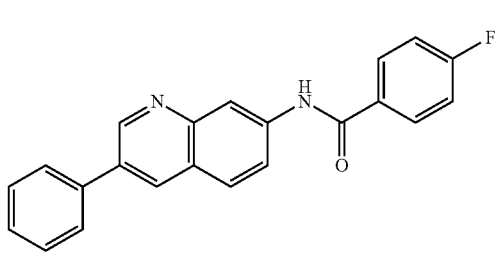 [SMILES: O=C(Nc1ccc2cc(-c3ccccc3)cnc2c1)c1ccc(F)cc1]

I-97
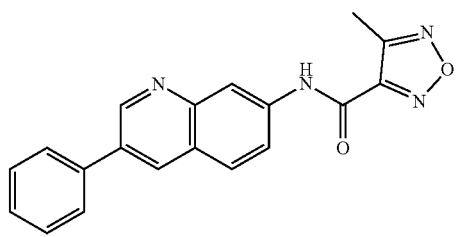 [SMILES: Cc1nonc1C(=O)Nc1ccc2cc(-c3ccccc3)cnc2c1]

I-98
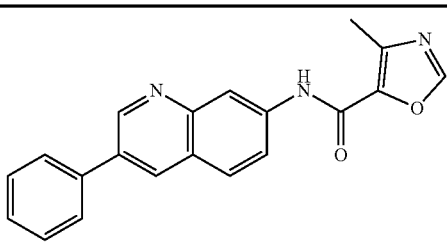

I-99
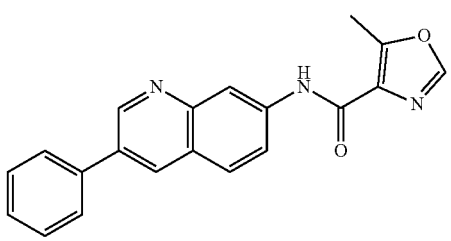 [SMILES: Cc1ocnc1C(=O)Nc1ccc2cc(-c3ccccc3)cnc2c1]

I-100
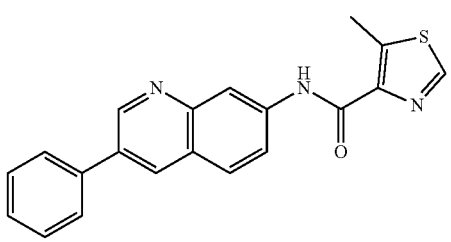 [SMILES: Cc1scnc1C(=O)Nc1ccc2cc(-c3ccccc3)cnc2c1]

In certain embodiments, the present invention provides any compound selected from those depicted in Table 1, above, or a pharmaceutically acceptable salt thereof, for the inhibition of AHR.

4. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit AHR, in a biological sample or in a patient. In certain embodiments, the amount of compound in compositions of this invention is such that is effective to measurably inhibit AHR, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The activity of a compound utilized in this invention as an inhibitor of AHR may be assayed in vitro or in vivo. An in vivo assessment of the efficacy of the compounds of the invention may be made using an animal model of obesity or metabolic syndrome, e.g., a rodent or primate model. Cell-based assays may be performed using, e.g., a cell line isolated from a tissue that expresses AHR. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate in vitro assays quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an inhibitor of AHR are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, the compounds and compositions, according to the method of the present invention, may be administered using any amount and any route of administration effective for treating or lessening the severity of a disease associated with AHR.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses and Methods of Treatment

According to one embodiment, the invention relates to a method of inhibiting AHR in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting AHR in a patient comprising the step of administering to said patient a compound of the present invention, or a composition comprising said compound.

Provided compounds are inhibitors of AHR and are therefore useful for treating one or more disorders associated with activity of AHR. Thus, in certain embodiments, the present invention provides a method for treating an AHR-mediated disorder comprising the step of administering to a patient in need thereof a compound of the present invention, or pharmaceutically acceptable composition thereof.

As used herein, the terms "AHR-mediated" disorders, diseases, and/or conditions as used herein means any disease or other deleterious condition in which AHR, or a mutant thereof, are known to play a role. Accordingly, another embodiment of the present invention relates to treating or lessening the severity of one or more diseases in which AHR, or a mutant thereof, are known to play a role.

AHR mediated disorders are well established in the art. The nexus between AHR and AHR mediated disorders diseases and/or conditions as recited herein is well established in the relevant arts. For example, see: Uyttenhove et al., "Evidence for a tumoral immune resistance mechanism based on tryptophan degradation by indoleamine 2,3-dioxygenase" *Nature Medicine,* 2003 vol. 9(10), 1038; Murray et al., "AH RECEPTOR LIGANDS IN CANCER: FRIEND AND FOE" *Nat. Rev. Cancer* December 2014, vol. 14(12), pages 801-814; Moon et al., "Targeting the indoleamine 2,3-dioxygenase pathway in cancer" *J. ImmunoTherapy of Cancer,* 2015 vol 3, page 51; Ishida et al., "Activation of aryl hydrocarbon receptor promotes invasion of clear cell renal cell carcinoma and is associated with poor prognosis and cigarette smoke" *Int. J. Cancer* July 2015 vol. 15, no. 137(2), pages 299-310; Ishida et al., "Activation of the aryl hydrocarbon receptor pathway enhances cancer cell invasion by upregulating the MMP expression and is associated with poor prognosis in upper urinary tract urothelial cancer" *Carcinogenesis* February 2010 vol. 31(2), pages 287-295. Su et al., "Prognostic value of nuclear translocation of aryl hydrocarbon receptor for non-small cell lung cancer" *Anticancer Res*. September 2013, vol. 33(9), pages 3953-3961; Peng et al., "Aryl hydrocarbon receptor pathway activation enhances gastric cancer cell invasiveness likely through a c-Jun-dependent induction of matrix metalloproteinase-9" *BMC Cell Biol*. April 2009 vol. 16; pages 10-27; Jin et al., "Aryl Hydrocarbon Receptor Activation Reduces Dendritic Cell Function during Influenza Virus Infection" Toxicol Sci. August 2010, vol. 116(2), pages 514-522; Head et al., "The aryl hydrocarbon receptor is a modulator of anti-viral immunity" *Biochem. Pharmacol.* February 2009 vol. 15; no. 77(4), pages 642-53; Jin et al., "New insights into the role of the aryl hydrocarbon receptor in the function of $CD11c^+$ cells during respiratory viral infection" *Eur. J. Immunol.* June 2014, vol. 44(6), pages 1685-98; Nguyen et al., "Aryl hydrocarbon receptor and kynurenine: recent advances in autoimmune disease research" *Front Immunol*. October 2014, vol. 29, no. 5, page 551; Esser et al., "The aryl hydrocarbon receptor in immunity" *Trends in Immunology,* Vol. 30, No. 9.

In some embodiments, the present invention provides a method for treating one or more disorders, diseases, and/or conditions wherein the disorder, disease, or condition is a proliferative disease such as cancer, an inflammatory disorder, or a viral infection.

In certain embodiments, the present invention provides a method of treating cancer or another proliferative disorder, comprising administering a compound or composition of the present invention to a patient with cancer or another proliferative disorder. In certain embodiments, the method of treating cancer or another proliferative disorder comprises administering compounds and compositions of the present invention to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL).

Compounds of the current invention are useful in the treatment of a proliferative disease selected from a benign or malignant tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, Waldenström's macroglobulinemia, a mammary carcinoma, follicular carcinoma, undifferentiated carcinoma, papillary carcinoma, seminoma, melanoma, an MYD88-driven disorder, DLBCL, ABC DLBCL, an IL-1-driven disorder, Smoldering of indolent multiple myeloma, or a leukemia.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Graves' disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, dermatomyositis, polymyositis, inclusion body myositis, myasthenia gravis, thyroiditis, Addison's disease, lichen planus, Type 1 diabetes, or Type 2 diabetes.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin-Associated Periodic Syndromes (CAPS), or osteoarthritis.

In some embodiments, the inflammatory disease which can be treated according to the methods of this invention is selected from a TH17-mediated disease. In some embodiments, the TH17-mediated disease is selected from Systemic lupus erythematosus, Multiple sclerosis, inflammatory bowel disease including Crohn's or ulcerative colitis.

In some embodiments, the inflammatory disease which can be treated according to the methods of this invention is selected from Sjogren's syndrome allergic disorders, osteoarthritis. Conditions of the eye such as ocular allergy, conjunctivitis, keratoconjunctivitis sicca, and vernal conjunctivitis, diseases affecting the nose including allergic rhinitis.

In some embodiments, the inflammatory disease which can be treated according to the methods of this invention is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In certain embodiments, a provided compound is useful for treating a viral infection, disease, or condition. In some embodiments, the present invention provides a method of treating a viral disease selected from retroviral diseases, such as, HIV-1, HIV-2, human T-cell leukemia virus-I (HTLV-I), HTLV-II, HTLV-III, simian immunodeficiency virus (SIV), lymphadenopathy-associated virus (LAV-2), simian T-lymphotrophic virus-I (STLV-I), STLV-II, STLV-III, simian B-lymphotrophic (SBL) virus. Gibbon ape leukemia virus (GALV), bovine leukemia virus (BLV), equine infectious anemia virus (EIAV), feline leukemia virus (FELV), murine leukemia virus (MuLV), avian leukosis virus (ALV); other virus infections such as hepadnaviridae (Hepatitis B); herpesviridae (Herpes simplex I, Herpes simplex II, Varicella-Zoster, Epstein-Barr virus and cytomegalovirus); parvoviridae (human parvovirus B-19); papovaviridae (human papilloma virus types 1 to 60, JC and BK viruses); pox viruses (variola major, variola minor, vaccinia, monkey pox, cowpox, paravaccinia or milker's node virus, parapox or ORF virus, molluscum contagiosum) and cancers, lymphomas and other leukemias.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or a composition thereof, is administered in combination with another anti-cancer, cytotoxin, or chemotherapeutic agent, to a patient in need thereof.

In certain embodiments, the anti-cancer or chemotherapeutic agents used in combination with compounds or compositions of the invention include, but are not limited to metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™ Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation:

vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, mTOR inhibitors, CPT1 inhibitors, AMPK activators, PCSK9 inhibitors, SREBP site 1 protease inhibitors, HMG CoA-reductase inhibitors, antiemetics (e.g. 5-HT3 receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In some embodiments, a provided compound is administered in combination with an antiviral agent, including, e.g., acyclovir, pencyclovir, cidofovir, idoxuridine, zidovudine, ribavarin, amantadine, foscarnet, didanosine, acyclovir, ganciclovir, cidofovir, zalcitabine, rimantadine, calacyclovir, famiciclovir, abacavir, didanosine, emtricitabine, lamivudine, stavudine, tenofovir, zalcitabine, zidovudine, zidovudine-lamivudine, TRIZIVIR (zidovudine, lamivudine, abacavir), EPZICOM (aba-cavir-lamivudine), TRUVADA (tenofovir-emtricitabine), efavirenz, nevirapine, and delavirdine, amprenavir, atazanavir, fosamprenavir, indinavir, lopinavir-ritonavir, nelfinavir, ritonavir, saquinavir, and tipranavir. In some embodiments, the antiviral agent is anti-influenza agent including, e.g., rimantadine, amantadine, oseltamivir, and zanamivir.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the present invention, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of the present invention and one or more additional therapeutic agents. The therapeutic agent may be administered together with a compound of the present invention, or may be administered prior to or following administration of a compound of the present invention. Suitable therapeutic agents are described in further detail below. In certain embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a medicament comprising at least one compound of the present invention or a pharmaceutically acceptable salt thereof and a pharmaceutically acceptable carrier.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1A

DRE-Luciferase Reporter Assay

AHR binds to Dioxin Responsive Elements (DRE) upstream of genes that it activates. One measure of AHR activity is activation of a reporter gene, such as luciferase, downstream of one or multiple DRE elements. Luciferase activity will reflect activation and inhibition of AHR in the cells expressing his reporter.

Murine Hepa1-6 or Hepa-1c1c7 or other murine cell line with a DRE-luciferase reporter either stably or transiently transfected were plated in media in plates (96-well, 384-well or other plates) and incubated overnight at 37° C. in a $CO_2$ incubator. Likewise, human HepG2 or other human cell line with a DRE-luciferase reporter either stably or transiently transfected were plated in media in plates (96-well, 384-well or other plates) and incubated overnight at 37° C. in a $CO_2$ incubator.

The next day, an AHR activating ligand, such as TCDD, kynurenine, ITE (2-(1H-indole-3-ylcarbonyl)-4-thiazolecarboxylic methyl ester), VAF347, BNF (beta-naphthoflavone), FICZ (6-formylindolo(3,2-b) carbazole or other AHR ligands, was added with or without AHR antagonist.

Cells were incubated for 4, 15 or 24 hours or another time point and then lysed for determination of luciferase activity as a read-out of the AHR activation or inhibition. Luciferase was measured with a commercial kit such as the Promega Luciferase kit or any kit or reagents that provide the luciferin substrate for measuring luciferase activity. The level of luciferase with only activating ligand added was the maximum signal while the luciferase with no ligand was the minimum signal. $IC_{50}$ values were determined as the concentration which inhibits half of the luciferase activity. Compounds assayed and their $IC_{50}$ values are shown in Table 2, below.

In some embodiments, compounds have an $IC_{50}$ of 5-20 µM. In some embodiments, compounds have an $IC_{50} \leq 5$ µM. In some embodiments, compounds have an $IC_{50} \leq 1$ µM. In some embodiments, compounds have an $IC_{50} \leq 0.1$ µM. In some embodiments, compounds have an $IC_{50} \leq 0.01$ µM. In some embodiments, compounds have an $IC_{50} \leq 0.001$ µM.

In Table 2, $IC_{50}$ values are reported as A, B, C and D, whereby A represents an $IC_{50}$ of <0.5 µM; B represents an $IC_{50}$ of between 0.5 and 1.0 µM; and C represents an $IC_{50}$ of between 1.0 and 1.5 µM; and D represents an $IC_{50}$ of >1.5 µM. Compound numbers recited in Table 2 correspond to compound numbers, and corresponding structures, recited in Table 1, supra.

TABLE 2

IC$_{50}$ Values for Select Compounds Assayed According to Example 1A.

| Compound | IC$_{50}$ |
|---|---|
| I-1 | D |
| I-2 | D |
| I-3 | D |
| I-4 | D |
| I-5 | A |
| I-6 | D |
| I-7 | D |
| I-8 | D |
| I-9 | D |
| I-10 | D |
| I-11 | D |
| I-12 | B |
| I-13 | D |
| I-14 | D |
| I-15 | C |
| I-16 | D |
| I-17 | — |
| I-18 | A |
| I-19 | D |
| I-20 | A |
| I-21 | D |
| I-22 | A |
| I-23 | A |
| I-24 | A |
| I-25 | A |
| I-26 | D |
| I-27 | B |
| I-28 | — |
| I-29 | A |
| I-30 | D |
| I-31 | D |
| I-32 | D |
| I-33 | — |
| I-34 | — |
| I-35 | — |
| I-36 | D |
| I-37 | D |
| I-38 | — |
| I-39 | — |
| I-40 | — |
| I-41 | — |
| I-42 | — |
| I-43 | — |

Example 1B

DRE-Luciferase Reporter Assay (Alternate Method)

AHR binds to Dioxin Responsive Elements (DRE) upstream of genes that it activates. One measure of AHR activity is activation of a reporter gene, such as luciferase, downstream of one or multiple DRE elements. Luciferase activity will reflect activation and inhibition of AHR in the cells expressing his reporter.

Murine Hepa1-6 or Hepa-1c1c7 or other murine cell line with a DRE-luciferase reporter either stably or transiently transfected were plated in media in plates (96-well, 384-well or other plates) and incubated overnight at 37° C. in a CO$_2$ incubator or compound and agonist were added at the time of plating. Likewise, human HepG2 or other human cell line with a DRE-luciferase reporter either stably or transiently transfected were plated in media in plates (96-well, 384-well or other plates) and incubated overnight at 37° C. in a CO$_2$ incubator or compound and agonist were added at the time of plating.

At the time that cells are plated or following incubation overnight, an AHR activating ligand, such as TCDD, kynurenine, ITE (2-(1H-indole-3-ylcarbonyl)-4-thiazolecarboxylic methyl ester), VAF347, BNF (beta-naphthoflavone), FICZ (6-formylindolo(3,2-b) carbazole or other AHR ligands, was added with or without AHR antagonist.

Cells were incubated for 4, 15 or 24 hours or another time point and then lysed for determination of luciferase activity as a read-out of the AHR activation or inhibition. Luciferase was measured with a commercial kit such as the Promega Luciferase kit or any kit or reagents that provide the luciferin substrate for measuring luciferase activity. The level of luciferase with only activating ligand added was the maximum signal while the luciferase with no ligand was the minimum signal. IC$_{50}$ values were determined as the concentration which inhibits half of the luciferase activity. Compounds assayed and their IC$_{50}$ values are shown in Table 3, below.

In some embodiments, compounds have an IC$_{50}$ of 5-20 µM. In some embodiments, compounds have an IC$_{50}$≤5 µM. In some embodiments, compounds have an IC$_{50}$≤1 µM. In some embodiments, compounds have an IC$_{50}$≤0.1 µM. In some embodiments, compounds have an IC$_{50}$≤0.01 µM. In some embodiments, compounds have an IC$_{50}$≤0.001 µM.

Activity of certain compounds of the present invention as obtained by the above assay is set forth in Table 3, below.

In Table 3, IC$_{50}$ values are reported as A, B, C and D, whereby A represents an IC$_{50}$ of <0.5 µM; B represents an IC$_{50}$ of between 0.5 and 1.0 µM; and C represents an IC$_{50}$ of between 1.0 and 1.5 M; and D represents an IC$_{50}$ of >1.5 M.

TABLE 3

IC$_{50}$ Values for Select Compounds Assayed According to Example 1B.

| Compound | IC$_{50}$ |
|---|---|
| I-44 | A |
| I-45 | B |
| I-46 | A |
| I-47 | D |
| I-48 | A |
| I-49 | D |
| I-50 | D |
| I-51 | A |
| I-52 | D |
| I-53 | D |
| I-54 | D |
| I-55 | D |
| I-56 | D |
| I-57 | D |
| I-58 | D |
| I-59 | D |
| I-60 | D |
| I-61 | D |
| I-62 | D |
| I-63 | D |
| I-64 | D |
| I-65 | B |
| I-66 | B |
| I-67 | B |
| I-68 | D |
| I-69 | D |
| I-70 | A |
| I-71 | D |
| I-72 | D |
| I-73 | D |
| I-74 | D |
| I-75 | B |
| I-76 | D |
| I-77 | D |
| I-78 | B |
| I-79 | D |
| I-80 | D |
| I-81 | C |
| I-82 | C |
| I-83 | D |
| I-84 | A |

TABLE 3-continued

IC$_{50}$ Values for Select Compounds Assayed According to Example 1B.

| Compound | IC$_{50}$ |
|---|---|
| I-85 | D |
| I-86 | D |
| I-87 | D |
| I-88 | D |

Example 2

AHR-Dependent Gene Expression

Murine Hepa1-6 or Hepa-1c1c7 or other murine cell line are plated in media in plates (6, well, 12 well or other plates) and incubated overnight at 37° C. in a $CO_2$ incubator; or human HepG2 or other human cell line are plated in media in plates (6-well, 12-well or other plates) and incubated overnight at 37° C. in a $CO_2$ incubator.

The next day AHR activating ligand, such as TCDD, kynurenine, ITE (2-(1H-indole-3-ylcarbonyl)-4-thiazolecarboxylic methyl ester), VAF347, BNF (beta-naphthoflavone), ICZ (6-Formylindolo(3,2-b) carbazole or other AHR ligands added with or without AHR antagonist. Cells are incubated for 4, 15 or 24 hours or another time point and then cells are lysed for RNA collection. RNA can be collected via a RNA isolation kit such as Qiagen or any other RNA isolation method. Gene expression is determined by quantitative RT-PCR using probes for specific genes including a housekeeping gene such as Gapdh, p-actin or other constitutively expressed genes for normalization. AHR-dependent genes to be examined include but are not limited to: cyp1a1, cyp1b1, AHRR, IDO1, IDO2, cox2, IL6, VEGFA, cyclinD1, cdc2, MMP-9, c-myc.

Example 3

AHR-dependent gene expression is measured in tissue samples such as tumor or liver. RNA is extracted from the tissue via methods such as RNA isolation kit such as Qiagen or any other RNA isolation method known to one of ordinary skill in the art. The RNA extraction could be done from total cells or cells post-sorting for specific populations of cells such as tumor cells, tumor associated-T cells, tumor associated-myeloid cells or others. Gene expression is determined by quantitative RT-PCR using probes for specific genes including a housekeeping gene such as Gapdh, p-actin or other constitutively expressed genes for normalization. AHR-dependent genes to be examined include but are not limited to: cyp1a1, cyp1b1, AHRR, IDO1, IDO2, cox2, IL6, VEGFA, cyclinD1, cdc2, MMP-9, c-myc.

Example 4

Synthesis of Compound I-17

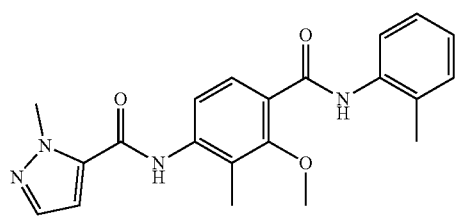

I-17

Synthetic Scheme:

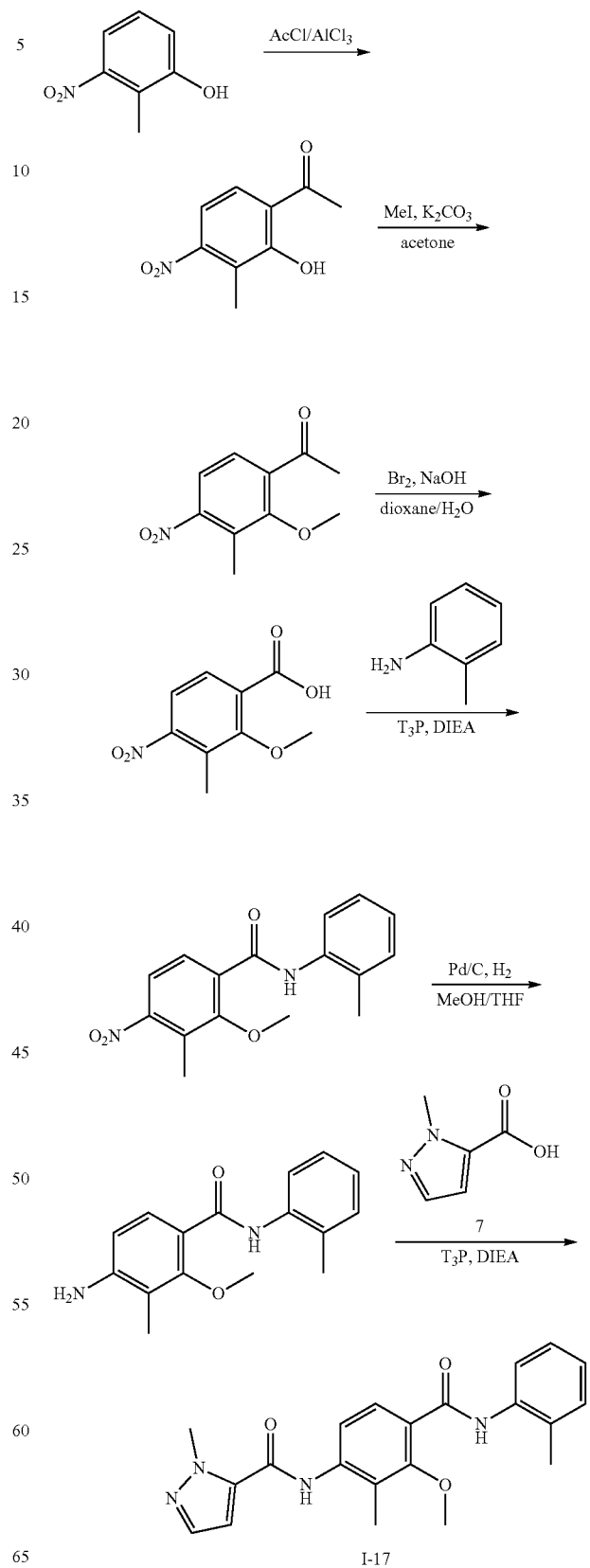

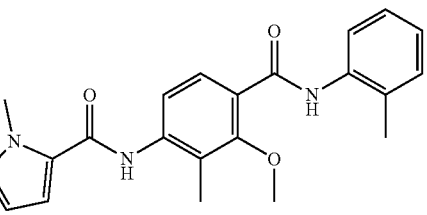

I-17

Step 1: 1-(2-Hydroxy-3-methyl-4-nitrophenyl)ethanone

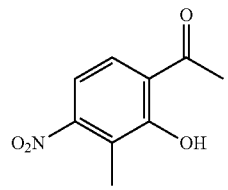

To a solution of 2-methyl-3-nitro-phenol (2 g, 13.06 mmol, 1 eq) in nitrobenzene (30 mL) was added AlCl$_3$ (2.09 g, 15.67 mmol, 1.2 eq) and acetyl chloride (1.33 g, 16.98 mmol, 1.21 mL, 1.3 eq). The mixture was stirred at 120° C. for 12 h. The reaction mixture was quenched by addition 1 N NaOH (80 mL) then filtered. The filtrate was extracted with ethyl acetate (50 mL×3). The combined aqueous layers were acidified with con. HCl to adjusted to pH=3-4, extracted with DCM (50 mL×3). The combined organic layers were dried over anhydrous Na$_2$SO$_4$, filtered and concentrated under reduced pressure to give a residue which was purified by flash silica gel chromatography (ISCO®; 24 g SepaFlash® Silica Flash Column, Eluent of 8-10% Ethyl acetate/Petroleum ether gradient @ 50 mL/min) to give 1-(2-hydroxy-3-methyl-4-nitro-phenyl)ethanone (800 mg, 3.93 mmol, 30.1% yield, 96% purity) as yellow oil. $^1$H NMR (400 MHz, DMSO) δ ppm 12.84 (s, 1H), 8.02 (d, J=8.8 Hz, 1H), 7.41 (d, J=8.8 Hz, 1H), 2.71 (s, 3H), 2.23 (s, 3H); ES-LCMS m/z 196.1 [M+H]$^+$.

Step 2: 1-(2-Methoxy-3-methyl-4-nitrophenyl)ethanone

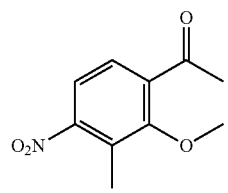

To a solution of 1-(2-hydroxy-3-methyl-4-nitro-phenyl) ethanone (200 mg, 983.75 umol, 1 eq) in acetone (12 mL) was added K$_2$CO$_3$ (679.82 mg, 4.92 mmol, 5.0 eq) and MeI (1.40 g, 9.84 mmol, 612.43 µL, 10 eq). The mixture was stirred at 50° C. for 12 h. The reaction mixture was filtered and the filtrate was concentrated under reduced pressure to give a residue which was purified by flash silica gel chromatography (ISCO®; 4 g SepaFlash® Silica Flash Column, Eluent of 5-10% Ethyl acetate/Petroleum ether gradient @ 50 mL/min) to give 1-(2-methoxy-3-methyl-4-nitro-phenyl) ethanone (200 mg, 927.35 µmol, 94.3% yield, 97% purity) as yellow oil. $^1$H NMR (400 MHz, DMSO-d$_6$) δ ppm; 7.76 (d, J=8.4 Hz, 1H), 7.60 (d, J=8.4 Hz, 1H), 3.76 (s, 3H), 2.59 (s, 3H), 2.36 (s, 3H); ES-LCMS m/z 210.2 [M+H]$^+$.

Step 3: 2-Methoxy-3-methyl-4-nitrobenzoic Acid

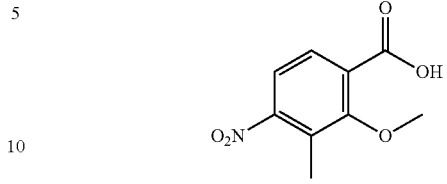

To a solution of NaOH (556.41 mg, 13.91 mmol, 15 eq) in H$_2$O (8 mL) was added Br$_2$ (592.80 mg, 3.71 mmol, 191.23 µL, 4.0 eq) at 0° C. The mixture was stirred at 0° C. for 1 h. A solution of 1-(2-methoxy-3-methyl-4-nitro-phenyl)ethanone (200 mg, 927.35 µmol, 1 eq) in 1,4-dioxane (10 mL) was added to the above solution. After addition, the reaction mixture was warmed to 20° C. and stirred for 12 h. 3 M HCl solution was added to adjusted pH=3-4 then diluted with H$_2$O (15 mL). The mixture was extracted with EtOAc (15 mL×3), dried over Na$_2$SO$_4$, filtered and concentrated under reduced pressure to give 2-methoxy-3-methyl-4-nitro-benzoic acid (180 mg, 767.15 µmol, 82.7% yield, 90% purity) as a white solid which was used in the next step without further purification. $^1$H NMR (400 MHz, DMSO-d$_6$) δ ppm 13.44 (br s, 1H), 7.85-7.49 (m, 2H), 3.80 (s, 3H), 2.35 (s, 3H); ES-LCMS m/z 194.0 [M+H]$^+$.

Step 4: 2-Methoxy-3-methyl-4-nitro-N-(o-tolyl)benzamide

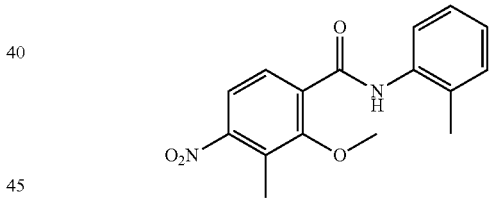

To a solution of 2-methoxy-3-methyl-4-nitro-benzoic acid (180 mg, 767.15 umol, 1 eq) in EtOAc (5 mL) was added 2-methylaniline (164.40 mg, 1.53 mmol, 164.40 uL, 2.0 eq), T$_3$P (2.44 g, 3.84 mmol, 2.28 mL, 50%, 5.0 eq) and DIPEA (495.74 mg, 3.84 mmol, 668.12 uL, 5.0 eq). The mixture was stirred at 60° C. for 3 h. The reaction mixture was diluted with H$_2$O (15 mL) and extracted with EtOAc (20 mL×3). The combined organic layers were washed with brine (15 mL×3), dried over Na$_2$SO$_4$, filtered and concentrated under reduced pressure to give a residue which was purified by flash silica gel chromatography (ISCO®; 4 g SepaFlash® Silica Flash Column, Eluent of 10-15% Ethyl acetate/Petroleum ether gradient @ 50 mL/min) to give 2-methoxy-3-methyl-4-nitro-N-(o-tolyl)benzamide (160 mg, 527.46 umol, 68.8% yield, 99% purity) as a yellow solid. $^1$H NMR (400 MHz, CDCl$_3$) δ ppm 9.54 (br s, 1H), 8.21 (d, J=7.9 Hz, 1H), 8.14 (d, J=8.6 Hz, 1H), 7.76 (d, J=8.6 Hz, 1H), 7.32-7.21 (m, 2H), 7.16-7.06 (m, 1H), 3.92 (s, 3H), 2.53 (s, 3H), 2.37 (s, 3H); ES-LCMS m/z 301.0 [M+H]$^+$.

Step 5:
4-Amino-2-methoxy-3-methyl-N-(o-tolyl)benzamide

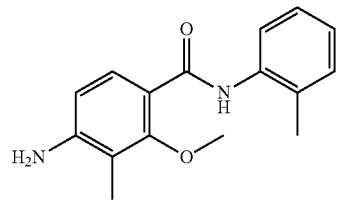 [SMILES: COc1c(C(=O)Nc2ccccc2C)ccc([N+](=O)[O-])c1C]

To a solution of 2-methoxy-3-methyl-4-nitro-N-(o-tolyl) benzamide (160 mg, 527.46 µmol, 1 eq) in MeOH (6 mL) and THF (4 mL) was added Pd/C (70 mg, 10%). The suspension was degassed under vacuum and purged with $H_2$ several times. The mixture was stirred at 20° C. under $H_2$ (15 psi) for 12 h. The reaction mixture was filtered and concentrated under reduced pressure to give 4-amino-2-methoxy-3-methyl-N-(o-tolyl)benzamide (140 mg, 486.82 µmol, 92.3% yield, 94% purity) as a white solid which was used in the next step without further purification. $^1$H NMR (400 MHz, CD$_3$OD) δ ppm 7.91 (d, J=7.7 Hz, 1H), 7.68 (d, J=8.6 Hz, 1H), 7.26-7.16 (m, 2H), 7.10-7.03 (m, 1H), 6.59 (d, J=8.6 Hz, 1H), 3.87-3.81 (m, 3H), 2.35 (s, 3H), 2.13 (s, 3H); ES-LCMS m/z 284.9 [M+H]$^+$.

Step 6: N-(3-Methoxy-2-methyl-4-(o-tolylcarbamoyl)phenyl)-1-methyl-1H-pyrazole-5-carboxamide (I-17)

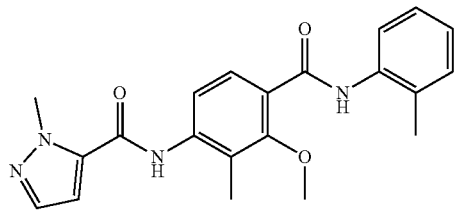 [SMILES: COc1c(C(=O)Nc2ccccc2C)ccc(NC(=O)c2ccnn2C)c1C]

To a solution of 4-amino-2-methoxy-3-methyl-N-(o-tolyl) benzamide (70 mg, 243.41 umol, 1 eq) in EtOAc (5 mL) was added 2-methylpyrazole-3-carboxylic acid (46.05 mg, 365.12 umol, 1.5 eq), DIEA (157.29 mg, 1.22 mmol, 211.98 µL, 5.0 eq) and T$_3$P (774.48 mg, 1.22 mmol, 723.82 uL, 50%, 5.0 eq). The mixture was stirred at 60° C. for 1 h. The reaction mixture was diluted with H$_2$O (10 mL) and extracted with EtOAc (15 mL×3). The combined organic layers were dried over Na$_2$SO$_4$, filtered and concentrated under reduced pressure to give a residue which was purified by preparative HPLC (HCl condition; column: Phenomenex Kinetex XB-C18 150 mm*30 mm, 5 µm; mobile phase: [water(0.05% HCl)-ACN]; B %: 33%-53%, 12 min) to give N-[3-methoxy-4-(o-tolylcarbamoyl)phenyl]-2-methyl-pyrazole-3-carboxamide (compound I-17, 24.56 mg, 67.13 µmol, 27.6% yield, 99.6% purity) as a white solid. $^1$H NMR (400 MHz, CD$_3$OD) δ ppm 7.77 (dd, J=5.5, 7.7 Hz, 2H), 7.57 (d, J=2.2 Hz, 1H), 7.35 (d, J=8.4 Hz, 1H), 7.29-7.20 (m, 2H), 7.16-7.11 (m, 1H), 7.02 (d, J=2.0 Hz, 1H), 4.16 (s, 3H), 3.92 (s, 3H), 2.38 (s, 3H), 2.30 (s, 3H); ES-LCMS m/z 379.1 [M+H]$^+$.

Example 5

Synthesis of Compound I-12

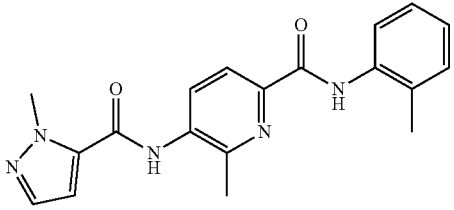

Synthetic Scheme:

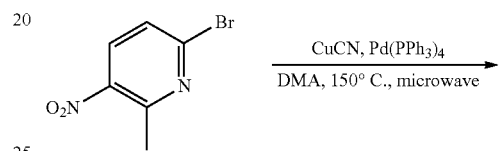

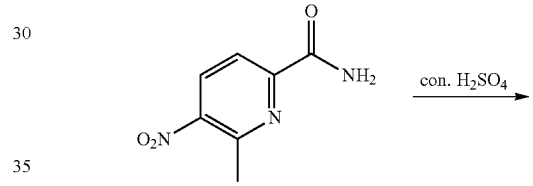

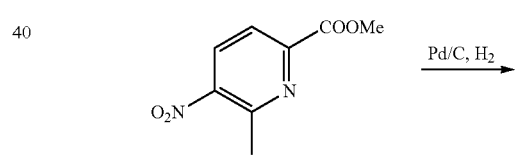

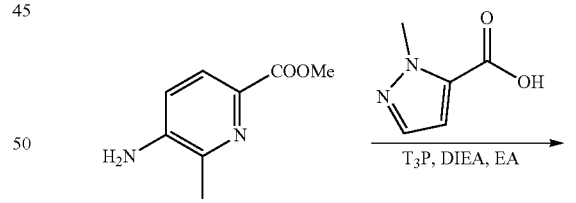

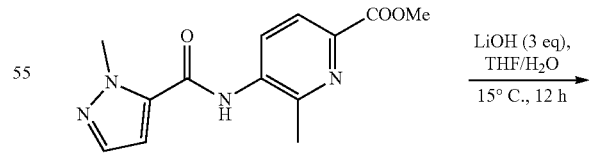

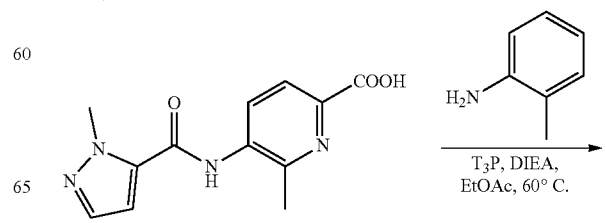

-continued

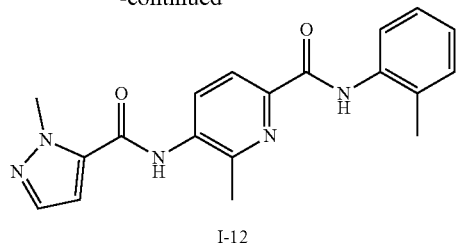

I-12

Step 1: 6-Methyl-5-nitropicolinamide

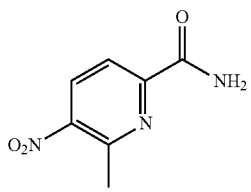

To a solution of 6-bromo-2-methyl-3-nitro-pyridine (8 g, 36.86 mmol, 1 eq) in DMA (15 mL) was added CuCN (13.21 g, 147.45 mmol, 32.21 mL, 4 eq) and Pd(PPh$_3$)$_4$ (2.13 g, 1.84 mmol, 0.05 eq) under N$_2$. The mixture was stirred at 150° C. under microwave for 4 h. TLC (PE/EtOAc=2/1, R$_f$=0.30) indicated the starting material was consumed completely and one new spot formed. The mixture was diluted with water (20 mL) and filtered. The filtrate was extracted with EtOAc (30 mL×3), dried over anhydrous Na$_2$SO$_4$, filtered and concentrated to give a residue which was purified on silica gel column chromatography (from PE/EtOAc=1/0 to 3/2, TLC: PE/EtOAc=2/1, R$_f$=0.3) to yield 6-methyl-5-nitropicolinamide (690 mg, 3.76 mmol, 10.2% yield, 98.8% purity) as a yellow solid. $^1$H NMR (400 MHz, CDCl$_3$) δ ppm 8.35 (d, J=8.4 Hz, 1H), 8.17 (d, J=8.4 Hz, 1H), 7.75 (s, 1H), 5.98 (br s, 1H), 2.82 (s, 3H); ES-LCMS m/z 182.1 [M+H]$^+$.

Step 2: Methyl 6-methyl-5-nitropicolinate

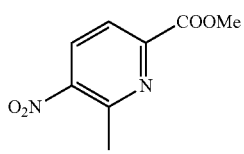

To a solution of 6-methyl-5-nitro-pyridine-2-carboxamide (690 mg, 3.76 mmol, 1 eq) in anhydrous MeOH (10 mL) was added con. H$_2$SO$_4$ (1.85 g, 18.82 mmol, 1.00 mL, 5 eq). The mixture was stirred at 60° C. for 16 h. The mixture was concentrated to remove the solvent. Saturated NaHCO$_3$ solution (10 mL) was added, the mixture was extracted with EtOAc (10 mL×3). The combined organic layers were washed with brine (10 mL), dried over anhydrous Na$_2$SO$_4$, filtered and concentrated to afford crude methyl 6-methyl-5-nitropicolinate (660 mg, 3.11 mmol, 82.5% yield, 92.3% purity) as a white solid which was used in next step without further purification. $^1$H NMR (400 MHz, CDCl$_3$) δ ppm 8.37 (d, J=8.4 Hz, 1H), 8.14 (d, J=8.4 Hz, 1H), 4.04 (s, 3H), 2.93 (s, 3H); ES-LCMS m/z 197.1 [M+H]$^+$.

Step 3: Methyl 5-amino-6-methylpicolinate

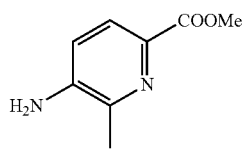

To a solution of methyl 6-methyl-5-nitro-pyridine-2-carboxylate (730 mg, 3.43 mmol, 1 eq) in anhydrous MeOH (10 mL) was added Pd/C (80 mg, 10% purity) under N$_2$ atmosphere. The suspension was degassed and purged with H$_2$ for 3 times. The mixture was stirred under H$_2$ (15 Psi) at 13° C. for 1 h. TLC (PE/EtOAc=0/1, R$_f$=0.50) indicated the starting material was consumed completely and one new spot formed. The mixture was filtered and the filtrate was concentrated to afford the crude methyl 5-amino-6-methylpicolinate (577 mg, 3.29 mmol, 95.7% yield, 94.7% purity) as a yellow solid which was used in next step without further purification. $^1$H NMR (400 MHz, CD$_3$OD) δ ppm 7.75 (d, J=8.4 Hz, 1H), 6.98 (d, J=8.4 Hz, 1H), 3.89-3.84 (m, 3H), 2.38-2.36 (m, 3H); ES-LCMS m/z 167.1 [M+H]$^+$.

Step 4: Methyl 6-methyl-5-(1H-pyrazole-5-carboxamido)picolinate

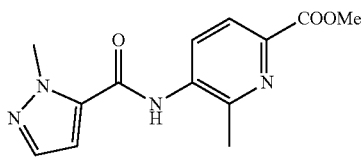 [SMILES: COC(=O)c1ccc(NC(=O)c2ccnn2C)c(C)n1]

To a solution of methyl 5-amino-6-methyl-pyridine-2-carboxylate (100 mg, 569.87 umol, 1 eq) in EtOAc (2 mL) was added DIEA (220.95 mg, 1.71 mmol, 297.78 uL, 3 eq), 2-methylpyrazole-3-carboxylic acid (71.87 mg, 569.87 umol, 1 eq) and T$_3$P (1.09 g, 1.71 mmol, 1.02 mL, 50% purity, 3 eq). The mixture was stirred at 60° C. for 1.5 h. Saturated NaHCO$_3$ solution (5 mL) was added, the mixture was extracted with EtOAc (10 mL×3). The combined organic layers were washed with brine (10 mL), dried over anhydrous Na$_2$SO$_4$, filtered and concentrated to afford a residue which was purified on silica gel column chromatography (from PE/EtOAc=1/0 to 1/4, TLC: PE/EtOAc=0/1, R$_f$=0.62) to yield methyl 6-methyl-5-(1H-pyrazole-5-carboxamido)picolinate (145 mg, 503.82 umol, 88.4% yield, 95.3% purity) as a white solid. $^1$H NMR (400 MHz, CDCl$_3$) δ ppm 8.61 (d, J=8.6 Hz, 1H), 8.06 (d, J=8.4 Hz, 1H), 7.75 (s, 1H), 7.53 (d, J=2.0 Hz, 1H), 6.70 (d, J=2.2 Hz, 1H), 4.27-4.18 (m, 3H), 3.98 (s, 3H), 2.66 (s, 3H); ES-LCMS m/z 274.9 [M+H]$^+$.

Step 5: 6-Methyl-5-(1-methyl-1H-pyrazole-5-carboxamido)picolinic Acid

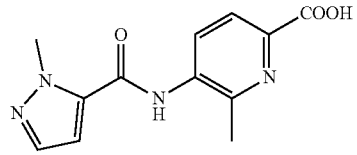 [SMILES: Cc1nc(C(=O)O)ccc1NC(=O)c1ccnn1C]

To a solution of methyl 6-methyl-5-[(2-methylpyrazole-3-carbonyl)amino]pyridine-2-carboxylate (145 mg, 503.82 umol, 1 eq) in THF (3 mL) and H$_2$O (1 mL) was added LiOH (36.20 mg, 1.51 mmol, 3 eq). The mixture was stirred at 12° C. for 12 h. H$_2$O (5 mL) was added, the mixture was adjusted to pH=3-4 with 3 N HCl solution, extracted with DCM/i-PrOH (20 mL×3, v/v=3/1). The combined organic layers dried over anhydrous Na$_2$SO$_4$, filtered and concentrated to afford crude 6-methyl-5-(1-methyl-1H-pyrazole-5-carboxamido)picolinic acid (120 mg, 461.10 umol, 91.5% yield, 100% purity) as a white solid which was used in next step without further purification. $^1$H NMR (400 MHz, CD$_3$OD) δ ppm 8.20-7.98 (m, 2H), 7.54 (d, J=2.0 Hz, 1H), 7.02 (d, J=2.0 Hz, 1H), 4.15 (s, 3H), 2.60 (s, 3H); ES-LCMS m/z 261.0 [M+H]$^+$.

Step 6: 6-Methyl-5-(1-methyl-1H-pyrazole-5-carboxamido)-N-(o-tolyl)picolinamide (I-12)

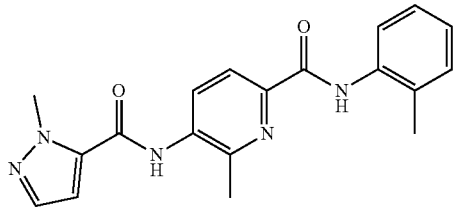 [SMILES: Cc1ccccc1NC(=O)c1ccc(NC(=O)c2ccnn2C)c(C)n1]

To a solution of 6-methyl-5-[(2-methylpyrazole-3-carbonyl)amino]pyridine-2-carboxylic acid (120 mg, 461.10 umol, 1 eq) in EtOAc (2 mL) was added DIEA (178.78 mg, 1.38 mmol, 240.94 uL, 3 eq), 2-methylaniline (74.11 mg, 691.65 umol, 74.11 uL, 1.5 eq) and T$_3$P (880.27 mg, 1.38 mmol, 822.68 uL, 50% purity in EtOAc, 3 eq). The mixture was stirred at 60° C. for 2 h. Saturated NaHCO$_3$ solution (10 mL) was added and the mixture was extracted with EtOAc (10 mL×3). The combined organic layers were washed with brine (10 mL), dried over anhydrous Na$_2$SO$_4$, filtered and concentrated to afford a residue which was purified by preparative HPLC (Instrument: Phenomenex Kinetex XB-C18 150 mm*30 mm, 5 μm/Mobile phase A: water (0.05% HCl)-ACN/Mobile phase B: Acetonitrile/Gradient: 40-70(B %)/Flowrate: 25 ml/min/Run time: 12 min) to yield 6-methyl-5-(1-methyl-1H-pyrazole-5-carboxamido)-N-(o-tolyl)picolinamide (compound I-12, 73.56 mg, 190.65 umol, 41.3% yield, 100% purity, HCl salt) as a white solid; $^1$H NMR (400 MHz, CD$_3$OD) δ ppm 8.29-8.24 (m, 1H), 8.21-8.16 (m, 1H), 7.79 (d, J=7.9 Hz, 1H), 7.57 (d, J=2.2 Hz, 1H), 7.32-7.21 (m, 2H), 7.19-7.11 (m, 1H), 7.05 (d, J=2.2 Hz, 1H), 4.16 (s, 3H), 2.69 (s, 3H), 2.37 (s, 3H); ES-LCMS m/z 350.2 [M+H]$^+$.

Example 6

Synthesis of I-15

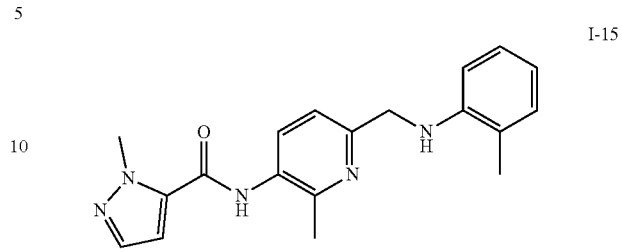

Synthetic Scheme:

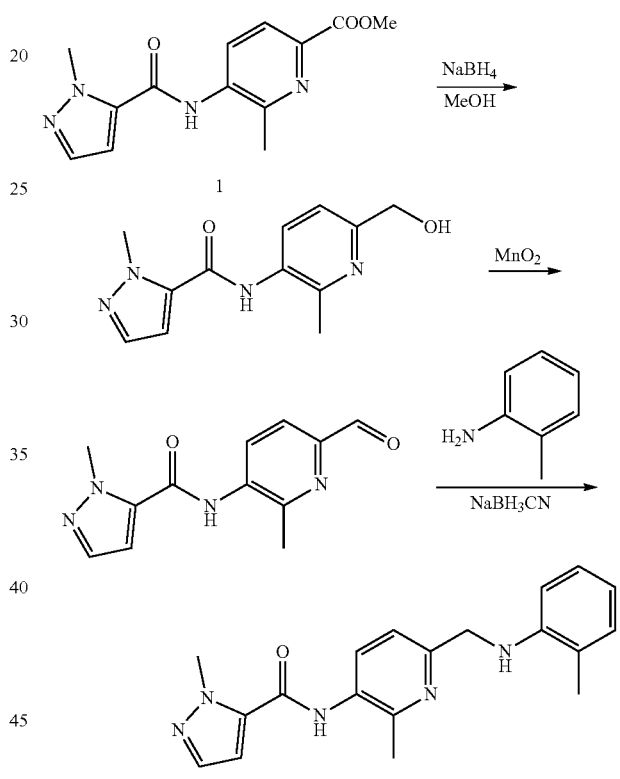

Step 1: N-[6-(Hydroxymethyl)-2-methyl-3-pyridyl]-2-methyl-pyrazole-3-carboxamide

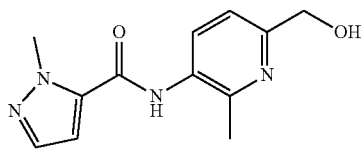 [SMILES: Cc1nc(CO)ccc1NC(=O)c1ccnn1C]

To a solution of methyl 6-methyl-5-[(2-methylpyrazole-3-carbonyl)amino]pyridine-2-carboxylate (250 mg, 884.15 umol, 1 eq) in anhydrous MeOH (2 mL) was added NaBH$_4$ (100.34 mg, 2.65 mmol, 3 eq). The mixture was stirred at 15° C. for 0.5 h. H$_2$O (10 mL) was added and extracted with ethyl acetate (10 mL×3). The combined organic layers were washed with brine (10 mL), dried over anhydrous $Na_2SO_4$, filtered and concentrated to afford the crude product which was purified on silica gel column chromatography (from PE/EtOAc=1/0 to 0/1, TLC: PE/EtOAc=0/1, $R_f$=0.20) to give N-[6-(hydroxymethyl)-2-methyl-3-pyridyl]-2-methyl-pyrazole-3-carboxamide (136 mg, 552.25 umol, 62.5% yield, 100% purity) as a white solid. $^1$H NMR (400 MHz, $CD_3OD$) δ ppm 7.80 (d, J=8.2 Hz, 1H), 7.53 (d, J=2.2 Hz, 1H), 7.44 (d, J=8.2 Hz, 1H), 6.99 (d, J=1.8 Hz, 1H), 4.67 (s, 2H), 4.19-4.10 (m, 3H), 2.48 (s, 3H); ES-LCMS m/z 246.9 $[M+H]^+$.

Step 2: N-(6-formyl-2-methyl-3-pyridyl)-2-methyl-pyrazole-3-carboxamide

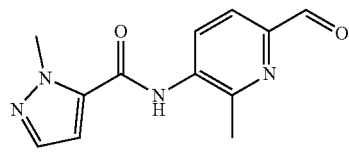 [SMILES: Cc1nc(C=O)ccc1NC(=O)c1ccnn1C]

To a solution of N-[6-(hydroxymethyl)-2-methyl-3-pyridyl]-2-methyl-pyrazole-3-carboxamide (116 mg, 471.04 umol, 1 eq) in anhydrous DCM (3 mL) was added $MnO_2$ (204.76 mg, 2.36 mmol, 5 eq). The mixture was stirred at 30° C. for 3 h. TLC (PE/EA=0/1, $R_f$=0.65) indicated the starting material was consumed completely and one new spot formed. The mixture was filtered and concentrated to afford the crude product N-(6-formyl-2-methyl-3-pyridyl)-2-methyl-pyrazole-3-carboxamide (110 mg, 362.99 umol, 77.1% yield, 80.6% purity) as a yellow solid which was used in the next step without further purification. $^1$H NMR (400 MHz, $CD_3OD$) δ ppm 9.95 (s, 1H), 8.14 (d, J=7.7 Hz, 1H), 7.88 (d, J=7.9 Hz, 1H), 7.50 (br s, 1H), 7.03 (br s, 1H), 5.50 (s, 3H), 2.62 (br s, 3H); ES-LCMS m/z 244.9 $[M+H]^+$.

Step 3: 2-Methyl-N-[2-methyl-6-[(2-methylanilino)methyl]-3-pyridyl]pyrazole-3-carboxamide (I-15)

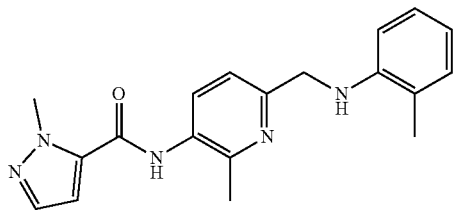 [SMILES: Cc1ccccc1NCc1ccc(NC(=O)c2ccnn2C)c(C)n1]

To a solution of N-(6-formyl-2-methyl-3-pyridyl)-2-methyl-pyrazole-3-carboxamide (110 mg, 362.99 umol, 1 eq) in anhydrous MeOH (3 mL) was added 2-methylaniline (58.34 mg, 544.49 umol, 58.34 uL, 1.5 eq). After stirring for 5 min, $NaBH_3CN$ (68.43 mg, 1.09 mmol, 3 eq) was added in one portion. The mixture was stirred at 50° C. for 16 h. The mixture was concentrated to afford the crude product which was purified by preparative HPLC (MeCN/$H_2O$ as eluents, acidic condition, Instrument: Phenomenex Gemini 150*25 mm*10 um/Mobile phase: water(0.05% HCl)-ACN/Gradient: B from 15% to 35% in 10 min/Flow rate: 25 mL/min) followed by lyophilization to yield 2-methyl-N-[2-methyl-6-[(2-methylanilino)methyl]-3-pyridyl]pyrazole-3-carboxamide (compound I-15, 37.73 mg, 100.75 μmol, 23.2% yield, 99.3% purity, 3HCl salt) as a white solid. $^1$H NMR (400 MHz, $CD_3OD$) δ ppm 8.47 (d, J=8.6 Hz, 1H), 7.82 (d, J=8.6 Hz, 1H), 7.58 (d, J=2.2 Hz, 1H), 7.17-7.08 (m, 2H), 7.03 (t, J=7.7 Hz, 1H), 6.75 (t, J=7.4 Hz, 1H), 6.57 (d, J=7.9 Hz, 1H), 4.80 (s, 2H), 4.15 (s, 3H), 2.76 (s, 3H), 2.31 (s, 3H); ES-LCMS m/z 336.1 $[M+H]^+$.

Example 7

Synthesis of I-5

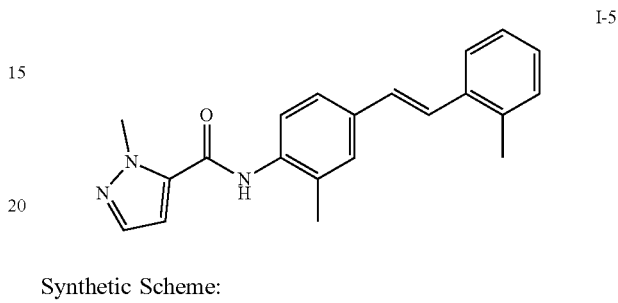

Synthetic Scheme:

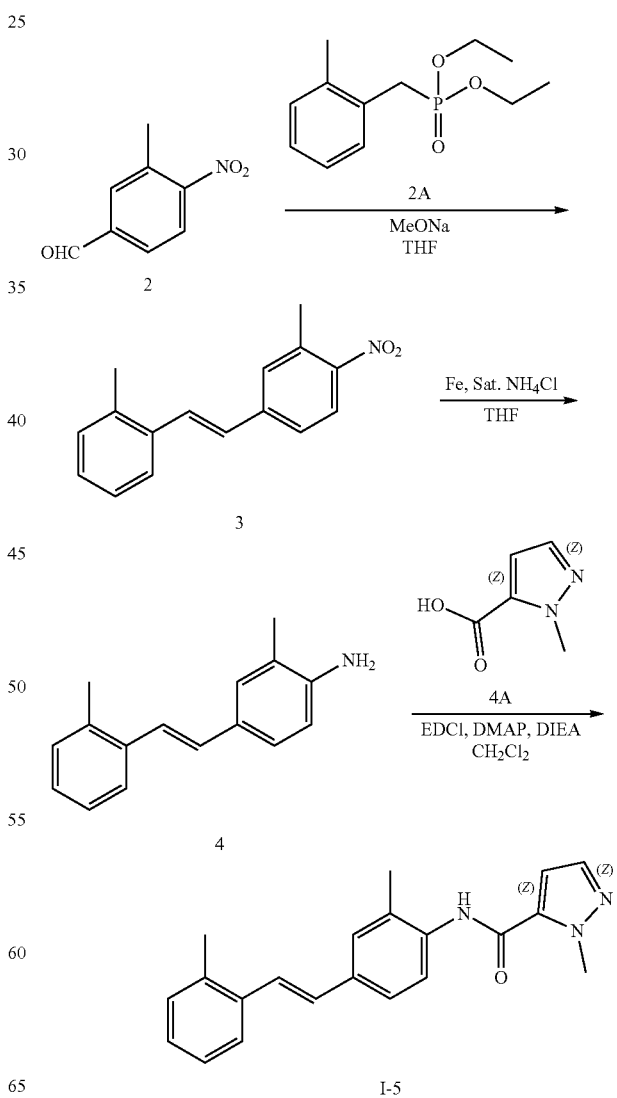

71

Step 1: (E)-2-methyl-4-(2-methylstyryl)-1-nitrobenzene

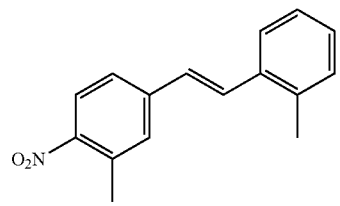 [SMILES: Cc1ccccc1/C=C/c1ccc([N+](=O)[O-])c(C)c1]

To a solution of diethyl 2-methylbenzyl-phosphonate (compound 2A, 500 mg, 2.06 mmol) in THF (6 mL) was added $CH_3ONa$ (123 mg, 2.27 mmol) at 0° C., the mixture was stirred at 25° C. for 30 min, then cooled to 0° C., a solution of 3-methyl-4-nitrobenzaldehyde (compound 2, 375 mg, 2.27 mmol) in THF (6 mL) was added, the mixture was stirred at 25° C. for 2 hrs. TLC (petroleum ether:ethyl acetate=1:1, $R_f$=0.92) showed one new point formed. The mixture was concentrated in vacuum to give yellow oil. The oil was purified by silica gel column chromatography (petroleum ether:ethyl acetate=100:0 to 50:50) to give (E)-2-methyl-4-(2-methylstyryl)-1-nitrobenzene (compound 3, 290 mg, 56% yield) as yellow solid.

Step 2: (E)-2-methyl-4-(2-methylstyryl)aniline

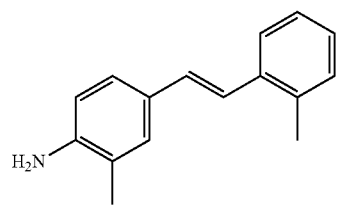

To a solution of (E)-2-methyl-4-(2-methylstyryl)-1-nitrobenzene (compound 3, 290 mg, 1.14 mmol) in THF (15 mL) was added Fe (320 mg, 5.72 mmol), sat. $NH_4Cl$ (15 mL), the mixture was stirred at 25° C. for 12 hrs. TLC (petroleum ether:ethyl acetate=1:1, $R_f$=0.60) showed starting material consumed completely. The mixture was filtered, filter cake was washed with 10 mL $CH_2Cl_2$ for three times. The filtrate was separated, then aqueous layer was extracted with $CH_2Cl_2$ (5 mL*3), combined organic layer, dried with anhydrous $Na_2SO_4$, filtered and concentrated in vacuum to give yellow solid. The solid was purified by silica gel column chromatograph (petroleum ether:ethyl acetate=100:0 to 50:50) to give (E)-2-methyl-4-(2-methylstyryl)aniline (compound 4, 110 mg, 43% yield) as yellow solid.

72

Step 3: (E)-1-methyl-N-(2-methyl-4-(2-methylstyryl)phenyl)-1H-pyrazole-5-carboxamide (I-5)

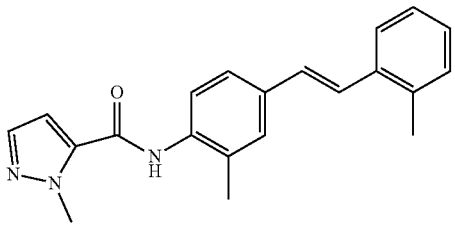 [SMILES: Cc1ccccc1/C=C/c1ccc(NC(=O)c2ccnn2C)c(C)c1]

To a solution of 1-methyl-1H-pyrazole-5-carboxylic acid (compound 4A, 81 mg, 0.640 mmol), DIEA (286 mg, 2.22 mmol) in $CH_2Cl_2$ (10 mL) was added EDCI (189 mg, 0.985 mmol), DMAP (90 mg, 0.739 mmol) at −5° C., then the mixture was stirred at −5° C. for 30 min, (E)-2-methyl-4-(2-methylstyryl)aniline (compound 4, 110 mg, 0.493 mmol) was added, the mixture was stirred at −5° C. for 30 min, warmed to 25° C. and stirred for 11 hrs. TLC (petroleum ether:ethyl acetate=1:1, $R_f$=0.60) showed starting material consumed completely. The mixture was concentrated in vacuum to give yellow oil. The oil was purified by silica gel column chromatography (petroleum ether:ethyl acetate=100:0 to 60:40) to give (E)-1-methyl-N-(2-methyl-4-(2-methylstyryl)phenyl)-1H-pyrazole-5-carboxamide (compound I-5, 65 mg, 39% yield) as white solid. $^1H$ NMR (400 MHz, DMSO-$d_6$) δ ppm 9.86 (s, 1H), 7.66 (d, J=7.4 Hz, 1H), 7.52-7.58 (m, 2H), 7.49 (d, J=8.2 Hz, 1H), 7.32-7.44 (m, 2H), 7.16-7.23 (m, 3H), 7.05~7.14 (m, 2H), 4.09 (s, 3H), 2.42 (s, 3H), 2.27 (s, 3H); ES-LCMS m/z 332.3 $[M+H]^+$.

Example 8

Synthesis of I-6

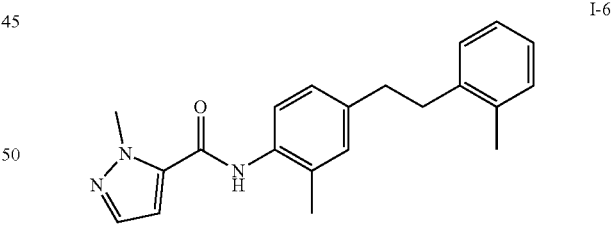

Synthetic Scheme:

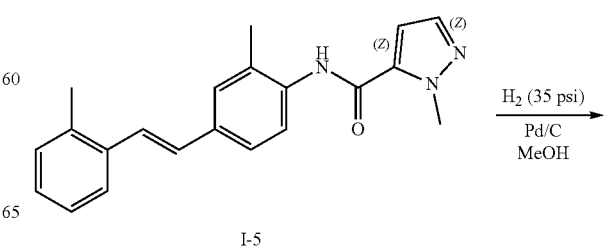

-continued

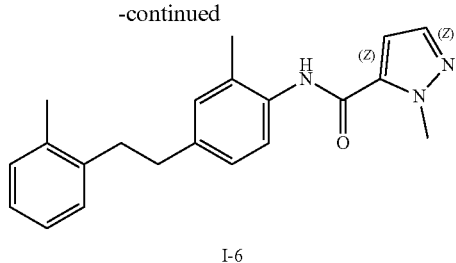

I-6

To a solution of (E)-1-methyl-N-(2-methyl-4-(2-methylstyryl)phenyl)-1H-pyrazole-5-carboxamide (compound I-5, 40 mg, 0.121 mmol) in MeOH (10 mL) was added Pd/C (10 mg), the mixture was stirred at 25° C. for 4 hrs under H$_2$ atmosphere, the pressure was 35 psi. TLC (petroleum ether: ethyl acetate=1:1, R$_f$=0.57) showed starting material consumed completely. The mixture was filtered, filter cake was washed with MeOH (10 mL*3), the filtrate was concentrated in vacuum to give 1-methyl-N-(2-methyl-4-(2-methylphenethyl)phenyl)-1H-pyrazole-5-carboxamide (compound I-6, 19 mg, 47% yield) as light yellow solid. $^1$H NMR (400 MHz, CDCl$_3$) δ ppm 7.74 (d, J=8.2 Hz, 1H), 7.44-7.55 (m, 2H), 7.06-7.19 (m, 6H), 6.64 (s, 1H), 4.24 (s, 3H), 2.81-2.93 (m, 4H), 2.33 (s, 3H), 2.31 (s, 3H); ES-LCMS m/z 334.3 [M+H]$^+$.

Example 9

Synthesis of I-7

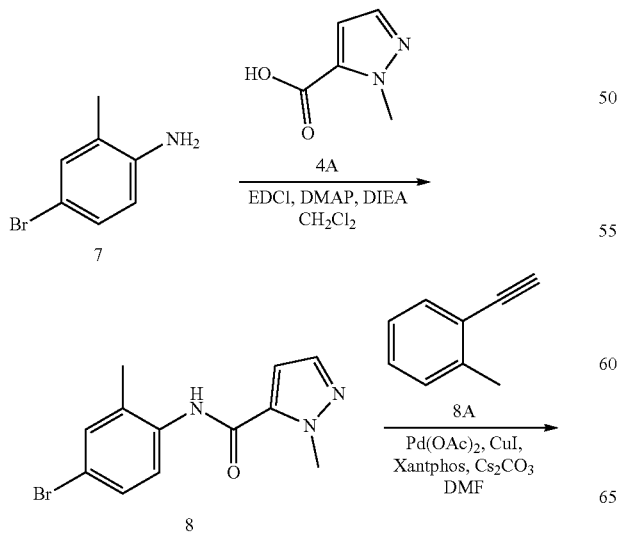

Synthetic Scheme:

-continued

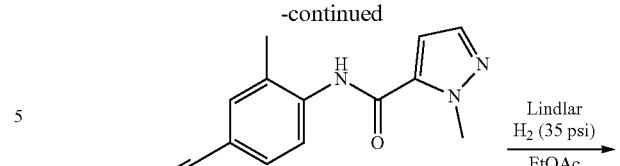

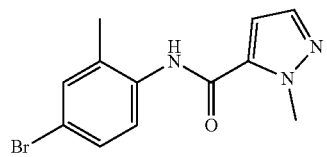 [SMILES: Cc1cc(Br)ccc1NC(=O)c1ccnn1C]

I-7

Step 1 N-(4-bromo-2-methylphenyl)-1-methyl-1H-pyrazole-5-carboxamide

To a solution of 1-methyl-1H-pyrazole-5-carboxylic acid (compound 4A, 4.07 g, 32.2 mmol), DIEA (12.2 g, 94.1 mmol) in CH$_2$Cl$_2$ (30 mL) was added EDCI (10.3 g, 53.7 mmol) and DMAP (3.94 g, 32.2 mmol) at −5° C., the mixture was stirred at −5° C. for 30 min under N$_2$. Then 4-bromo-2-methylaniline (compound 7, 5.00 g, 26.9 mmol) was added, the mixture was stirred at −5° C. for 30 min, then warmed to 25° C., stirred for 11 hrs. TLC (petroleum ether:ethyl acetate=1:1, R$_f$=0.27) showed one new point formed. The mixture was concentrated in vacuum to give light yellow oil. The oil was purified by silica gel column chromatography (petroleum ether: ethyl acetate=80:20 to 50:50) to give N-(4-bromo-2-methylphenyl)-1-methyl-1H-pyrazole-5-carboxamide (compound 8, 6.40 g, 81% yield) as light yellow solid. $^1$H NMR (400 MHz, CDCl$_3$) δ δ ppm 7.72 (d, J=8.2 Hz, 1H), 7.47-7.58 (m, 2H), 7.33-7.41 (m, 2H), 6.64 (s, 1H), 4.20 (s, 3H), 2.28 (s, 3H); ES-LCMS m/z 294.1 [M+H]$^+$.

Step 2: 1-methyl-N-(2-methyl-4-(o-tolylethynyl)phenyl)-1H-pyrazole-5-carboxamide

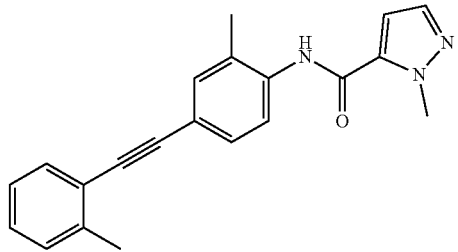 [SMILES: Cc1ccccc1C#Cc1ccc(NC(=O)c2ccnn2C)c(C)c1]

To a solution of N-(4-bromo-2-methylphenyl)-1-methyl-1H-pyrazole-5-carboxamide (compound 8, 2.2 g, 7.48 mmol), 1-ethynyl-2-methylbenzene (compound 8A, 1.04 g, 8.98 mmol) in DMF (10 mL) was added Pd(OAc)$_2$ (168 mg, 0.748 mmol), CuI (142 mg, 0.748 mmol), Xantphos (433 mg, 0.748 mmol) and Cs$_2$CO$_3$ (4.87 g, 15.0 mmol), the mixture was stirred at 60° C. for 12 hrs under N$_2$ atmosphere. TLC (petroleum ether:ethyl acetate=1:1, R$_f$=0.49) showed starting material consumed completely. The mixture was filtered, filter cake was washed with CH$_2$Cl$_2$ (20 mL*3), 50 mL H$_2$O was added to the filtrate, then separated, organic layer was dried with anhydrous Na$_2$SO$_4$, filtered and concentrated in vacuum to give black oil. The oil was purified by silica gel column chromatograph (petroleum ether:ethyl acetate=100:0 to 50:50) to give 1-methyl-N-(2-methyl-4-(o-tolylethynyl)phenyl)-1H-pyrazole-5-carboxamide (compound 9, 1.90 g, 77% yield) as brown solid. ES-LCMS m/z 330.3 [M+H]$^+$.

Step 3: (Z)-1-methyl-N-(2-methyl-4-(2-methylstyryl)phenyl)-1H-pyrazole-5-carboxamide (I-7)

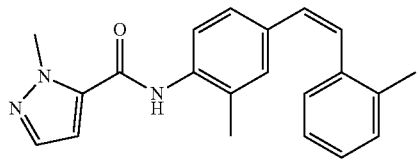 [SMILES: Cc1ccccc1/C=C\c1ccc(NC(=O)c2ccnn2C)c(C)c1]

To a solution of 1-methyl-N-(2-methyl-4-(o-tolylethynyl)phenyl)-1H-pyrazole-5-carboxamide (compound 9, 400 mg, 1.21 mmol) in EtOAc (10 mL) was added LINDLAR CATALYST (200 mg, 0.968 mmol), the mixture was stirred at 25° C. for 2 h under H$_2$ atmosphere and the pressure was 35 psi. TLC (petroleum ether:ethyl acetate=1:1, R$_f$=0.55) showed starting material consumed completely. The mixture was filtered, the filter cake was washed with EtOAc (10 mL*3), the organic layer was concentrated in vacuum to give yellow solid. The solid was purified by SFC (column: AD (250 mm*30 mm, 5 um); mobile phase: [0.1% NH$_3$H$_2$O MEOH]; B %: 30%-30%, min) to give (Z)-1-methyl-N-(2-methyl-4-(2-methylstyryl)phenyl)-1H-pyrazole-5-carboxamide (compound I-7, 50.0 mg, 12% yield) as white solid. $^1$H NMR (400 MHz, DMSO-d$_6$) δ ppm 9.76 (s, 1H), 7.50 (d, J=2.0 Hz, 1H), 7.23-7.26 (m, 1H), 7.16-7.21 (m, 1H), 7.07~7.12 (m, 3H), 6.99-7.03 (m, 2H), 6.88 (d, J=8.2 Hz, 1H), 6.62-6.71 (m, 2H), 4.05 (s, 3H), 2.22-2.22 (m, 1H), 2.23 (s, 2H), 2.07 (s, 3H); ES-LCMS m/z 332.2 [M+H]$^+$.

Example 10

Synthesis of I-8

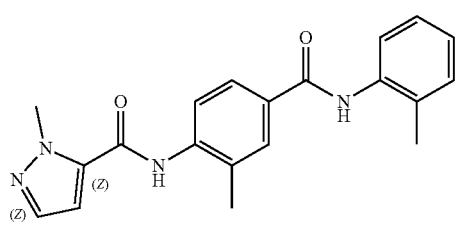

I-8

Synthetic Scheme:

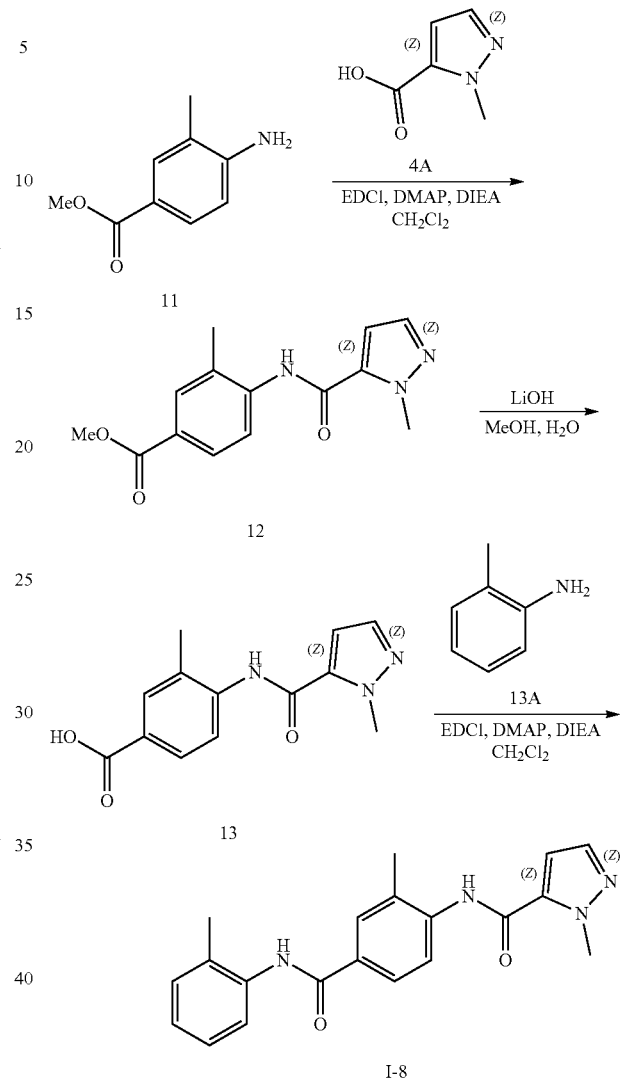

Step 1: Methyl 3-methyl-4-(1-methyl-1H-pyrazole-5-carboxamido)benzoate

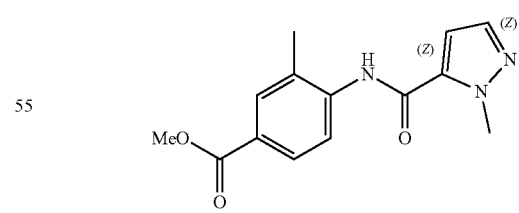

To a solution of 1-methyl-1H-pyrazole-5-carboxylic acid (compound 4A, 4.58 g, 36.3 mmol), DIEA (13.7 g, 106 mmol) in CH$_2$Cl$_2$ (30 mL) was added EDCI (11.6 g, 60.5 mmol) and DMAP (4.44 g, 36.3 mmol) at −5° C., the mixture was stirred at −5° C. for 30 min. Then methyl 4-amino-3-methylbenzoate (compound 11, 5.00 g, 30.3 mmol) was added, stirred at −5° C. for 30 min. The mixture was warmed to 25° C., stirred for 11 hrs. TLC (petroleum ether:ethyl acetate=1:1, $R_f$=0.52) showed starting material consumed completely. The mixture was concentrated in vacuum to give light yellow oil. The oil was purified by silica gel column chromatography (petroleum ether:ethyl acetate=90:10 to 50:50) to give methyl 3-methyl-4-(1-methyl-1H-pyrazole-5-carboxamido)benzoate (compound 12, 5.70 g, 69% yield) as light yellow solid.

Step 2: methyl 3-methyl-4-(1-methyl-1H-pyrazole-5-carboxamido)benzoate

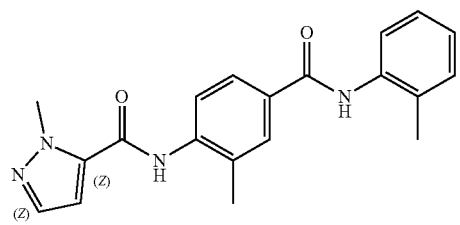

To a solution of methyl 3-methyl-4-(1-methyl-1H-pyrazole-5-carboxamido)benzoate (compound 12, 2.00 g, 7.32 mmol) in MeOH (15 mL) and H$_2$O (5 mL) was added LiOH.H$_2$O (614 mg, 14.6 mmol), the mixture was stirred at 25° C. for 12 hrs. TLC (petroleum ether:ethyl acetate=1:1, $R_f$=0.5) showed starting material consumed completely. The mixture was extracted with EtOAc (10 mL*2), organic layer was discard, aqueous layer was adjust pH to ~2, then extracted with EtOAc (10 mL*3), combined organic layer, dried with anhydrous Na$_2$SO$_4$, filtered and concentrated in vacuum to give 3-methyl-4-(1-methyl-1H-pyrazole-5-carboxamido)benzoic acid (compound 13, 1.30 g, crude) as yellow solid.

Step 3: 1-methyl-N-(2-methyl-4-(o-tolylcarbamoyl)phenyl)-1H-pyrazole-5-carboxamide (Compound I-8)

To a solution of 3-methyl-4-(1-methyl-1H-pyrazole-5-carboxamido)benzoic acid (compound 13, 532 mg, 2.05 mmol), DIEA (844 mg, 6.53 mmol) in CH$_2$Cl$_2$ (15 mL) was added EDCI (644 mg, 3.36 mmol), DMAP (274 mg, 2.24 mmol) at −5° C., then the mixture was stirred at −5° C. for 30 min, o-toluidine (compound 13A, 200 mg, 1.87 mmol) was added, the mixture was stirred at −5° C. for 30 min, warmed to 25° C., stirred for 11 hrs. TLC (petroleum ether:ethyl acetate=1:1, $R_f$=0.63) showed starting material consumed completely. The mixture was filtered, filter cake was washed with CH$_2$Cl$_2$ (20 mL*3) to give 1-methyl-N-(2-methyl-4-(o-tolylcarbamoyl)phenyl)-1H-pyrazole-5-carboxamide (compound I-8, 36 mg, 5.5% yield) as white solid. $^1$H NMR (400 MHz, DMSO-d$_6$) δ ppm 9.99 (s, 1H), 9.86 (s, 1H), 7.91 (s, 1H), 7.84 (d, J=8.0 Hz, 1H), 7.56 (d, J=2.0 Hz, 1H), 7.51 (d, J=8.0 Hz, 1H), 7.34 (d, J=7.4 Hz, 1H), 7.28 (d, J=7.4 Hz, 1H), 7.15-7.25 (m, 2H), 7.10 (d, J=1.4 Hz, 1H), 4.09 (s, 3H), 2.33 (s, 3H), 2.24 (s, 3H); ES-LCMS m/z 349.3 [M+H]$^+$.

Example 11

Synthesis of I-9

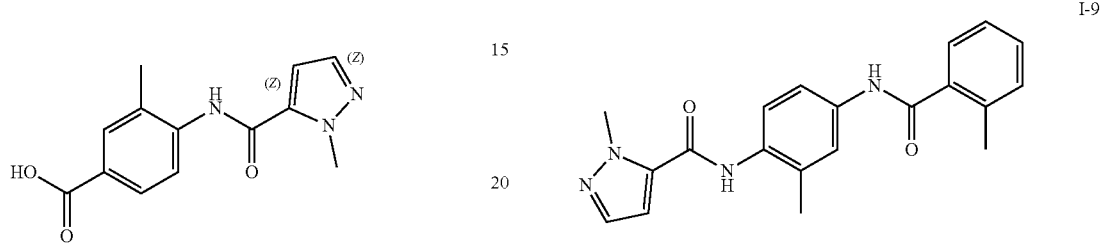

Synthetic Scheme:

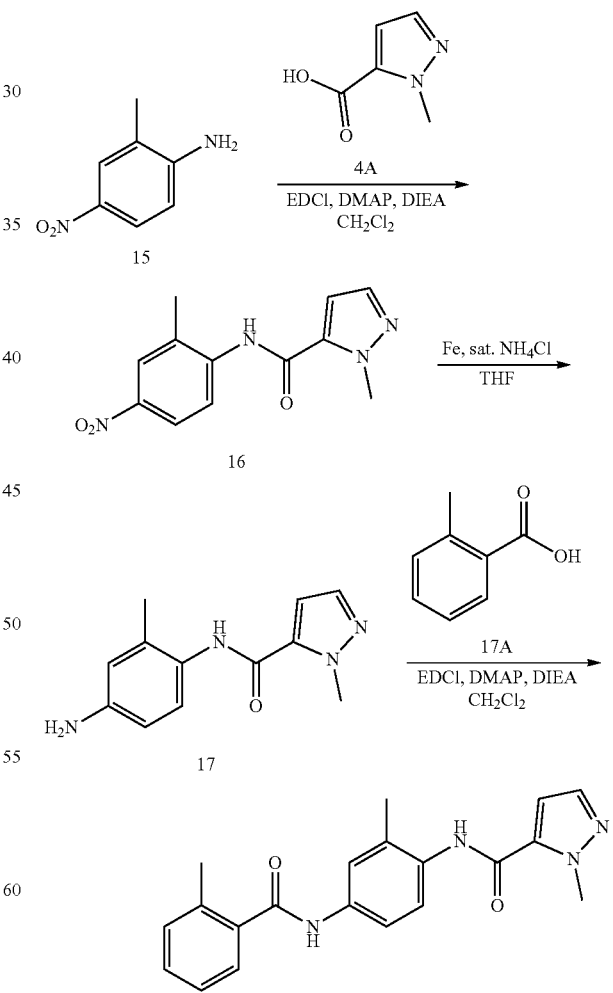

Step 1: 1-methyl-N-(2-methyl-4-nitrophenyl)-1H-pyrazole-5-carboxamide

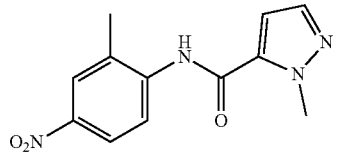 [SMILES: Cc1cc([N+](=O)[O-])ccc1NC(=O)c1ccnn1C]

To a solution of 1-methyl-1H-pyrazole-5-carboxylic acid (compound 4A, 1.99 g, 15.8 mmol), DIEA (5.95 g, 46.0 mmol) in CH$_2$Cl$_2$ (20 mL) was added EDCI (5.04 g, 26.3 mmol) and DMAP (1.93 g, 15.8 mmol) at −5° C., the mixture was stirred at −5° C. for 30 min under N$_2$. Then 2-methyl-4-nitroaniline (compound 15, 2.00 g, 13.1 mmol) was added, the mixture was stirred at −5° C. for 30 min, then warmed to 25° C., stirred for 11 hrs. TLC (petroleum ether:ethyl acetate=1:1, R$_f$=0.55) showed starting material consumed completely. The mixture was concentrated in vacuum to give light yellow oil. The oil was purified by silica gel column chromatograph (petroleum ether:ethyl acetate=100:0 to 50:50) to give 1-methyl-N-(2-methyl-4-nitrophenyl)-1H-pyrazole-5-carboxamide (compound 16, 2.60 g, 76% yield) as light yellow solid.

Step 2: N-(4-amino-2-methylphenyl)-1-methyl-1H-pyrazole-5-carboxamide

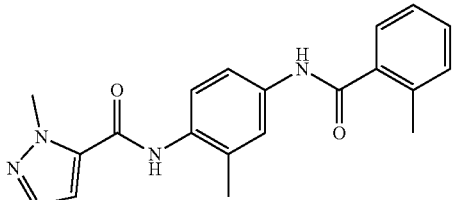

To a solution of 1-methyl-N-(2-methyl-4-nitrophenyl)-1H-pyrazole-5-carboxamide (compound 16, 2.60 g, 9.99 mmol) in THF (20 mL) was added Fe (2.79 g, 50.0 mmol), sat. NH$_4$C$_1$ (15 mL), the mixture was stirred at 25° C. for 12 hrs. TLC (petroleum ether:ethyl acetate=1:1, R$_f$=0.46) showed starting material consumed completely. The mixture was filtered, filter cake was washed with CH$_2$Cl$_2$ (10 mL*3), filtrate was separated, organic layer was dried with anhydrous Na$_2$SO$_4$, filtered and concentrated in vacuum to give yellow solid. The solid was purified by silica gel column chromatograph (petroleum ether:ethyl acetate=100:0 to 50:50) to give N-(4-amino-2-methylphenyl)-1-methyl-1H-pyrazole-5-carboxamide (compound 17, 1.90 g, 83% yield) as yellow solid. ES-LCMS m/z 483.4 [M+H]$^+$.

Step 3: 1-methyl-N-(2-methyl-4-(2-methylbenzamido)phenyl)-1H-pyrazole-5-carboxamide (I-9)

To a solution of 2-methylbenzoic acid (compound 17A, 355 mg, 2.61 mmol), DIEA (982 mg, 7.60 mmol) in CH$_2$Cl$_2$ (15 mL) was added EDCI (833 mg, 4.34 mmol), DMAP (398 mg, 3.26 mmol) at −5° C., then the mixture was stirred at −5° C. for 30 min, N-(4-amino-2-methylphenyl)-1-methyl-1H-pyrazole-5-carboxamide (compound 17, 500 mg, 2.17 mmol) was added, the mixture was stirred at −5° C. for 30 min, warmed to 25° C. for 11 hrs. TLC (petroleum ether:ethyl acetate=1:1, R$_f$=0.63) showed starting material consumed completely. The mixture was filtered, filter cake was washed with CH$_2$Cl$_2$ (20 mL*3) to give 1-methyl-N-(2-methyl-4-(2-methylbenzamido)phenyl)-1H-pyrazole-5-carboxamide (compound I-9, 30 mg, 3.8% yield) as white solid. $^1$H NMR (400 MHz, DMSO-d$_6$) δ ppm 10.28 (s, 1H), 9.84 (s, 1H), 7.69 (s, 1H), 7.57 (d, J=8.4 Hz, 1H), 7.53 (d, J=2.0 Hz, 1H), 7.46 (d, J=7.4 Hz, 1H), 7.36-7.42 (m, 1H), 7.31 (d, J=7.4 Hz, 2H), 7.23-7.29 (m, 1H), 7.06 (s, 1H), 4.08 (s, 3H), 2.39 (s, 3H), 2.21 (s, 3H); ES-LCMS m/z 349.2 [M+H]$^+$.

Example 12

Synthesis of I-10

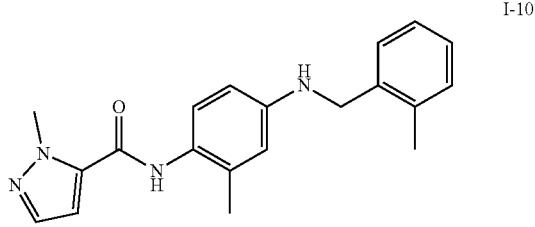 [SMILES: Cc1ccccc1CNc1ccc(NC(=O)c2ccnn2C)c(C)c1]

Synthetic Scheme:

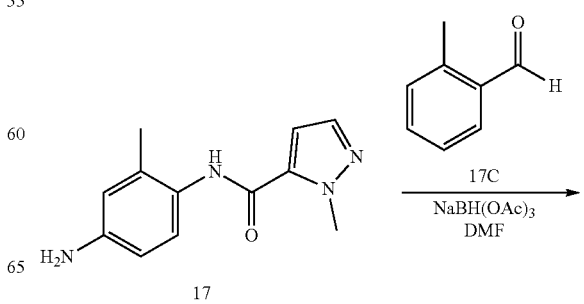

-continued

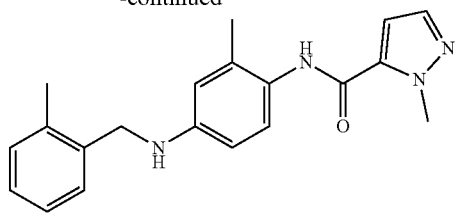

I-9

To a solution of N-(4-amino-2-methylphenyl)-1-methyl-1H-pyrazole-5-carboxamide (compound 17, 500 mg, 2.17 mmol) and 2-methylbenzaldehyde (compound 17C, 313 mg, 2.61 mmol) in DMF (15 mL) was added NaBH(OAc)₃ (4.60 g, 21.7 mmol), the mixture was stirred at 25° C. for 12 hrs. TLC (petroleum ether:ethyl acetate=1:1, R$_f$=0.54) showed starting material consumed completely. The mixture was quenched with 20 mL H₂O, then extracted with CH₂Cl₂ (10 mL*3), combined organic layer, dried with anhydrous Na₂SO₄, filtered and concentrated in vacuum to give yellow oil. The oil was purified by pre-HPLC (column: Waters Xbridge Prep OBD C18 150*30 5 u; mobile phase: [water (10 mM NH₄HCO₃)-ACN]; B %: 25%-55%, 12 min) to give 1-methyl-N-(2-methyl-4-((2-methylbenzyl)amino)phenyl)-1H-pyrazole-5-carboxamide (compound I-9, 20.0 mg, 2.7% yield) as white solid. ¹H NMR (400 MHz, DMSO-d₆) δ ppm 9.55 (s, 1H), 7.49 (s, 1H), 7.27 (d, J=5.4 Hz, 1H), 7.10-7.22 (m, 3H), 6.99 (s, 1H), 6.92 (d, J=8.6 Hz, 1H), 6.50 (s, 1H), 6.42 (d, J=7.8 Hz, 1H), 6.01 (t, J=5.8 Hz, 1H), 4.21 (d, J=5.4 Hz, 2H), 4.05 (s, 3H), 2.33 (s, 3H), 2.07 (s, 3H); ES-LCMS m/z 335.3 [M+H]⁺.

Example 13

Synthesis of I-11

I-11

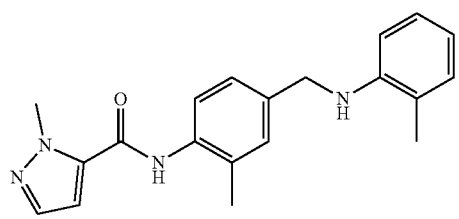

Synthetic Scheme:

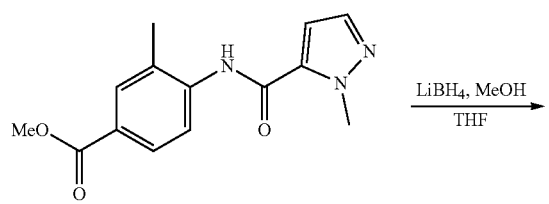

12

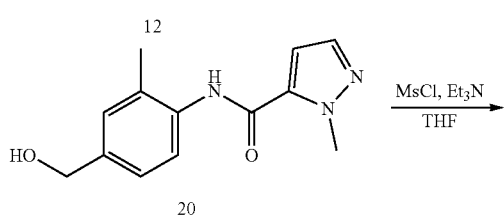

20

-continued

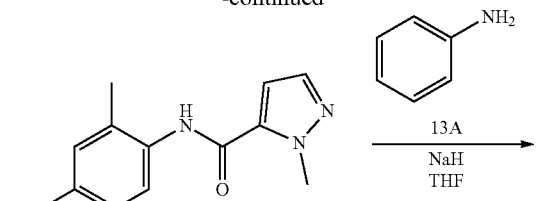

20-1

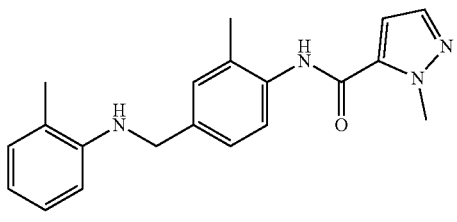

I-11

Step 1: N-(4-(hydroxymethyl)-2-methylphenyl)-1-methyl-1H-pyrazole-5-carboxamide

To a solution of methyl 3-methyl-4-(1-methyl-1H-pyrazole-5-carboxamido)benzoate (compound 12, 1.00 g, 3.66 mmol) in THF (7 mL) was added LiBH₄ (239 mg, 11.0 mmol) and MeOH (234 mg, 7.32 mmol), the mixture was stirred at 70° C. for 2 hrs. The mixture was adjusted to pH-2, then extracted with EtOAc, organic layer was analysed. TLC (petroleum ether:ethyl acetate=1:1, R$_f$=0.71) showed starting material consumed completely. The mixture was quenched with 10 mL H₂O, adjusted pH to ~2, then extracted with EtOAc (5 mL*2), combined organic layer, dried with anhydrous Na₂SO₄, filtered and concentrated in vacuum to give white solid. The solid was purified by silica gel column chromatograph (petroleum ether:ethyl acetate=100:0 to 50:50) to give N-(4-(hydroxymethyl)-2-methylphenyl)-1-methyl-1H-pyrazole-5-carboxamide (compound 20, 500 mg, 56% yield) as white solid. ES-LCMS m/z 246.2 [M+H]⁺.

Step 2: N-(4-(hydroxymethyl)-2-methylphenyl)-1-methyl-1H-pyrazole-5-carboxamide

To a solution of N-(4-(hydroxymethyl)-2-methylphenyl)-1-methyl-1H-pyrazole-5-carboxamide (compound 20, 100 mg, 0.408 mmol), TEA (82.5 mg, 0.815 mmol) in THF (5 mL) was added MsCl (42.0 mg, 0.367 mmol) at 0° C., the mixture was stirred at 25° C. for 30 min. The mixture was filtered, and filtrate was used in next step.

Step 3: 1-methyl-N-(2-methyl-4-((o-tolylamino)methyl)phenyl)-1H-pyrazole-5-carboxamide (I-11)

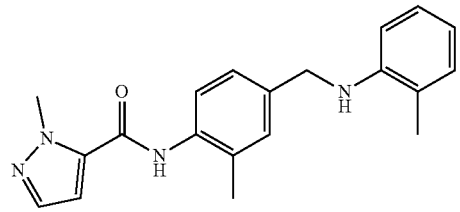

To a solution of aniline (compound 13A, 86.2 mg, 0.804 mmol) in THF (5 mL) was added NaH (32.2 mg, 0.804 mmol, 60% purity) at 0° C., the mixture was stirred at 0° C. for 30 min, a solution of 3-methyl-4-(1-methyl-1H-pyrazole-5-carboxamido)phenyl methanesulfonate (compound 20-1, 130 mg, theoretical value) in THF (5 mL) was added to the above cold mixture, the mixture was warmed to 25° C. and stirred for 10 hrs. TLC (petroleum ether:ethyl acetate=1:1, $R_f$=0.82) showed one new point formed. The mixture was quenched with 10 mL $H_2O$, then extracted with EtOAc (10 mL*3), combined organic layer, dried with anhydrous $Na_2SO_4$, filtered and concentrated in vacuum to give light yellow oil. The oil was purified by pre-TLC (petroleum ether:ethyl acetate=1:1) to give 1-methyl-N-(2-methyl-4-((o-tolylamino)methyl)phenyl)-1H-pyrazole-5-carboxamide (compound I-11, 20 mg, 15% yield) as white solid. $^1$H NMR (400 MHz, $CDCl_3$) δ ppm 7.82 (d, J=8.4 Hz, 1H), 7.53 (d, J=1.4 Hz, 1H), 7.48 (s, 1H), 7.28-7.33 (m, 2H), 7.06-7.14 (m, 2H), 6.59 6.73 (m, 3H), 4.35 (s, 2H), 4.24 (s, 3H), 3.86 (s, 1H), 3.83~3.87 (m, 1H), 2.33 (s, 3H), 2.19 (s, 3H); ES-LCMS m/z 228.1 $[M+H]^+$.

Example 14

Synthesis of I-18

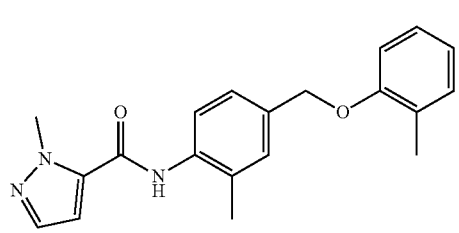

Synthetic Scheme:

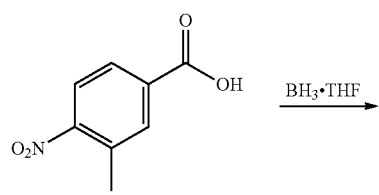

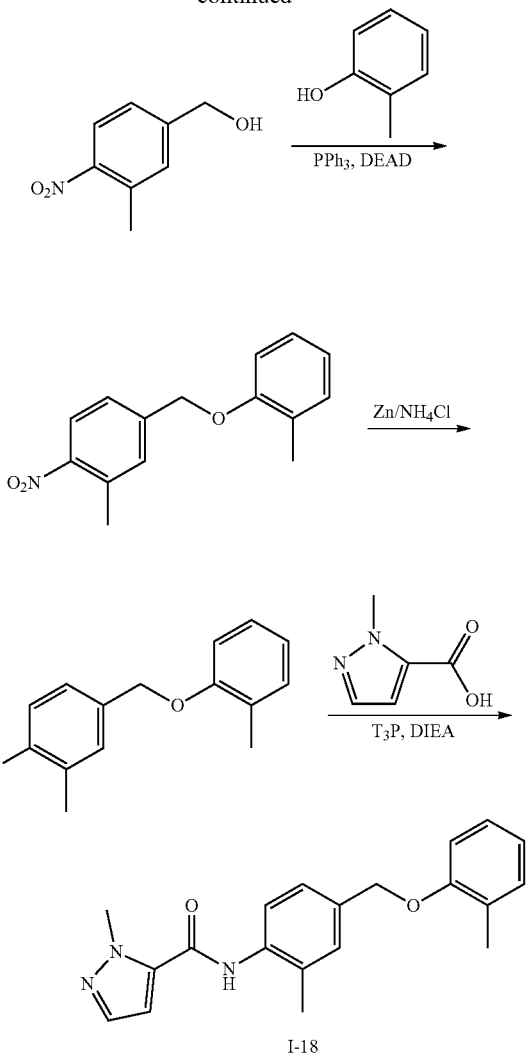

Step 1: (3-Methyl-4-nitro-phenyl)methanol

To a solution of 3-methyl-4-nitro-benzoic acid (2 g, 11.04 mmol, 1 eq) in anhydrous THF (20 mL) was added $BH_3$-THF (1 M, 27.60 mL, 2.5 eq) at 0-5° C. under $N_2$ atmosphere. The mixture was stirred at 20° C. for 3 h. The reaction mixture was quenched by addition of MeOH (30 mL) at 20° C. then stirred at 20° C. for 0.5 h. The mixture was concentrated to afford the crude product (3-methyl-4-nitro-phenyl)methanol (1.66 g, 9.93 mmol, 89.9% yield, 100% purity) as an off-white solid which was used in the next step without further purification. $^1$H NMR (400 MHz, $CD_3OD$) δ ppm 7.97 (d, J=8.3 Hz, 1H), 7.46-7.35 (m, 2H), 4.90 (s, 2H), 2.59 (s, 3H); ES-LCMS m/z 168.2 $[M+H]^+$.

Step 2: 2-Methyl-4-[(2-methylphenoxy)methyl]-1-nitro-benzene

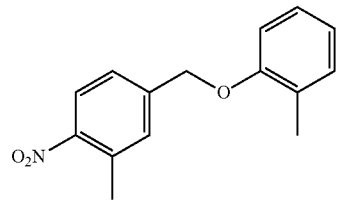 [SMILES: Cc1ccccc1OCc1ccc([N+](=O)[O-])c(C)c1]

To a solution of (3-methyl-4-nitro-phenyl)methanol (200 mg, 1.20 mmol, 1 eq) in THF (5 mL) was added o-cresol (142.32 mg, 1.32 mmol, N/A, 1.1 eq) and PPh$_3$ (345.20 mg, 1.32 mmol, 1.1 eq). After stirring for 5 min, DEAD (229.21 mg, 1.32 mmol, 239.26 uL, 1.1 eq) was added at 0° C. under N$_2$ atmosphere. The mixture was stirred at 21° C. for 12 h. H$_2$O (10 mL) was added, the mixture was extracted with ethyl acetate (10 mL×3). The combined organic layers were washed with brine (10 mL), dried over anhydrous Na$_2$SO$_4$, filtered and concentrated to afford the crude product which was purified on silica gel column chromatography (from PE/EtOAc=1/0 to 20/1, TLC: PE/EtOAc=10/1, R$_f$=0.74) to give 2-methyl-4-[(2-methylphenoxy)methyl]-1-nitro-benzene (163 mg, 631.01 µmol, 52.7% yield, 99.6% purity) as a white solid. $^1$H NMR (400 MHz, CDCl$_3$) δ ppm 8.01 (d, J=9.0 Hz, 1H), 7.47-7.36 (m, 2H), 7.21-7.12 (m, 2H), 6.91 (t, J=7.4 Hz, 1H), 6.82 (d, J=8.2 Hz, 1H), 5.11 (s, 2H), 2.63 (s, 3H), 2.31 (s, 3H); ES-LCMS m/z 258.0 [M+H]$^+$.

Step 3: 2-Methyl-4-[(2-methylphenoxy)methyl]aniline

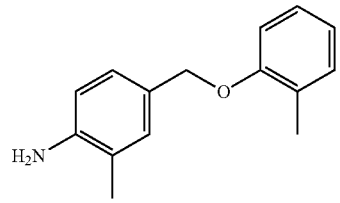

To a solution of 2-methyl-4-[(2-methylphenoxy)methyl]-1-nitro-benzene (163 mg, 631.00 umol, 1 eq) in EtOH (5 mL) was added NH$_4$Cl (337.52 mg, 6.31 mmol, 10 eq) and Zn (412.61 mg, 6.31 mmol, 10 eq). The mixture was stirred at 18° C. for 5 h. The mixture was filtered and concentrated to give the crude 2-methyl-4-[(2-methylphenoxy)methyl]aniline (170 mg, 160.05 µmol, 25.36% yield, 21.4% purity) as a yellow solid which was used in the next step without further purification. $^1$H NMR (400 MHz, CD$_3$OD) δ ppm 7.21-7.07 (m, 2H), 7.05 (m, 1H), 6.98 (m, 1H), 6.89-6.79 (m, 1H), 6.77-6.68 (m, 2H), 3.37 (s, 2H), 2.24-2.13 (m, 6H); ES-LCMS m/z 228.1 [M+H]$^+$.

Step 4: 2-Methyl-N-[2-methyl-4-[(2-methylphenoxy)methyl]phenyl]pyrazole-3-carboxamide (I-18)

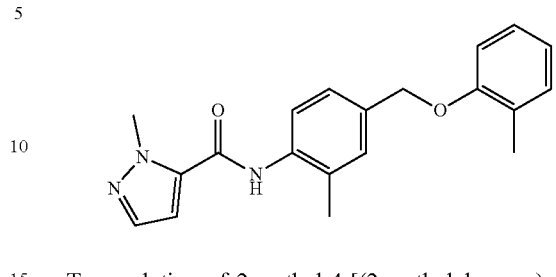

To a solution of 2-methyl-4-[(2-methylphenoxy)methyl]aniline (120 mg, 112.98 µmol, 1 eq) in EtOAc (5 mL) was added DIEA (43.80 mg, 338.93 µmol, 59.03 uL, 3 eq), 2-methylpyrazole-3-carboxylic acid (14.25 mg, 112.98 µmol, 1 eq) and T$_3$P (215.68 mg, 338.93 µmol, 201.57 uL, 50% purity, 3 eq). The mixture was stirred at 60° C. for 16 h. Saturated NaHCO$_3$ solution (10 mL) was added, extracted with ethyl acetate (10 mL×3). The combined organic layers were washed with brine (10 mL), dried over anhydrous Na$_2$SO$_4$, filtered and concentrated to afford the crude product which was purified by preparative HPLC (MeCN/H$_2$O as eluents, acidic condition, Instrument: Phenomenex Gemini 150*25 mm*10 um/Mobile phase: water(0.05% HCl)-ACN/Gradient: B from 45% to 75% in 10 min/Flow rate: 25 mL/min) followed by lyophilization to yield 2-methyl-N-[2-methyl-4-[(2-methylphenoxy)methyl]phenyl]pyrazole-3-carboxamide (compound I-18, 4.77 mg, 12.08 µmol, 10.7% yield, 94.2% purity, HCl) as a yellow solid. $^1$H NMR (400 MHz, CD$_3$OD) δ ppm 7.56 (s, 1H), 7.35-7.45 (m, 3H), 7.17-7.10 (m, 2H), 7.04-6.92 (m, 2H), 6.89-6.80 (m, 1H), 5.11 (s, 2H), 4.17 (s, 3H), 2.33 (s, 3H), 2.26 (s, 3H); ES-LCMS m/z 336.1 [M+H]$^+$.

Example 15

Synthesis of I-20

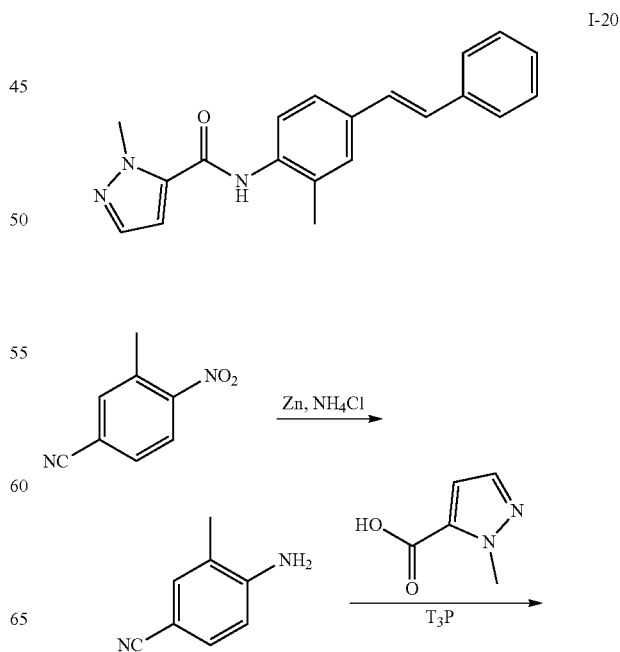

I-20

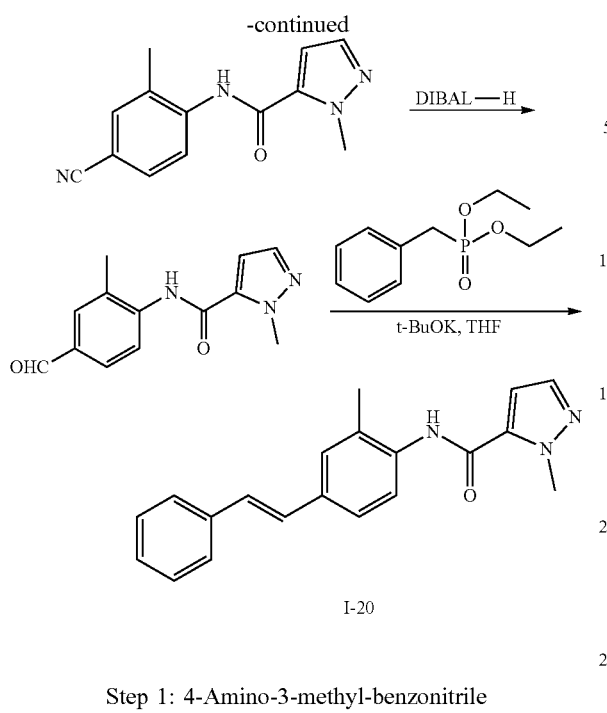

I-20

Step 1: 4-Amino-3-methyl-benzonitrile

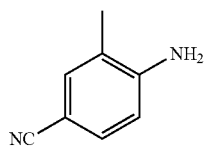

To a solution of 3-methyl-4-nitro-benzonitrile (3 g, 18.50 mmol, 1 eq) in MeOH (30 mL) was added Zn (12.10 g, 185.00 mmol, 10 eq) and NH₄Cl (9.90 g, 185.00 mmol, 10 eq). The mixture was stirred at 15° C. for 16 h. The mixture was filtered through celite, and the filtrate was concentrated under reduced pressure. The residue was diluted with EtOAc (50 mL), washed with brine (10 mL), dried over Na₂SO₄, filtered and concentrated under reduced pressure to yield crude 4-amino-3-methyl-benzonitrile (2.3 g, 17.05 mmol, 92.2% yield, 98.0% purity) as a white solid which was used in the next step without further purification. ¹H NMR (400 MHz, CDCl₃) δ ppm 7.32 (dd, J=2.9, 3.9 Hz, 2H), 6.68-6.61 (m, 1H), 4.24-3.90 (m, 2H), 2.16 (s, 3H); ES-LCMS m/z 155.1 [M+Na]⁺.

Step 2: N-(4-Cyano-2-methyl-phenyl)-2-methyl-pyrazole-3-carboxamide

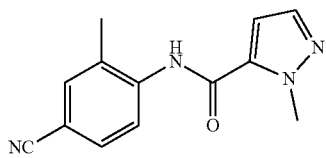 [SMILES: Cc1cc(C#N)ccc1NC(=O)c1ccnn1C]

To a solution of 4-amino-3-methyl-benzonitrile (1.5 g, 11.12 mmol, 1 eq) and 2-methylpyrazole-3-carboxylic acid (1.54 g, 12.23 mmol, 1.1 eq) in pyridine (15 mL) was added T₃P (21.23 g, 33.37 mmol, 19.84 mL, 50%, 3 eq). The mixture was stirred at 15° C. for 1.5 h. The reaction mixture was concentrated under reduced pressure to remove pyridine (15 mL). The residue was dissolved in water (100 mL), extracted with EtOAc (50 mL×3). The combined organic layers were washed with brine (20 mL), dried over Na₂SO₄, filtered and concentrated under reduced pressure to yield crude N-(4-cyano-2-methyl-phenyl)-2-methyl-pyrazole-3-carboxamide (2.3 g, 8.71 mmol, 78.3% yield, 91.0% purity) as a pink solid which was used in the next step without further purification. ¹H NMR (400 MHz, CDCl₃) δ ppm 8.26 (d, J=8.5 Hz, 1H), 7.71 (s, 1H), 7.60-7.49 (m, 3H), 6.69 (d, J=2.0 Hz, 1H), 4.23 (s, 3H), 2.37 (s, 3H); ES-LCMS m/z 241.1 [M+H]⁺.

Step 3: N-(4-Formyl-2-methyl-phenyl)-2-methyl-pyrazole-3-carboxamide

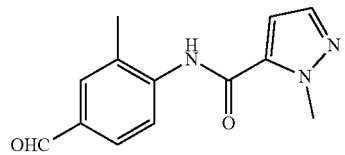 [SMILES: Cc1cc(C=O)ccc1NC(=O)c1ccnn1C]

To a solution of N-(4-cyano-2-methyl-phenyl)-2-methyl-pyrazole-3-carboxamide (2.0 g, 7.58 mmol, 1 eq) in toluene (50 mL) and DCM (10 mL) was added a solution of DIBAL-H (1 M in toluene, 22.73 mL, 3.0 eq) drop-wise at −78° C. under N₂. The reaction mixture was stirred at −78° C. for 0.5 h then warmed to 15° C. The resulting mixture was stirred at 15° C. for 2.5 h. The reaction mixture was quenched by addition of MeOH (10 mL) and aq. HCl (2 N, 10 mL) at 0° C., filtered. The filtrate was concentrated under reduced pressure to give a residue which was purified by flash silica gel chromatography (from PE/EtOAc=1/0 to 1/1, TLC: PE/EtOAc=1/1, R_f=0.33) to yield N-(4-formyl-2-methyl-phenyl)-2-methyl-pyrazole-3-carboxamide (1.0 g, 2.10 mmol, 27.6% yield, 51.0% purity) as a yellow solid. ¹H NMR (400 MHz, CD₃OD) δ ppm 9.94 (s, 1H), 7.84 (s, 1H), 7.74-7.68 (m, 1H), 7.62-7.54 (m, 2H), 7.00 (d, J=1.8 Hz, 1H), 4.16 (s, 3H), 2.41 (s, 3H); ES-LCMS m/z 244.1 [M+H]⁺.

Step 4: 2-Methyl-N-[2-methyl-4-[(E)-styryl]phenyl]pyrazole-3-carboxamide (I-20)

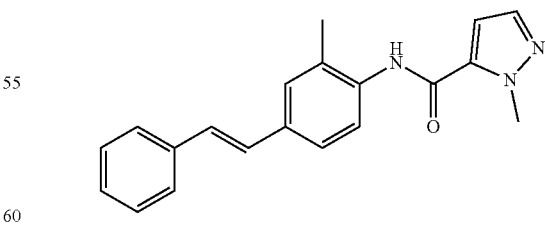

To a solution of diethoxyphosphorylmethylbenzene (342.11 mg, 1.50 mmol, 1.1 eq) in THF (15 mL) was added t-BuOK (458.75 mg, 4.09 mmol, 3 eq) and N-(4-formyl-2-methyl-phenyl)-2-methyl-pyrazole-3-carboxamide (650 mg, 1.36 mmol, 1 eq). The mixture was stirred at 15° C. for 16 h. The reaction mixture was quenched by addition of water (50 mL), extracted with EtOAc (30 mL×3). The combined organic layers were washed with brine, dried over Na$_2$SO$_4$, filtered and concentrated under reduced pressure to give a residue which was purified by flash silica gel chromatography (from PE/EA=1/0 to 3/1, TLC: PE/EA=1/1, R$_f$=0.57) to yield 2-methyl-N-[2-methyl-4-[(E)-styryl]phenyl]pyrazole-3-carboxamide (compound I-20, 170 mg, 524.92 umol, 38.5% yield, 98.0% purity) as a white solid. $^1$H NMR (400 MHz, CDCl$_3$) δ ppm 7.93 (d, J=8.2 Hz, 1H), 7.62-7.47 (m, 4H), 7.45-7.32 (m, 4H), 7.24 (m, 1H), 7.13-7.01 (m, 2H), 6.65 (s, 1H), 4.24 (s, 3H), 2.35 (s, 3H); ES-LCMS m/z 318.1 [M+H]$^+$.

Example 16

Synthesis of I-22

I-22

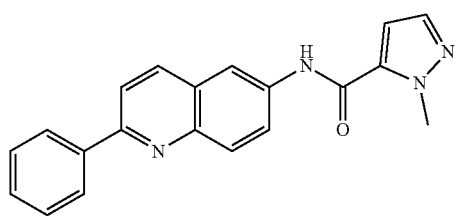

Synthetic Scheme:

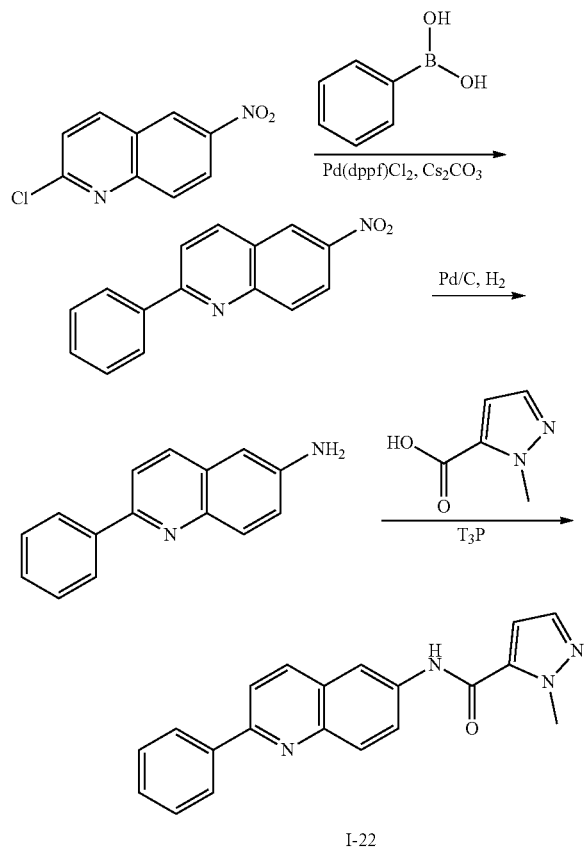

I-22

Step 1: 6-Nitro-2-phenyl-quinoline

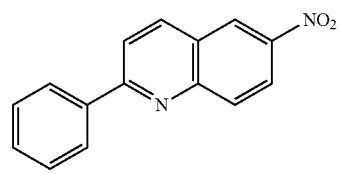 [SMILES: O=[N+]([O-])c1ccc2nc(-c3ccccc3)ccc2c1]

2-Chloro-6-nitro-quinoline (200 mg, 958.77 μmol, 1 eq), phenylboronic acid (140.28 mg, 1.15 mmol, 1.2 eq), Cs$_2$CO$_3$ (937.15 mg, 2.88 mmol, 3.0 eq) and Pd(dppf)Cl$_2$ (70.15 mg, 95.88 μmol, 0.1 eq) were taken up into a microwave tube in 1,4-dioxane (6 mL) and water (1.2 mL). The sealed tube was heated at 80° C. for 30 min under microwave. The reaction mixture was diluted with EtOAc (50 mL) and filtered through a pad of celite. The filtrate was concentrated under reduced pressure to give a residue which was purified by flash silica gel chromatography (from PE/EtOAc=100/1 to 5/1, TLC: PE/EtOAc=5/1, R$_f$=0.65) to yield 6-nitro-2-phenyl-quinoline (194 mg, 577.54 μmol, 60.2% yield, 74.5% purity) as a yellow solid. $^1$H NMR (400 MHz, CDCl$_3$) δ ppm 8.81 (d, J=2.3 Hz, 1H), 8.50 (dd, J=2.4, 9.2 Hz, 1H), 8.41 (d, J=8.8 Hz, 1H), 8.28 (d, J=9.3 Hz, 1H), 8.23 (d, J=6.8 Hz, 2H), 8.06 (d, J=8.8 Hz, 1H), 7.62-7.51 (m, 3H); ES-LCMS m/z 251.0 [M+H]$^+$.

Step 2: 2-Phenylquinolin-6-amine

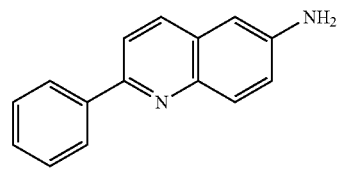

To a solution of 6-nitro-2-phenyl-quinoline (194 mg, 577.54 umol, 1 eq) in THF (10 mL) and MeOH (10 mL) was added Pd/C (10%, 200 mg) under N$_2$ atmosphere. The suspension was degassed under vacuum and purged with H$_2$ three times. The mixture was stirred under H$_2$ (15 psi) at 28° C. for 14 h. The reaction mixture was filtered through a pad of celite and the filtrate was concentrated under reduced pressure to give the desired product 2-phenylquinolin-6-amine (120 mg, 470.70 umol, 81.5% yield, 86.4% purity) as a yellow solid which was used in the next step without further purification. $^1$H NMR (400 MHz, CD$_3$OD) δ ppm 8.06 (d, J=8.5 Hz, 1H), 8.00 (d, J=7.5 Hz, 2H), 7.86 (d, J=9.0 Hz, 1H), 7.77 (d, J=8.5 Hz, 1H), 7.54-7.48 (m, 2H), 7.45 (d, J=7.5 Hz, 1H), 7.26 (dd, J=2.5, 9.0 Hz, 1H), 6.98 (d, J=2.5 Hz, 1H); ES-LCMS m/z 221.1 [M+H]$^+$.

Step 3: 2-Methyl-N-(2-phenyl-6-quinolyl)pyrazole-3-carboxamide (I-22)

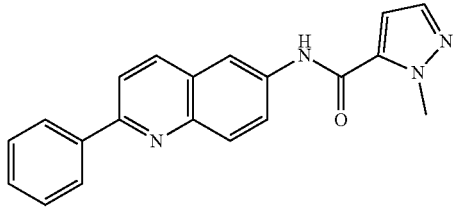 [SMILES: Cn1nccc1C(=O)Nc1ccc2nc(-c3ccccc3)ccc2c1]

To a solution of 2-phenylquinolin-6-amine (80 mg, 313.80 μmol, 1 eq) in EtOAc (3 mL) was added T₃P (535.00 mg, 840.72 μmol, 0.5 mL, 50%, 2.68 eq), DIEA (148.40 mg, 1.15 mmol, 0.2 mL, 3.66 eq) and 2-methylpyrazole-3-carboxylic acid (50 mg, 396.47 μmol, 1.26 eq). The mixture was stirred at 70° C. for 4 h. The reaction mixture was concentrated under reduced pressure to give a residue which was purified by preparative HPLC (HCl condition; column: Phenomenex Gemini 150×25 mm×10 um; mobile phase: [water (0.05% HCl)-ACN]; B %: 20%-50%, 10 min). The desired fraction was lyophilized to yield 2-methyl-N-(2-phenyl-6-quinolyl)pyrazole-3-carboxamide (compound I-22, 24.36 mg, 57.61 μmol, 18.4% yield, 94.9% purity, 2HCl salt) as a yellow solid. ¹H NMR (400 MHz, CD₃OD) δ ppm 9.14 (d, J=8.6 Hz, 1H), 8.92 (d, J=2.0 Hz, 1H), 8.46-8.34 (m, 3H), 8.16-8.11 (m, 2H), 7.83-7.73 (m, 3H), 7.59 (d, J=2.2 Hz, 1H), 7.12 (d, J=2.2 Hz, 1H), 4.22 (s, 3H); ES-LCMS m/z 329.1 [M+H]⁺.

Example 17

Synthesis of I-23

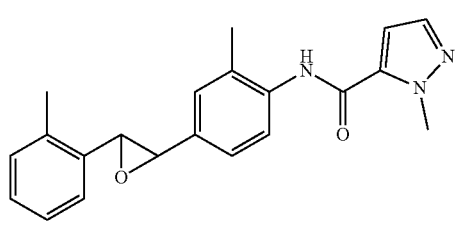

I-23

Synthetic Scheme:

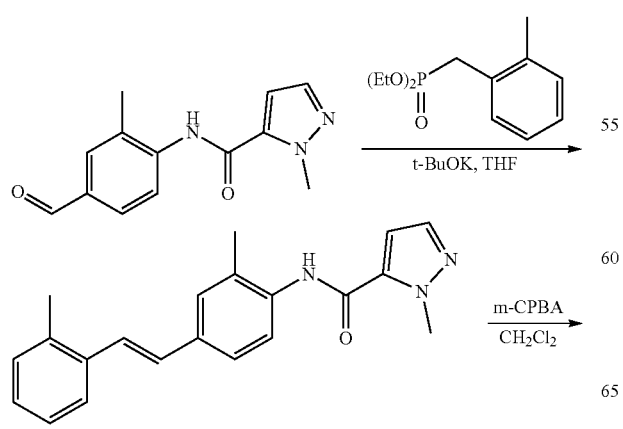

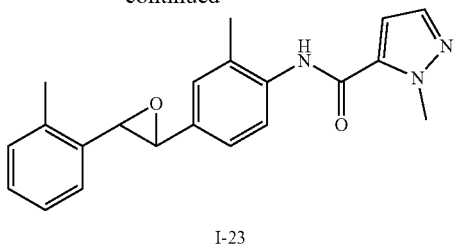

I-23

Step 1: 2-Methyl-N-[2-methyl-4-[(E)-2-(o-tolyl)vinyl]phenyl]pyrazole-3-carboxamide

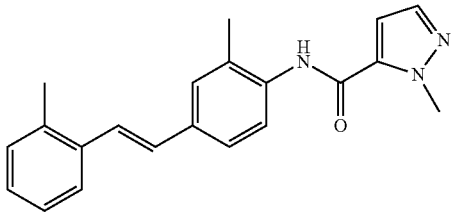 [SMILES: Cc1ccccc1/C=C/c1ccc(NC(=O)c2ccnn2C)c(C)c1]

To a solution of N-(4-formyl-2-methyl-phenyl)-2-methyl-pyrazole-3-carboxamide (300 mg, 912.60 μmol, 1 eq) in anhydrous THF (5 mL) was added potassium; 2-methylpropan-2-olate (307.21 mg, 2.74 mmol, 3 eq) and 1-(diethoxyphosphorylmethyl)-2-methyl-benzene (265.29 mg, 1.10 mmol, 1.2 eq). The mixture was stirred at 25° C. for 16 h. The mixture was concentrated to remove THF. H₂O (10 mL) was added and the mixture was extracted with ethyl acetate (10 mL×3). The combined organic layers were washed with brine (10 mL), dried over anhydrous Na₂SO₄, filtered and concentrated to afford the crude product which was purified on silica gel column chromatography (from PE/EtOAc=1/0 to 2/1, TLC: PE/EtOAc=1/1, R_f=0.59) to give 2-methyl-N-[2-methyl-4-[(E)-2-(o-tolyl)vinyl]phenyl]pyrazole-3-carboxamide (147 mg, 416.50 μmol, 45.6% yield, 93.9% purity) as a yellow solid. ¹H NMR (400 MHz, CDCl₃) δ ppm 7.91 (d, J=8.6 Hz, 1H), 7.58 (d, J=7.1 Hz, 1H), 7.52 (d, J=2.0 Hz, 2H), 7.43-7.37 (m, 2H), 7.29 (d, J=16.3 Hz, 1H), 7.21-7.14 (m, 3H), 6.95 (d, J=16.1 Hz, 1H), 6.68-6.60 (m, 1H), 4.23 (s, 3H), 2.44 (s, 3H), 2.35 (s, 3H); ES-LCMS m/z 332.0 [M+H]⁺.

Step 2: 2-Methyl-N-[2-methyl-4-[3-(o-tolyl)oxiran-2-yl]phenyl]pyrazole-3-carboxamide (I-23)

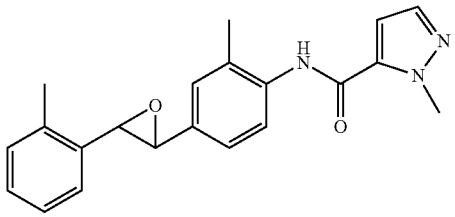 [SMILES: Cc1cc(C2OC2c2ccccc2C)ccc1NC(=O)c1ccnn1C]

To a solution of 2-methyl-N-[2-methyl-4-[(E)-2-(o-tolyl)vinyl]phenyl]pyrazole-3-carboxamide (70 mg, 198.33 μmol, 1 eq) in anhydrous DCM (3 mL) was added m-CPBA (100.67 mg, 495.84 μmol, 85% purity, 2.5 eq). The mixture was stirred at 25° C. for 1 h. Sat.NaHCO₃ (5 mL) solution was added and the mixture was extracted with ethyl acetate (10 mL×2). The combined organic layers were washed with aq.Na₂SO₃ (10 mL, 10 M), dried over anhydrous Na₂SO₄, filtered and concentrated to afford the crude product which was purified by preparative TLC (SiO₂, PE/EtOAc=1/1, R$_f$=0.50) followed by lyophilization to yield 2-methyl-N-[2-methyl-4-[3-(o-tolyl)oxiran-2-yl]phenyl]pyrazole-3-carboxamide (compound I-23, 24.69 mg, 70.50 μmol, 35.6% yield, 99.2% purity) as a white solid. ¹H NMR (400 MHz, CD₃OD) δ ppm 7.53 (d, J=2.0 Hz, 1H), 7.39-7.34 (m, 2H), 7.28 (d, J=5.5 Hz, 2H), 7.23-7.17 (m, 3H), 7.01-6.96 (m, 1H), 4.15 (s, 3H), 4.05 (d, J=1.8 Hz, 1H), 3.75 (d, J=1.8 Hz, 1H), 2.33 (d, J=5.7 Hz, 6H); ES-LCMS m/z 348.1 [M+H]⁺.

Example 18

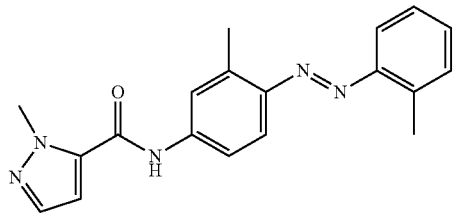

I-24

Synthesis of I-24

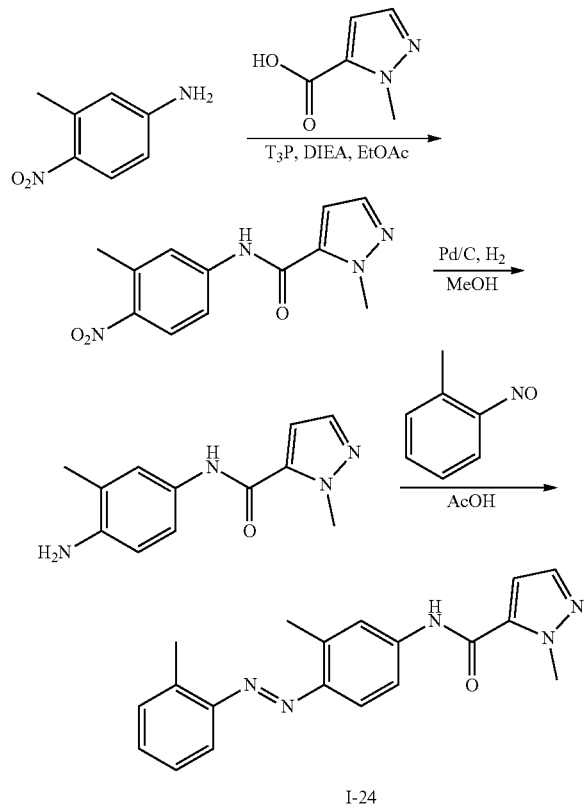

I-24

Step 1: 2-Methyl-N-(3-methyl-4-nitro-phenyl)pyrazole-3-carboxamide

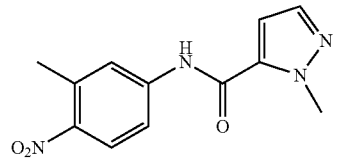 [SMILES: Cc1cc(NC(=O)c2ccnn2C)ccc1[N+](=O)[O-]]

To a solution of 3-methyl-4-nitro-aniline (500 mg, 3.29 mmol, 1 eq) in EtOAc (5 mL) was added 2-methylpyrazole-3-carboxylic acid (414.43 mg, 3.29 mmol, 1 eq), DIEA (1.27 g, 9.86 mmol, 1.72 mL, 3 eq) and T₃P (6.27 g, 9.86 mmol, 5.86 mL, 3 eq). The mixture was stirred at 60° C. for 16 h. Sat. NaHCO₃ solution (10 mL) was added and the mixture was extracted with ethyl acetate (10 mL×3). The combined organic layers were washed with brine (10 mL), dried over anhydrous Na₂SO₄, filtered and concentrated to afford the crude product which was purified on silica gel column chromatography (from PE/EtOAc=1/0 to 3/1, TLC: PE/EtOAc=2/1, R$_f$=0.60) to give 2-methyl-N-(3-methyl-4-nitro-phenyl)pyrazole-3-carboxamide (600 mg, 2.27 mmol, 69.0% yield, 98.3% purity) as a yellow solid. ¹H NMR (400 MHz, CDCl₃) δ ppm 8.10 (d, J=9.0 Hz, 1H), 7.82 (s, 1H), 7.65 (d, J=2.0 Hz, 1H), 7.58 (dd, J=2.3, 9.0 Hz, 1H), 7.54 (d, J=2.3 Hz, 1H), 6.70 (d, J=2.3 Hz, 1H), 4.23 (s, 3H), 2.67 (s, 3H); ES-LCMS m/z 261.0 [M+H]⁺.

Step 2: N-(4-Amino-3-methyl-phenyl)-2-methyl-pyrazole-3-carboxamide

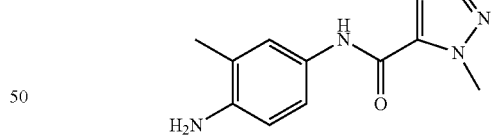

To a solution of 2-methyl-N-(3-methyl-4-nitro-phenyl) pyrazole-3-carboxamide (203.46 mg, 768.49 μmol, 1 eq) in anhydrous MeOH (10 mL) was added Pd/C (10%, 0.02 g) under N₂ atmosphere. The suspension was degassed and purged with H₂ for 3 times. The mixture was stirred under H₂ (15 Psi) at 25° C. for 1 h. The mixture was filtered and concentrated to afford the crude product N-(4-amino-3-methyl-phenyl)-2-methyl-pyrazole-3-carboxamide (177 mg, 694.89 μmol, 90.4% yield, 90.4% purity) as a white solid which was used in the next step without further purification. ¹H NMR (400 MHz, CDCl₃) δ ppm 7.47 (d, J=1.8 Hz, 2H), 7.27 (s, 1H), 7.18-7.12 (m, 1H), 6.65 (d, J=8.4 Hz, 1H), 6.58 (s, 1H), 4.19 (s, 3H), 3.58 (br s, 2H), 2.17 (s, 3H); ES-LCMS m/z 231.3 [M+H]⁺.

Step 3: 2-Methyl-N-[3-methyl-4-[(E)-o-tolylazo]phenyl]pyrazole-3-carboxamide (I-24)

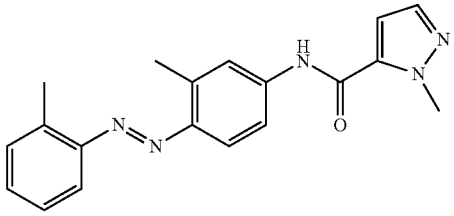 [SMILES: Cc1ccccc1/N=N/c1ccc(NC(=O)c2ccnn2C)cc1C]

To a solution of N-(4-amino-3-methyl-phenyl)-2-methyl-pyrazole-3-carboxamide (157 mg, 681.82 μmol, 1 eq) in AcOH (5 mL) was added 1-methyl-2-nitroso-benzene (91.77 mg, 681.82 μmol, 1 eq). The mixture was stirred at 25° C. for 15 h under $N_2$ atmosphere under dark. The mixture was concentrated to remove AcOH. Sat. $NaHCO_3$ solution (10 mL) was added and the mixture was extracted with ethyl acetate (10 mL×3). The combined organic layers were washed with brine (10 mL), dried over anhydrous $Na_2SO_4$, filtered and concentrated to afford the crude product which was purified by preparative TLC ($SiO_2$, PE/EtOAc=2/1, $R_f$=0.65) to give 2-methyl-N-[3-methyl-4-[(E)-o-tolylazo]phenyl]pyrazole-3-carboxamide (74 mg, 91.9% purity). The product was then purified by preparative HPLC (MeCN/$H_2O$ as eluents, basic condition, Instrument: Phenomenex Gemini 150*25 mm*10 um/Mobile phase: water (0.05% ammonia hydroxide v/v)-ACN/Gradient: B from 60% to 90% in 10 min/Flow rate: 25 mL/min) followed by lyophilization to yield product of 2-methyl-N-[3-methyl-4-[(E)-o-tolylazo]phenyl]pyrazole-3-carboxamide (compound I-24, 33 mg, 95.82 umol, 14.05% yield, 96.8% purity) as a yellow solid. $^1$H NMR (400 MHz, DMSO-$d_6$) δ ppm 10.37 (s, 1H), 7.86 (s, 1H), 7.71-7.59 (m, 2H), 7.56-7.50 (m, 2H), 7.39 (m, 2H), 7.29 (d, J=4.1, 8.3 Hz, 1H), 7.09 (d, J=2.2 Hz, 1H), 4.08 (s, 3H), 2.67 (s, 3H), 2.65 (s, 3H); ES-LCMS m/z 334.3 [M+H]$^+$.

Example 19

Synthesis of I-25

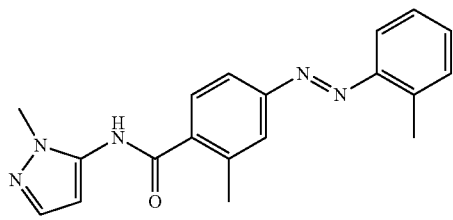

I-25

Synthetic Scheme:

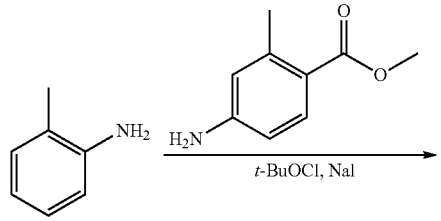

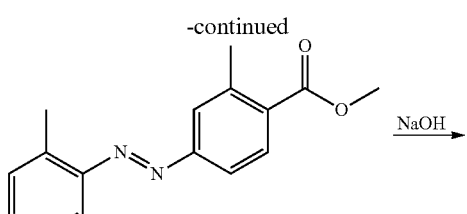

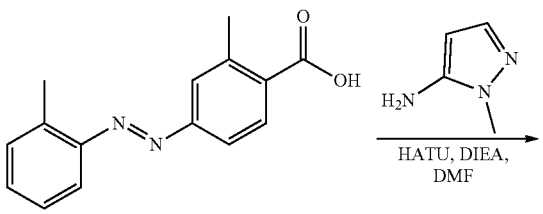

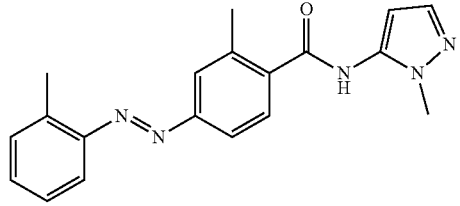

I-25

Step 1: Methyl 2-methyl-4-[(E)-o-tolylazo]benzoate

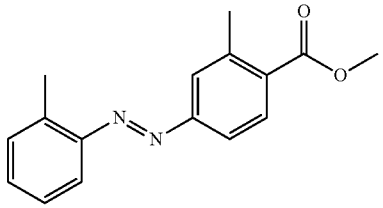 [SMILES: COC(=O)c1ccc(/N=N/c2ccccc2C)cc1C]

To a solution of 2-methylaniline (454.07 mg, 4.24 mmol, 454.07 μL, 1 eq), methyl 4-amino-2-methyl-benzoate (1 g, 6.05 mmol, 1.43 eq), NaI (2.54 g, 16.95 mmol, 4 eq) in THF (70 mL) was added tert-butyl hypochlorite (1.84 g, 16.95 mmol, 4 eq) at 0° C. The mixture was stirred at 0° C. for 6 h. The reaction mixture was quenched by addition of water (100 mL), extracted with EtOAc (80 mL×3). The combined organic layers were washed with brine (30 mL), dried over $Na_2SO_4$, filtered and concentrated under reduced pressure to give a residue which was purified by flash silica gel chromatography (from PE/EtOAc=1/0 to 5/1, TLC: PE/EtOAc=5/1, $R_f$=0.62) to yield methyl 2-methyl-4-[(E)-o-tolylazo]benzoate (120 mg, 384.63 umol, 9.1% yield, 86.0% purity) as yellow oil. $^1$H NMR (400 MHz, $CD_3OD$) δ ppm 8.05 (d, J=8.6 Hz, 1H), 7.80 (s, 1H), 7.76 (d, J=8.2 Hz, 1H), 7.62 (dd, J=7.8, 17.3 Hz, 1H), 7.43-7.36 (m, 2H), 7.29-7.26 (m, 1H), 3.92 (s, 3H), 2.75-2.72 (m, 3H), 2.68 (s, 3H); ES-LCMS m/z 269.1 [M+H]$^+$.

Step 2: 2-Methyl-4-[(E)-o-tolylazo]benzoic acid

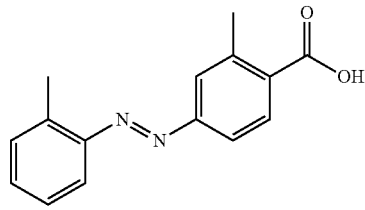 [SMILES: Cc1ccccc1/N=N/c1ccc(C(=O)O)c(C)c1]

To a solution of methyl 2-methyl-4-[(E)-o-tolylazo]benzoate (120 mg, 384.63 umol, 1 eq) in MeOH (5 mL) and H$_2$O (1 mL) was added NaOH (30.77 mg, 769.26 µmol, 2 eq). The mixture was stirred at 15° C. for 16 h. The reaction mixture was concentrated under reduced pressure. To the residue was added water (20 mL) and EtOAc (10 mL) then separated. The aqueous layer was adjusted to pH to 5 by addition with 1 N HCl, extracted with EtOAc (20 mL×3). The organic layer was dried over Na$_2$SO$_4$, filtered, and concentrated under reduced pressure to give crude 2-methyl-4-[(E)-o-tolylazo]benzoic acid (65 mg, 199.38 umol, 51.8% yield, 78.0% purity) as a yellow solid which was used in the next step without further purification. $^1$H NMR (400 MHz, CD$_3$OD) δ ppm 8.07 (d, J=8.4 Hz, 1H), 7.83-7.72 (m, 2H), 7.64 (d, J=7.5 Hz, 1H), 7.46-7.38 (m, 2H), 7.33-7.25 (m, 1H), 2.74 (s, 3H), 2.70 (s, 3H); ES-LCMS m/z 255.1 [M+H]$^+$.

Step 3: 2-Methyl-N-(2-methylpyrazol-3-yl)-4-[(E)-o-tolylazo]benzamide (I-25)

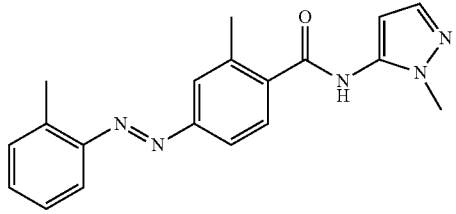 [SMILES: Cc1ccccc1/N=N/c1ccc(C(=O)Nc2ccnn2C)c(C)c1]

To a solution of 2-methyl-4-[(E)-o-tolylazo]benzoic acid (65 mg, 199.38 µmol, 1 eq), 2-methylpyrazol-3-amine (38.73 mg, 398.77 µmol, 2 eq) in DMF (5 mL) was added HATU (98.56 mg, 259.20 µmol, 1.3 eq) and DIEA (77.31 mg, 598.15 µmol, 104.19 µL, 3.0 eq). The mixture was stirred at 15° C. for 2 h. TLC (PE/EtOAc=1/1, R$_f$=0.71) showed the starting material was consumed completely and two new spots were formed. The reaction mixture was quenched by addition of water (30 mL), extracted with EtOAc (20 mL×3). The combined organic layers were washed with brine (10 mL), dried over Na$_2$SO$_4$, filtered and concentrated under reduced pressure to give a residue, which was purified by preparative TLC (PE/EtOAc=0/1, R$_f$=0.71) to yield crude which was further purified by preparative HPLC (column: Agela DuraShell 150 mm_25 mm_5 um; mobile phase: [water (10 mM NH$_4$HCO$_3$)-ACN]; B %: 50%-80%, 10 min) followed by lyophilization to yield 2-methyl-N-(2-methylpyrazol-3-yl)-4-[(E)-o-tolylazo]benzamide (compound I-25, 16.41 mg, 46.76 umol, 23.4% yield, 95.0% purity) as a yellow solid. $^1$H NMR (400 MHz, DMSO-d$_6$) δ ppm 10.48 (s, 1H), 7.86-7.74 (m, 3H), 7.60 (d, J=7.9 Hz, 1H), 7.52-7.44 (m, 2H), 7.41-7.31 (m, 2H), 6.33 (d, J=1.8 Hz, 1H), 3.75 (s, 3H), 2.71 (s, 3H), 2.54 (s, 3H); ES-LCMS m/z 334.2 [M+H]$^+$.

Example 20

Synthesis of I-27

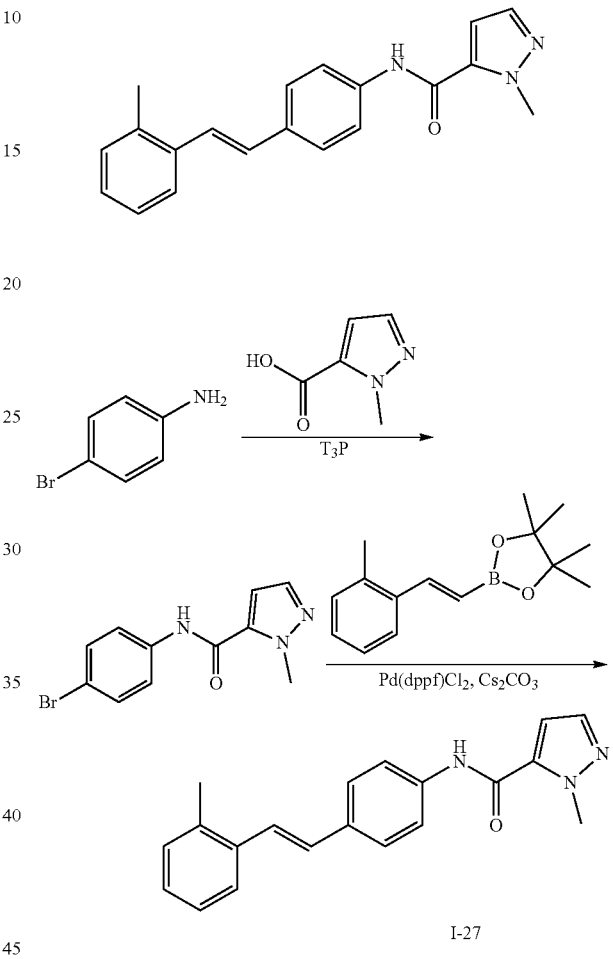

Step 1: N-(4-Bromophenyl)-2-methyl-pyrazole-3-carboxamide

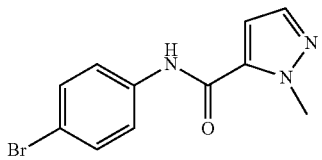 [SMILES: Cn1nccc1C(=O)Nc1ccc(Br)cc1]

To a solution of 4-bromoaniline (200 mg, 1.16 mmol, 1 eq) in EtOAc (5 mL) was added 2-methylpyrazole-3-carboxylic acid (175.95 mg, 1.40 mmol, 1.2 eq), DIEA (450.78 mg, 3.49 mmol, 607.52 µL, 3 eq) and T$_3$P (2.22 g, 3.49 mmol, 2.07 mL, 3 eq). The mixture was stirred at 60° C. for 12 h. Sat. NaHCO$_3$ solution (10 mL) was added and the mixture was extracted with ethyl acetate (10 mL×3). The combined organic layers were washed with brine (10 mL), dried over anhydrous Na₂SO₄, filtered and concentrated to afford the crude product which was purified on silica gel column chromatography (from PE/EtOAc=1/0 to 3/1, TLC: PE/EtOAc=2/1, R_f=0.47) to give N-(4-bromophenyl)-2-methyl-pyrazole-3-carboxamide (198 mg, 699.77 μmol, 60.2% yield, 99.0% purity) as a white solid. $^1$H NMR (400 MHz, CDCl₃) δ ppm 7.61 (s, 1H), 7.49 (d, J=2.0 Hz, 1H), 7.47 (s, 4H), 6.63 (d, J=2.0 Hz, 1H), 4.20 (s, 3H); ES-LCMS m/z 279.6 [M+H]⁺.

Step 2: 2-Methyl-N-[4-[(E)-2-(o-tolyl)vinyl]phenyl]pyrazole-3-carboxamide (I-27)

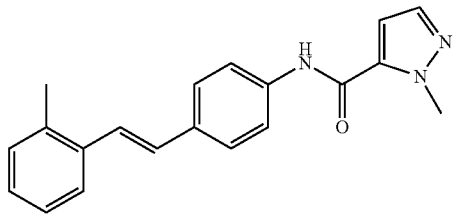 [SMILES: Cc1ccccc1/C=C/c1ccc(NC(=O)c2ccnn2C)cc1]

To a solution of 4,4,5,5-tetramethyl-2-[(E)-2-(o-tolyl)vinyl]-1,3,2-dioxaborolane (103 mg, 304.61 μmol, 1 eq) in 1,4-dioxane (5 mL) and H₂O (1 mL) was added N-(4-bromophenyl)-2-methyl-pyrazole-3-carboxamide (86.19 mg, 304.61 μmol, 1 eq), Cs₂CO₃ (297.74 mg, 913.83 μmol, 3 eq) and Pd(dppf)Cl₂ (11.14 mg, 15.23 μmol, 0.05 eq). The mixture was stirred under N₂ atmosphere at 110° C. for 0.5 h under microwave. H₂O (10 mL) was added, the mixture was extracted with ethyl acetate (10 mL×3). The combined organic layers were washed with brine (10 mL), dried over anhydrous Na₂SO₄, filtered and concentrated to afford the crude product which was purified by preparative HPLC (MeCN/H₂O as eluents, acidic condition, Instrument: Phenomenex Synergi C18 150*30 mm*4 um/Mobile phase: water(0.05% HCl)-ACN/Gradient: B from 55% to 85% in 12 min/Flow rate: 25 mL/min) followed by lyophilization to yield 2-methyl-N-[4-[(E)-2-(o-tolyl)vinyl]phenyl]pyrazole-3-carboxamide (compound I-27, 19.96 mg, 53.93 μmol, 17.7% yield, 95.6% purity, HCl) as a white solid. $^1$H NMR (400 MHz, CD₃OD) δ ppm 7.72 (m, 2H), 7.65-7.54 (m, 4H), 7.40 (d, J=16.1 Hz, 1H), 7.23-7.13 (m, 3H), 7.05 (d, J=16.1 Hz, 1H), 7.00 (d, J=2.0 Hz, 1H), 4.18 (s, 3H), 2.45 (s, 3H); ES-LCMS m/z 318.1 [M+H]⁺.

Example 21

Synthesis of I-28

I-28

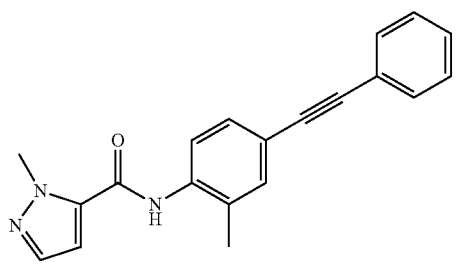

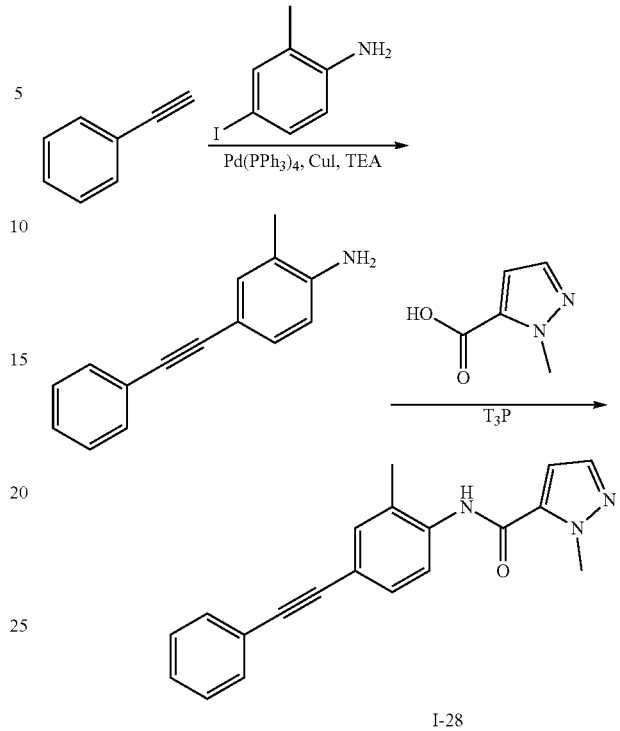

Step 1: 2-Methyl-4-(2-phenylethynyl)aniline

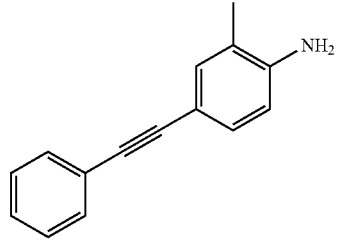 [SMILES: Cc1cc(C#Cc2ccccc2)ccc1N]

A mixture of ethynylbenzene (200 mg, 1.96 mmol, 215.05 μL, 1 eq), 4-iodo-2-methyl-aniline (456.36 mg, 1.96 mmol, 1 eq), TEA (594.46 mg, 5.87 mmol, 817.69 μL, 3.0 eq), CuI (74.59 mg, 391.65 μmol, 0.2 eq) and Pd(PPh₃)₄ (226.29 mg, 195.82 μmol, 0.1 eq) in DMF (10 mL) was degassed and purged with N₂ for 3 times, the mixture was stirred at 100° C. for 16 h under N₂. The reaction mixture was quenched by addition of water (50 mL), extracted with EtOAc (30 mL×3). The combined organic layers were washed with brine (10 mL), dried over Na₂SO₄, filtered and concentrated under reduced pressure to give a residue which was purified by flash silica gel chromatography (from PE/EtOAc=1/0 to 5/1, TLC: PE/EtOAc=5/1, R_f=0.28) to yield 2-methyl-4-(2-phenylethynyl)aniline (160 mg, 725.62 umol, 37.1% yield, 94.0% purity) as a yellow solid. $^1$H NMR (400 MHz, DMSO-d₆) δ ppm 7.48-7.29 (m, 5H), 7.15-7.04 (m, 2H), 6.60 (d, J=8.2 Hz, 1H), 5.33 (s, 2H), 2.05 (s, 3H); ES-LCMS m/z 208.1 [M+H]⁺.

Step 2: 2-Methyl-N-[2-methyl-4-(2-phenylethynyl)phenyl]pyrazole-3-carboxamide (I-28)

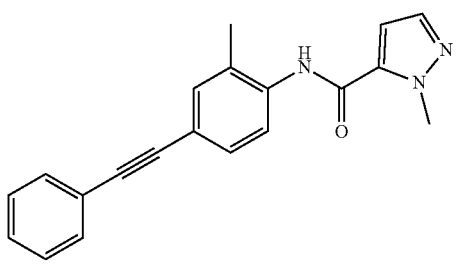 [SMILES: Cc1cc(C#Cc2ccccc2)ccc1NC(=O)c1ccnn1C]

To a solution of 2-methyl-4-(2-phenylethynyl)aniline (50 mg, 226.76 µmol, 1 eq) in pyridine (3 mL) was added T₃P (288.60 mg, 453.51 µmol, 269.72 µL, 50%, 2 eq) and 2-methylpyrazole-3-carboxylic acid (28.60 mg, 226.76 µmol, 1 eq). The mixture was stirred at 20° C. for 16 h. The reaction mixture was quenched by addition water (50 mL), extracted with EtOAc (30 mL×3). The combined organic layers were washed with brine (10 mL), dried over Na₂SO₄, filtered and concentrated under reduced pressure to give a residue which was purified by preparative HPLC (column: Phenomenex Gemini 150×25 mm×10 um; mobile phase: [water(0.05% HCl)-ACN]; B %: 47%-77%, 10 min) followed by lyophilization to yield 2-methyl-N-[2-methyl-4-(2-phenylethynyl)phenyl]pyrazole-3-carboxamide (compound I-28, 32.57 mg, 92.57 µmol, 40.8% yield, 100% purity, HCl) as a light yellow solid. ¹H NMR (400 MHz, CD₃OD) δ ppm 7.56-7.49 (m, 3H), 7.47 (s, 1H), 7.42-7.35 (m, 5H), 6.98 (s, 1H), 4.15 (s, 3H), 2.31 (s, 3H); ES-LCMS m/z 316.0 [M+H]⁺.

Example 22

Synthesis of I-29

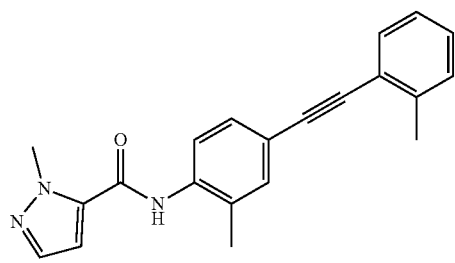

I-29

Synthetic Scheme:

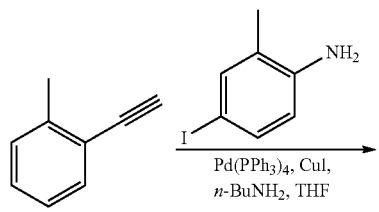

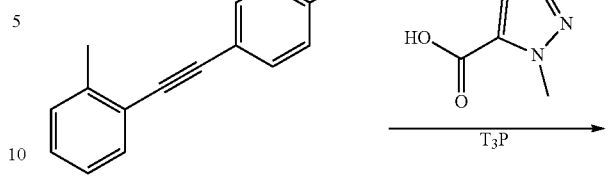

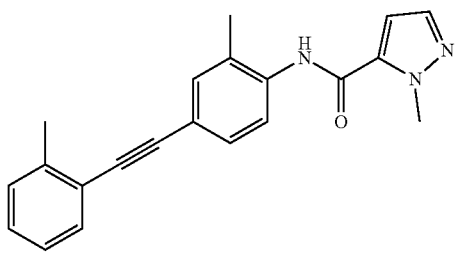

I-29

Step 1: 2-Methyl-4-[2-(o-tolyl)ethynyl]aniline

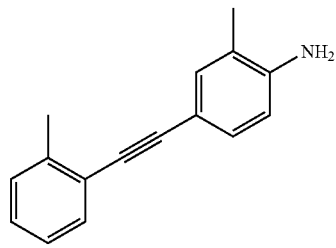 [SMILES: Cc1cc(C#Cc2ccccc2C)ccc1N]

A mixture of 1-ethynyl-2-methyl-benzene (70 mg, 602.62 µmol, 75.92 µL, 1 eq), 4-iodo-2-methyl-aniline (140.44 mg, 602.62 µmol, 1 eq), CuI (22.95 mg, 120.52 µmol, 0.2 eq), Pd(PPh₃)₄ (69.64 mg, 60.26 µmol, 0.1 eq) and butan-1-amine (132.23 mg, 1.81 mmol, 178.68 uL, 3 eq) in THF (5 mL) was degassed and purged with N₂ for 3 times. The mixture was stirred at 20° C. for 16 h under N₂. The reaction mixture was quenched by addition of water (50 mL), extracted with EtOAc (30 mL×3). The combined organic layers were washed with brine (10 mL), dried over Na₂SO₄, filtered and concentrated under reduced pressure to give a residue which was purified by flash silica gel chromatography (from PE/EtOAc=1/0 to 5/1, TLC: PE/EtOAc=5/1, R_f=0.23) to yield 2-methyl-4-[2-(o-tolyl)ethynyl]aniline (100 mg, 451.88 µmol, 75.0% yield, 100% purity) as a yellow solid. ¹H NMR (400 MHz, CDCl₃) δ ppm 7.50-7.43 (m, 1H), 7.27-7.12 (m, 5H), 6.65 (d, J=8.2 Hz, 1H), 3.78 (s, 2H), 2.51 (s, 3H), 2.18 (s, 3H); ES-LCMS m/z 222.2 [M+H]⁺.

Step 2: 2-Methyl-N-[2-methyl-4-[2-(o-tolyl)ethynyl]phenyl]pyrazole-3-carboxamide (I-29)

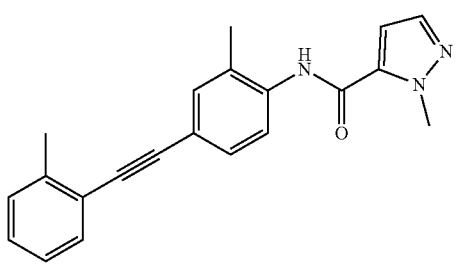 [SMILES: Cc1ccccc1C#Cc1ccc(NC(=O)c2ccnn2C)c(C)c1]

To a solution of 2-methyl-4-[2-(o-tolyl)ethynyl]aniline (50 mg, 225.94 μmol, 1 eq) in pyridine (3 mL) was added T₃P (287.56 mg, 451.88 μmol, 268.75 uL, 50%, 2 eq) and 2-methylpyrazole-3-carboxylic acid (28.49 mg, 225.94 μmol, 1 eq). The mixture was stirred at 20° C. for 16 h. The reaction mixture was quenched by addition of water (50 mL), extracted with EtOAc (30 mL×3). The combined organic layers were washed with brine (10 mL), dried over Na₂SO₄, filtered and concentrated under reduced pressure to give a residue, which was purified by preparative HPLC (column: Phenomenex Synergi C18 150×30 mm×4 um; mobile phase: [water(0.05% HCl)-ACN]; B %: 50%-80%, 12 min) followed by lyophilization to yield 2-methyl-N-[2-methyl-4-[2-(o-tolyl)ethynyl]phenyl]pyrazole-3-carboxamide (compound I-29, 28.27 mg, 76.50 μmol, 33.9% yield, 99.0% purity, HCl) as a white solid. ¹H NMR (400 MHz, CD₃OD) δ ppm 7.54 (d, J=2.2 Hz, 1H), 7.49-7.44 (m, 2H), 7.43-7.37 (m, 2H), 7.30-7.22 (m, 2H), 7.21-7.15 (m, 1H), 6.99 (s, 1H), 4.16 (s, 3H), 2.51 (s, 3H), 2.32 (s, 3H); ES-LCMS m/z 330.1 [M+H]⁺.

Example 23

Synthesis of I-33

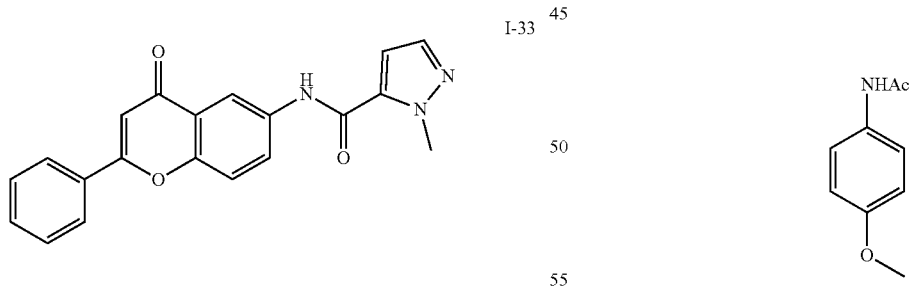

Synthetic Scheme:

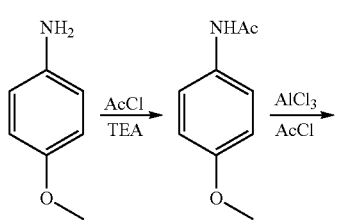

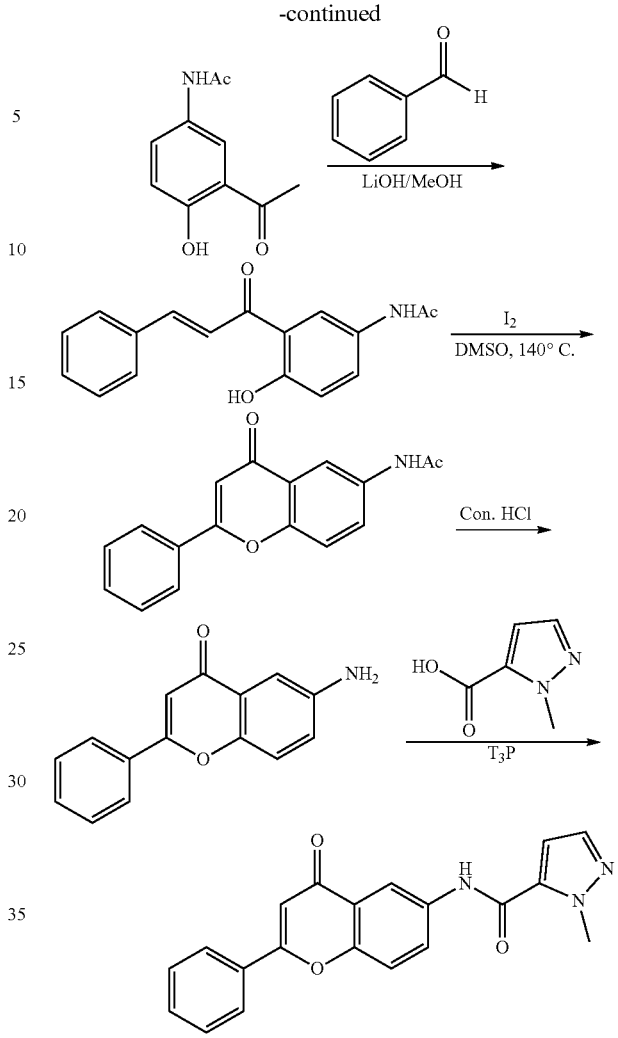

Step 1: N-(4-Methoxyphenyl)acetamide

To a solution of 4-methoxyaniline (5 g, 40.60 mmol, 1 eq) and TEA (8.22 g, 81.20 mmol, 11.30 mL, 2 eq) in DCM (50 mL) was added acetyl chloride (3.82 g, 48.72 mmol, 3.48 mL, 1.2 eq) dropwise at 0° C. After addition, the mixture was stirred at 15° C. for 2 h. The reaction mixture was concentrated and extracted with EtOAc (20 mL×2). The combined organic layers were washed with brine (20 mL), dried over Na₂SO₄, filtered and concentrated under reduced pressure to give N-(4-methoxyphenyl)acetamide (4 g, 22.33 mmol, 55.0% yield, 92.2% purity) as a brown solid which was used in the next step without further purification. ¹H NMR (400 MHz, CD₃OD) δ ppm 7.41-7.37 (m, 2H), 6.86-6.83 (m, 2H), 3.75 (s, 3H), 2.07-2.06 (m, 3H); ES-LCMS m/z 166.2 [M+H]⁺.

Step 2: N-(3-Acetyl-4-hydroxy-phenyl)acetamide

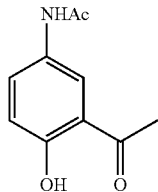

To a solution of N-(4-methoxyphenyl)acetamide (500 mg, 2.79 mmol, 1 eq) in CS₂ (50 mL) was added acetyl chloride (680.26 mg, 8.67 mmol, 618.42 μL, 3.11 eq). Then AlCl₃ (1.32 g, 9.87 mmol, 3.54 eq) was added to above solution in portions. After addition, the mixture was stirred at 90° C. for 2 h. The reaction mixture was concentrated and ice water was added slowly, extracted with EtOAc (20 mL×2). The combined organic layers were washed with brine (20 mL), dried over Na₂SO₄, filtered and concentrated under reduced pressure to give N-(3-acetyl-4-hydroxy-phenyl)acetamide (570 mg, 2.33 mmol, 83.5% yield, 79% purity) as brown solid which was used in the next step without further purification. ¹H NMR (400 MHz, CD₃OD) δ ppm 8.16 (d, J=2.6 Hz, 1H), 7.54 (dd, J=2.6, 8.8 Hz, 1H), 6.89 (d, J=8.8 Hz, 1H), 2.62 (s, 3H), 2.12 (s, 3H); ES-LCMS m/z 194.1 [M+H]⁺.

Step 3: N-[4-Hydroxy-3-[(E)-3-phenylprop-2-enoyl]phenyl]acetamide

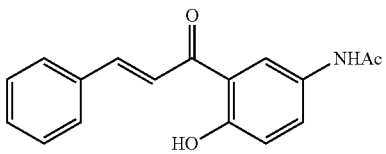 [SMILES: CC(=O)Nc1ccc(O)c(C(=O)/C=C/c2ccccc2)c1]

To a solution of N-(4-methoxyphenyl)acetamide (370 mg, 1.77 mmol, 1 eq) in MeOH (5 mL) was added benzaldehyde (187.78 mg, 1.77 mmol, 178.84 μL, 1 eq) and LiOH—H₂O (519.78 mg, 12.39 mmol, 7 eq), the mixture was stirred at 80° C. for 3 h. The reaction mixture was concentrated and extracted with EtOAc (20 mL×2). The combined organic layers were washed with brine (20 mL), dried over Na₂SO₄, filtered and concentrated under reduced pressure to give N-[4-hydroxy-3-[(E)-3-phenylprop-2-enoyl]phenyl]acetamide (470 mg, 918.93 μmol, 51.9% yield, 55% purity) as brown solid which was used in the next step without further purification. ¹H NMR (400 MHz, DMSO-d₆) δ ppm 11.71 (s, 1H), 9.91 (s, 1H), 8.15 (d, J=2.5 Hz, 1H), 7.85-7.77 (m, 3H), 7.73-7.69 (m, 1H), 7.58-7.40 (m, 4H), 6.97 (d, J=9.0 Hz, 1H), 2.06-2.03 (m, 3H); ES-LCMS m/z 282.2 [M+H]⁺.

Step 4: N-(4-Oxo-2-phenyl-chromen-6-yl)acetamide

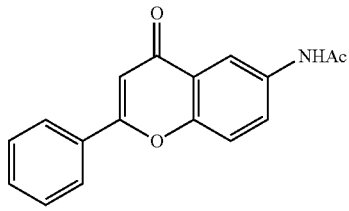 [SMILES: CC(=O)Nc1ccc2oc(-c3ccccc3)cc(=O)c2c1]

To a solution of N-[4-hydroxy-3-[(E)-3-phenylprop-2-enoyl]phenyl]acetamide (430 mg, 840.72 μmol, 1 eq) in DMSO (5 mL) was added 12 (21.34 mg, 84.07 μmol, 0.1 eq), the mixture was stirred at 140° C. for 0.5 h under microwave. To the reaction mixture was added 1 N HCl solution (2 mL) and the mixture was stirred for 1 h. The precipitate was collected and dried to yield N-(4-oxo-2-phenyl-chromen-6-yl)acetamide (180 mg, 560.71 μmol, 66.7% yield, 87% purity) as a brown solid which was used in the next step without further purification. ¹H NMR (400 MHz, DMSO-d₆) δ ppm 10.25 (s, 1H), 8.31 (d, J=2.6 Hz, 1H), 8.07 (dd, J=2.0, 7.7 Hz, 2H), 7.93 (dd, J=2.6, 9.0 Hz, 1H), 7.73 (d, J=9.0 Hz, 1H), 7.62-7.52 (m, 3H), 6.98 (s, 1H), 2.06 (s, 3H); ES-LCMS m/z 280.2 [M+H]⁺.

Step 5: 6-Amino-2-phenyl-chromen-4-one

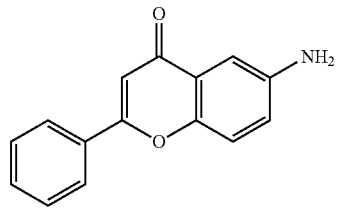 [SMILES: Nc1ccc2oc(-c3ccccc3)cc(=O)c2c1]

A suspension of N-(4-oxo-2-phenyl-chromen-6-yl)acetamide (60 mg, 186.90 umol, 1 eq) in HCl solution (12 M, 2 mL, 128.41 eq) and water (2 mL) was stirred at 100° C. for 0.5 h. The mixture was concentrated to yield 6-amino-2-phenyl-chromen-4-one (50 mg, 173.54 μmol, 92.9% yield, 95% purity, HCl) as a brown solid which was used in the next step without further purification. ¹H NMR (400 MHz, DMSO-d₆) δ ppm 8.10-8.02 (m, 2H), 7.71 (d, J=9.0 Hz, 1H), 7.60-7.50 (m, 4H), 7.44 (dd, J=2.5, 8.7 Hz, 1H), 6.97 (s, 1H); ES-LCMS m/z 238.2 [M+H]⁺.

Step 6: 2-Methyl-N-(4-oxo-2-phenyl-chromen-6-yl)pyrazole-3-carboxamide (I-33)

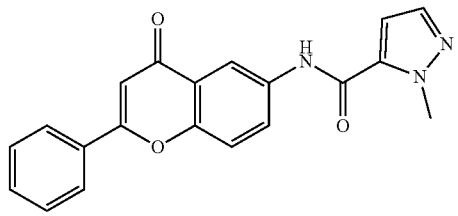 [SMILES: Cn1nccc1C(=O)Nc1ccc2oc(-c3ccccc3)cc(=O)c2c1]

To a solution of 6-amino-2-phenyl-chromen-4-one (50 mg, 173.54 μmol, 1 eq, HCl salt) and 2-methylpyrazole-3-carboxylic acid (22.98 mg, 182.22 μmol, 1.05 eq) in pyridine (3 mL) was added T$_3$P (331.30 mg, 520.62 μmol, 309.63 μL, 50% purity, 3 eq) at 25° C. The mixture was stirred at 25° C. for 0.5 h. The reaction mixture was concentrated under reduced pressure to remove solvent. The residue was diluted with DCM (50 mL) and extracted with DCM (50 mL×2). The combined organic layers were washed with brine (30 mL), dried over Na$_2$SO$_4$, filtered and concentrated under reduced pressure to yield a residue which was purified by preparative HPLC (column: Phenomenex Gemini 150*25 mm*10 um; mobile phase: [water(0.05% HCl)-ACN]; B %: 38%-68%, 10 min). The desired fraction was lyophilized to afford 2-methyl-N-(4-oxo-2-phenyl-chromen-6-yl)pyrazole-3-carboxamide (compound I-33, 19.56 mg, 51.23 μmol, 29.52% yield, 100% purity, HCl salt) as an off-white solid. $^1$H NMR (400 MHz, DMSO-d$_6$) δ ppm 10.49 (s, 1H), 8.46 (d, J=2.6 Hz, 1H), 8.14 (dd, J=2.8, 9.2 Hz, 1H), 8.11-8.04 (m, 2H), 7.80 (d, J=9.0 Hz, 1H), 7.63-7.49 (m, 4H), 7.10 (d, J=2.0 Hz, 1H), 7.01 (s, 1H), 4.09 (s, 3H); ES-LCMS m/z 346.3 [M+H]$^+$.

Example 24

Synthesis of I-34

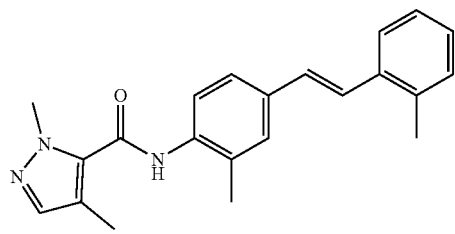

I-34

Synthetic Scheme:

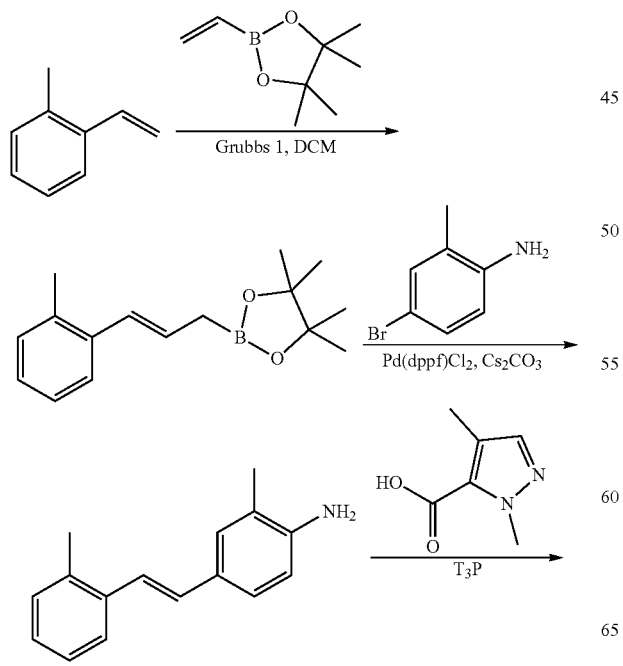

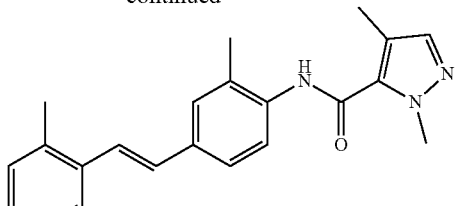

I-34

Step 1: 4,4,5,5-Tetramethyl-2-[(E)-2-(o-tolyl)vinyl]-1,3,2-dioxaborolane

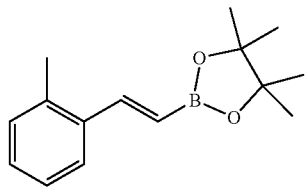 [SMILES: Cc1ccccc1/C=C/B1OC(C)(C)C(C)(C)O1]

To a solution of 1-methyl-2-vinyl-benzene (3 g, 25.39 mmol, 1 eq) in anhydrous DCM (50 mL) was added 4,4,5,5-tetramethyl-2-vinyl-1,3,2-dioxaborolane (3.91 g, 25.39 mmol, 4.31 mL, 1 eq) and Grubbs catalyst, first generation (2.09 g, 2.54 mmol, 0.1 eq). The mixture was stirred at 25° C. for 16 h. H$_2$O (50 mL) was added and extracted with DCM (50 mL×3). The combined organic layers were washed with brine (50 mL), dried over anhydrous Na$_2$SO$_4$, filtered and concentrated to afford the crude product which was purified on silica gel column chromatography (from PE/EtOAc=1/0 to 20/1, TLC: PE/EtOAc=10/1, R$_f$=0.53) to give 4,4,5,5-tetramethyl-2-[(E)-2-(o-tolyl)vinyl]-1,3,2-dioxaborolane (3 g, 6.57 mmol, 25.9% yield, 53.5% purity) as black brown oil. $^1$H NMR (400 MHz, CDCl$_3$) δ ppm 7.64 (d, J=18.4 Hz, 1H), 7.59-7.52 (m, 1H), 7.22-7.12 (m, 3H), 6.08 (dd, J=1.1, 18.4 Hz, 1H), 2.42 (s, 3H), 1.31 (s, 12H); ES-LCMS m/z 245.1 [M+H]$^+$.

Step 2: 2-Methyl-4-[(E)-2-(o-tolyl)vinyl]aniline

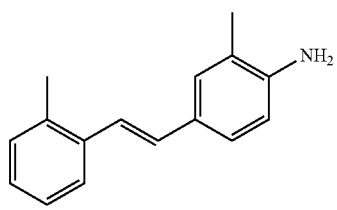 [SMILES: Cc1cc(/C=C/c2ccccc2C)ccc1N]

A mixture of 4,4,5,5-tetramethyl-2-[(E)-2-(o-tolyl)vinyl]-1,3,2-dioxaborolane (1.87 g, 4.10 mmol, 1 eq), 4-iodo-2-methyl-aniline (959.18 mg, 4.12 mmol, 1.00 eq), Pd(dppf)Cl$_2$ (299.71 mg, 410.00 μmol, 0.1 eq) and Cs$_2$CO$_3$ (4.00 g, 12.30 mmol, 3 eq) in 1,4-dioxane (20 mL) and H$_2$O (10 mL) was stirred under N$_2$ atmosphere at 90° C. for 4 h. The mixture was diluted with water (20 mL) and extracted with EtOAc (50 mL×3). The organic layer was dried over Na$_2$SO$_4$, filtered and concentrated under reduced pressure to give a residue which was purified by silica gel column chromatography (PE/EtOAc=20/1 to 5/1). The desired fraction was concentrated under reduced pressure to give 2-methyl-4-[(E)-2-(o-tolyl)vinyl]aniline (640 mg, 2.46 mmol, 60.1% yield, 86.0% purity) as a black brown solid. $^1$H NMR (400 MHz, CDCl$_3$) δ ppm 7.54 (d, J=7.6 Hz, 1H), 7.27-7.08 (m, 6H), 6.89 (d, J=16.0 Hz, 1H), 6.66 (d, J=8.0 Hz, 1H), 3.68 (br s, 2H), 2.40 (s, 3H), 2.19 (s, 3H); ES-LCMS m/z 224.1 [M+H]$^+$.

Step 3: 2,4-Dimethyl-N-[2-methyl-4-[(E)-2-(o-tolyl)vinyl]phenyl]pyrazole-3-carboxamide (I-34)

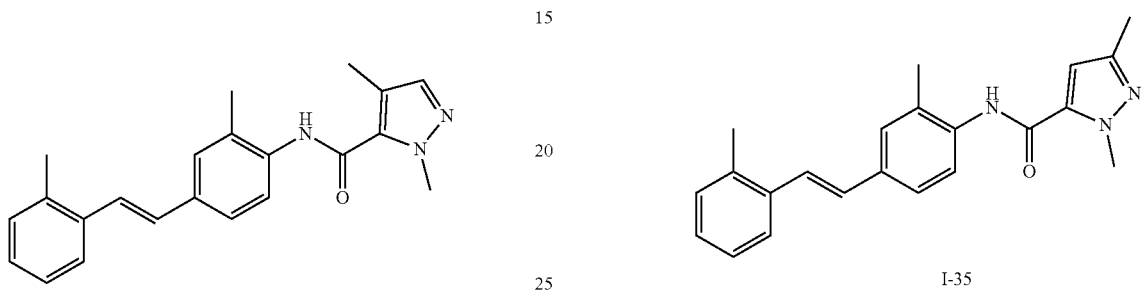

A mixture of 2-methyl-4-[(E)-2-(o-tolyl)vinyl]aniline (50 mg, 192.55 μmol, 1 eq), 2,4-dimethylpyrazole-3-carboxylic acid (32.38 mg, 231.07 μmol, 1.2 eq) and T$_3$P (612.67 mg, 962.77 μmol, 572.59 μL, 50%, 5 eq) in pyridine (3 mL) was stirred at 25° C. for 19 h. The reaction mixture was diluted with water (20 mL) and extracted with EtOAc (20 mL×3). The organic layer was dried over Na$_2$SO$_4$, filtered and concentrated under reduced pressure to give a residue which was purified by preparative HPLC (column: Phenomenex Synergi C18 150×30 mm×4 um; mobile phase: [water (0.05% HCl)-ACN]; B %: 50%-80%, 12 min). The desired fraction was lyophilized to give 2,4-dimethyl-N-[2-methyl-4-[(E)-2-(o-tolyl)vinyl]phenyl]pyrazole-3-carboxamide (compound I-34, 7.16 mg, 18.37 μmol, 9.5% yield, 98.0% purity, HCl) as an off-white solid. $^1$H NMR (400 MHz, DMSO-d$_6$) δ ppm 9.67 (s, 1H), 7.63 (d, J=7.6 Hz, 1H), 7.53 (s, 1H), 7.46 (br s, 2H), 7.36 (d, J=16.4 Hz, 1H), 7.31 (s, 1H), 7.21-7.14 (m, 3H), 7.06 (d, J=16.4 Hz, 1H), 3.90 (s, 3H), 2.38 (s, 3H), 2.27 (s, 3H), 2.20 (s, 3H); ES-LCMS m/z 346.2 [M+H]$^+$.

Example 25

Synthesis of I-35

I-35

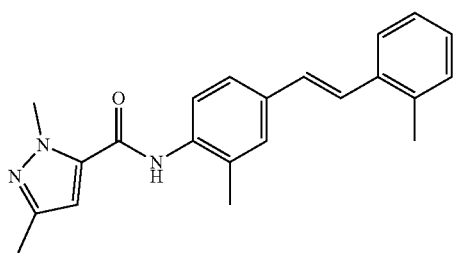

Synthetic Scheme:

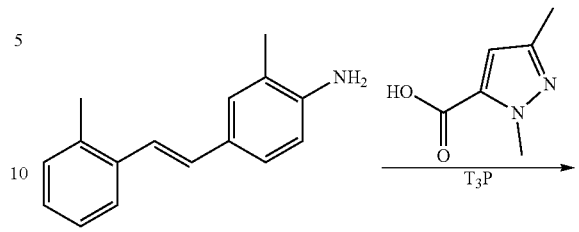

Step 1: 2,5-Dimethyl-N-[2-methyl-4-[(E)-2-(o-tolyl)vinyl]phenyl]pyrazole-3-carboxamide (I-35)

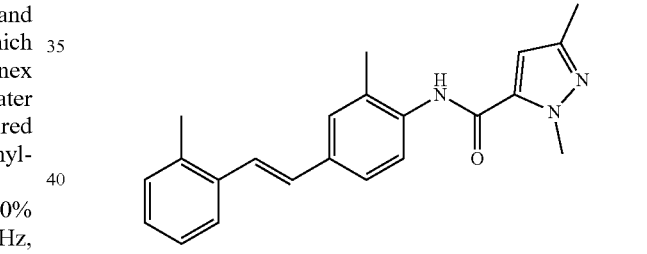

I-35

To a mixture of 2,5-dimethylpyrazole-3-carboxylic acid (29.68 mg, 211.81 μmol, 1.1 eq) and 2-methyl-4-[(E)-2-(o-tolyl)vinyl]aniline (50 mg, 192.56 μmol, 1 eq) in pyridine (2 mL) was added T$_3$P (612.68 mg, 962.78 μmol, 3.85 μL, 50%, 5 eq) dropwise at 25° C. and the mixture was stirred at 25° C. for 3 h. The reaction mixture was concentrated under reduced pressure to dryness. The residue was diluted with water (10 mL), extracted with EtOAc (10 mL×3). The organic layer was dried over Na$_2$SO$_4$, filtered and concentrated under reduced pressure to give a residue which was purified by preparative HPLC (column: Phenomenex Synergi C18 150×30 mm×4 um; mobile phase: [water(0.05% HCl)-ACN]; B %: 60%-90%, 12 min). The desired fraction was lyophilized to give 2,5-dimethyl-N-[2-methyl-4-[(E)-2-(o-tolyl)vinyl]phenyl]pyrazole-3-carboxamide (compound I-35, 26.24 mg, 65.53 μmol, 34.0% yield, 95.4% purity, HCl) was obtained as an off-white solid. $^1$H NMR (400 MHz, DMSO-d$_6$) δ ppm 9.73 (s, 1H), 7.63 (d, J=7.6 Hz, 1H), 7.51 (s, 1H), 7.45 (dd, J=1.6, 8.4 Hz, 1H), 7.36 (d, J=16.4 Hz, 1H), 7.31 (d, J=8.4 Hz, 1H), 7.21-7.12 (m, 3H), 7.06 (d, J=16.4 Hz, 1H), 6.79 (s, 1H), 3.96 (s, 3H), 2.38 (s, 3H), 2.22 (s, 3H), 2.17 (s, 3H); ES-LCMS m/z 346.2 [M+H]$^+$.

Example 26

Synthesis of I-38

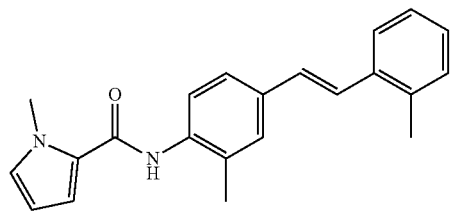
I-38

Synthetic Scheme:

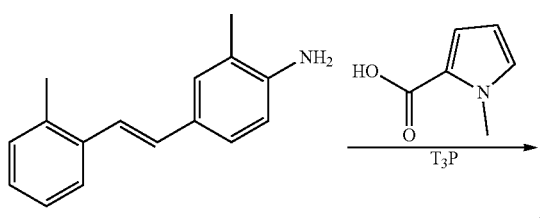

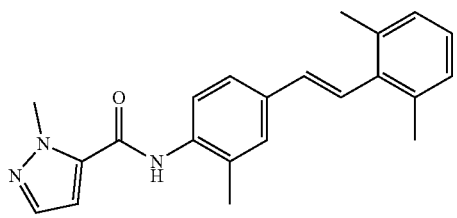
I-38

Step 1: 1-Methyl-N-[2-methyl-4-[(E)-2-(o-tolyl)vinyl]phenyl]pyrrole-2-carboxamide (I-38)

A mixture of 2-methyl-4-[(E)-2-(o-tolyl)vinyl]aniline (50 mg, 192.55 μmol, 1 eq), 1-methylpyrrole-2-carboxylic acid (26.50 mg, 211.81 μmol, 1.1 eq) and T$_3$P (122.53 mg, 192.55 μmol, 114.52 μL, 50%, 1 eq) in pyridine (2 mL) was degassed and purged with N$_2$ for 3 times. The mixture was stirred at 55° C. for 16 h under N$_2$ atmosphere. The combined reaction mixture was quenched by addition of NaHCO$_3$ solution then extracted with EtOAc (30 mL×3), washed with water (10 mL), brine (10 mL), dried over Na$_2$SO$_4$, filtered and concentrated under reduced pressure to give a residue which was purified by preparative HPLC (Column: Phenomenex Synergi C18 150×30 mm×4 um; mobile phase: [water (0.05% HCl)-ACN]; B %: 60%-90%, 12 min). The desired fraction was lyophilized to yield 1-methyl-N-[2-methyl-4-[(E)-2-(o-tolyl)vinyl]phenyl]pyrrole-2-carboxamide (compound I-38, 28.74 mg, 77.61 μmol, 40.3% yield, 99.1% purity, HCl) as a white solid. $^1$H NMR (400 MHz, CD$_3$OD) δ ppm 7.59 (d, J=7.1 Hz, 1H), 7.46-7.39 (m, 2H), 7.39-7.32 (m, 2H), 7.19-7.10 (m, 3H), 7.00 (d, J=16.1 Hz, 1H), 6.95 (d, J=1.7, 4.1 Hz, 1H), 6.88 (t, J=2.1 Hz, 1H), 6.11 (d, J=2.6, 4.0 Hz, 1H), 3.91 (s, 3H), 2.41 (s, 3H), 2.31 (s, 3H); ES-LCMS m/z 446.2 [M+H]$^+$.

Example 27

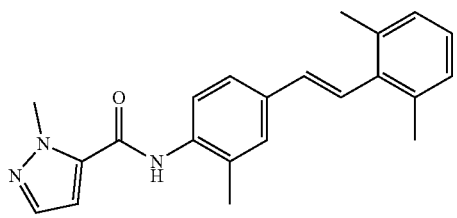
I-39

Synthesis of I-39

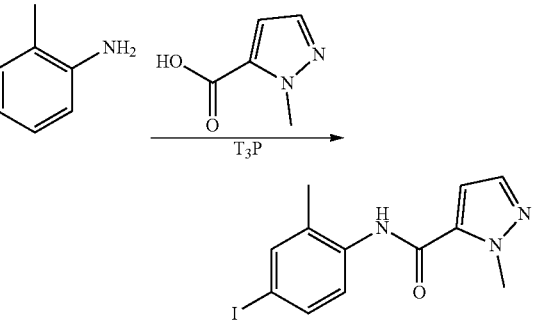

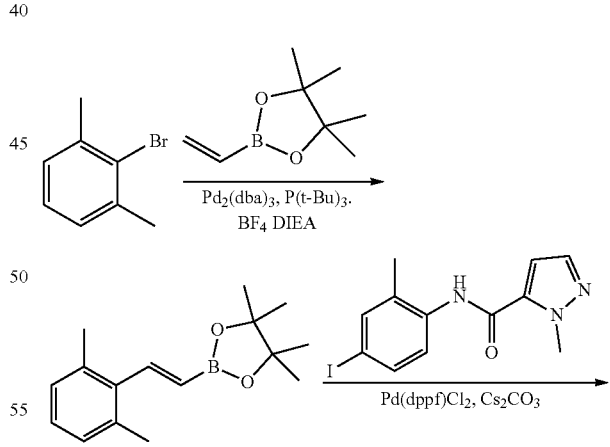

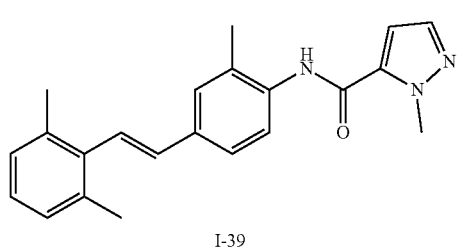
I-39

Step 1: N-(4-Iodo-2-methyl-phenyl)-2-methyl-pyrazole-3-carboxamide

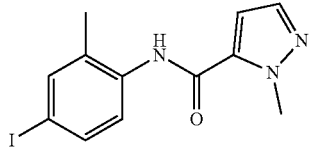 [SMILES: Cc1cc(I)ccc1NC(=O)c1ccnn1C]

To a solution of 4-iodo-2-methyl-aniline (200 mg, 858.19 µmol, 1 eq) and 2-methylpyrazole-3-carboxylic acid (129.87 mg, 1.03 mmol, 1.2 eq) in EtOAc (10 mL) was added T₃P (1.64 g, 2.57 mmol, 1.53 mL, 50%, 3.0 eq) and DIEA (332.74 mg, 2.57 mmol, 448.44 µL, 3.0 eq). The mixture was stirred at 60° C. for 3 h. The mixture was stirred at 60° C. for 16 h. The reaction mixture was diluted with NaHCO₃ solution (20 mL), extracted with ethyl acetate (20 mL×3). The combined organic layers were dried over anhydrous Na₂SO₄, filtered and concentrated under reduced pressure to give a residue which was purified on silica gel column chromatography (from PE/EtOAc=1/0 to 10/3, TLC: PE/EtOAc=3/1, R$_f$=0.49) to give the product of N-(4-iodo-2-methyl-phenyl)-2-methyl-pyrazole-3-carboxamide (100 mg, 284.34 µmol, 33.1% yield, 97.0% purity) as a white solid. ¹H NMR (400 MHz, CDCl₃) δ ppm 7.69 (d, J=8.4 Hz, 1H), 7.63-7.56 (m, 2H), 7.53 (d, J=2.2 Hz, 1H), 7.45 (br s, 1H), 6.64 (d, J=2.0 Hz, 1H), 4.23 (s, 3H), 2.28 (s, 3H); ES-LCMS m/z 341.8 [M+H]⁺.

Step 2: 2-[(E)-2-(2,6-Dimethylphenyl)vinyl]-4,4,5,5-tetramethyl-1,3,2-dioxaborolane

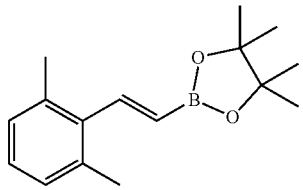 [SMILES: Cc1cccc(C)c1/C=C/B1OC(C)(C)C(C)(C)O1]

To a solution of 2-bromo-1,3-dimethyl-benzene (200 mg, 1.08 mmol, 1 eq), 4,4,5,5-tetramethyl-2-vinyl-1,3,2-dioxaborolane (183.09 mg, 1.19 mmol, 1.1 eq) and DIEA (279.35 mg, 2.16 mmol, 2 eq) in toluene (5 mL) was added Pd₂(dba)₃ (49.48 mg, 54.04 µmol, 0.05 eq) and tritert-butylphosphonium tetrafluoroborate (31.35 mg, 108.07 µmol, 0.1 eq). The mixture was purged with N₂ for 3 times and stirred at 95° C. for 3 h. TLC (PE/EtOAc=20/1, R$_f$=0.91) indicated the starting material was consumed and three main new spots with larger polarity were detected. The reaction mixture was concentrated under reduced pressure to give a residue which was purified on silica gel column chromatography (from PE/EtOAc=1/0 to 20/3, TLC: PE/EtOAc=20/1, R$_f$=0.63) to give the product 2-[(E)-2-(2,6-dimethylphenyl)vinyl]-4,4,5,5-tetramethyl-1,3,2-dioxaborolane (100 mg, 348.62 µmol, 32.3% yield, 90.0% purity) as yellow oil. ¹H NMR (400 MHz, CDCl₃) δ ppm 7.46 (d, J=18.7 Hz, 1H), 7.11-6.98 (m, 3H), 5.71 (d, J=19.0 Hz, 1H), 2.38-2.30 (m, 6H), 1.38-1.30 (m, 12H).

Step 3: N-[4-[(E)-2-(2,6-Dimethylphenyl)vinyl]-2-methyl-phenyl]-2-methyl-pyrazole-3-carboxamide (I-39)

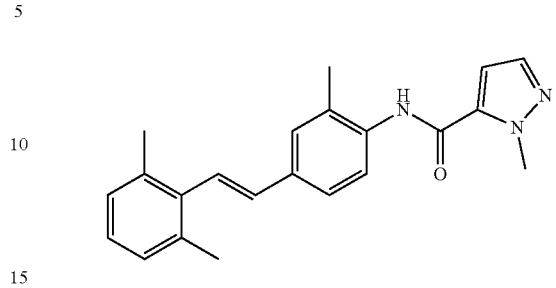

To a solution of N-(4-iodo-2-methyl-phenyl)-2-methyl-pyrazole-3-carboxamide (61 mg, 173.44 µmol, 1 eq) and 2-[(E)-2-(2,6-dimethylphenyl)vinyl]-4,4,5,5-tetramethyl-1,3,2-dioxaborolane (74.63 mg, 260.17 µmol, 1.5 eq) in 1,4-dioxane (2 mL) and H₂O (0.5 mL) was added Pd(dppf)Cl₂ (12.69 mg, 17.34 µmol, 0.1 eq) and Cs₂CO₃ (169.53 mg, 520.33 µmol, 3.0 eq). The mixture was purged with N₂ for 3 min. The sealed tube was heated at 110° C. for 40 min under microwave. The reaction mixture was filtered and concentrated under reduced pressure to give a residue which was purified by preparative HPLC (column: Phenomenex Gemini 150*25 mm*10 um; mobile phase: [water(0.05% HCl)-ACN]; B %: 57%-77%, 10 min) followed by lyophilization to yield N-[4-[(E)-2-(2,6-dimethylphenyl)vinyl]-2-methyl-phenyl]-2-methyl-pyrazole-3-carboxamide (compound I-39, 44.86 mg, 116.53 µmol, 67.2% yield, 99.2% purity, HCl) as a light brown solid. ¹H NMR (400 MHz, DMSO-d₆) δ ppm 9.90 (br s, 1H), 7.52 (d, J=10.4 Hz, 2H), 7.45 (d, J=7.1 Hz, 1H), 7.33 (d, J=7.9 Hz, 1H), 7.20 (d, J=16.5 Hz, 1H), 7.06 (br s, 4H), 6.64 (d, J=16.8 Hz, 1H), 4.08 (s, 3H), 2.33 (s, 6H), 2.25 (s, 3H); ES-LCMS m/z 346.1 [M+H]⁺.

Example 28

Synthesis of I-40

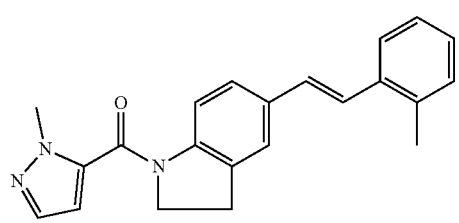

I-40

Synthetic Scheme:

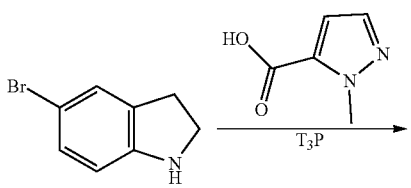

Step 1: (5-Bromoindolin-1-yl)-(2-methylpyrazol-3-yl)methanone

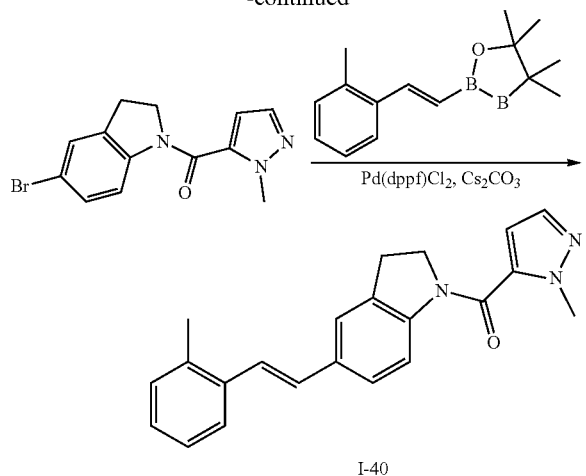

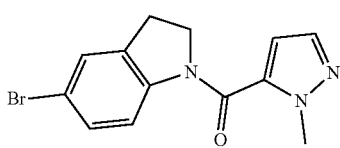 [SMILES: Cn1nccc1C(=O)N1CCc2cc(Br)ccc21]

To a solution of 5-bromoindoline (200 mg, 1.01 mmol, 1 eq) and 2-methylpyrazole-3-carboxylic acid (127.35 mg, 1.01 mmol, 1.0 eq) in EtOAc (10 mL) was added T₃P (1.93 g, 3.03 mmol, 1.80 mL, 50%, 3.0 eq) and DIEA (652.54 mg, 5.05 mmol, 879.44 μL, 5.0 eq). The mixture was stirred at 60° C. for 3 h. The reaction mixture was concentrated under reduced pressure to give a residue which was purified on silica gel column chromatography (from PE/EtOAc=1/0 to 10/3, TLC: PE/EtOAc=3/1, R$_f$=0.42) to give the product (5-bromoindolin-1-yl)-(2-methylpyrazol-3-yl)methanone (300 mg, 960.29 μmol, 95.1% yield, 98.0% purity) as a white solid ¹H NMR (400 MHz, CDCl₃) δ ppm 8.08 (s, 1H), 7.52 (d, J=2.2 Hz, 1H), 7.30-7.37 (m, 2H), 6.53 (d, J=2.0 Hz, 1H), 4.24 (t, J=8.3 Hz, 2H), 4.08 (s, 3H), 3.18 (t, J=8.3 Hz, 2H); ES-LCMS m/z 306.0, 308.0 [M+H]⁺.

Step 2: (2-Methylpyrazol-3-yl)-[5-[(E)-2-(o-tolyl)vinyl]indolin-1-yl]methanone (I-40)

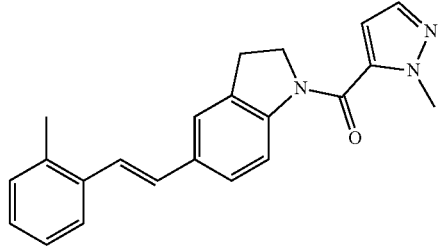 [SMILES: Cc1ccccc1/C=C/c1ccc2c(c1)CCN2C(=O)c1ccnn1C]

5-Bromoindolin-1-yl)-(2-methylpyrazol-3-yl)methanone (51.02 mg, 163.31 μmol, 1 eq), 4,4,5,5-tetramethyl-2-[(E)-2-(o-tolyl)vinyl]-1,3,2-dioxaborolane (111.79 mg, 244.97 μmol, 1.5 eq), Cs₂CO₃ (159.63 mg, 489.94 μmol, 3.0 eq) and Pd(dppf)Cl₂ (11.95 mg, 16.33 umol, 0.1 eq) were taken up into a microwave tube in 1,4-dioxane (2 mL) and H₂O (0.5 mL). The mixture was purged with N₂ for 3 min. The sealed tube was heated at 110° C. for 40 min under microwave. The reaction mixture was concentrated under reduced pressure to give a residue which was purified by preparative HPLC twice (column: Phenomenex Synergi C18 150*30 mm*4 um; mobile phase: [water(0.05% HCl)-ACN]; B %: 45%-75%, 12 min) followed by lyophilization to yield (compound 1-40, 2-methylpyrazol-3-yl)-[5-[(E)-2-(o-tolyl)vinyl]indolin-1-yl]methanone (22.79 mg, 59.69 μmol, 36.6% yield, 99.5% purity, HCl) as a white solid. ¹H NMR (400 MHz, CDCl₃) δ ppm 8.18 (br s, 1H), 7.59 (d, J=7.1 Hz, 1H), 7.53 (d, J=2.0 Hz, 1H), 7.44 (s, 1H), 7.38 (br s, 1H), 7.31-7.27 (m, 1H), 7.26-7.17 (m, 3H), 6.98 (d, J=16.1 Hz, 1H), 6.55 (d, J=1.8 Hz, 1H), 4.25 (t, J 8.3 Hz, 2H), 4.09 (br s, 3H), 3.21 (t, J=8.2 Hz, 2H), 2.45 (s, 3H); ES-LCMS m/z 344.2 [M+H]⁺.

Example 29

Synthesis of I-41

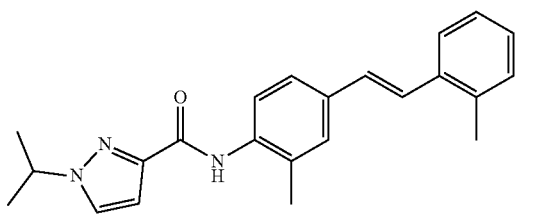

Synthetic Scheme:

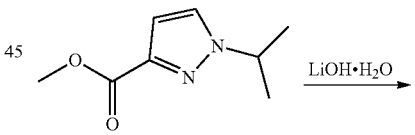

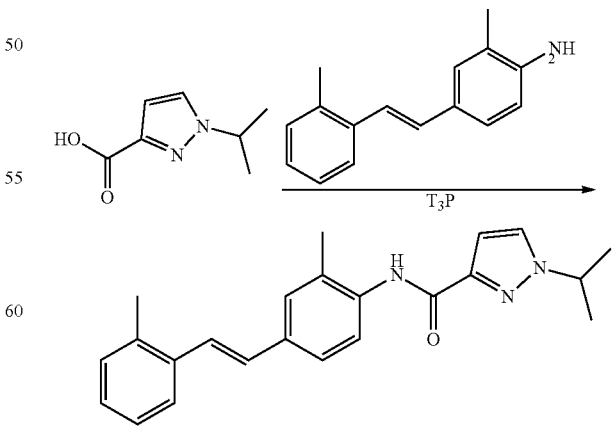

117

Step 1: 1-Isopropylpyrazole-3-carboxylic acid

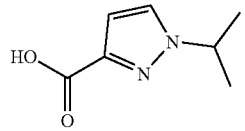

A mixture of methyl 1-isopropylpyrazole-3-carboxylate (compound 1, 200.00 mg, 1.07 mmol, 1 eq) and LiOH—H$_2$O (179.62 mg, 4.28 mmol, 4 eq) in MeOH (10 mL) was stirred at 25° C. for 2 h. The mixture was concentrated under reduced pressure to give a residue which was diluted with water (20 mL) and EtOAc (20 mL), adjusted pH to 2 with 2 N HCl, extracted with EtOAc (20 mL×3), dried over Na$_2$SO$_4$, filtered and concentrated under reduced pressure to give 1-isopropylpyrazole-3-carboxylic acid (145 mg, 846.49 µmol, 79.1% yield, 90.0% purity) as colorless oil which was used in the next step without further purification. $^1$H NMR (400 MHz, CD$_3$OD) δ ppm 7.73 (d, J=2.0 Hz, 1H), 6.76 (d, J=2.4 Hz, 1H), 4.60 (m, 1H), 1.51 (d, J=6.8 Hz, 6H); ES-LCMS m/z 155.2 [M+H]$^+$.

Step 2: 1-Isopropyl-N-[2-methyl-4-[(E)-2-(o-tolyl)vinyl]phenyl]pyrazole-3-carboxamide (I-41)

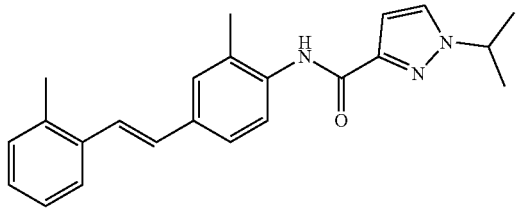 [SMILES: Cc1ccccc1/C=C/c1ccc(NC(=O)c2ccn(C(C)C)n2)c(C)c1]

A mixture of methyl 1-isopropylpyrazole-3-carboxylate (50 mg, 267.55 µmol, 1.2 eq), 2-methyl-4-[(E)-2-(o-tolyl)vinyl]aniline (71.13 mg, 222.96 µmol, 1 eq), T$_3$P (425.65 mg, 668.88 umol, 397.80 µL, 50% purity, 3 eq) in pyridine (5 mL) was stirred at 60° C. for 2 h. The mixture was concentrated under reduced pressure to give a residue which was purified by preparative HPLC (column: Phenomenex Gemini 150*25 mm*10 um; mobile phase: [water (0.05% ammonia hydroxide v/v)-ACN]; B %: 62%-92%, 10 min). The mixture was lyophilized, purified by preparative TLC (SiO$_2$, PE/EtOAc=5/1, R$_f$=0.56) to give 1-isopropyl-N-[2-methyl-4-[(E)-2-(o-tolyl)vinyl]phenyl]pyrazole-3-carboxamide (compound I-41, 35.09 mg, 97.62 µmol, 43.8% yield, 100% purity) as colorless oil. $^1$H NMR (400 MHz, CD$_3$OD) δ ppm 7.78 (d, J=2.4 Hz, 1H), 7.72 (d, J=8.2 Hz, 1H), 7.61 (d, J=7.2 Hz, 1H), 7.49-7.43 (m, 2H), 7.39 (d, J=16.4 Hz, 1H), 7.17-7.16 (m, 3H), 7.02 (d, J=16.4 Hz, 1H), 6.82 (d, J=2.0 Hz, 1H), 4.69-4.61 (m, 1H), 2.43 (s, 3H), 2.37 (s, 3H), 1.57 (d, J=6.8 Hz, 6H); ES-LCMS m/z 360.1 [M+H]$^+$.

118

Example 30

Synthesis of I-42

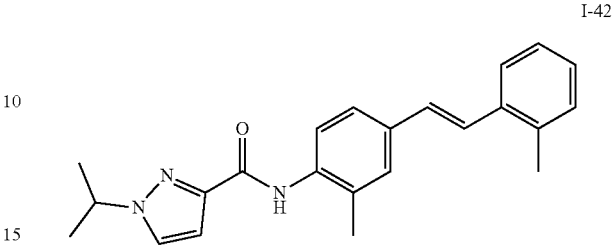

I-42

Synthetic Scheme:

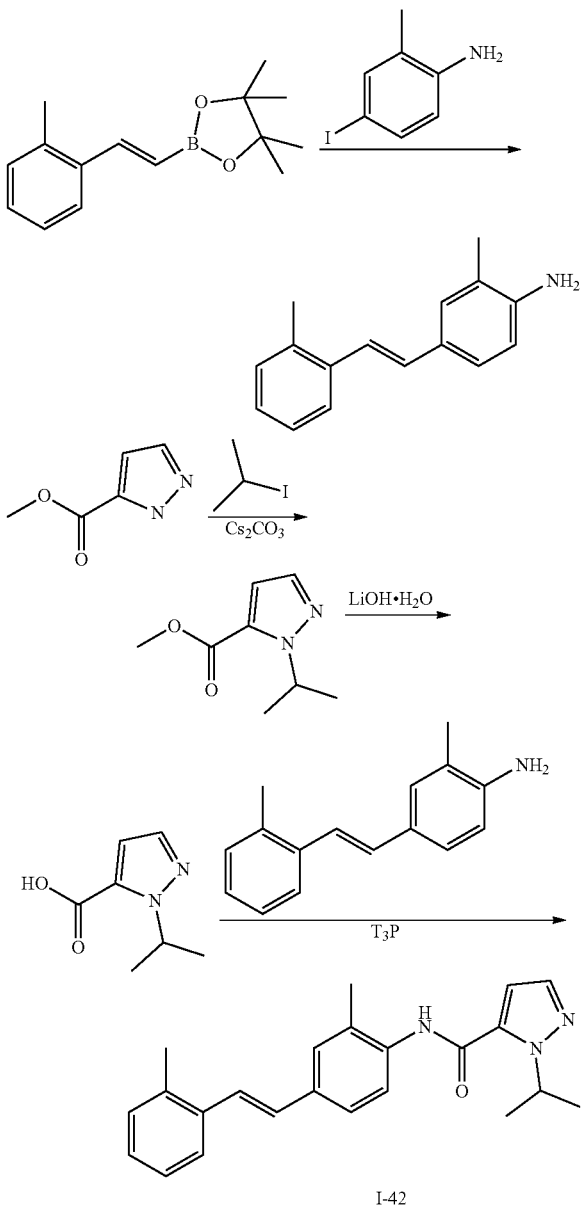

Step 1: 2-Methyl-4-[(E)-2-(o-tolyl)vinyl]aniline

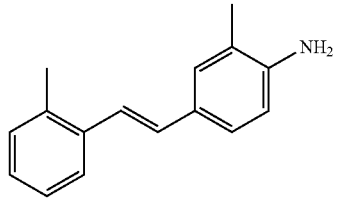 [SMILES: Cc1cc(/C=C/c2ccccc2C)ccc1N]

A solution of 4,4,5,5-tetramethyl-2-[(E)-2-(o-tolyl)vinyl]-1,3,2-dioxaborolane (1 g, 2.19 mmol, 1 eq), 4-iodo-2-methyl-aniline (612.84 mg, 2.63 mmol, 1.2 eq), $Cs_2CO_3$ (2.14 g, 6.57 mmol, 3 eq) and $Pd(dppf)Cl_2$ (160.35 mg, 219.14 umol, 0.1 eq) in 1,4-dioxane (8 mL) and $H_2O$ (4 mL) was de-gassed and heated to 90° C. for 12 h under $N_2$. The mixture was concentrated under reduced pressure to give a residue which was diluted with DCM (20 mL) and water (20 mL), extracted with DCM (20 mL×3), dried over $Na_2SO_4$, filtered and concentrated under reduced pressure to give a residue which was purified by column chromatography ($SiO_2$, PE/EtOAc=10/1 to 5/1, TLC: PE/EtOAc=5/1, $R_f$=0.61) to give 2-methyl-4-[(E)-2-(o-tolyl)vinyl]aniline (464 mg, 1.45 mmol, 66.4% yield, 70% purity) as a brown solid. $^1$H NMR (400 MHz, $CD_3OD$) δ ppm 7.54 (d, J=8.0 Hz, 1H), 7.21-7.11 (m, 6H), 6.92-6.87 (m, 1H), 6.70 (d, J=8.4 Hz, 1H), 2.39 (s, 3H), 2.19 (s, 3H); ES-LCMS m/z 224.0 [M+H]$^+$.

Step 2: Methyl 2-isopropylpyrazole-3-carboxylate & Methyl 1-isopropylpyrazole-3-carboxylate

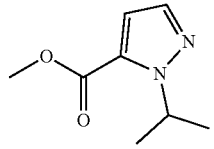 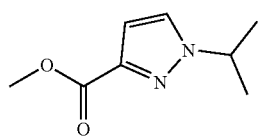

To a solution of 2-iodopropane (809.20 mg, 4.76 mmol, 476.00 μL, 1 eq) in MeCN (50 mL) was added $Cs_2CO_3$ (3.10 g, 9.52 mmol, 2 eq) and methyl 1H-pyrazole-5-carboxylate (600.33 mg, 4.76 mmol, 1 eq). The mixture was stirred at 25° C. for 12 h. The mixture was concentrated under reduced pressure to give a residue which was partitioned between water (20 mL) and DCM (20 mL), extracted with DCM (20 mL×3), dried over $Na_2SO_4$, filtered and concentrated under reduced pressure to give a residue which was purified by column chromatography ($SiO_2$, PE/EtOAc=10/1 to 5/1, TLC: PE/EtOAc=5/1, $R_f$=0.8 & $R_f$=0.51) to yield methyl 2-isopropylpyrazole-3-carboxylate (240 mg, 1.28 mmol, 27.0% yield, 90% purity) as colorless oil, and methyl 1-isopropylpyrazole-3-carboxylate (260 mg, 1.39 mmol, 29.23% yield, 90% purity) as colorless oil. $^1$H NMR (400 MHz, $CD_3OD$) δ ppm 7.52 (d, J=2.0 Hz, 1H), 6.85 (d, J=2.0 Hz, 1H), 5.61-5.50 (m, 1H), 3.91-3.83 (m, 3H), 1.46 (d, J=6.4 Hz, 6H). $^1$H NMR (400 MHz, $CD_3OD$) δ ppm 7.74 (d, J=2.4 Hz, 1H), 6.77 (d, J=2.8 Hz, 1H), 4.60 (m, 1H), 3.88 (s, 3H), 1.51 (d, J=6.8 Hz, 6H); ES-LCMS m/z 168.8 [M+H]$^+$.

Step 3: 2-Isopropylpyrazole-3-carboxylic acid

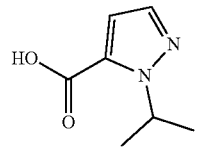

A mixture of methyl 2-isopropylpyrazole-3-carboxylate (120 mg, 642.12 μmol, 1 eq) and $LiOH.H_2O$ (107.78 mg, 2.57 mmol, 4 eq) in MeOH (10 mL) was stirred at 25° C. for 2 h. The mixture was concentrated under reduced pressure to give a residue which was diluted with water (20 mL) and EtOAc (20 mL), adjusted pH to 2 with 2 N HCl, extracted with EtOAc (20 mL×3), dried over $Na_2SO_4$, filtered and concentrated under reduced pressure to give 2-isopropylpyrazole-3-carboxylic acid (98 mg, crude) as colorless oil which was used in the next step without further purification. $^1$H NMR (400 MHz, $CD_3OD$) δ ppm 7.50 (d, J=1.6 Hz, 1H), 6.83 (d, J=2.0 Hz, 1H), 5.65-5.55 (m, 1H), 1.45 (d, J=6.8 Hz, 6H); ES-LCMS m/z 155.0 [M+H]$^+$.

Step 4: 2-Isopropyl-N-[2-methyl-4-[(E)-2-(o-tolyl)vinyl]phenyl]pyrazole-3-carboxamide (I-42)

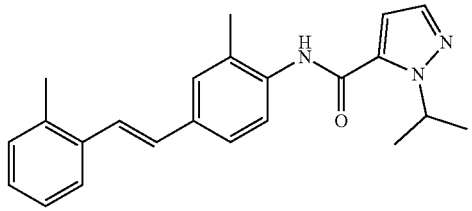 [SMILES: Cc1ccccc1/C=C/c1ccc(NC(=O)c2ccnn2C(C)C)c(C)c1]

A mixture of 2-isopropylpyrazole-3-carboxylic acid (50 mg, 291.89 μmol, 1 eq), 2-methyl-4-[(E)-2-(o-tolyl) vinyl]aniline (93.12 mg, 291.89 μmol, 1 eq), $T_3P$ (1.86 g, 2.92 mmol, 1.74 mL, 50%, 10 eq) in pyridine (5 mL) was stirred at 60° C. for 2 h. The mixture was concentrated under reduced pressure to give a residue which was purified by preparative HPLC (column: Phenomenex Gemini 150*25 mm*10 um; mobile phase: [water(0.05% HCl)-ACN]; B %: 55%-85%, 10 min). The mixture was lyophilized, purified by preparative TLC ($SiO_2$, PE/EtOAc=5/1, $R_f$=0.57) to give 2-isopropyl-N-[2-methyl-4-[(E)-2-(o-tolyl)vinyl]phenyl] pyrazole-3-carboxamide (compound I-42, 18.26 mg, 48.58 μmol, 16.6% yield, 95.6% purity) as an off-white solid. $^1$H NMR (400 MHz, $CDCl_3$) δ ppm 7.95 (d, J=8.0 Hz, 1H), 7.60-7.55 (m, 3H), 7.40-7.39 (m, 2H), 7.30 (d, J=16.0 Hz, 1H), 7.19-7.17 (m, 3H), 6.96 (d, J=16.0 Hz, 1H), 6.61 (s, 1H), 5.57-5.47 (m, 1H), 2.44 (s, 3H), 2.35 (s, 3H), 1.54 (d, J=6.8 Hz, 6H); ES-LCMS m/z 360.2 [M+H]$^+$.

Example 31

Synthesis of I-43

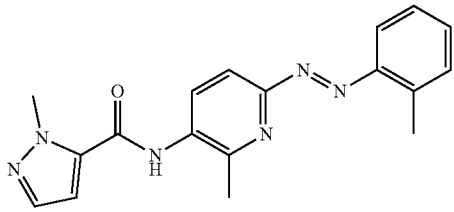

Synthetic Scheme:

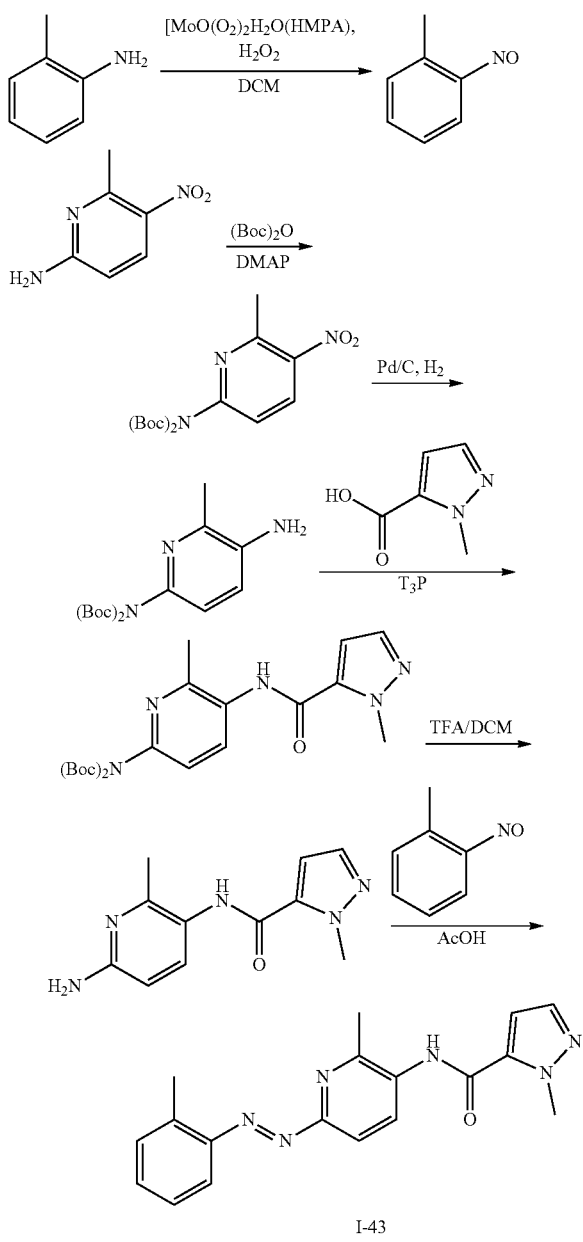

Step 1: tert-Butyl N-tert-butoxycarbonyl-N-(6-methyl-5-nitro-2-pyridyl)carbamate

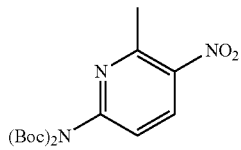

To a solution of 6-methyl-5-nitro-pyridin-2-amine (500 mg, 3.27 mmol, 1 eq) in anhydrous DCM (10 mL) was added DMAP (79.78 mg, 653.00 mol, 0.2 eq) and $(Boc)_2O$ (1.78 g, 8.16 mmol, 1.88 mL, 2.5 eq). The mixture was stirred at 25° C. for 12 h. $H_2O$ (10 mL) was added and the mixture was extracted with DCM (10 mL×3). The combined organic layers were washed with brine (10 mL), dried over anhydrous $Na_2SO_4$, filtered and concentrated to afford the crude product which was purified on silica gel column chromatography (from PE/EtOAc=1/0 to 10/1, TLC: PE/EtOAc=2/1, $R_f$=0.73) to give tert-butyl N-tert-butoxycarbonyl-N-(6-methyl-5-nitro-2-pyridyl)carbamate (847 mg, 1.65 mmol, 50.7% yield, 69.0% purity) $^1$H NMR (400 MHz, $CDCl_3$) 8.39-8.32 (m, 1H), 7.97-7.60 (m, 1H), 2.81-2.77 (m, 3H), 1.56-1.53 (m, 18H); ES-LCMS m/z 198.0 [M-t-Bu+H]$^+$.

Step 2: tert-Butyl N-(5-amino-6-methyl-2-pyridyl)-N-tert-butoxycarbonyl-carbamate

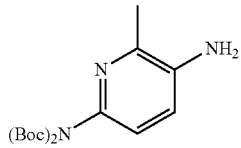

To a solution of tert-butyl N-tert-butoxycarbonyl-N-(6-methyl-5-nitro-2-pyridyl)carbamate (847 mg, 1.65 mmol, 1 eq) in anhydrous MeOH (10 mL) was added Pd/C (10%, 100 mg) under $N_2$ atmosphere. The suspension was degassed and purged with $H_2$ for 3 times. The mixture was stirred under $H_2$ (15 psi) at 25° C. for 16 h. The mixture was filtered and the filtrate was concentrated to afford the crude product tert-butyl N-(5-amino-6-methyl-2-pyridyl)-N-tert-butoxycarbonyl-carbamate (730 mg, 1.57 mmol, 95.00% yield, 69.6% purity) as a yellow solid which was used in the next step without further purification. $^1$H NMR (400 MHz, $CD_3OD$) δ ppm 7.10 (d, J=8.4 Hz, 1H), 6.84 (d, J=8.4 Hz, 1H), 2.32 (s, 3H), 1.39-1.37 (m, 18H); ES-LCMS m/z 324.3 [M+H]$^+$.

Step 3: Tert-Butyl N-tert-butoxycarbonyl-N-[6-methyl-5-[(2-methylpyrazole-3-carbonyl) Amino]-2-pyridyl]carbamate

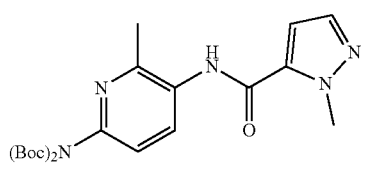

To a solution of tert-butyl N-(5-amino-6-methyl-2-pyridyl)-N-tert-butoxycarbonyl-carbamate (730 mg, 1.57 mmol, 1 eq) in EtOAc (10 mL) was added DIEA (609.16 mg, 4.71 mmol, 820.97 μL, 3 eq), 2-methylpyrazole-3-carboxylic acid (297.21 mg, 2.36 mmol, 1.5 eq) and $T_3P$ (3.00 g, 4.71 mmol, 2.80 mL, 50%, 3 eq). The mixture was stirred at 60° C. for 12 h. Sat. $NaHCO_3$ solution (10 mL) was added and the mixture was extracted with ethyl acetate (10 mL×3). The combined organic layers were washed with brine (10 mL), dried over anhydrous $Na_2SO_4$, filtered and concentrated to afford the crude product which was purified on silica gel column chromatography (from PE/EtOAc=1/0 to 3/1, TLC: PE/EtOAc=2/1, $R_f$=0.23) to give tert-butyl N-tert-butoxycarbonyl-N-[6-methyl-5-[(2-methylpyrazole-3-carbonyl)amino]-2-pyridyl]carbamate (770 mg, 999.34 μmol, 63.6% yield, 56.0% purity) as a yellow solid. $^1$H NMR (400 MHz, $CDCl_3$) δ ppm 7.55-7.51 (m, 2H), 7.16 (d, J=8.4 Hz, 1H), 6.67 (d, J=2.0 Hz, 1H), 4.22 (s, 3H), 2.52 (s, 3H), 1.45 (s, 18H); ES-LCMS m/z 432.0 $[M+H]^+$.

Step 4: N-(6-Amino-2-methyl-3-pyridyl)-2-methyl-pyrazole-3-carboxamide

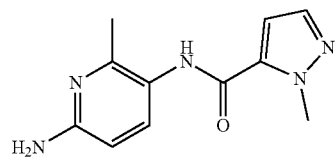 [SMILES: Cc1nc(N)ccc1NC(=O)c1ccnn1C]

To a solution of tert-butyl N-tert-butoxycarbonyl-N-[6-methyl-5-[(2-methylpyrazole-3-carbonyl)amino]-2-pyridyl] carbamate (770 mg, 999.34 μmol, 1 eq) in anhydrous DCM (12 mL) was added TFA (3 mL). The mixture was stirred at 25° C. for 1 h. The mixture was concentrated to remove the solvent and TFA. Sat. $NaHCO_3$ solution (10 mL) was added and the mixture was extracted with DCM (10 mL×3). The combined organic layers were washed with brine (10 mL), dried over anhydrous $Na_2SO_4$, filtered and concentrated to afford the crude product N-(6-amino-2-methyl-3-pyridyl)-2-methyl-pyrazole-3-carboxamide (520 mg, crude) as a yellow solid which was used in the next step without further purification. $^1$H NMR (400 MHz, $CD_3OD$) δ ppm 7.50 (d, J=2.2 Hz, 1H), 7.33 (d, J=8.6 Hz, 1H), 6.93 (d, J=2.0 Hz, 1H), 6.45 (d, J=8.4 Hz, 1H), 4.11 (s, 3H), 2.26 (s, 3H); ES-LCMS m/z 232.3 $[M+H]^+$.

Step 5: 1-Methyl-2-nitroso-benzene

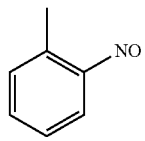

$Na_2MoO_4$ (10 g, 41 mmol) was dissolved in a minimum volume of water and the mixture was adjusted by $H_2SO_4$ (30% w/w) to pH=2. Then 29 mL of $H_2O_2$ (30%, 0.35 mol) were added at 0° C. HMPT (7.15 mL, 41 mmol) was added and a yellow precipitate was immediately formed. The mixture was filtered, washed with MeOH (10 mL), dried over reduced pressure to give $[MoO(O_2)_2(H_2O)(HMPA)]$ (6.1 g). To a solution of 2-methylaniline (1 g, 9.33 mmol, 1.00 mL, 1 eq) in anhydrous DCM (10 mL) was added $[MoO(O_2)_2(H_2O)(HMPA)]$ (348.24 mg, 933.24 μmol, 0.1 eq) and $H_2O_2$ (5.29 g, 46.66 mmol, 1.56 mL, 30%, 5 eq). The mixture was stirred at 25° C. for 16 h under. TLC (PE/EtOAc=10/1, $R_f$=0.75) indicated the starting material was almost consumed and two new spots formed. $H_2O$ (10 mL) was added and the mixture was extracted with DCM (10 mL×3). The combined organic layers were washed with brine (10 mL), dried over anhydrous $Na_2SO_4$, filtered and concentrated to afford the crude product which was purified on silica gel column chromatography (from PE/EtOAc=1/0 to 10/1, TLC: PE/EtOAc=10/1, $R_f$=0.75) to give 1-methyl-2-nitroso-benzene (620 mg, 4.61 mmol, 49.4% yield, 90% purity) as a brown solid. $^1$H NMR (400 MHz, $CDCl_3$) δ ppm 7.64-7.52 (m, 2H), 7.21-7.12 (m, 1H), 6.29 (d, J=7.9 Hz, 1H), 3.35 (s, 3H).

Step 6: 2-Methyl-N-[2-methyl-6-[(E)-o-tolylazo]-3-pyridyl]pyrazole-3-carboxamide (I-43)

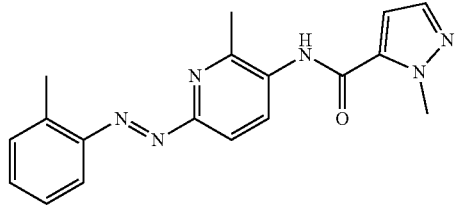 [SMILES: Cc1ccccc1/N=N/c1ccc(NC(=O)c2ccnn2C)c(C)n1]

To a solution of N-(6-amino-2-methyl-3-pyridyl)-2-methyl-pyrazole-3-carboxamide (100 mg, 421.62 umol, 1 eq) in toluene (1 mL) and $H_2O$ (4 mL) was added NaOH (168.65 mg, 4.22 mmol, 10 eq). After stirring for 10 min, 1-methyl-2-nitroso-benzene (113.50 mg, 843.23 μmol, 2 eq) was added. The mixture was stirred at 50° C. for 12 h. TLC (PE/EtOAc=2/1, $R_f$=0.24) detected a major new spot. $H_2O$ (5 mL) was added and the mixture was extracted with DCM (10 mL×3). The combined organic layers were washed with brine (10 mL), dried over anhydrous $Na_2SO_4$, filtered and concentrated to afford the crude product which was purified by preparative HPLC (MeCN/$H_2O$ as eluents, neutral condition, Instrument: Agela DuraShell 150 mm_25 mm_5 um/Mobile phase: [water(10 mM $NH_4HCO_3$)-ACN]: B from 40% to 70% in 10 min/Flow rate: 25 mL/min) followed by lyophilization to yield 2-methyl-N-[2-methyl-6-[(E)-o-tolylazo]-3-pyridyl]pyrazole-3-carboxamide (compound I-43, 4.02 mg, 11.46 umol, 2.7% yield, 95.4% purity) as a yellow solid. $^1$H NMR (400 MHz, DMSO-$d_6$) δ ppm 10.19 (s, 1H), 8.03 (d, J=8.5 Hz, 1H), 7.63 (m, 2H), 7.58 (s, 1H), 7.55-7.47 (m, 2H), 7.40-7.33 (m, 1H), 7.14 (s, 1H), 4.11 (s, 3H), 2.71 (s, 3H), 2.58 (s, 3H); ES-LCMS m/z 335.0 $[M+H]^+$.

Example 32

Synthesis of I-44

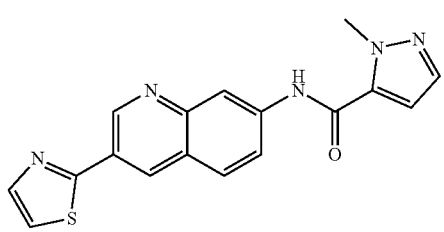 [SMILES: Cn1nccc1C(=O)Nc1ccc2cc(-c3nccs3)cnc2c1]

Synthetic Scheme:

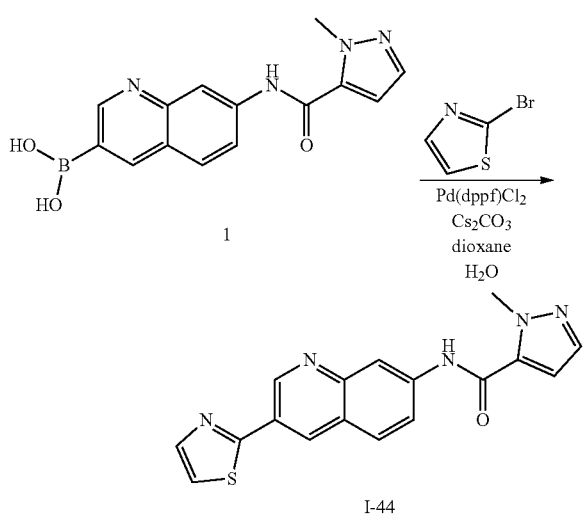

Step 1: 2-Methyl-N-(3-thiazol-2-yl-7-quinolyl)pyrazole-3-carboxamide (I-44)

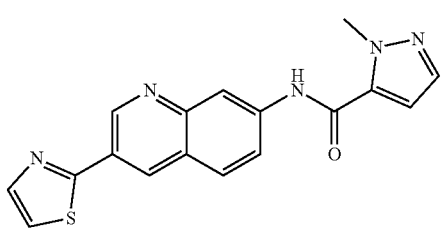

A mixture of [7-[(2-methylpyrazole-3-carbonyl)amino]-3-quinolyl]boronic acid (60 mg, 141.85 μmol, 1 eq), 2-bromothiazole (25.59 mg, 156.03 μmol, 14.06 μL, 1.1 eq), Cs$_2$CO$_3$ (231.09 mg, 709.25 μmol, 5 eq) and Pd(dppf)Cl$_2$ (10.38 mg, 14.18 μmol, 0.1 eq) in 1,4-dioxane (3 mL) and H$_2$O (1 mL) were taken up into a microwave tube and then purged with N$_2$ for 1 min. The sealed tube was heated at 110° C. for 1 h under microwave (1 bar). The reaction mixture was concentrated to give the residue which was purified by preparative HPLC (column: Agela ASB 150*25 mm*5 um; mobile phase: [water (0.05% HCl)-ACN]; B %: 25%-55%, 9 min) followed by lyophilization to yield 2-methyl-N-(3-thiazol-2-yl-7-quinolyl)pyrazole-3-carboxamide (20.88 mg, 46.95 μmol, 33.1% yield, 100.0% purity, 3HCl) as a yellow solid. $^1$H NMR (400 MHz, CD$_3$OD) δ ppm 9.67 (s, 1H), 9.54 (s, 1H), 9.15 (s, 1H), 8.37 (d, J=8.2 Hz, 1H), 8.09 (d, J=9.5 Hz, 1H), 8.03 (s, 1H), 7.84 (s, 1H), 7.54 (s, 1H), 7.13 (s, 1H), 4.18 (s, 3H); ES-LCMS m/z 336.1 [M+H]$^+$.

Example 33

Synthesis of I-45

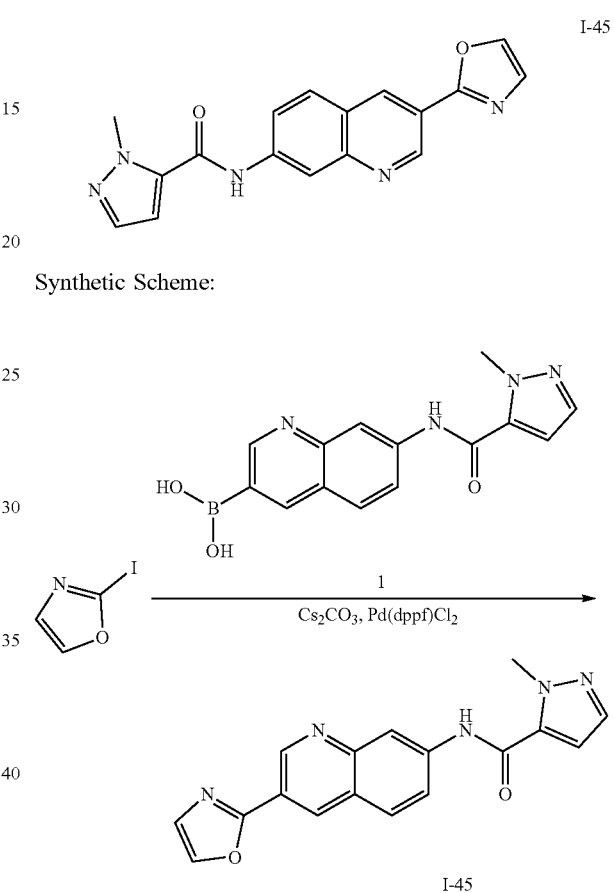

Step 1: 2-Methyl-N-(3-oxazol-2-yl-7-quinolyl)pyrazole-3-carboxamide (I-45)

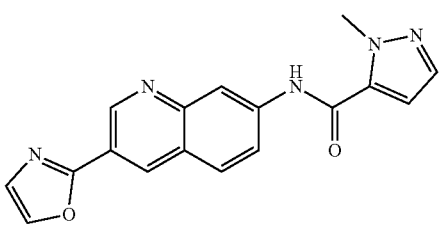 [SMILES: Cn1nccc1C(=O)Nc1ccc2cc(-c3ncco3)cnc2c1]

To a solution of 2-iodooxazole (30 mg, 153.88 μmol, 1 eq) in 1,4-dioxane (3 mL) and water (1 mL) was added Pd(dppf)Cl$_2$ (11.26 mg, 15.39 μmol, 0.1 eq), Cs$_2$CO$_3$ (150.41 mg, 461.64 μmol, 3 eq) and [7-[(2-methylpyrazole-3-carbonyl)amino]-3-quinolyl]boronic acid (78.11 mg, 184.66 μmol, 1.2 eq). The mixture was bubbled with N$_2$ for 3 min and stirred at 110° C. for 30 min under microwave. The reaction mixture was diluted with EtOAc (20 mL) and filtered through a pad of celite. The filtrate was concentrated under reduced pressure to yield a residue which was purified by preparative HPLC (HCl condition; column: Phenomenex Gemini C18 250*50 mm*10 µm; mobile phase: [water (0.05% HCl)-ACN]; B %: 20%-50%, 10 min) followed by lyophilized to yield 2-methyl-N-(3-oxazol-2-yl-7-quinolyl)pyrazole-3-carboxamide (8.41 mg, 19.62 µmol, 12.8% yield, 100.0% purity, 3HCl) as a yellow solid. $^1$H NMR (400 MHz, CD$_3$OD) δ ppm 9.68 (d, J=2.0 Hz, 1H), 9.59 (d, J=1.0 Hz, 1H), 9.20 (d, J=1.8 Hz, 1H), 8.44 (d, J=9.0 Hz, 1H), 8.22 (s, 1H), 8.15 (dd, J=1.9, 9.2 Hz, 1H), 7.59 (d, J=2.3 Hz, 1H), 7.50 (d, J=0.8 Hz, 1H), 7.18 (d, J=2.3 Hz, 1H), 4.22 (s, 3H); ES-LCMS m/z 320.2 [M+H]$^+$.

Example 34

Synthesis of I-46

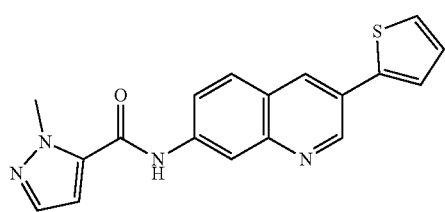

Synthetic Scheme:

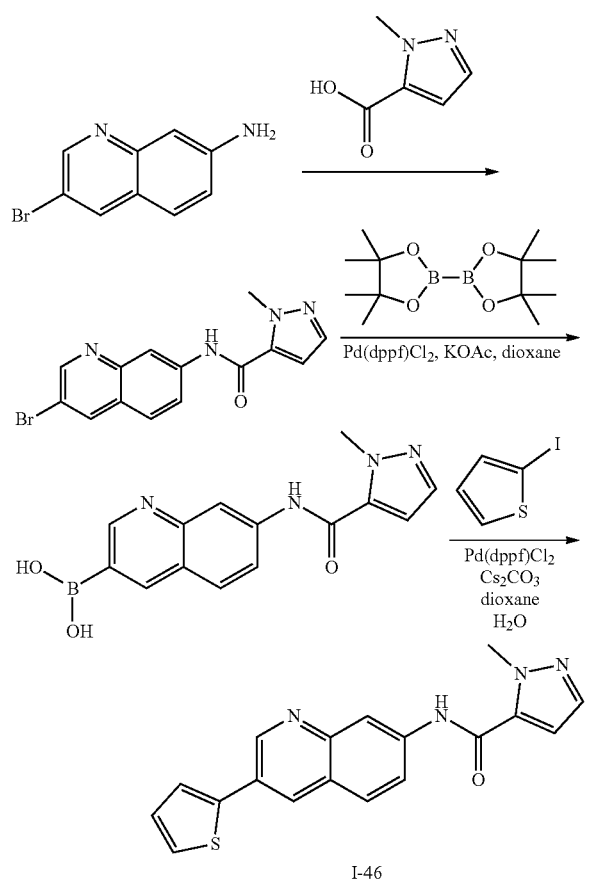

Step 1: [7-[(2-Methylpyrazole-3-carbonyl)amino]-3-quinolyl]boronic Acid

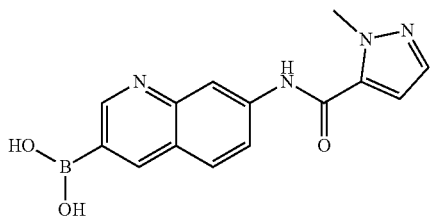 [SMILES: Cn1nccc1C(=O)Nc1ccc2cc(B(O)O)cnc2c1]

A mixture of N-(3-bromo-7-quinolyl)-2-methyl-pyrazole-3-carboxamide (300 mg, 887.77 µmol, 1 eq), 4,4,5,5-tetramethyl-2-(4,4,5,5-tetramethyl-1,3,2-dioxaborolan-2-yl)-1,3,2-dioxaborolane (405.79 mg, 1.60 mmol, 1.8 eq), Pd(dppf)Cl$_2$ (64.96 mg, 88.78 µmol, 0.1 eq) and KOAc (348.50 mg, 3.55 mmol, 4 eq) in 1,4-dioxane (10 mL) was stirred at 90° C. for 3 h under N$_2$ atmosphere. The reaction mixture was filtered and concentrated to yield [7-[(2-methylpyrazole-3-carbonyl)amino]-3-quinolyl]boronic acid (300 mg, 709.25 µmol, 79.9% yield, 70.0% purity) as a brown solid. $^1$H NMR (400 MHz, CDCl$_3$) δ ppm 9.14 (s, 1H), 8.56 (s, 1H), 8.15 (s, 2H), 7.97 (s, 1H), 7.83 (d, J=8.2 Hz, 1H), 7.50 (s, 1H), 6.73 (s, 1H), 4.22 (s, 3H); ES-LCMS m/z 297.1 [M+H]$^+$.

Step 2: 2-Methyl-N-[3-(2-thienyl)-7-quinolyl]pyrazole-3-carboxamide (I-46)

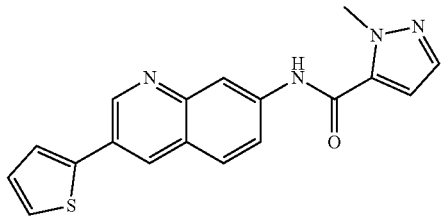 [SMILES: Cn1nccc1C(=O)Nc1ccc2cc(-c3cccs3)cnc2c1]

[7-[(2-Methylpyrazole-3-carbonyl)amino]-3-quinolyl]boronic acid (80 mg, 189.13 mol, 1 eq), 2-iodothiophene (43.70 mg, 208.05 µmol, 21.21 µL, 1.1 eq), Cs$_2$CO$_3$ (308.12 mg, 945.66 µmol, 5 eq) and Pd(dppf)Cl$_2$ (13.84 mg, 18.91 µmol, 0.1 eq) in 1,4-dioxane (3 mL) and H$_2$O (1 mL) were taken up into a microwave tube and purged with N$_2$ for 1 min. The sealed tube was heated at 110° C. for 1 h under microwave (1 bar). The reaction mixture was concentrated to yield the residue which was purified by preparative HPLC (column: Phenomenex Gemini 150*25 mm*10 um; mobile phase: [water (0.05% HCl)-ACN]; B %: 26%-56%, 9 min) followed by lyophilization to yield 2-methyl-N-[3-(2-thienyl)-7-quinolyl]pyrazole-3-carboxamide (34.14 mg, 83.82 µmol, 44.3% yield, 100.0% purity, 2HCl) as a yellow solid. $^1$H NMR (400 MHz, CD$_3$OD) δ ppm 9.49 (d, J=2.0 Hz, 1H), 9.28 (s, 1H), 9.15 (s, 1H), 8.35 (d, J=9.0 Hz, 1H), 8.09 (dd, J=1.5, 9.0 Hz, 1H), 7.86 (d, J=3.0 Hz, 1H), 7.72 (d, J=5.0 Hz, 1H), 7.60 (d, J=2.0 Hz, 1H), 7.33-7.27 (m, 1H), 7.17 (d, J=2.0 Hz, 1H), 4.24 (s, 3H); ES-LCMS m/z 335.2 [M+H]$^+$.

Example 35

Synthesis of I-47

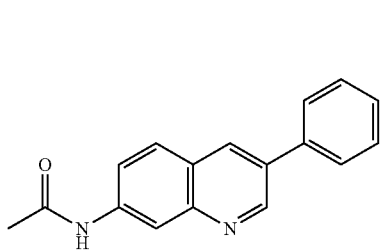

Synthetic Scheme:

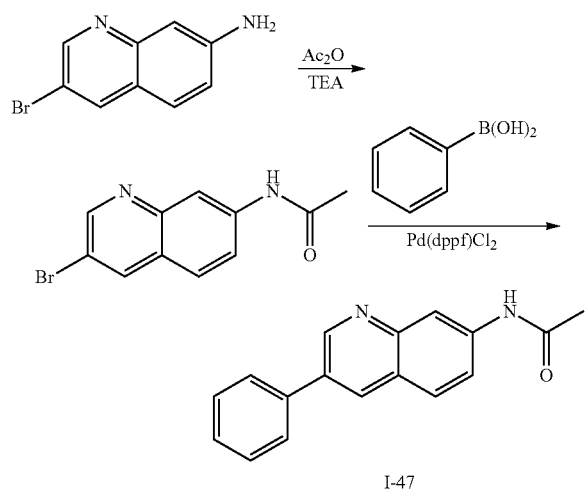

Step 1: N-(3-Bromo-7-quinolyl)acetamide

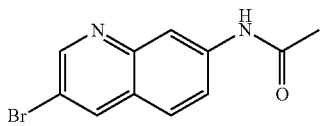

To a solution of 3-bromoquinolin-7-amine (100 mg, 448.29 μmol, 1 eq) in DCM (10 mL) was added Ac₂O (68.65 mg, 672.44 μmol, 1.5 eq) and TEA (136.09 mg, 1.34 μmol, 187.19 uL, 3.0 eq). The mixture was stirred at 25° C. for 16 h. TLC (TLC: PE/EtOAc=1/1, R$_f$=0.44) indicated 50% of starting material was remained. Ac₂O (68.65 mg, 672.44 μmol, 1.5 eq) and TEA (136.09 mg, 1.34 μmol, 187.19 uL, 3.0 eq) was added and the mixture was stirred at 25° C. for 16 h. The reaction mixture was concentrated under reduced pressure to yield a residue which was purified on silica gel column chromatography (from PE/EtOAc=1/0 to 1/2, TLC: PE/EtOAc=1/1, R$_f$=0.44) to yield the product N-(3-bromo-7-quinolyl)acetamide (110 mg, 394.18 μmol, 87.9% yield, 95.0% purity) as a white solid. ¹H NMR (400 MHz, CD₃OD) δ ppm 8.29 (d, J=2.2 Hz, 1H), 8.50 (d, J=2.2 Hz, 1H), 8.81 (s, 1H), 7.88-7.82 (m, 1H), 7.80-7.72 (m, 1H), 2.20 (s, 3H).

Step 2: N-(3-Phenyl-7-quinolyl)acetamide (I-47)

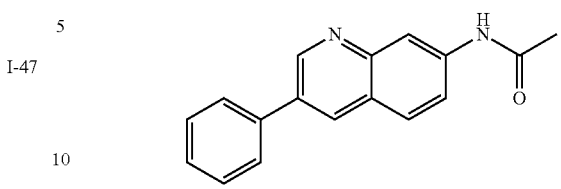

A solution of N-(3-bromo-7-quinolyl)acetamide (70 mg, 250.84 μmol, 1 eq), phenylboronic acid (45.88 mg, 376.26 μmol, 1.5 eq) and Cs₂CO₃ (245.19 mg, 752.53 μmol, 3 eq) in 1,4-dioxane (2 mL) and H₂O (0.5 mL) was purged with N₂ for 2 min. Pd(dppf)Cl₂ (18.35 mg, 25.08 μmol, 0.1 eq) was added and the mixture was stirred at 110° C. for 30 min under microwave. The reaction mixture was filtered and concentrated under reduced pressure to yield a residue which was purified by preparative HPLC (column: Phenomenex Gemini 150*25 mm*10 um; mobile phase: [water (0.05% HCl)-ACN]; B %: 3%-30%, 10 min) followed by lyophilization to yield the product N-(3-phenyl-7-quinolyl)acetamide (32.31 mg, 106.20 μmol, 42.3% yield, 98.2% purity, HCl) as a yellow solid. ¹H NMR (400 MHz, CD₃OD) δ ppm 9.38 (d, J=2.2 Hz, 1H), 9.30 (d, J=1.5 Hz, 1H), 9.02 (d, J=1.8 Hz, 1H), 8.31 (d, J=9.0 Hz, 1H), 7.91-7.87 (m, 2H), 7.80 (dd, J=2.0, 9.0 Hz, 1H), 7.63-7.57 (m, 2H), 7.57-7.51 (m, 1H), 2.26 (s, 3H); ES-LCMS m/z 263.2 [M+H]⁺.

Example 36

Synthesis of I-48

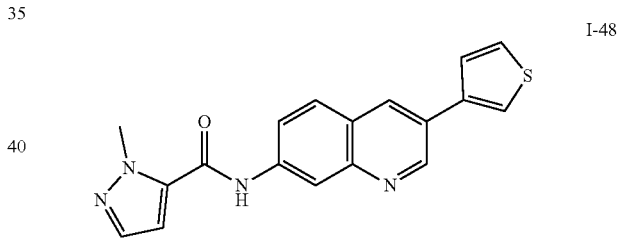

Synthetic Scheme:

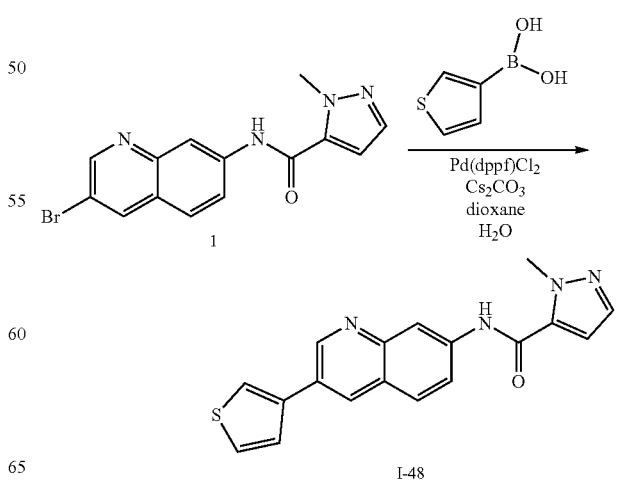

131

Step 1: 2-Methyl-N-[3-(3-thienyl)-7-quinolyl]pyrazole-3-carboxamide (I-48)

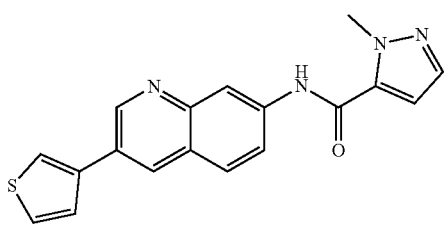 [SMILES: Cn1nccc1C(=O)Nc1ccc2cc(-c3ccsc3)cnc2c1]

A mixture of N-(3-bromo-7-quinolyl)-2-methyl-pyrazole-3-carboxamide (50 mg, 134.37 μmol, 1 eq), 3-thienylboronic acid (22.35 mg, 174.69 μmol, 1.3 eq), $Cs_2CO_3$ (218.91 mg, 671.87 μmol, 5 eq) and $Pd(dppf)Cl_2$ (9.83 mg, 13.44 μmol, 0.1 eq) in 1,4-dioxane (3 mL) and $H_2O$ (1 mL) were taken up into a microwave tube and purged with $N_2$ for 1 min. The sealed tube was heated at 110° C. for 1 h under microwave (1 bar). The reaction mixture was concentrated to yield the residue which was purified by preparative HPLC (column: Phenomenex Gemini C18 250*50 mm*10 um; mobile phase: [water (0.05% HCl)-ACN]; B %: 10%-40%, 10 min) followed by lyophilization to yield 2-methyl-N-[3-(3-thienyl)-7-quinolyl]pyrazole-3-carboxamide (33.41 mg, 81.54 μmol, 60.7% yield, 99.4% purity, 2HCl) as a yellow solid. $^1$H NMR (400 MHz, $CD_3OD$) δ ppm 9.52 (d, J=2.0 Hz, 1H), 9.37 (s, 1H), 9.13 (d, J=1.5 Hz, 1H), 8.34 (d, J=9.5 Hz, 1H), 8.20 (d, J=1.5 Hz, 1H), 8.09 (dd, J=2.0, 9.0 Hz, 1H), 7.81-7.77 (m, 1H), 7.72 (dd, J=3.0, 5.0 Hz, 1H), 7.60 (d, J=2.0 Hz, 1H), 7.18 (d, J=2.0 Hz, 1H), 4.23 (s, 3H); ES-LCMS m/z 335.1 [M+H]$^+$.

Example 37

Synthesis of I-49

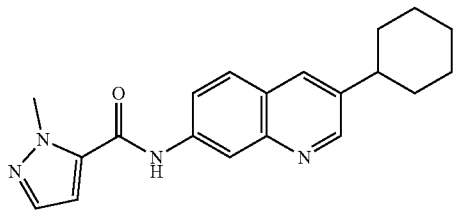
I-49

Synthetic Scheme:

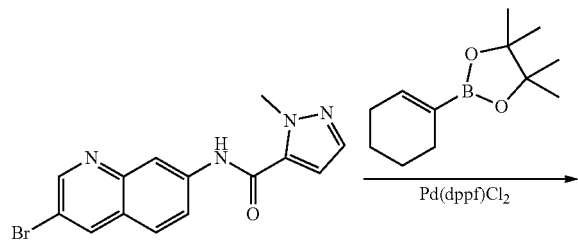

132

-continued

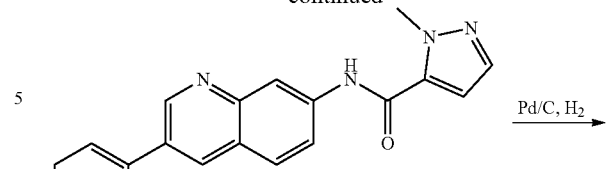

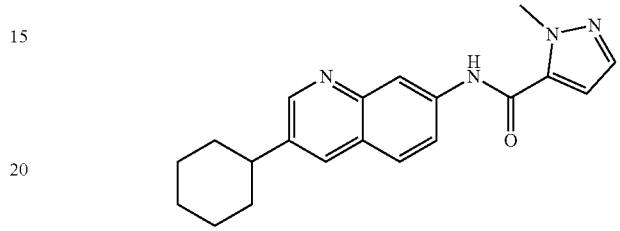
I-49

Step 1: N-[3-(Cyclohexen-1-yl)-7-quinolyl]-2-methyl-pyrazole-3-carboxamide

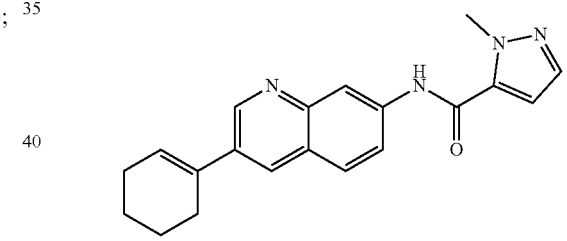

N-(3-Bromo-7-quinolyl)-2-methyl-pyrazole-3-carboxamide (100 mg, 295.92 μmol, 1 eq), 2-(cyclohexen-1l-yl)-4,4,5,5-tetramethyl-1,3,2-dioxaborolane (64.66 mg, 310.72 μmol, 66.80 L, 1.05 eq), $Cs_2CO_3$ (289.25 mg, 887.77 μmol, 3 eq), $Pd(dppf)Cl_2$ (21.65 mg, 29.59 μmol, 0.1 eq) and $H_2O$ (1 mL) were taken up into a microwave tube in 1,4-dioxane (3 mL). The sealed tube was heated at 110° C. for 1 h under microwave. The reaction mixture was diluted with $H_2O$ (10 mL), extracted with EtOAc (20 mL×3). The combined organic layers were dried over $Na_2SO_4$, filtered and concentrated under reduced pressure to yield a residue which was purified by flash silica gel chromatography (from PE/EtOAC=100/1 to 1/1, TLC: PE/EtOAc=1/1, $R_f$=0.2) to yield N-[3-(cyclohexen-1-yl)-7-quinolyl]-2-methyl-pyrazole-3-carboxamide (80 mg, 240.68 μmol, 81.3% yield, 100.0% purity) as a yellow solid. $^1$H NMR (400 MHz, $CD_3OD$) δ ppm 8.92 (d, J=2.0 Hz, 1H), 8.49 (s, 1H), 8.18 (d, J=2.0 Hz, 1H), 7.92-7.84 (m, 2H), 7.54 (d, J=2.0 Hz, 1H), 7.05 (d, J=2.0 Hz, 1H), 6.41 (t, J=4.0 Hz, 1H), 4.19 (s, 3H), 2.58-2.50 (m, 2H), 2.31 (dd, J=2.4, 6.4 Hz, 2H), 1.92-1.84 (m, 2H), 1.78-1.70 (m, 2H); ES-LCMS m/z 333.1 [M+H]$^+$.

Step 2: N-(3-Cyclohexyl-7-quinolyl)-2-methyl-pyrazole-3-carboxamide (I-49)

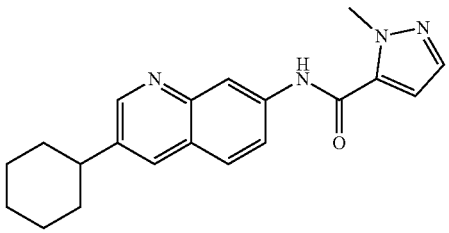 [SMILES: Cn1nccc1C(=O)Nc1ccc2cc(C3CCCCC3)cnc2c1]

To a solution of N-[3-(cyclohexen-1-yl)-7-quinolyl]-2-methyl-pyrazole-3-carboxamide (80 mg, 240.68 μmol, 1 eq) in MeOH (3 mL) was added Pd/C under Ar atmosphere. The suspension was degassed and purged with $H_2$ for 3 times. The mixture was stirred under $H_2$ (15 Psi) at 25° C. for 2 h. The mixture was filtered through a pad of celiet and concentrated under reduced pressure to yield a residue which was purified by preparative HPLC (column: Phenomenex Gemini 150*25 mm*10 um; mobile phase: [water (0.05% HCl)-ACN]; B %: 10%-40%, 9.5 min) followed by lyophilization to yield N-(3-cyclohexyl-7-quinolyl)-2-methyl-pyrazole-3-carboxamide (43.41 mg, 106.57 μmol, 44.3% yield, 100.0% purity, 2HCl) as a white solid. $^1$H NMR (400 MHz, CD$_3$OD) δ ppm 9.11 (d, J=1.8 Hz, 1H), 9.06 (d, J=2.0 Hz, 1H), 8.99 (s, 1H), 8.27 (d, J=8.8 Hz, 1H), 8.04 (dd, J=2.0, 8.8 Hz, 1H), 7.59 (d, J=2.0 Hz, 1H), 7.14 (d, J=2.0 Hz, 1H), 4.22 (s, 3H), 2.98 (tt, J=3.2, 11.6 Hz, 1H), 2.07 (d, J=11.6 Hz, 2H), 1.97 (d, J=13.2 Hz, 2H), 1.85 (d, J=12.8 Hz, 1H), 1.74-1.51 (m, 4H), 1.47-1.34 (m, 1H); ES-LCMS m/z 335.2 [M+H]$^+$.

Example 38

Synthesis of I-50

I-50

Synthetic Scheme:

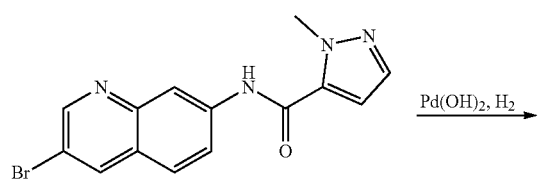

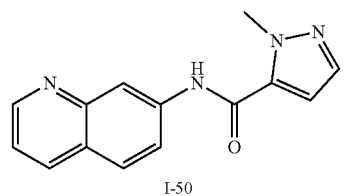

I-50

Step 1: 2-Methyl-N-(7-quinolyl)pyrazole-3-carboxamide (I-50)

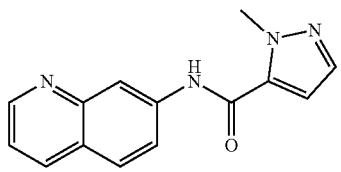 [SMILES: Cn1nccc1C(=O)Nc1ccc2cccnc2c1]

To a solution of N-(3-bromo-7-quinolyl)-2-methyl-pyrazole-3-carboxamide (78.65 mg, 211.37 μmol, 1 eq) in MeOH (5 mL) was added Pd(OH)$_2$ (0.05 g, 71.21 μmol, 20%, 1 eq) under $N_2$. The suspension was degassed under vacuum and purged with $H_2$ 3 times. The mixture was stirred under $H_2$ (15 psi) at 25° C. for 1 h. TLC (PE/EtOAc=3/1, R$_f$=0.5) showed the starting material was consumed completely. The reaction mixture was filtered and the filtrate was concentrated to give the residue which was purified by preparative HPLC (column: Phenomenex Gemini C18 250*50 mm*10 um; mobile phase: [water (0.05% HCl)-ACN]; B %: 0%-30%, 10 min). The desired fraction was lyophilized to yield 2-methyl-N-(7-quinolyl)pyrazole-3-carboxamide (37.89 mg, 110.97 μmol, 52.5% yield, 95.2% purity, 2HCl) as a white solid. $^1$H NMR (400 MHz, CD$_3$OD) δ ppm 9.13-9.04 (m, 3H), 8.29 (d, J=9.2 Hz, 1H), 8.05 (dd, J=2.0, 8.8 Hz, 1H), 7.93 (dd, J=5.6, 8.4 Hz, 1H), 7.54 (d, J=2.0 Hz, 1H), 7.11 (d, J=2.4 Hz, 1H), 4.17 (s, 3H); ES-LCMS m/z 253.2 [M+H]$^+$.

Example 39

Synthesis of I-51

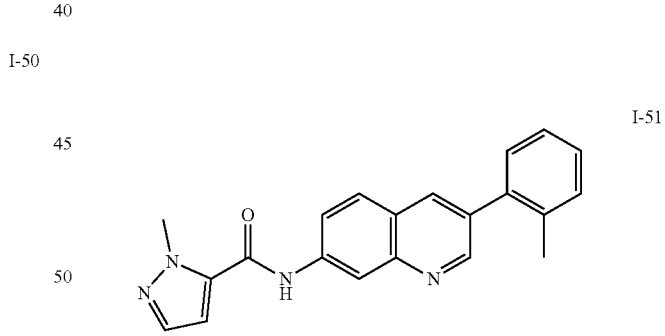

I-51

Synthetic Scheme:

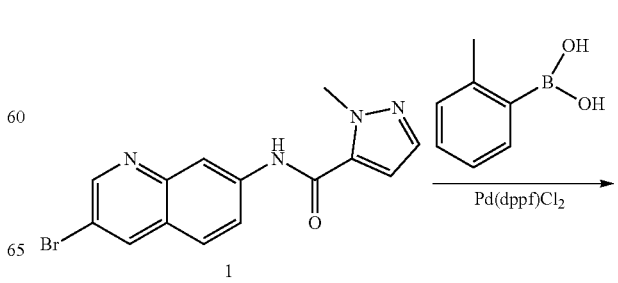

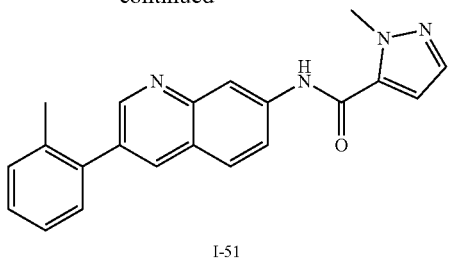

I-51

Step 1: 2-Methyl-N-[3-(o-tolyl)-7-quinolyl]pyrazole-3-carboxamide (I-51)

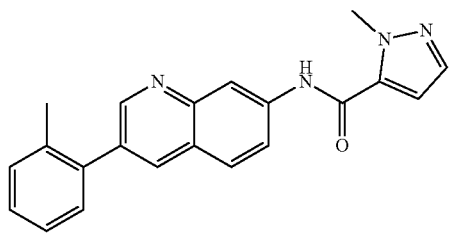 [SMILES: Cc1ccccc1-c1cnc2cc(NC(=O)c3ccnn3C)ccc2c1]

N-(3-Bromo-7-quinolyl)-2-methyl-pyrazole-3-carboxamide (80 mg, 236.74 µmol, 1 eq), o-tolylboronic acid (32.19 mg, 236.74 µmol, 1 eq), Cs₂CO₃ (231.40 mg, 710.22 µmol, 3 eq) and Pd(dppf)Cl₂ (17.32 mg, 23.67 µmol, 0.1 eq) were taken up into a microwave tube in 1,4-dioxane (6 mL) and H₂O (2 mL). The sealed tube was heated at 110° C. for 1 h under microwave (2 bar). The mixture was concentrated and water (8 mL) was added, extracted with EtOAc (8 mL×3). The combined organic layers were dried over Na₂SO₄, filtered and concentrated and purified by preparative HPLC (column: Phenomenex Gemini 150*25 mm*10 µm; mobile phase: [water (0.05% HCl)-ACN]; B %: 18%-48%, 9 min) followed by lyophilization to yield 2-methyl-N-[3-(o-tolyl)-7-quinolyl]pyrazole-3-carboxamide (49.17 mg, 118.39 µmol, 50.0% yield, 100.0% purity, 2HCl) as a white solid. H NMR (400 MHz, CD₃OD) δ ppm 9.22 (s, 1H), 9.19 (d, J=2.0 Hz, 1H), 9.11 (s, 1H), 8.36 (d, J=9.0 Hz, 1H), 8.10 (dd, J=2.0, 9.0 Hz, 1H), 7.60 (d, J=2.2 Hz, 1H), 7.47-7.44 (m, 3H), 7.43-7.38 (m, 1H), 7.15 (d, J=2.2 Hz, 1H), 4.23 (s, 3H), 2.40 (s, 3H); ES-LCMS m/z 343.0 [M+H]⁺.

Example 40

Synthesis of I-52

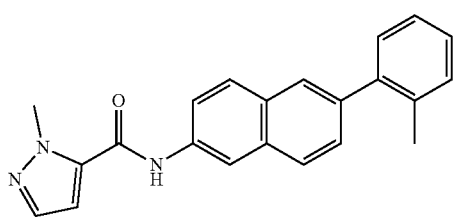

I-52

Synthetic Scheme:

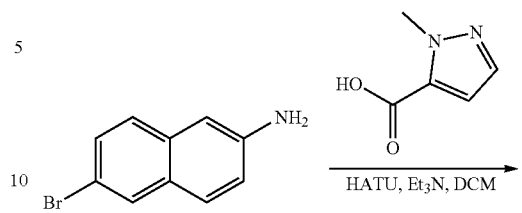

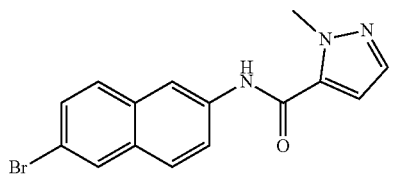 [SMILES: Cn1nccc1C(=O)Nc1ccc2cc(Br)ccc2c1]

I-52

Step 1: N-(6-Bromo-2-naphthyl)-2-methyl-pyrazole-3-carboxamide

To a mixture of 6-bromonaphthalen-2-amine (100 mg, 450.29 µmol, 1 eq), 2-methylpyrazole-3-carboxylic acid (56.79 mg, 450.29 µmol, 1 eq), HATU (222.58 mg, 585.37 µmol, 1.3 eq) in DCM (10 mL) was added Et₃N (136.69 mg, 1.35 mmol, 188.02 µL, 3 eq). The mixture was stirred at 25° C. under N₂ atmosphere for 19 h. The mixture was concentrated and saturated NaHCO₃ (10 mL) was added, extracted with EtOAc (10 mL×3). The combined organic layers were dried over Na₂SO₄, filtered and concentrated to yield the residue which was purified on silica gel column chromatography (from PE/EtOAc=1/0 to 10/3, TLC: PE/EtOAc=3/1, R_f=0.45) to yield N-(6-bromo-2-naphthyl)-2-methyl-pyrazole-3-carboxamide (120 mg, 363.44 µmol, 80.7% yield, 100.0% purity) as a white solid. ¹H NMR (400 MHz, CDCl₃) δ ppm 8.29 (d, J=1.8 Hz, 1H), 7.98 (s, 1H), 7.84-7.75 (m, 2H), 7.71 (d, J=8.8 Hz, 1H), 7.61-7.49 (m, 3H), 6.71 (d, J 2.2 Hz, 1H), 4.26 (s, 3H); ES-LCMS m/z 332.0, 334.0 [M+H]⁺.

Step 2: 2-Methyl-N-[6-(o-tolyl)-2-naphthyl]pyrazole-3-carboxamide (I-52)

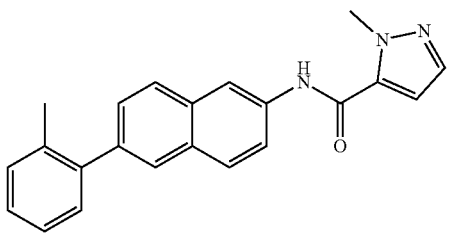 [SMILES: Cc1ccccc1-c1ccc2cc(NC(=O)c3ccnn3C)ccc2c1]

N-(6-Bromo-2-naphthyl)-2-methyl-pyrazole-3-carboxamide (120 mg, 363.44 μmol, 1 eq), o-tolylboronic acid (49.41 mg, 363.44 μmol, 1 eq), Cs$_2$CO$_3$ (355.25 mg, 1.09 mmol, 3 eq) and Pd(dppf)Cl$_2$ (26.59 mg, 36.34 μmol, 0.1 eq) were taken up into a microwave tube in 1,4-dioxane (6 mL) and H$_2$O (2 mL). The sealed tube was heated at 110° C. for 1 h under microwave (2 bar). The reaction mixture was concentrated and water (10 mL) was added, extracted with EtOAc (10 mL×3). The combined organic layers were dried over Na$_2$SO$_4$, filtered and concentrated to yield the residue which was purified by preparative HPLC (Phenomenex Gemini 150*25 mm*10 μm; mobile phase: [water (0.05% HCl)-ACN]; B %: 50%-80%, 9 min) to yield 2-methyl-N-[6-(o-tolyl)-2-naphthyl]pyrazole-3-carboxamide (29.88 mg, 79.08 μmol, 21.8% yield, 100.0% purity, HCl) as a yellow solid. $^1$H NMR (400 MHz, CD$_3$OD) δ ppm 8.36 (d, J=1.8 Hz, 1H), 7.88 (t, J=7.8 Hz, 2H), 7.77-7.71 (m, 2H), 7.57 (d, J=2.2 Hz, 1H), 7.46 (dd, J=1.7, 8.5 Hz, 1H), 7.33-7.23 (m, 4H), 7.05 (d, J=2.2 Hz, 1H), 4.20 (s, 3H), 2.29 (s, 3H); ES-LCMS m/z 342.1 [M+H]$^+$.

Example 41

Synthesis of I-53

I-53

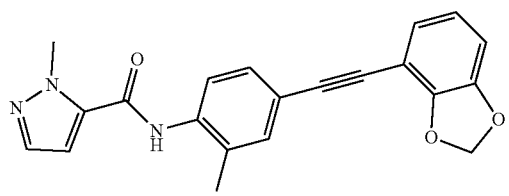

Synthetic Scheme:

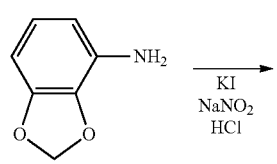

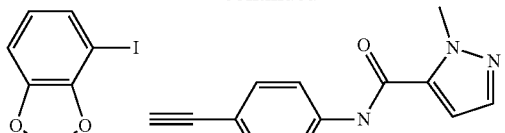

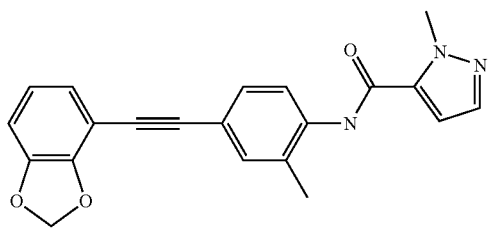

Step 1: 4-Iodo-1,3-benzodioxole

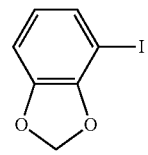

To a solution of 1,3-benzodioxol-4-amine (1.5 g, 8.64 mmol, 1 eq, HCl) and con. HCl (6.12 g, 62.10 mmol, 6 mL, 37%, 7.19 eq) in water (25 mL) and acetone (15 mL) was added a solution of NaNO$_2$ (1.49 g, 21.60 mmol, 2.5 eq) in water (15 mL) at ice-water and the mixture was stirred at 0° C. for 0.5 h. KI (3.73 g, 22.47 mmol, 2.6 eq) was added to the mixture portion wise at 0° C. After being stirred for 0.5 h, the mixture was stirred for 12 h at 80° C. TLC (PE/EtOAc=3/1, R$_f$=0.94) indicated starting material disappeared, one major new spot with lower polarity was detected. The mixture was concentrated, diluted with water (20 mL) and extracted with EtOAc (40 mL×2). The combined organic layers were washed with brine (30 mL), dried over Na$_2$SO$_4$, filtered and concentrated under reduced pressure to yield a residue which was purified by flash silica gel chromatography (from PE/EtOAc=100/1 to 80/1, TLC: PE/EtOAc=3/1, R$_f$=0.94). The desired fraction was concentrated to give 4-iodo-1,3-benzodioxole (2.1 g, 8.47 mmol, 97.9% yield, 100.0% purity) as black brown oil. $^1$H NMR (400 MHz, CDCl$_3$) δ ppm 7.14 (m, 1H), 6.78 (m, 1H), 6.64-6.59 (m, 1H), 6.02 (s, 2H).

139

Step 2: N-[4-[2-(1,3-Benzodioxol-4-yl)ethynyl]-2-methyl-phenyl]-2-methyl-pyrazole-3-carboxamide (I-53)

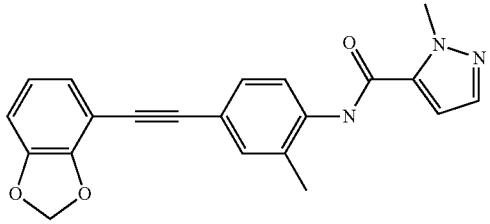 [SMILES: Cc1cc(C#Cc2cccc3c2OCO3)ccc1NC(=O)c1ccnn1C]

A mixture of N-(4-ethynyl-2-methyl-phenyl)-2-methyl-pyrazole-3-carboxamide (237.96 mg, 967.67 μmol, 1.2 eq), 4-iodo-1,3-benzodioxole (200 mg, 806.40 μmol, 1 eq), TEA (204.00 mg, 2.02 mmol, 280.60 μL, 2.5 eq), Pd(PPh$_3$)$_2$Cl$_2$ (566.01 mg, 806.40 μmol, 1 eq) and CuI (30.72 mg, 161.28 μmol, 0.2 eq) in THF (5 mL) was degassed and purged with N$_2$ for 3 times, The mixture was stirred at 70° C. for 12 h under N$_2$ atmosphere. 1 mL TMT solution was added to the solution. After 2 h, the mixture was filtered and the filtrate was concentrated to give the residue which was purified by preparative HPLC (column: Phenomenex Gemini 150*25 mm*10 um; mobile phase: [water (0.05% HCl)-ACN]; B %: 45%-75%, 10 min). The desired fraction was lyophilized to yield N-[4-[2-(1,3-benzodioxol-4-yl)ethynyl]-2-methyl-phenyl]-2-methyl-pyrazole-3-carboxamide (96.75 mg, 244.42 μmol, 30.3% yield, 100.0% purity, HCl) as a white solid. $^1$H NMR (400 MHz, CD$_3$OD) δ ppm 7.53 (d, J=2.0 Hz, 1H), 7.46-7.44 (m, 1H), 7.42-7.39 (m, 1H), 7.39-7.36 (m, 1H), 6.98 (s, 1H), 6.93 (m, 1H), 6.84 (s, 2H), 6.04 (s, 2H), 4.15 (s, 3H), 2.31 (s, 3H); ES-LCMS m/z 360.1 [M+H]$^+$.

Example 42

Synthesis of I-54

I-54

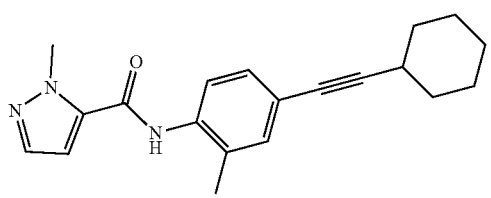

Synthetic Scheme:

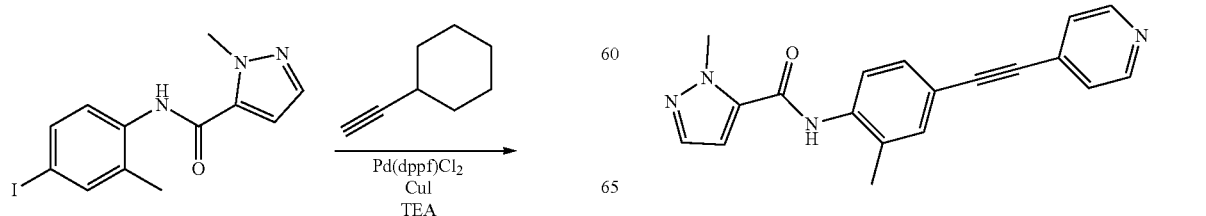

140

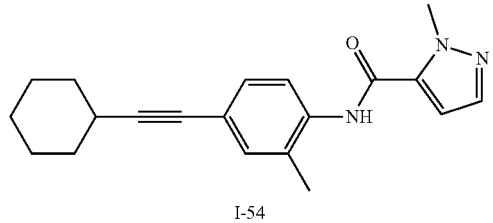

I-54

Step 1: N-[4-(2-Cyclohexylethynyl)-2-methyl-phenyl]-2-methyl-pyrazole-3-carboxamide (I-54)

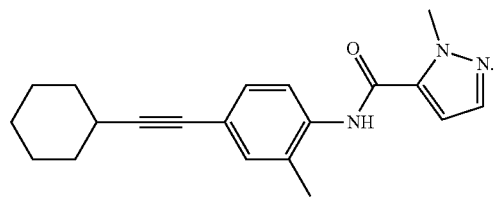 [SMILES: Cc1cc(C#CC2CCCCC2)ccc1NC(=O)c1ccnn1C]

A mixture of N-(4-iodo-2-methyl-phenyl)-2-methyl-pyrazole-3-carboxamide (60 mg, 175.88 μmol, 1 eq), ethynyl-cyclohexane (38.05 mg, 351.75 μmol, 2 eq), Pd(dppf)Cl$_2$ (12.87 mg, 17.59 μmol, 0.1 eq), CuI (6.70 mg, 35.18 μmol, 0.2 eq) and TEA (53.39 mg, 527.63 μmol, 73.44 L, 3 eq) in DMF (2 mL) was degassed and purged with N$_2$ for 3 times. The mixture was stirred at 100° C. for 12 h under N$_2$ atmosphere. The reaction mixture was quenched by addition H$_2$O (20 mL), extracted with EtOAc (30 mL×3). The combined organic layers were dried over Na$_2$SO$_4$, filtered and concentrated under reduced pressure to yield a residue which was purified by preparative HPLC (column: Phenomenex Gemini C18 250*50 mm*10 um; mobile phase: [water (0.05% HCl)-ACN]; B %: 50%-80%, 10 min) followed by lyophilization to yield N-[4-(2-cyclohexylethynyl)-2-methyl-phenyl]-2-methyl-pyrazole-3-carboxamide (20.53 mg, 57.37 μmol, 32.6% yield, 100.0 purity, HCl) as a white solid. $^1$H NMR (400 MHz, CD$_3$OD) δ ppm 7.55 (s, 1H), 7.32-7.27 (m, 2H), 7.24-7.19 (m, 1H), 6.98 (s, 1H), 4.15 (s, 3H), 2.69-2.51 (m, 1H), 2.26 (s, 3H), 2.02 (s, 1H), 2.00-1.84 (m, 2H), 1.77 (s, 2H), 1.62-1.43 (m, 3H), 1.42-1.35 (m, 2H); ES-LCMS m/z 322.2 [M+H]$^+$.

Example 43

Synthesis of I-55

I-55

Synthetic Scheme:

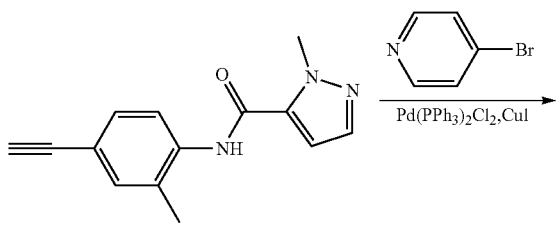

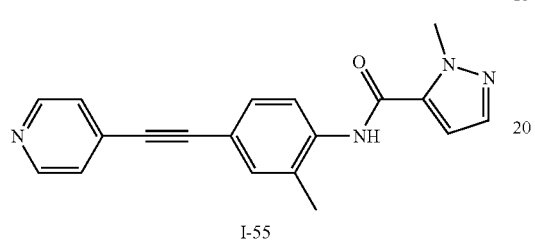

Step 1: 2-Methyl-N-[2-methyl-4-[2-(4-pyridyl)ethynyl]phenyl]pyrazole-3-carboxamide (I-55)

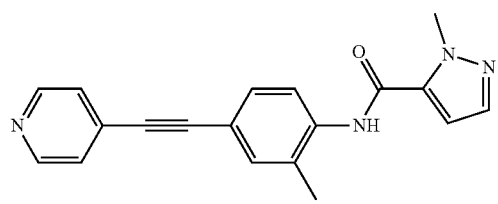 [SMILES: Cc1cc(C#Cc2ccncc2)ccc1NC(=O)c1ccnn1C]

To a solution of N-(4-ethynyl-2-methyl-phenyl)-2-methyl-pyrazole-3-carboxamide (100 mg, 406.65 µmol, 1 eq) in THF (5 mL) was added 4-bromopyridine (96.37 mg, 609.98 µmol, 1.5 eq), TEA (123.45 mg, 1.22 mmol, 169.80 µL, 3 eq), CuI (7.74 mg, 40.67 µmol, 0.1 eq) and Pd(PPh$_3$)$_2$Cl$_2$ (14.27 mg, 20.33 µmol, 0.05 eq). The mixture was stirred at 70° C. for 12 h under N$_2$ atmosphere. The mixture was concentrated under reduced pressure, water (30 mL) was added. The mixture was extracted with EtOAc (20 mL×3). The combined organic layers were washed with brine (30 mL), dried over Na$_2$SO$_4$, filtered and concentrated to yield a residue which was purified by preparative HPLC (column: Phenomenex Gemini C18 250*50 mm*10 µm; mobile phase: [water (0.05% HCl)-ACN]; B %: 15%-45%, 10 min) followed by lyophilization to yield 2-methyl-N-[2-methyl-4-[2-(4-pyridyl)ethynyl]phenyl]pyrazole-3-carboxamide (15.24 mg, 48.17 µmol, 11.8% yield, 100% purity) as a yellow solid. $^1$H NMR (400 MHz, CD$_3$OD) δ ppm 8.85 (d, J=6.8 Hz, 2H), 8.17 (d, J=6.8 Hz, 2H), 7.66 (s, 1H), 7.60 (s, 2H), 7.58 (d, J=2.3 Hz, 1H), 7.02 (d, J=2.3 Hz, 1H), 4.17 (s, 3H), 2.36 (s, 3H); ES-LCMS m/z 317.1 [M+H]$^+$.

Example 44

Synthesis of I-56

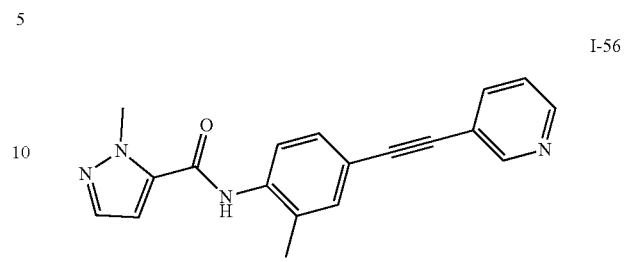

Synthetic Scheme:

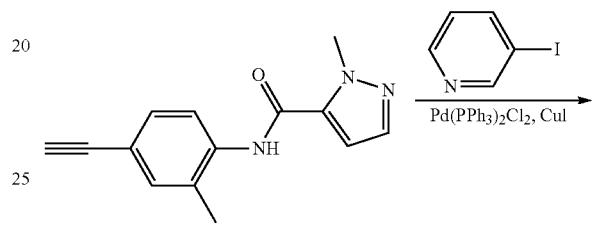

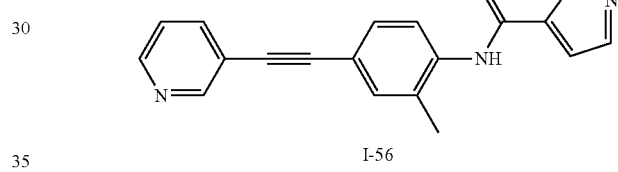

Step 1: 2-Methyl-N-[2-methyl-4-[2-(3-pyridyl)ethynyl]phenyl]pyrazole-3-carboxamide (I-56)

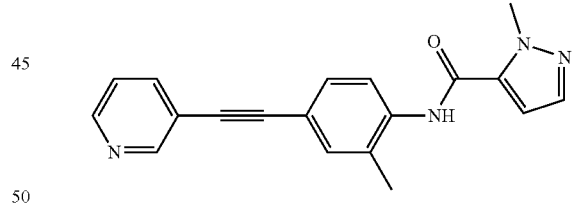

To a solution of N-(4-ethynyl-2-methyl-phenyl)-2-methyl-pyrazole-3-carboxamide (100 mg, 406.65 µmol, 1 eq) in DMF (4 mL) was added 3-iodopyridine (125.04 mg, 609.98 µmol, 1.5 eq), TEA (123.45 mg, 1.22 mmol, 169.80 µL, 3 eq), Pd(PPh$_3$)$_2$Cl$_2$ (14.27 mg, 20.33 µmol, 0.05 eq) and CuI (7.74 mg, 40.67 µmol, 0.1 eq). The mixture was stirred at 100° C. for 12 h under N$_2$ atmosphere. The mixture was concentrated under reduced pressure, water (30 mL) was added. The mixture was extracted with EtOAc (30 mL×3). The combined organic layers were washed with brine (30 mL), dried over Na$_2$SO$_4$, filtered and concentrated to yield a residue which was purified by preparative HPLC (column: Phenomenex Gemini C18 250*50 mm*10 µm; mobile phase: [water (0.05% HCl)-ACN]; B %: 20%-50%, 10 min), followed by lyophilization to yield 2-methyl-N-[2-methyl-4-[2-(3-pyridyl)ethynyl]phenyl]pyrazole-3-carboxamide (85.56 mg, 219.79 μmol, 54.0% yield, 100% purity, 2HCl) as a brown yellow solid. $^1$H NMR (400 MHz, CD$_3$OD) δ ppm 9.10 (s, 1H), 8.83 (d, J=5.7 Hz, 1H), 8.75 (td, J=1.6, 8.3 Hz, 1H), 8.12 (dd, J=6.1, 8.0 Hz, 1H), 7.60 (s, 1H), 7.55 (d, J=2.2 Hz, 1H), 7.53 (d, J=0.9 Hz, 2H), 7.00 (d, J=2.2 Hz, 1H), 4.16 (s, 3H), 2.35 (s, 3H); ES-LCMS m/z 316.9 [M+H]$^+$.

Example 45

Synthesis of I-57

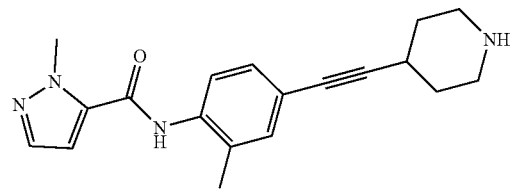
I-57

Synthetic Scheme:

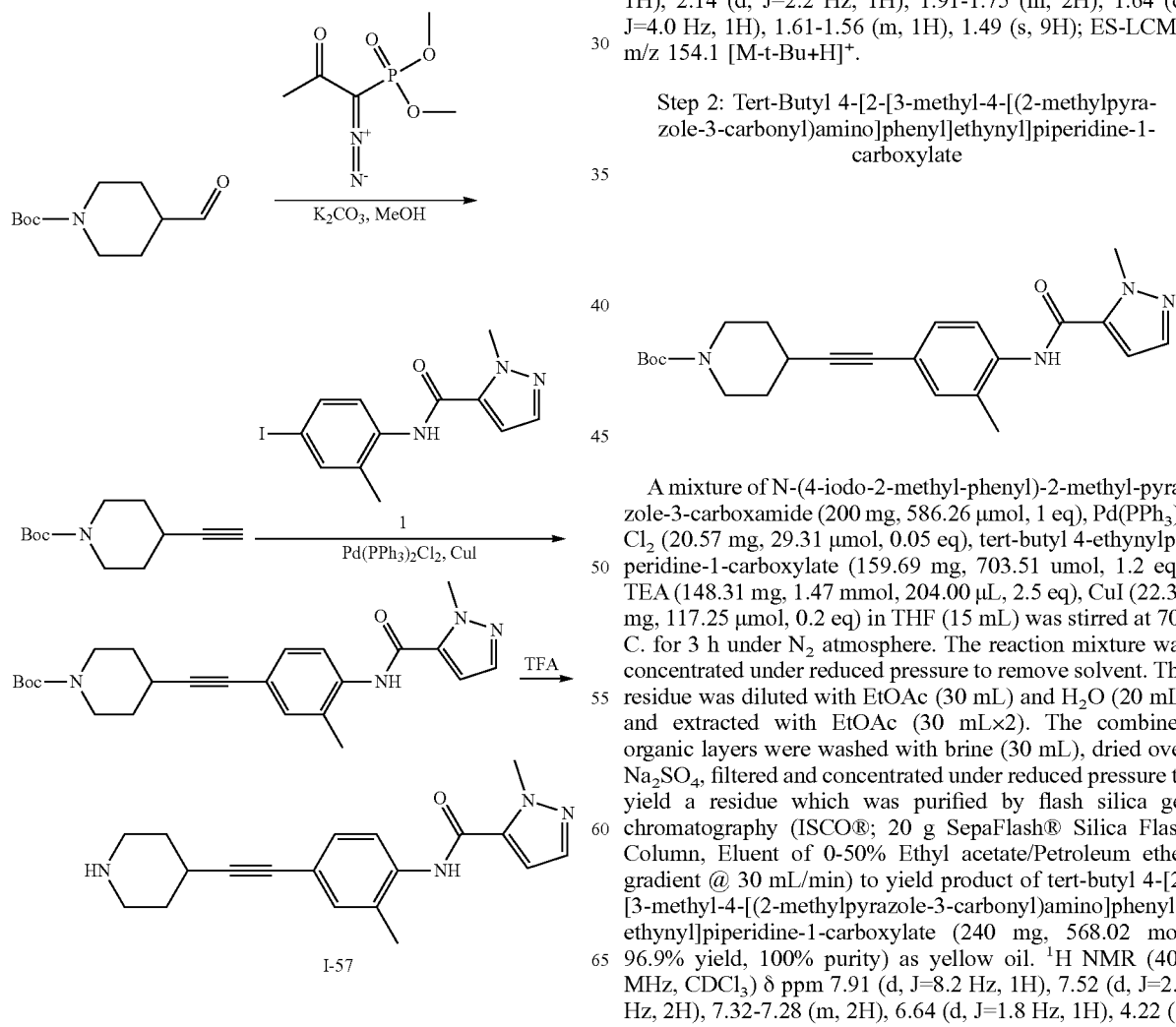

Step 1: tert-Butyl 4-ethynylpiperidine-1-carboxylate

To a mixture of tert-butyl 4-formylpiperidine-1-carboxylate (1 g, 4.69 mmol, 1 eq), K$_2$CO$_3$ (1.30 g, 9.38 mmol, 2 eq) in MeOH (15 mL) was added a solution of 1-diazo-1-dimethoxyphosphoryl-propan-2-one (901.00 mg, 4.69 mmol, 1 eq) in MeOH (5 mL) at 0° C. Then the mixture was stirred at 25° C. for 12 h under N$_2$ atmosphere. The reaction mixture was concentrated under reduced pressure to remove solvent. The residue was diluted with EtOAc (30 mL) and H$_2$O (20 mL) and extracted with EtOAc (30 mL×2). The combined organic layers were washed with brine (30 mL), dried over Na$_2$SO$_4$, filtered and concentrated under reduced pressure to yield a residue which was purified by flash silica gel chromatography (ISCO®; 20 g SepaFlash® Silica Flash Column, Eluent of 0-15% Ethyl acetate/Petroleum ether gradient @ 30 mL/min) to yield tert-butyl 4-ethynylpiperidine-1-carboxylate (1 g, 4.41 mmol, 93.9% yield, 92.2% purity) as colorless oil. $^1$H NMR (400 MHz, CDCl$_3$) δ ppm 3.72 (d, J=6.8 Hz, 2H), 3.28-3.14 (m, 2H), 2.69-2.51 (m, 1H), 2.14 (d, J=2.2 Hz, 1H), 1.91-1.75 (m, 2H), 1.64 (d, J=4.0 Hz, 1H), 1.61-1.56 (m, 1H), 1.49 (s, 9H); ES-LCMS m/z 154.1 [M-t-Bu+H]$^+$.

Step 2: Tert-Butyl 4-[2-[3-methyl-4-[(2-methylpyrazole-3-carbonyl)amino]phenyl]ethynyl]piperidine-1-carboxylate A mixture of N-(4-iodo-2-methyl-phenyl)-2-methyl-pyrazole-3-carboxamide (200 mg, 586.26 μmol, 1 eq), Pd(PPh$_3$)$_2$Cl$_2$ (20.57 mg, 29.31 μmol, 0.05 eq), tert-butyl 4-ethynylpiperidine-1-carboxylate (159.69 mg, 703.51 umol, 1.2 eq), TEA (148.31 mg, 1.47 mmol, 204.00 μL, 2.5 eq), CuI (22.33 mg, 117.25 μmol, 0.2 eq) in THF (15 mL) was stirred at 70° C. for 3 h under N$_2$ atmosphere. The reaction mixture was concentrated under reduced pressure to remove solvent. The residue was diluted with EtOAc (30 mL) and H$_2$O (20 mL) and extracted with EtOAc (30 mL×2). The combined organic layers were washed with brine (30 mL), dried over Na$_2$SO$_4$, filtered and concentrated under reduced pressure to yield a residue which was purified by flash silica gel chromatography (ISCO®; 20 g SepaFlash® Silica Flash Column, Eluent of 0-50% Ethyl acetate/Petroleum ether gradient @ 30 mL/min) to yield product of tert-butyl 4-[2-[3-methyl-4-[(2-methylpyrazole-3-carbonyl)amino]phenyl]ethynyl]piperidine-1-carboxylate (240 mg, 568.02 mol, 96.9% yield, 100% purity) as yellow oil. $^1$H NMR (400 MHz, CDCl$_3$) δ ppm 7.91 (d, J=8.2 Hz, 1H), 7.52 (d, J=2.0 Hz, 2H), 7.32-7.28 (m, 2H), 6.64 (d, J=1.8 Hz, 1H), 4.22 (s, 3H), 3.81-3.67 (m, 2H), 3.29-3.20 (m, 2H), 2.80 (tt, J=4.1, 8.0 Hz, 1H), 2.29 (s, 3H), 1.86 (dd, J=3.3, 13.5 Hz, 2H), 1.72-1.61 (m, 2H), 1.47 (s, 9H); ES-LCMS m/z 367.2 [M-t-Bu+H]⁺.

Step 3: 2-Methyl-N-[2-methyl-4-[2-(4-piperidyl)ethynyl]phenyl]pyrazole-3-carboxamide (I-57)

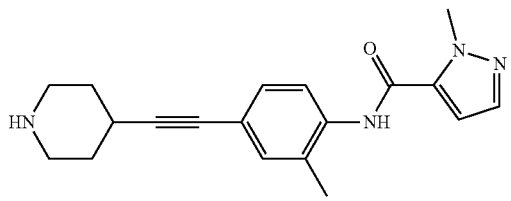 [SMILES: Cc1cc(C#CC2CCNCC2)ccc1NC(=O)c1ccnn1C]

To a solution of tert-butyl 4-[2-[3-methyl-4-[(2-methyl-pyrazole-3-carbonyl)amino]phenyl]ethynyl]piperidine-1-carboxylate (100 mg, 236.68 µmol, 1 eq) in DCM (8 mL) was added TFA (3.08 g, 27.01 mmol, 2 mL, 114.13 eq) and the mixture was stirred at 20° C. for 0.5 h. The reaction mixture was concentrated to yield the residue which was purified by preparative HPLC (column: Phenomenex Gemini 150*25 mm*10 um; mobile phase: [water (0.05% HCl)-ACN]; B %: 5%-35%, 10 min). The desired fraction was lyophilized to afford 2-methyl-N-[2-methyl-4-[2-(4-piperidyl)ethynyl]phenyl]pyrazole-3-carboxamide (79.72 mg, 201.66 µmol, 85.2% yield, 100% purity, 2HCl) as a white solid. ¹H NMR (400 MHz, CD₃OD) δ ppm 7.52 (d, J=2.2 Hz, 1H), 7.33 (d, J=7.9 Hz, 2H), 7.28-7.24 (m, 1H), 6.95 (d, J=1.3 Hz, 1H), 4.12 (s, 3H), 3.40 (td, J=3.7, 12.8 Hz, 2H), 3.25-3.11 (m, 2H), 3.04 (tt, J=4.0, 8.0 Hz, 1H), 2.25 (s, 3H), 2.19-2.09 (m, 2H), 1.97-1.87 (m, 2H); ES-LCMS m/z 323.2 [M+H]⁺.

Example 46

Synthesis of I-58

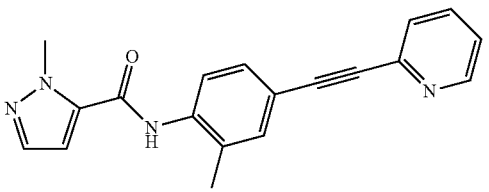

Synthetic Scheme:

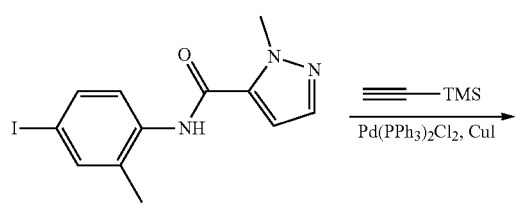

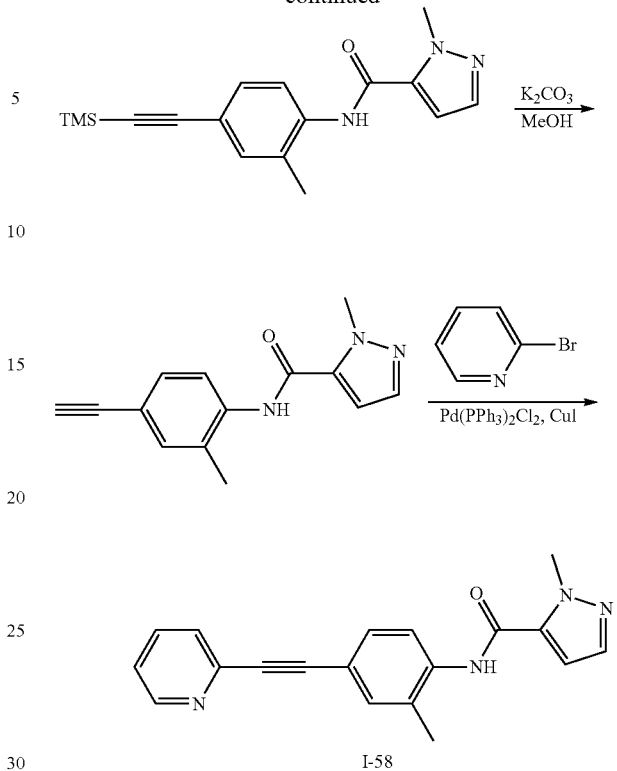

Step 1: 2-Methyl-N-[2-methyl-4-(2-trimethylsilyl-ethynyl)phenyl]pyrazole-3-carboxamide

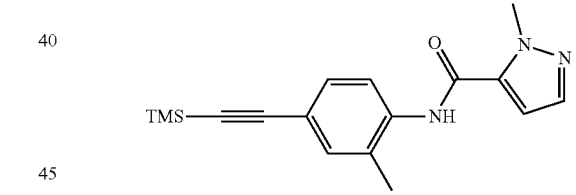

A mixture of N-(4-iodo-2-methyl-phenyl)-2-methyl-pyrazole-3-carboxamide (200 mg, 586.26 µmol, 1 eq), ethynyl (trimethyl)silane (86.37 mg, 879.39 µmol, 121.82 µL, 1.5 eq), TEA (177.97 mg, 1.76 mmol, 244.80 µL, 3 eq), CuI (11.17 mg, 58.63 µmol, 0.1 eq) and Pd(PPh₃)₂Cl₂ (20.57 mg, 29.31 µmol, 0.05 eq) in DMF (4 mL) was stirred at 100° C. for 16 h under N₂ atmosphere. The mixture was concentrated under reduced pressure, water (30 mL) was added. The mixture was extracted with EtOAc (30 mL×3). The combined organic layers were washed with brine (30 mL), dried over Na₂SO₄, filtered and concentrated to yield a residue which was purified by silica gel column chromatography (from PE/EtOAc=1/0 to 3/1, TLC: PE/EtOAc=3/1, R_f=0.6) to yield 2-methyl-N-[2-methyl-4-(2-trimethylsilylethynyl)phenyl]pyrazole-3-carboxamide (95 mg, 298.92 µmol, 50.9% yield, 98% purity) as yellow oil. ¹H NMR (400 MHz, CD₃OD) δ ppm 7.53 (d, J=2.2 Hz, 1H), 7.42-7.26 (m, 3H), 6.97 (s, 1H), 4.14 (s, 3H), 2.28 (s, 3H), 0.28-0.15 (m, 9H); ES-LCMS m/z 312.1 [M+H]⁺.

Step 2: N-(4-Ethynyl-2-methyl-phenyl)-2-methyl-pyrazole-3-carboxamide

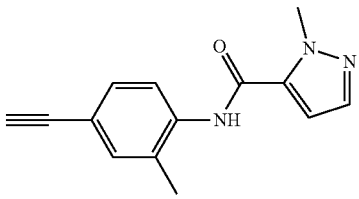 [SMILES: C#Cc1ccc(NC(=O)c2ccnn2C)c(C)c1]

To a solution of 2-methyl-N-[2-methyl-4-(2-trimethylsilylethynyl)phenyl]pyrazole-3-carboxamide (95 mg, 298.92 µmol, 1 eq) in MeOH (10 mL) was added $K_2CO_3$ (82.63 mg, 597.84 µmol, 2 eq). The mixture was stirred at 25° C. for 3 h under $N_2$ atmosphere. The mixture was concentrated under reduced pressure, water (30 mL) was added. The mixture was extracted with EtOAc (20 mL×3). The combined organic layers were washed with brine (30 mL), dried over $Na_2SO_4$, filtered and concentrated under reduced pressure to yield N-(4-ethynyl-2-methyl-phenyl)-2-methyl-pyrazole-3-carboxamide (50 mg, 202.91 µmol, 67.8% yield, 97.1% purity) as a yellow solid which was used in the next step without further purification. $^1$H NMR (400 MHz, $CD_3OD$) δ ppm 7.51 (d, J=2.2 Hz, 1H), 7.38 (s, 1H), 7.31 (s, 2H), 6.92 (s, 1H), 4.16-4.12 (m, 3H), 3.36-3.36 (m, 1H), 2.27 (s, 3H); ES-LCMS m/z 240.1 $[M+H]^+$.

Step 3: 2-Methyl-N-[2-methyl-4-[2-(2-pyridyl)ethynyl]phenyl]pyrazole-3-carboxamide (I-58)

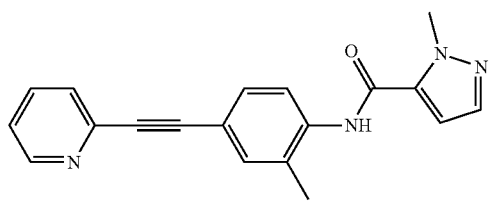

To a solution of N-(4-ethynyl-2-methyl-phenyl)-2-methyl-pyrazole-3-carboxamide (50 mg, 202.91 µmol, 1 eq) in THF (4 mL) was added TEA (61.60 mg, 608.72 µmol, 84.73 µL, 3 eq), $Pd(PPh_3)_2Cl_2$ (7.12 mg, 10.15 µmol, 0.05 eq), CuI (3.86 mg, 20.29 µmol, 0.1 eq) and 2-bromopyridine (48.09 mg, 304.36 µmol, 28.97 µL, 1.5 eq). The mixture was stirred at 100° C. for 12 h under $N_2$ atmosphere. The mixture was concentrated under reduced pressure, water (30 mL) was added. The mixture was extracted with EtOAc (20 mL×3). The combined organic layers were washed with brine (30 mL), dried over $Na_2SO_4$, filtered and concentrated to yield a residue which was purified by preparative HPLC (column: Phenomenex Gemini C18 250*50 mm*10 µm; mobile phase: [water (0.05% HCl)-ACN]; B %: 15%-45%, 10 min) followed by lyophilization to yield 2-methyl-N-[2-methyl-4-[2-(2-pyridyl)ethynyl]phenyl]pyrazole-3-carboxamide (28.57 mg, 73.39 µmol, 36.1% yield, 100% purity, 2HCl) as a yellow solid. $^1$H NMR (400 MHz, $CD_3OD$) δ ppm 8.84 (d, J=6.0 Hz, 1H), 8.62 (dt, J=1.5, 8.0 Hz, 1H), 8.24 (d, J=8.3 Hz, 1H), 8.03 (ddd, J=1.3, 6.1, 7.7 Hz, 1H), 7.69 (s, 1H), 7.63 (s, 2H), 7.56 (d, J=2.0 Hz, 1H), 7.01 (d, J=2.0 Hz, 1H), 4.16 (s, 3H), 2.37 (s, 3H); ES-LCMS m/z 317.1 $[M+H]^+$.

Example 47

Synthesis of I-59

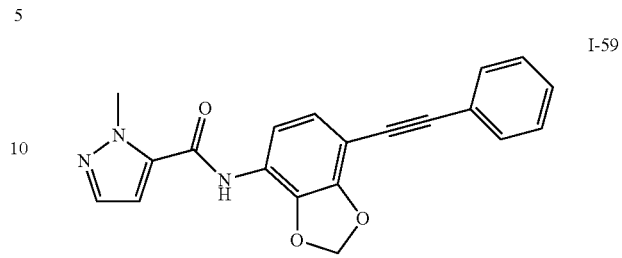

Synthetic Scheme:

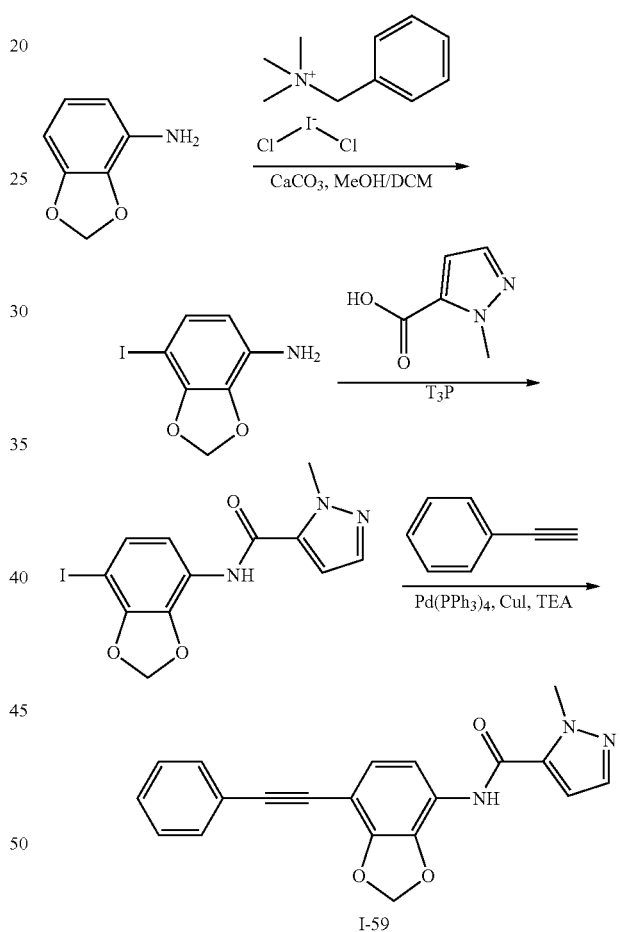

Step 1: 7-Iodo-1,3-benzodioxol-4-amine

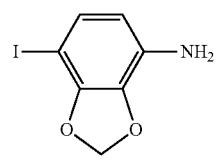

To a mixture of benzyltrimethylammonium dichloroiodate (558.36 mg, 1.60 mmol, 1.1 eq) and CaCO$_3$ (190.00 mg, 1.90 mmol, 1.30 eq) in MeOH (3 mL) and DCM (6 mL) was added portionwise 1,3-benzodioxol-4-amine (200 mg, 1.46 mmol, 1 eq) over 5 min. The mixture was stirred at 30° C. for 1.5 h. The reaction mixture was diluted with H$_2$O (20 mL), extracted with DCM (20 mL×3). The combined organic layers were washed with brine (50 mL) solution, dried over anhydrous Na$_2$SO$_4$, filtered and concentrated under reduced pressure to give a residue which was purified on silica gel column chromatography (from PE/EtOAc=1/0 to 5/1, TLC: PE/EtOAc=5/1, R$_f$=0.51) to give the product 7-iodo-1,3-benzodioxol-4-amine (170 mg, 646.31 μmol, 44.3% yield, 100.0% purity) as a brown solid. $^1$H NMR (400 MHz DMSO-d$_6$) δ ppm 6.81 (d, J=8.8 Hz, 1H), 6.14 (d, J=8.5 Hz, 1H), 5.95 (s, 2H), 5.06 (s, 2H); ES-LCMS m/z 263.9 [M+H]$^+$.

Step 2: N-(7-Iodo-1,3-benzodioxol-4-yl)-2-methyl-pyrazole-3-carboxamide

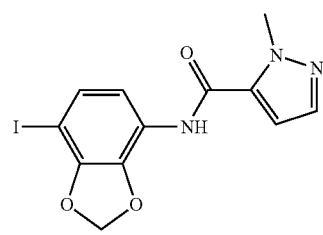 [SMILES: Cn1nccc1C(=O)Nc1ccc(I)c2c1OCO2]

To a solution of 7-iodo-1,3-benzodioxol-4-amine (170 mg, 646.31 umol, 1 eq) and 2-methylpyrazole-3-carboxylic acid (85.58 mg, 678.62 μmol, 1.05 eq) in pyridine (5 mL) was added T$_3$P (1.23 g, 1.94 mmol, 1.15 mL, 50%, 3.0 eq). The mixture was stirred at 25° C. for 2 h. The reaction mixture was quenched by addition NaHCO$_3$ solution (50 mL), extracted with EtOAc (50 mL×3). The combined organic layers were dried over anhydrous Na$_2$SO$_4$, filtered and concentrated under reduced pressure to give a residue which was purified on silica gel column chromatography (from PE/EtOAc=1/0 to 10/3, TLC: PE/EtOAc=5/1, R$_f$=0.36) to give the product N-(7-iodo-1,3-benzodioxol-4-yl)-2-methyl-pyrazole-3-carboxamide (205 mg, 521.99 μmol, 80.8% yield, 94.5% purity) as a white solid. $^1$H NMR (400 MHz, CDCl$_3$) δ ppm 7.58-7.49 (m, 2H), 7.18 (d, J=9.0 Hz, 1H), 6.66 (d, J=2.3 Hz, 1H), 6.09 (s, 2H), 4.23 (s, 3H); ES-LCMS m/z 371.9 [M+H]$^+$.

Step 3: 2-Methyl-N-[7-(2-phenylethynyl)-1,3-benzodioxol-4-yl]pyrazole-3-carboxamide (I-59)

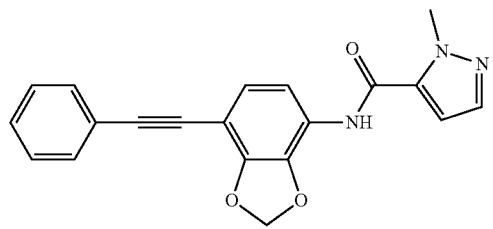 [SMILES: Cn1nccc1C(=O)Nc1ccc(C#Cc2ccccc2)c2c1OCO2]

To a solution of N-(7-iodo-1,3-benzodioxol-4-yl)-2-methyl-pyrazole-3-carboxamide (80 mg, 203.70 μmol, 1 eq) and ethynylbenzene (20.80 mg, 203.70 μmol, 22.37 μL, 1 eq) in DMF (10 mL) was added TEA (61.84 mg, 611.11 μmol, 85.06 μL, 3.0 eq), CuI (7.76 mg, 40.74 μmol, 0.2 eq) and Pd(PPh$_3$)$_4$ (23.54 mg, 20.37 μmol, 0.1 eq). The mixture was stirred at 100° C. for 16 h. The reaction mixture was filtered and concentrated under reduced pressure to give a residue which was purified by preparative HPLC (column: Phenomenex Gemini C18 250*50 mm*10 um; mobile phase: [water (0.05% HCl)-ACN]; B %: 35%-65%, 10 min) followed by lyophilization to yield 2-methyl-N-[7-(2-phenylethynyl)-1,3-benzodioxol-4-yl]pyrazole-3-carboxamide (42.52 mg, 110.92 μmol, 54.4% yield, 99.6% purity, HCl) as a gray solid. $^1$H NMR (400 MHz, CD$_3$OD) δ ppm 7.53-7.46 (m, 3H), 7.39-7.35 (m, 3H), 7.11 (d, J=8.5 Hz, 1H), 6.99-6.94 (m, 2H), 6.11 (s, 2H), 4.14 (s, 3H); ES-LCMS m/z 346.2 [M+H]$^+$.

Example 48

Synthesis of I-60

I-60

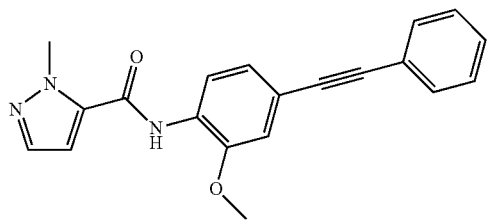

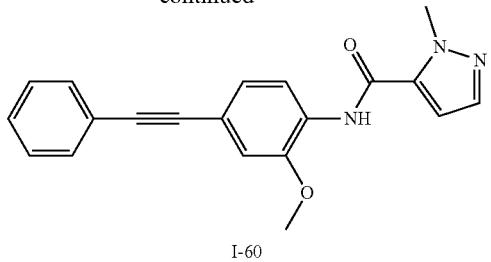

I-60

Step 1: 4-Bromo-2-methoxy-aniline

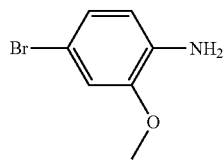

To a solution of 4-bromo-2-methoxy-1-nitro-benzene (1.07 g, 4.63 mmol, 1 eq) in MeOH (20 mL) was added Zn (3.03 g, 46.30 mmol, 10 eq) and NH$_4$Cl (2.48 g, 46.30 mmol, 1.62 mL, 10 eq). The mixture was stirred at 25° C. for 2 h under N$_2$ atmosphere. The reaction mixture was filtered, concentrated and water (80 mL) was added, extracted with EtOAc (50 mL×3). The combined organic layers were washed with brine (50 mL), dried over Na$_2$SO$_4$, filtered and concentrated to yield 4-bromo-2-methoxy-aniline (830 mg, 4.11 mmol, 88.7% yield, crude) as a black solid which was used in the next step without further purification. $^1$H NMR (400 MHz, DMSO-d$_6$) δ ppm 6.89 (d, J=2.2 Hz, 1H), 6.80 (dd, J=2.1, 8.3 Hz, 1H), 6.56 (d, J=8.4 Hz, 1H), 4.87 (s, 2H), 3.75 (s, 3H); ES-LCMS m/z 204.0, 206.0 [M+H]$^+$.

Step 2: N-(4-Bromo-2-methoxy-phenyl)-2-methyl-pyrazole-3-carboxamide

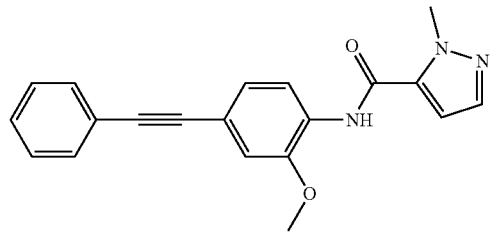 [SMILES: COc1cc(C#Cc2ccccc2)ccc1NC(=O)c1ccnn1C]

A mixture of 4-bromo-2-methoxy-aniline (750 mg, 3.71 mmol, 1 eq), 2-methylpyrazole-3-carboxylic acid (468.13 mg, 3.71 mmol, 1 eq) and T$_3$P (3.54 g, 5.57 mmol, 3.31 mL, 50%, 1.5 eq) in pyridine (15 mL) was degassed and purged with N$_2$ for 3 times. The mixture was stirred at 25° C. for 2 h under N$_2$ atmosphere. The mixture was concentrated and saturated NaHCO$_3$ (50 mL) was added, extracted with EtOAc (40 mL×3). The combined organic layers were washed with brine (40 mL), dried over Na$_2$SO$_4$, filtered and concentrated to yield a residue which was purified on silica gel column chromatography (from PE/EtOAc=1/0 to 10/3, TLC: PE/EtOAc=3/1, R$_f$=0.32) to yield N-(4-bromo-2-methoxy-phenyl)-2-methyl-pyrazole-3-carboxamide (370 mg, 1.19 mmol, 32.1% yield, 100.0% purity) as a brown solid. $^1$H NMR (400 MHz, CDCl$_3$) δ ppm 8.32 (d, J=8.8 Hz, 1H), 7.51 (d, J=2.3 Hz, 1H), 7.15 (dd, J=2.0, 8.8 Hz, 1H), 7.06 (d, J=2.3 Hz, 1H), 6.66 (d, J=2.0 Hz, 1H), 4.23 (s, 3H), 3.93 (s, 3H); ES-LCMS m/z 312.0, 314.0 [M+H]$^+$.

Step 3: N-[2-Methoxy-4-(2-phenylethynyl)phenyl]-2-methyl-pyrazole-3-carboxamide (I-60)

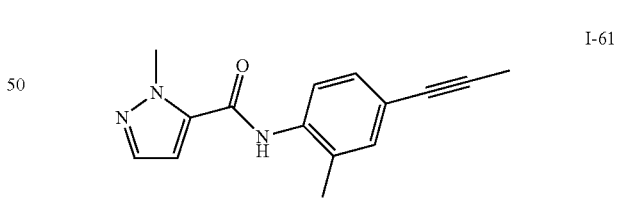

A mixture of N-(4-bromo-2-methoxy-phenyl)-2-methyl-pyrazole-3-carboxamide (100 mg, 322.43 μmol, 1 eq), ethynylbenzene (32.93 mg, 322.43 μmol, 35.41 μL, 1 eq), TEA (97.88 mg, 967.29 μmol, 134.64 μL, 3 eq), CuI (12.28 mg, 64.49 μmol, 0.2 eq) and Pd(PPh$_3$)$_4$ (37.26 mg, 32.24 μmol, 0.1 eq) in DMF (10 mL) was degassed and purged with N$_2$ for 3 times. The mixture was stirred at 100° C. for 16 h under N$_2$ atmosphere. The reaction mixture was filtered though a pad of celite and purified by preparative HPLC (column: Phenomenex Gemini C18 250*50 mm*10 μm; mobile phase: [water (0.05% HCl)-ACN]; B %: 50%-80%, 10 min) followed by lyophilization to yield N-[2-methoxy-4-(2-phenylethynyl)phenyl]-2-methyl-pyrazole-3-carboxamide (31.76 mg, 86.34 μmol, 26.8% yield, 100.0% purity, HCl) as a yellow solid. $^1$H NMR (400 MHz, CD$_3$OD) δ ppm 8.05 (d, J=8.2 Hz, 1H), 7.54-7.49 (m, 3H), 7.40-7.35 (m, 3H), 7.21-7.14 (m, 2H), 6.92 (s, 1H), 4.16 (s, 3H), 3.96 (s, 3H); ES-LCMS m/z 332.1 [M+H]$^+$.

Example 49

Synthesis of I-61

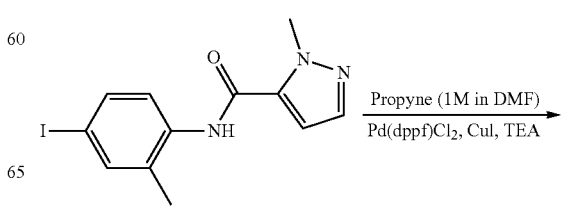

Synthetic Scheme:

Synthetic Scheme:

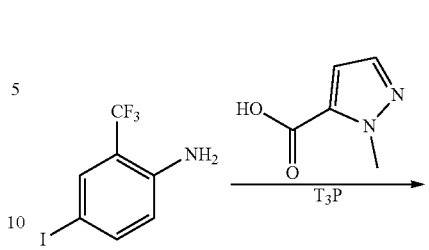

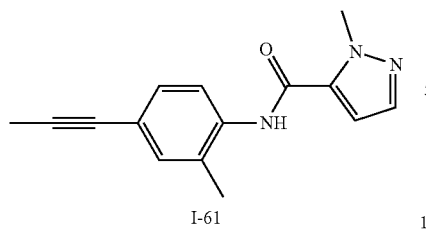

Step 1: 2-methyl-N-(2-methyl-4-prop-1-ynyl-phenyl)pyrazole-3-carboxamide (I-61)

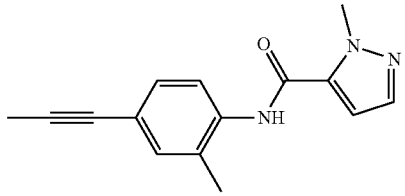 [SMILES: CC#Cc1ccc(NC(=O)c2ccnn2C)c(C)c1]

A mixture of N-(4-iodo-2-methyl-phenyl)-2-methyl-pyrazole-3-carboxamide (60 mg, 175.88 µmol, 1 eq), prop-1-yne (1 M, 879.39 µL, 5 eq), TEA (53.39 mg, 527.63 µmol, 73.44 µL, 3 eq), CuI (6.70 mg, 35.18 µmol, 0.2 eq) and Pd(dppf)Cl$_2$ (12.87 mg, 17.59 µmol, 0.1 eq) in DMF (1 mL) was degassed and purged with N$_2$ for 3 times. The mixture was stirred at 80° C. for 12 h under N$_2$ atmosphere. The reaction mixture was quenched by addition of water (20 mL), extracted with EtOAc (30 mL×3). The combined organic layers were dried over Na$_2$SO$_4$, filtered and concentrated under reduced pressure to yield a residue which was purified by preparative HPLC (column: Phenomenex Gemini C18 250*50 mm*10 um; mobile phase: [water (0.05% HCl)-ACN]; B %: 30%-60%, 10 min) followed by lyophilization to yield 2-methyl-N-(2-methyl-4-prop-1-ynyl-phenyl)pyrazole-3-carboxamide (25.99 mg, 89.70 µmol, 51.0% yield, 100.0% purity, HCl) as a gray solid. $^1$H NMR (400 MHz, CD$_3$OD) δ ppm 7.52 (s, 1H), 7.28 (d, J=3.6 Hz, 2H), 7.25-7.18 (m, 1H), 6.96 (s, 1H), 4.14 (s, 3H), 2.25 (s, 3H), 2.02 (s, 3H); ES-LCMS m/z 254.1 [M+H]$^+$.

Example 50

Synthesis of I-62

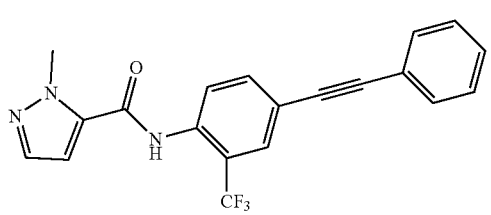

Step 1: N-[4-Iodo-2-(trifluoromethyl)phenyl]-2-methyl-pyrazole-3-carboxamide

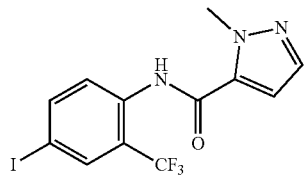 [SMILES: Cn1nccc1C(=O)Nc1ccc(I)cc1C(F)(F)F]

A mixture of 2-methylpyrazole-3-carboxylic acid (145.00 mg, 1.15 mmol, 1.1 eq), 4-iodo-2-(trifluoromethyl)aniline (300 mg, 1.05 mmol, 1 eq), T$_3$P (2.00 g, 3.14 mmol, 1.86 mL, 50%, 3 eq) in pyridine (3 mL) was degassed and purged with N$_2$ for 3 times. The mixture was stirred at 25° C. for 12 h under N$_2$ atmosphere The reaction mixture was quenched by addition H$_2$O (20 mL), extracted with EtOAc (30 mL×3). The combined organic layers were dried over Na$_2$SO$_4$, filtered and concentrated under reduced pressure to yield N-[4-iodo-2-(trifluoromethyl)phenyl]-2-methyl-pyrazole-3-carboxamide (350 mg, 708.65 µmol, 67.8% yield, 80.0% purity) as a white solid which was used in the next step without further purification. $^1$H NMR (400 MHz, CD$_3$OD) δ ppm 8.10-8.01 (m, 2H), 7.52 (d, J=2.0 Hz, 1H), 7.39 (d, J=8.2 Hz, 1H), 6.92 (d, J=2.2 Hz, 1H), 4.12 (s, 3H); ES-LCMS m/z 396.0 [M+H]$^+$.

Step 2: 2-Methyl-N-[2-methyl-4-(2-phenylethynyl)phenyl]pyrazole-3-carboxamide (I-62)

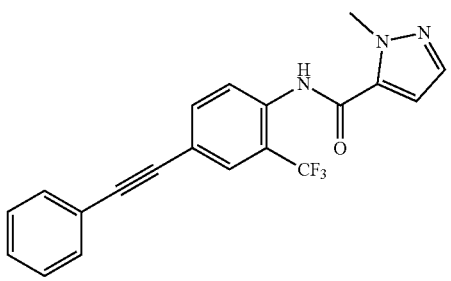 [SMILES: Cn1nccc1C(=O)Nc1ccc(C#Cc2ccccc2)cc1C(F)(F)F]

A mixture of N-(2-fluoro-4-iodo-phenyl)-2-methyl-pyrazole-3-carboxamide (80 mg, 231.81 µmol, 1 eq), ethynylbenzene (23.68 mg, 231.81 mol, 25.46 µL, 1 eq), Pd(PPh$_3$)$_4$ (26.79 mg, 23.18 µmol, 0.1 eq), TEA (70.37 mg, 695.43 µmol, 96.80 µL, 3 eq) and CuI (8.83 mg, 46.36 µmol, 0.2 eq) in DMF (2 mL) was degassed and purged with N$_2$ for 3 times. The mixture was stirred at 100° C. for 12 h under N$_2$ atmosphere The reaction mixture was quenched by addition H$_2$O (20 mL), extracted with EtOAc (30 mL×3). The combined organic layers were dried over Na$_2$SO$_4$, filtered and concentrated under reduced pressure to yield a residue which was purified by preparative HPLC (column: Phenomenex Gemini 150*25 mm*10 um; mobile phase: [water (0.05% HCl)-ACN]; B %: 50%-80%, 10 min) followed by lyophilization to yield 2-methyl-N-[2-methyl-4-(2-phenylethynyl)phenyl]pyrazole-3-carboxamide (22.38 mg, 55.15 µmol, 23.8% yield, 100.0% purity, HCl) as a white solid. $^1$H NMR (400 MHz, CD$_3$OD) δ ppm 7.90 (s, 1H), 7.84 (d, J=8.2 Hz, 1H), 7.69 (d, J=8.2 Hz, 1H), 7.61-7.52 (m, 3H), 7.45-7.38 (m, 3H), 6.96 (d, J=2.2 Hz, 1H), 4.15 (s, 3H); ES-LCMS m/z 370.1 [M+H]$^+$.

Example 51

Synthesis of I-63

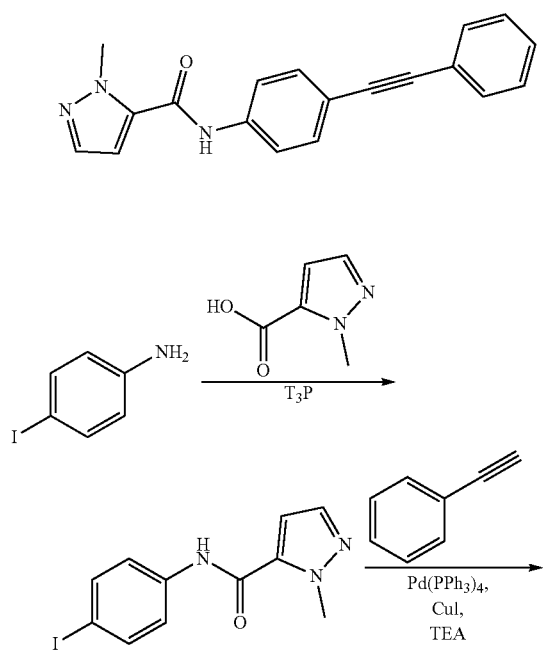

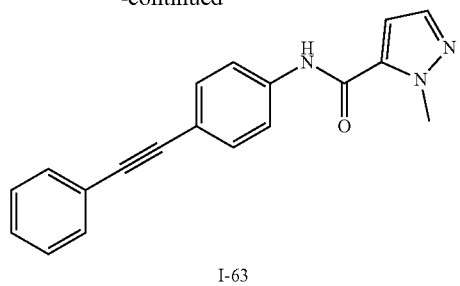

I-63

Step 1: N-(4-Iodophenyl)-2-methyl-pyrazole-3-carboxamide

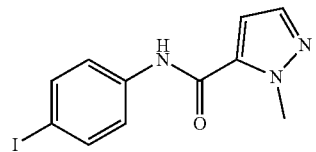 [SMILES: Cn1nccc1C(=O)Nc1ccc(I)cc1]

A mixture of 4-iodoaniline (500 mg, 2.28 mmol, 1 eq), 2-methylpyrazole-3-carboxylic acid (287.90 mg, 2.28 mmol, 1 eq), T$_3$P (4.36 g, 6.85 mmol, 4.07 mL, 50%, 3 eq) in pyridine (2 mL) was degassed and purged with N$_2$ for 3 times. The mixture was stirred at 25° C. for 12 h under N$_2$ atmosphere. The reaction mixture was quenched by addition H$_2$O (20 mL), extracted with EtOAc (30 mL×3). The combined organic layers were dried over Na$_2$SO$_4$, filtered and concentrated under reduced pressure to yield N-(4-iodophenyl)-2-methyl-pyrazole-3-carboxamide (450 mg, 1.10 mmol, 48.2% yield, 80.0% purity) as a white solid which was used in the next step without further purification. $^1$H NMR (400 MHz, CD$_3$OD) δ ppm 7.70-7.68 (m, 1H), 7.67-7.66 (m, 1H), 7.52-7.49 (m, 3H), 6.96 (d, J=2.0 Hz, 1H), 4.14 (s, 3H); ES-LCMS m/z 328.0 [M+H]$^+$.

Step 2: 2-Methyl-N-[4-(2-phenylethynyl)phenyl]pyrazole-3-carboxamide (I-63)

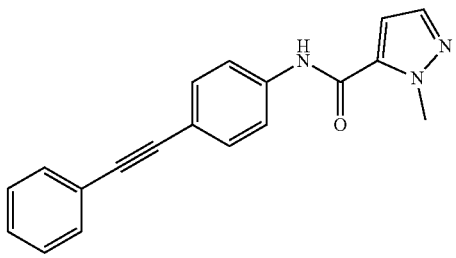 [SMILES: Cn1nccc1C(=O)Nc1ccc(C#Cc2ccccc2)cc1]

A mixture of N-(4-iodophenyl)-2-methyl-pyrazole-3-carboxamide (100 mg, 244.56 µmol, 1 eq), ethynylbenzene (24.98 mg, 244.56 µmol, 26.86 µL, 1 eq), TEA (74.24 mg, 733.68 umol, 102.12 µL, 3 eq), CuI (9.32 mg, 48.91 µmol, 0.2 eq) and Pd(PPh$_3$)$_4$ (28.26 mg, 24.46 µmol, 0.1 eq) in DMF (3 mL) was degassed and purged with N$_2$ for 3 times. The mixture was stirred at 100° C. for 12 h under N$_2$ atmosphere. The reaction mixture was quenched by addition H$_2$O (20 mL), extracted with EtOAc (30 mL×3). The combined organic layers were dried over Na$_2$SO$_4$, filtered and concentrated under reduced pressure to yield a residue which was purified by preparative HPLC (column: Phenomenex Gemini C18 250*50 mm*10 um; mobile phase: [water (0.05% HCl)-ACN]; B %: 40%-70%, 10 min) followed by lyophilization to yield 2-methyl-N-[4-(2-phenylethynyl)phenyl]pyrazole-3-carboxamide (41.71 mg, 123.47 μmol, 50.5% yield, 100.0% purity, HCl) as a gray solid. $^1$H NMR (400 MHz, CD$_3$OD) δ ppm 7.76-7.71 (m, 2H), 7.54-7.49 (m, 5H), 7.40-7.32 (m, 3H), 6.98 (d, J=2.2 Hz, 1H), 4.16 (s, 3H); ES-LCMS m/z 302.2 [M+H]$^+$.

Example 52

Synthesis of I-76

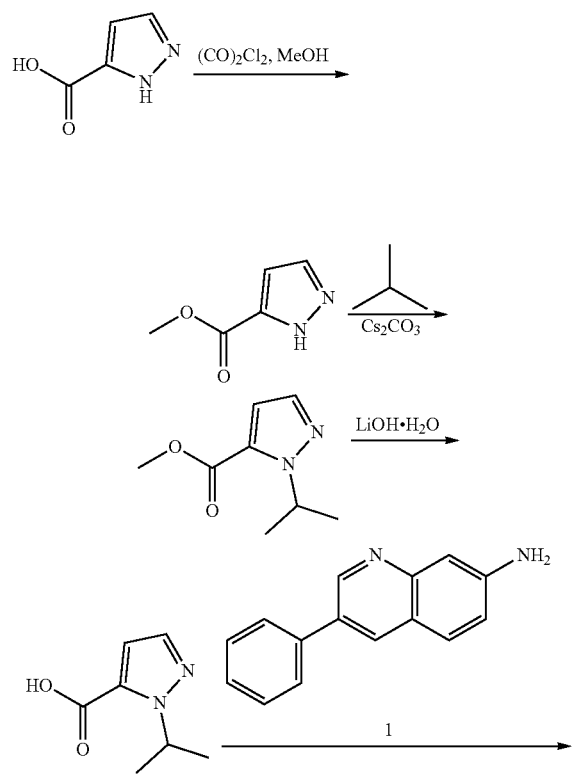

I-76

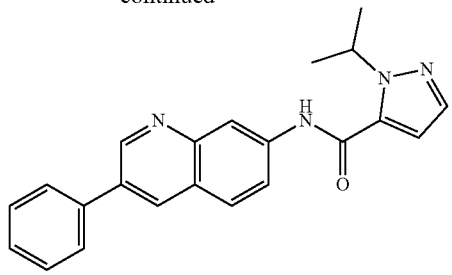

I-76

Step 1: Methyl 1H-pyrazole-5-carboxylate

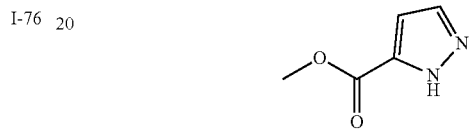

To a mixture of 1H-pyrazole-5-carboxylic acid (3 g, 26.77 mmol, 1 eq) and DMF (0.5 mL) in DCM (20 mL) was added oxalyl chloride (6.79 g, 53.53 mmol, 4.69 mL, 2 eq) dropwise at 0° C. under N$_2$ atmosphere. The mixture was stirred at 15° C. for 1 h. The mixture was concentrated and MeOH (20 mL) was added. After being stirred at 15° C. for 0.5 h, the mixture was concentrated under reduced pressure to yield methyl 1H-pyrazole-5-carboxylate (6 g, 25.83 mmol, 96.5% yield, 70% purity, HCl) as a yellow solid which was used in next step without further purification. $^1$H NMR (400 MHz, CD$_3$OD) δ ppm 7.87 (d, J=2.0 Hz, 1H), 6.92 (d, J=2.2 Hz, 1H), 3.92 (s, 3H); ES-LCMS m/z 150.1 [M+Na]$^+$ Step 2: Methyl 2-isopropylpyrazole-3-carboxylate

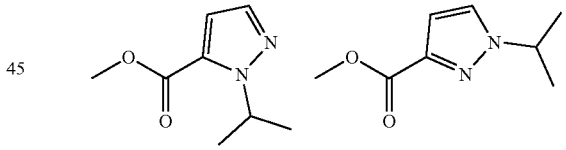

To a mixture of methyl 1H-pyrazole-5-carboxylate (6 g, 25.83 mmol, 1 eq, HCl) and Cs$_2$CO$_3$ (25.25 g, 77.50 mmol, 3 eq) in MeCN (60 mL) was added 2-iodopropane (4.83 g, 28.42 mmol, 2.84 mL, 1.1 eq). The mixture was stirred at 60° C. for 2 h. The mixture was filtered, the filtrate was concentrated to yield a residue which was purified on silica gel column chromatography (from pure PE to PE/EtOAc=3/1, TLC: PE/EtOAc=5/1, R$_f$=0.7 (P1), R$_f$=0.3 (P2)) to yield methyl 2-isopropylpyrazole-3-carboxylate (1.5 g, 8.47 mmol, 32.8% yield, 95% purity, R$_f$=0.7) as colorless oil. $^1$H NMR (400 MHz, CDCl$_3$) δ ppm 7.51 (d, J=2.0 Hz, 1H), 6.82 (d, J=2.0 Hz, 1H), 5.62-5.47 (m, 1H), 3.88 (s, 3H), 1.50 (d, J=6.6 Hz, 6H), and methyl 1-isopropylpyrazole-3-carboxylate (1.9 g, 10.73 mmol, 41.5% yield, 95% purity, R$_f$=0.3) as colorless oil. $^1$H NMR (400 MHz, CDCl$_3$) δ ppm 7.44 (d, J=2.2 Hz, 1H), 6.81 (d, J=2.4 Hz, 1H), 4.66-4.53 (m, 1H), 3.91 (s, 3H), 1.52 (d, J=6.8 Hz, 6H). ES-LCMS m/z 169.2 [M+H]$^+$.

159
Step 3: 2-Isopropylpyrazole-3-carboxylic Acid

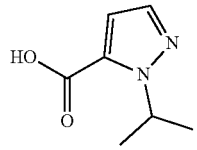

To a solution of methyl 2-isopropylpyrazole-3-carboxylate (500 mg, 2.82 mmol, 1 eq) in H$_2$O (5 mL) was added HCl solution (12 M, 5.00 mL, 21.25 eq). The mixture was stirred at 80° C. for 3 h. The mixture was concentrated under reduced pressure to yield 2-isopropylpyrazole-3-carboxylic acid (500 mg, 2.36 mmol, 83.6% yield, 90% purity, HCl) as a white solid which was used for the next step without purification. $^1$H NMR (400 MHz, CD$_3$OD) δ ppm 7.51 (d, J=1.7 Hz, 1H), 6.84 (d, J=2.0 Hz, 1H), 5.65-5.53 (m, 1H), 1.46 (d, J=6.6 Hz, 6H); ES-LCMS m/z 156.1 [M+H]$^+$.

Step 4: 2-Isopropyl-N-(3-phenyl-7-quinolyl)pyrazole-3-carboxamide (I-76)

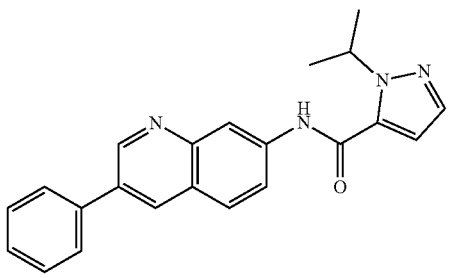 [SMILES: CC(C)n1nccc1C(=O)Nc1ccc2cc(-c3ccccc3)cnc2c1]

To a solution of 2-isopropylpyrazole-3-carboxylic acid (300 mg, 1.42 mmol, 1 eq, HCl) and T$_3$P (8.03 g, 12.61 mmol, 7.50 mL, 50% purity, 8.90 eq) in pyridine (10 mL) was added 3-phenylquinolin-7-amine (346.65 mg, 1.42 mmol, 1 eq). The mixture was stirred at 80° C. for 36 h under N$_2$ atmosphere. The mixture was concentrated and water (20 mL) was added. The mixture was extracted with EtOAc/MeOH (v/v=10/1, 50 mL×3). The combined organic layers were concentrated to yield a residue was purified by preparative HPLC (column: Xtimate C18 150*25 mm*5 μm; mobile phase: [water (0.05% HCl)-ACN]; B %: 30%-60%, 8 min), followed by lyophilization to yield 2-isopropyl-N-(3-phenyl-7-quinolyl)pyrazole-3-carboxamide (76.3 mg, 208.14 μmol, 14.7% yield, 97.2% purity) as a yellow solid. $^1$H NMR (400 MHz, CD$_3$OD) δ ppm 9.45 (s, 1H), 9.34 (s, 1H), 9.16 (s, 1H), 8.37 (d, J=9.0 Hz, 1H), 8.07 (d, J=9.0 Hz, 1H), 7.93 (d, J=7.8 Hz, 2H), 7.66-7.59 (m, 3H), 7.59-7.53 (m, 1H), 7.07 (s, 1H), 5.58-5.49 (m, 1H), 1.53 (d, J=6.6 Hz, 6H); ES-LCMS m/z 357.1 [M+H]$^+$.

160
Example 53

Synthesis of I-77

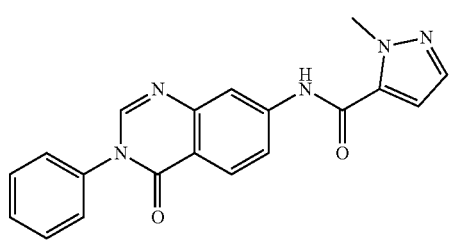

Synthetic Scheme:

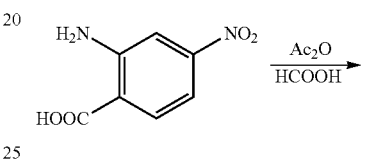

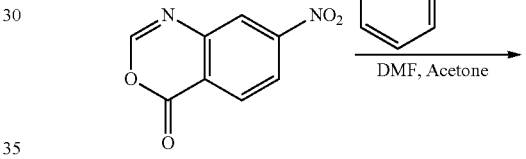

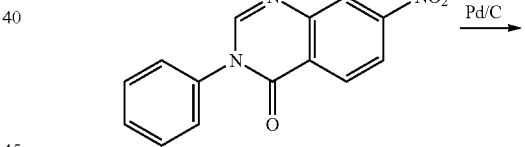

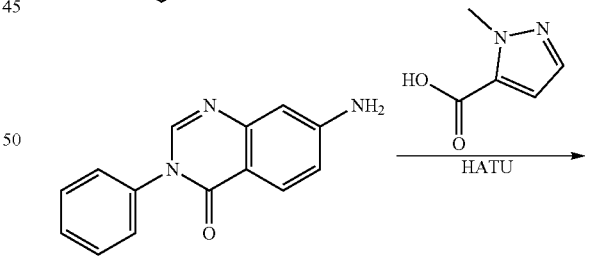

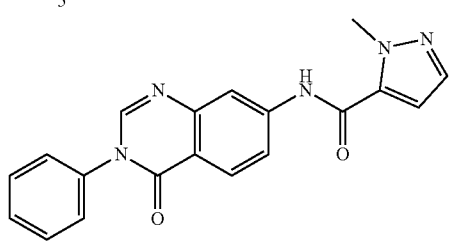

I-77

Step 1: 7-Nitro-3,1-benzoxazin-4-one

To a solution of Ac$_2$O (17.94 g, 175.69 mmol, 16.46 mL, 32 eq) cooled to 0° C. was added formic acid (10.02 g, 208.64 mmol, 38 eq) dropwise. The mixture was stirred at 0° C. for 30 min and warmed to 50° C. for 30 min. The mixture was cooled to 0° C. and 2-amino-4-nitro-benzoic acid (1 g, 5.49 mmol, 1 eq) was added portions. The mixture was heated to 50° C. for 30 min and stirred for 48 h at 20° C. The reaction mixture was concentrated under reduced pressure to yield the crude product 7-nitro-3,1-benzoxazin-4-one (1 g, 5.20 mmol, 94.8% yield, crude purity) as a gray solid which was used in the next step without further purification. $^1$H NMR (400 MHz, DMSO-d$_6$) δ ppm 8.37-8.32 (m, 3H), 7.97 (d, J=7.1 Hz, 1H).

Step 2: 7-Nitro-3,1-benzoxazin-4-one

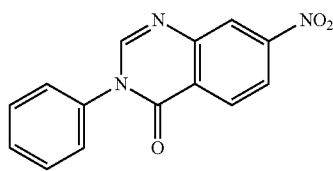 [SMILES: O=c1c2ccc([N+](=O)[O-])cc2ncn1-c1ccccc1]

To a solution of 7-nitro-3,1-benzoxazin-4-one (1 g, 5.20 mmol, 1 eq) in acetone (30 mL) was added a solution of aniline (581.65 mg, 6.25 mmol, 570.25 µL, 1.2 eq) in acetone (20 mL) drop-wise. The mixture was stirred at 20° C. for 3 h and concentrated under 20° C. to remove half of original. The residue was cooled to 0° C. and filtered to collect the solid. To a boiling DMF (30 mL) was added portion wise the above solid and the mixture was stirred at 155° C. for 1.5 h. The reaction mixture was concentrated under reduced pressure to remove 20 mL DMF, H$_2$O (30 mL) was added, filtered and collected the solid. The solid was diluted with MeOH (10 mL) and stirred for 10 min, filtered and collected the solid, dried to yield 7-nitro-3-phenyl-quinazolin-4-one (150 mg, 523.69 µmol, 10.1% yield, 93.3% purity) as a yellow solid which was used in the next step without further purification. $^1$H NMR (400 MHz, DMSO-d$_6$) δ ppm 8.49-8.46 (m, 1H), 8.44-8.42 (m, 1H), 8.33 (m, 1H), 8.33 (dd, J=2.1, 8.7 Hz, 1H), 7.91 (d, J=8.8 Hz, 2H), 7.63 (d, J 2.4 Hz, 2H), 7.58 (m, 2H), 7.24 (dd, J=2.4, 8.8 Hz, 2H); ES-LCMS m/z 268.1 [M+H]$^+$.

Step 3: 7-Amino-3-phenyl-quinazolin-4-one

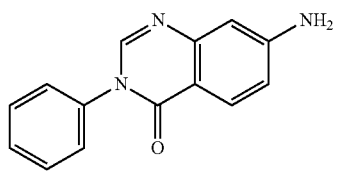

To a solution of 7-nitro-3-phenyl-quinazolin-4-one (150 mg, 561.30 µmol, 1 eq) in DMF (10 mL) was added Pd/C (100 mg, wet) under N$_2$ atmosphere. The mixture was purged with H$_2$ (15 psi) for 3 times and stirred at 20° C. for 1 h. The reaction mixture was filtered and concentrated under reduced pressure to yield the crude product 7-amino-3-phenyl-quinazolin-4-one (130 mg, 230.13 µmol, 41.0% yield, 42.0% purity) as yellow oil which was used in the next step without further purification. ES-LCMS m/z 238.2 [M+H]$^+$.

Step 4: 2-Methyl-N-(4-oxo-3-phenyl-quinazolin-7-yl)pyrazole-3-carboxamide (I-77)

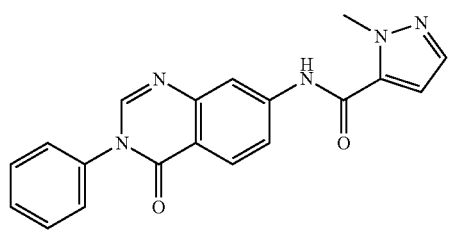 [SMILES: Cn1nccc1C(=O)Nc1ccc2c(=O)n(-c3ccccc3)cnc2c1]

To a solution of 7-amino-3-phenyl-quinazolin-4-one (110 mg, 194.73 µmol, 1 eq) and 2-methylpyrazole-3-carboxylic acid (36.84 mg, 292.09 µmol, 1.5 eq) in DMF (5 mL) was added HATU (148.08 mg, 389.45 µmol, 2.0 eq) and DIEA (75.50 mg, 584.18 µmol, 101.75 µL, 3.0 eq). The mixture was stirred at 40° C. for 12 h. The reaction mixture was concentrated under reduced pressure to give a residue which was purified by preparative HPLC (column: Xtimate C18 150*25 mm*5 um; mobile phase: [water (0.05% HCl)-ACN]; B %: 31%-51%, 9 min), followed by lyophilization to yield 2-methyl-N-(4-oxo-3-phenyl-quinazolin-7-yl)pyrazole-3-carboxamide (54.01 mg, 129.13 µmol, 66.3% yield, 100.0% purity, 2HCl) as a white solid. $^1$H NMR (400 MHz, DMSO-d$_6$) δ ppm 10.70 (s, 1H), 8.43 (s, 1H), 8.26 (d, J=1.8 Hz, 1H), 8.19 (d, J=8.5 Hz, 1H), 7.96 (dd, J=1.8, 8.8 Hz, 1H), 7.61-7.50 (m, 6H), 7.20 (d, J=2.0 Hz, 1H), 4.13 (s, 3H); ES-LCMS m/z 346.1 [M+H]$^+$.

Example 54

Synthesis of I-78

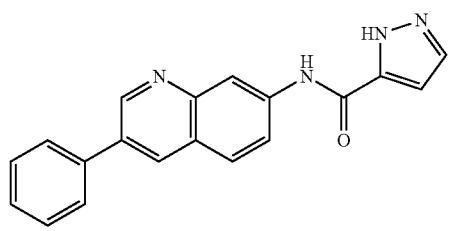

Synthetic Scheme:

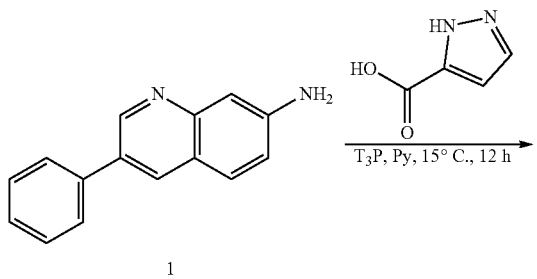

Step 1: N-(3-Phenyl-7-quinolyl)-1H-pyrazole-5-carboxamide (I-78)

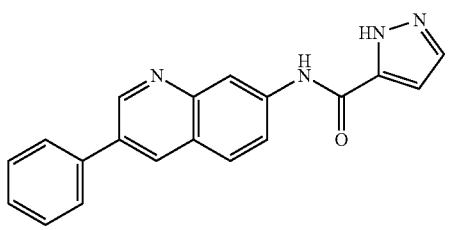 [SMILES: O=C(Nc1ccc2cc(-c3ccccc3)cnc2c1)c1ccn[nH]1]

To a solution of 3-phenylquinolin-7-amine (50 mg, 204.30 μmol, 1 eq) and 1H-pyrazole-5-carboxylic acid (25.19 mg, 224.73 μmol, 1.1 eq) in pyridine (5 mL) was added $T_3P$ (535.00 mg, 840.72 μmol, 0.5 mL, 50%, 4.12 eq) under $N_2$ atmosphere. The mixture was stirred at 15° C. for 2 h. The mixture was concentrated to yield a residue which was diluted with $H_2O$ (15 mL), extracted with EtOAc/MeOH (10/1, 20 mL×3). The combined organic layers were dried over $Na_2SO_4$, filtered and concentrated to yield a residue which was purified by preparative HPLC (column: Agela DuraShell 150 mm_25 mm_5 um; mobile phase: [water (0.05% HCl)-ACN]; B %: 20%-50%, 8 min), followed by lyophilization to yield a residue which was further purified by preparative HPLC (column: Agela ASB 150*25 mm*5 um; mobile phase: [water (0.05% HCl)-ACN]; B %: 22%-52%, 8 min), followed by lyophilization to yield N-(3-phenyl-7-quinolyl)-1H-pyrazole-5-carboxamide (21.03 mg, 53.50 μmol, 26.2% yield, 98.5% purity, 2 HCl) as a yellow solid. $^1$H NMR (400 MHz, $CD_3OD$) δ ppm 9.41 (d, J=2.2 Hz, 1H), 9.34 (d, J=1.7 Hz, 1H), 9.18 (d, J=1.7 Hz, 1H), 8.35 (d, J=9.0 Hz, 1H), 8.09 (dd, J=2.0, 9.0 Hz, 1H), 7.94-7.87 (m, 2H), 7.80 (d, J=2.4 Hz, 1H), 7.63-7.57 (m, 2H), 7.56-7.51 (m, 1H), 6.96 (d, J=2.4 Hz, 1H); ES-LCMS m/z 315.1 $[M+H]^+$.

Example 55

Synthesis of I-79

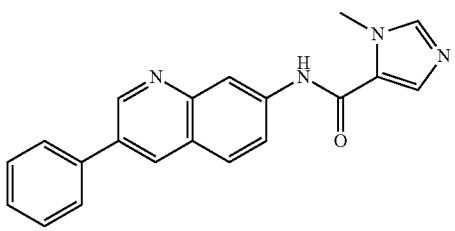

Synthetic Scheme:

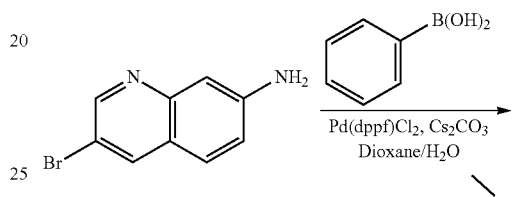

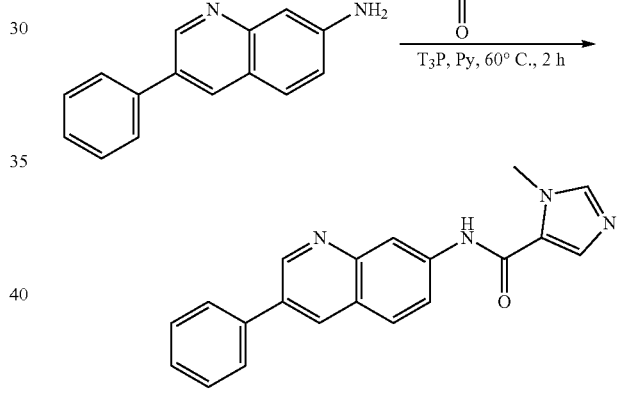

Step 1: 3-Phenylquinolin-7-amine

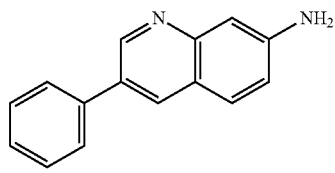 [SMILES: Nc1ccc2cc(-c3ccccc3)cnc2c1]

To a mixture of 3-bromoquinolin-7-amine (0.5 g, 2.24 mmol, 1 eq) and phenylboronic acid (355.29 mg, 2.91 mmol, 1.3 eq) in $H_2O$ (4 mL) and 1,4-dioxane (16 mL) was added $Cs_2CO_3$ (2.19 g, 6.72 mmol, 3 eq) and $Pd(dppf)Cl_2$ (164.01 mg, 224.15 μmol, 0.1 eq) under $N_2$ atmosphere. The mixture was stirred at 90° C. for 2 h under $N_2$ atmosphere. The mixture was extracted with EtOAc (30 mL×3). The combined organic layers were concentrated to yield a residue which was purified by flash silica gel chromatography (from pure PE to PE/EtOAc=2/1, TLC: PE/EtOAc=1/1, $R_f$=0.18) to yield 3-phenylquinolin-7-amine (500 mg, 2.04 mmol, 91.1% yield, 90% purity) as a yellow solid. $^1$H NMR (400 MHz, CD$_3$OD) δ ppm 8.84 (d, J=2.2 Hz, 1H), 8.30 (d, J=2.0 Hz, 1H), 7.70 (dd, J=5.5, 7.9 Hz, 3H), 7.47 (t, J=7.7 Hz, 2H), 7.37 (d, J=7.3 Hz, 1H), 7.12-7.05 (m, 2H); ES-LCMS m/z 221.2 [M+H]$^+$.

Step 2: 3-Methyl-N-(3-phenyl-7-quinolyl)imidazole-4-carboxamide (I-79)

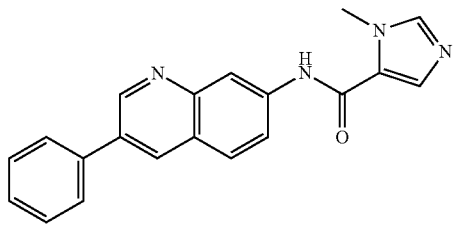 [SMILES: Cn1cncc1C(=O)Nc1ccc2cc(-c3ccccc3)cnc2c1]

To a solution of 3-phenylquinolin-7-amine (50 mg, 204.30 μmol, 1 eq) and 3-methylimidazole-4-carboxylic acid (28.34 mg, 224.73 μmol, 1.1 eq) in pyridine (5 mL) was added T$_3$P (535.00 mg, 840.72 μmol, 0.5 mL, 50%, 4.12 eq) under N$_2$ atmosphere. The mixture was stirred at 60° C. for 12 h. The mixture was concentrated to yield a residue which was diluted with H$_2$O (15 mL), extracted with EtOAc/MeOH (10/1, 20 mL×3). The combined organic layers were dried over Na$_2$SO$_4$, filtered and concentrated to yield a residue which was purified by preparative HPLC (column: Agela DuraShell 150 mm_25 mm_5 μm; mobile phase: [water (0.05% HCl)-ACN]; B %: 15%-45%, 8 min), followed by lyophilization to yield 3-methyl-N-(3-phenyl-7-quinolyl)imidazole-4-carboxamide (23.23 mg, 55.69 μmol, 27.3% yield, 96.2% purity, 2 HCl) as a yellow solid. $^1$H NMR (400 MHz, CD$_3$OD) δ ppm 9.36 (s, 1H), 9.18 (s, 1H), 8.92 (s, 1H), 8.85 (s, 1H), 8.35 (br s, 1H), 8.31 (d, J=9.0 Hz, 1H), 8.04 (d, J=8.8 Hz, 1H), 7.87 (d, J=7.6 Hz, 2H), 7.63-7.56 (m, 2H), 7.55-7.48 (m, 1H), 4.16 (s, 3H); ES-LCMS m/z 329.2 [M+H]$^+$.

Example 56

Synthesis of I-80

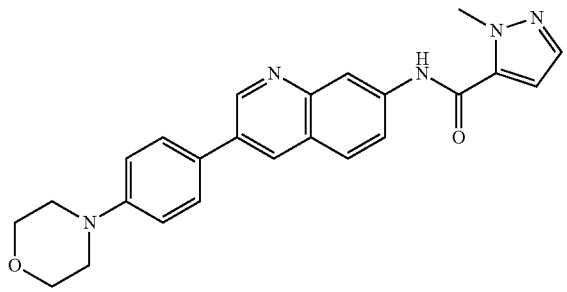 [SMILES: Cn1nccc1C(=O)Nc1ccc2cc(-c3ccc(N4CCOCC4)cc3)cnc2c1]

Synthetic Scheme:

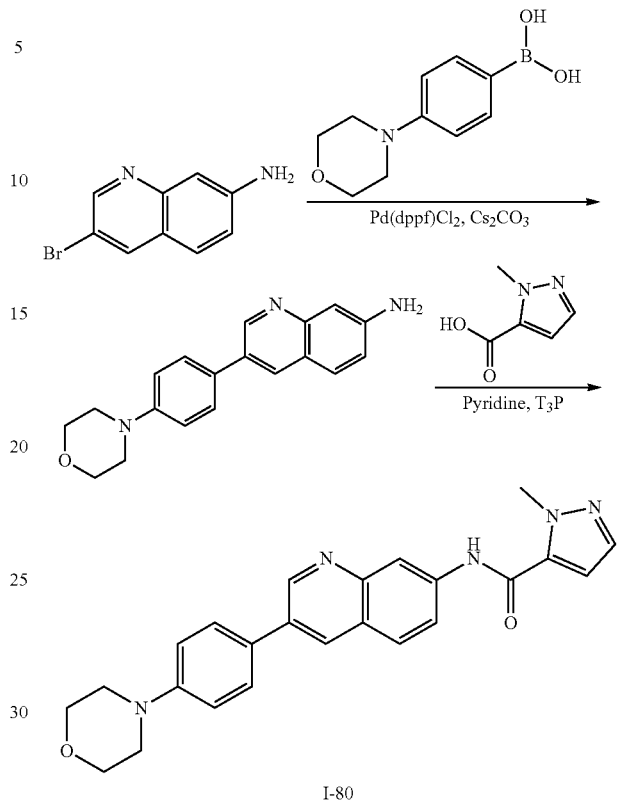

I-80

Step 1: 3-(4-Morpholinophenyl)quinolin-7-amine

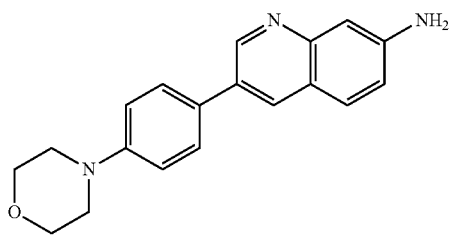 [SMILES: Nc1ccc2cc(-c3ccc(N4CCOCC4)cc3)cnc2c1]

A mixture of 3-bromoquinolin-7-amine (50 mg, 224.15 μmol, 1 eq), (4-morpholinophenyl)boronic acid (60.33 mg, 291.40 μmol, 1.3 eq), Cs$_2$CO$_3$ (219.10 mg, 672.45 μmol, 3 eq) and Pd(dppf)Cl$_2$ (8.20 mg, 11.21 μmol, 0.05 eq) were taken up into a sealed tube in 1,4-dioxane (2 mL) and H$_2$O (1 mL). The sealed tube was heated at 110° C. for 1 h under microwave. The reaction mixture was concentrated under reduced pressure to yield a residue which was purified by flash silica gel chromatography (from DCM/MeOH=100/1 to 10/1, TLC: DCM/MeOH=10/1, $R_f$=0.4) to yield 3-(4-morpholinophenyl)quinolin-7-amine (50 mg, 130.99 μmol, 58.4% yield, 80.0% purity) as a yellow solid. $^1$H NMR (400 MHz, CD$_3$OD) δ ppm 8.84 (d, J=2.2 Hz, 1H), 8.26 (d, J=2.0 Hz, 1H), 7.70 (d, J=8.6 Hz, 1H), 7.64 (d, J=8.8 Hz, 2H), 7.12-7.06 (m, 4H), 3.89-3.84 (m, 4H), 3.24-3.19 (m, 4H); ES-LCMS m/z 306.2 [M+H]$^+$

Step 2: 2-Methyl-N-[3-(4-morpholinophenyl)-7-quinolyl]pyrazole-3-carboxamide (I-80)

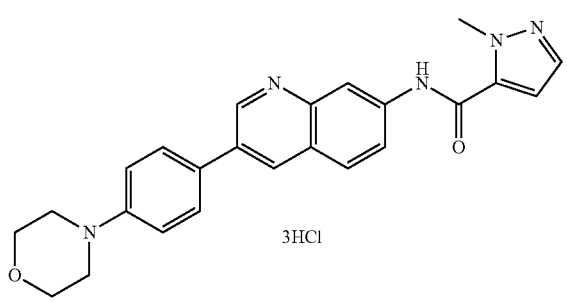 [SMILES: Cn1nccc1C(=O)Nc1ccc2cc(-c3ccc(N4CCOCC4)cc3)cnc2c1]

3HCl

To a solution of 3-(4-morpholinophenyl)quinolin-7-amine (50 mg, 130.99 μmol, 1 eq) in pyridine (3 mL) was added T$_3$P (250.07 mg, 392.96 μmol, 233.71 μL, 50%, 3 eq) and 2-methylpyrazole-3-carboxylic acid (24.78 mg, 196.48 μmol, 1.5 eq). The mixture was stirred at 20° C. for 12 h. The reaction mixture was concentrated under reduced pressure to give a residue which was purified by preparative HPLC (column: Agela ASB 150*25 mm*5 um; mobile phase: [water (0.05% HCl)-ACN]; B %: 30%-60%, 8 min), followed by lyophilization to yield 2-methyl-N-[3-(4-morpholinophenyl)-7-quinolyl]pyrazole-3-carboxamide (3.02 mg, 5.78 μmol, 4.4% yield, 100.0% purity, 3HCl) as a yellow solid. $^1$H NMR (400 MHz, CD$_3$OD) δ ppm 9.44 (s, 1H), 9.33 (s, 1H), 9.16 (s, 1H), 8.35 (d, J=9.3 Hz, 1H), 8.07 (d, J=9.0 Hz, 1H), 7.96 (d, J=8.1 Hz, 2H), 7.59 (d, J=2.0 Hz, 1H), 7.44 (d, J=7.3 Hz, 2H), 7.15 (d, J=2.0 Hz, 1H), 4.23 (s, 3H), 3.96 (d, J=4.2 Hz, 4H), 3.46 (s, 4H); ES-LCMS m/z 414.2 [M+H]$^+$.

Example 57

Synthesis of I-81

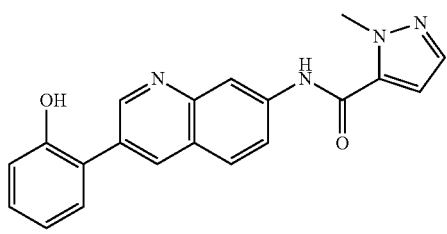 [SMILES: Cn1nccc1C(=O)Nc1ccc2cc(-c3ccccc3O)cnc2c1]

I-81

Synthetic Scheme:

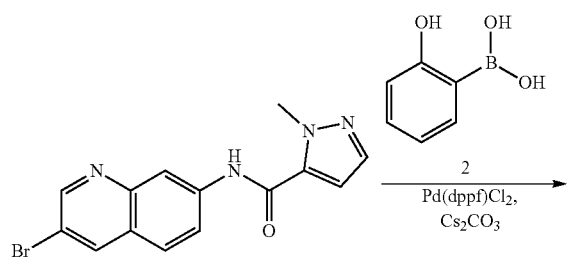

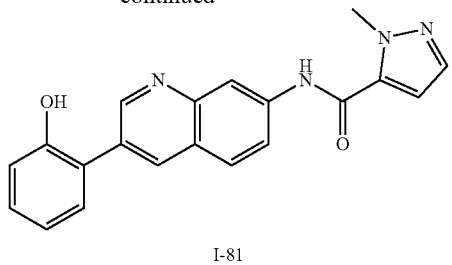

I-81

Step 1: N-[3-(2-Hydroxyphenyl)-7-quinolyl]-2-methyl-pyrazole-3-carboxamide (I-81)

A mixture of N-(3-Bromo-7-quinolyl)-2-methyl-pyrazole-3-carboxamide (50 mg, 150.98 μmol, 1 eq), (2-hydroxyphenyl)boronic acid (24.99 mg, 181.18 μmol, 1.2 eq) and Pd(dppf)Cl$_2$ (8.37 mg, 15.10 μmol, 0.1 eq) and Cs$_2$CO$_3$ (196.77 mg, 603.92 μmol, 4 eq) were taken up into a microwave tube in 1,4-dioxane (3 mL) and H$_2$O (1 mL). The sealed tube was heated at 110° C. for 1 h under microwave. The mixture was concentrated under reduced pressure to yield a residue which was purified by preparative HPLC (Agela ASB 150*25 mm*5 um; mobile phase: [water (0.05% HCl)-ACN]; B %: 20%-50%, 8 min), followed by lyophilization to yield N-[3-(2-hydroxyphenyl)-7-quinolyl]-2-methyl-pyrazole-3-carboxamide (35.55 mg, 84.43 μmol, 55.9% yield, 99.1% purity, 2HCl) as a yellow solid. $^1$H NMR (400 MHz, CD$_3$OD) δ ppm 9.43 (d, J=1.7 Hz, 1H), 9.28 (s, 1H), 9.17 (s, 1H), 8.35 (d, J=9.0 Hz, 1H), 8.05 (d, J=9.0 Hz, 1H), 7.64-7.59 (m, 2H), 7.39-7.35 (m, 1H), 7.14 (d, J=2.2 Hz, 1H), 7.11-7.03 (m, 2H), 4.23 (s, 3H); ES-LCMS m/z 345.2 [M+H]$^+$.

Example 58

Synthesis of I-82

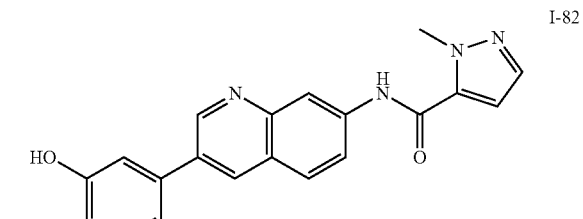

I-82

Synthetic Scheme:

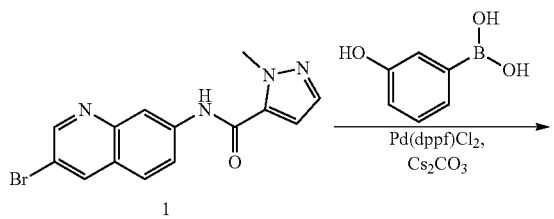

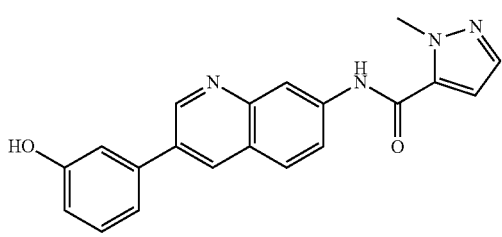 [SMILES: Cn1nccc1C(=O)Nc1ccc2cc(-c3cccc(O)c3)cnc2c1]

Step 1: N-[3-(3-Hydroxyphenyl)-7-quinolyl]-2-methyl-pyrazole-3-carboxamide (I-82)

A mixture of N-(3-bromo-7-quinolyl)-2-methyl-pyrazole-3-carboxamide (50 mg, 150.98 μmol, 1 eq), (3-hydroxyphenyl)boronic acid (24.99 mg, 181.18 μmol, 1.2 eq) and DPPF (8.37 mg, 15.10 μmol, 0.1 eq) and Cs₂CO₃ (196.77 mg, 603.92 μmol, 4 eq) were taken up into a microwave tube in 1,4-dioxane (3 mL) and H₂O (1 mL). The sealed tube was heated at 110° C. for 1 h under microwave. The mixture was concentrated under reduced pressure to yield a residue which was purified by preparative HPLC (Agela ASB 150*25 mm*5 um; mobile phase: [water (0.05% HCl)-ACN]; B %: 23%-51%, 8 min), followed by lyophilization to yield N-[3-(3-hydroxyphenyl)-7-quinolyl]-2-methyl-pyrazole-3-carboxamide (33.07 mg, 98.41 μmol, 65.2% yield, 100.0% purity, 3HCl) as a yellow solid. ¹H NMR (400 MHz, CD₃OD) δ ppm 9.43 (d, J=2.0 Hz, 1H), 9.31 (s, 1H), 9.19 (s, 1H), 8.37 (d, J=9.0 Hz, 1H), 8.07 (dd, J=2.0, 9.0 Hz, 1H), 7.59 (d, J=2.2 Hz, 1H), 7.48-7.40 (m, 1H), 7.38-7.30 (m, 2H), 7.14 (d, J=2.0 Hz, 1H), 6.98 (dd, J 1.6, 7.9 Hz, 1H), 4.23 (s, 3H); ES-LCMS m/z 345.2 [M+H]⁺.

Example 59

Synthesis of I-83

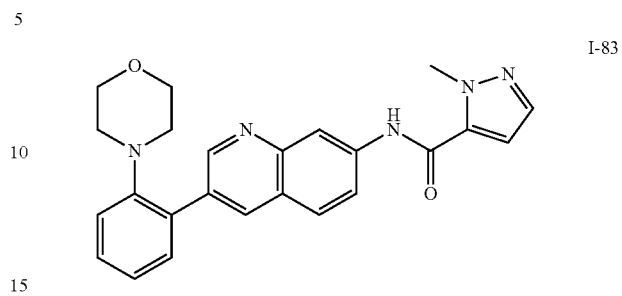

Synthetic Scheme:

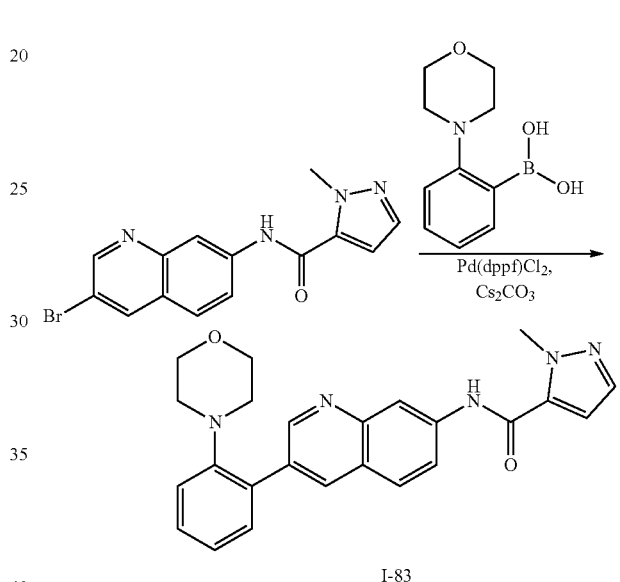

Step 1: 2-Methyl-N-[3-(2-morpholinophenyl)-7-quinolyl]pyrazole-3-carboxamide (I-83)

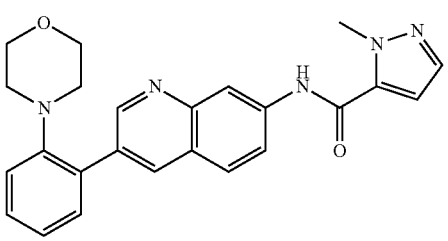 [SMILES: Cn1nccc1C(=O)Nc1ccc2cc(-c3ccccc3N3CCOCC3)cnc2c1]

A mixture of N-(3-bromo-7-quinolyl)-2-methyl-pyrazole-3-carboxamide (60 mg, 172.12 μmol, 1 eq), (2-morpholinophenyl)boronic acid (42.76 mg, 206.54 μmol, 1.2 eq), Cs₂CO₃ (168.24 mg, 516.36 μmol, 3 eq) and Pd(dppf)Cl₂ (12.59 mg, 17.21 μmol, 0.1 eq) were taken up into a microwave tube in 1,4-dioxane (3 mL) and H₂O (1 mL). The sealed tube was heated at 110° C. for 1 h under microwave. The reaction mixture was diluted with water (10 mL) and extracted with EtOAc (20 mL×3). The combined organic layers were dried over Na₂SO₄, filtered and concentrated under reduced pressure to yield a residue which was purified by preparative HPLC (column: Agela DuraShell 150 mm_25 mm_5 um; mobile phase: [water (0.05% HCl)-ACN]; B %: 20%-50%, 9 min), followed by lyophilization to yield 2-methyl-N-[3-(2-morpholinophenyl)-7-quinolyl]pyrazole-3-carboxamide (28.44 mg, 54.18 μmol, 31.5% yield, 99.6% purity, 3HCl) as a yellow solid. $^1$H NMR (400 MHz, CD$_3$OD) δ ppm 9.58 (d, J=1.7 Hz, 1H), 9.28 (s, 1H), 9.17 (d, J=1.7 Hz, 1H), 8.36 (d, J=9.0 Hz, 1H), 8.10 (dd, J=2.0, 8.8 Hz, 1H), 7.63-7.51 (m, 3H), 7.41-7.29 (m, 2H), 7.18 (d, J=2.2 Hz, 1H), 4.24 (s, 3H), 3.66-3.57 (m, 4H), 2.96-2.86 (m, 4H); ES-LCMS m/z 414.2 [M+H]$^+$.

Example 60

Synthesis of I-84

I-84

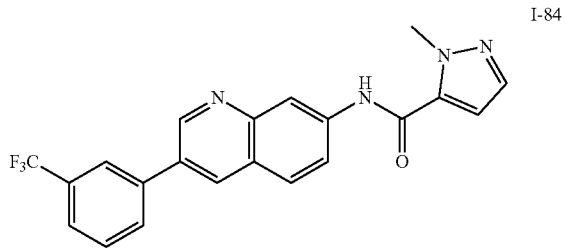 [SMILES: Cn1nccc1C(=O)Nc1ccc2cc(-c3cccc(C(F)(F)F)c3)cnc2c1]

Synthetic Scheme:

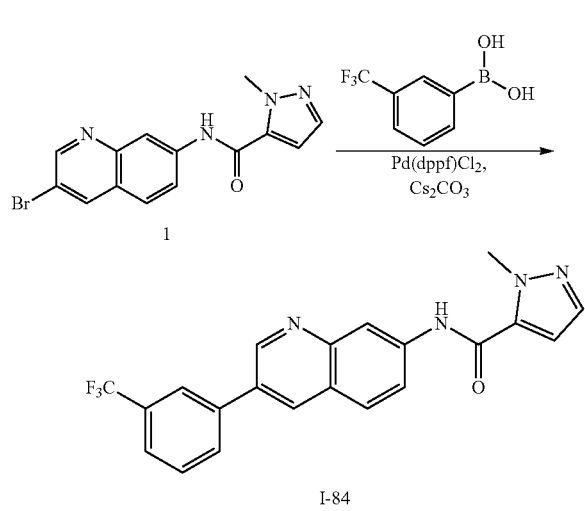

Step 1: 2-Methyl-N-[3-[3-(trifluoromethyl)phenyl]-7-quinolyl]pyrazole-3-carboxamide (I-84)

A mixture of N-(3-bromo-7-quinolyl)-2-methyl-pyrazole-3-carboxamide (50 mg, 143.43 μmol, 1 eq), [3-(trifluoromethyl)phenyl]boronic acid (27.24 mg, 143.43 μmol, 1 eq), Cs$_2$CO$_3$ (140.20 mg, 430.30 μmol, 3 eq) and Pd(dppf)Cl$_2$ (10.50 mg, 14.34 μmol, 0.1 eq) in 1,4-dioxane (3 mL) and water (1 mL) was taken up into a microwave tube and then purged with N$_2$ for 1 min. The sealed tube was heated at 110° C. for 1 h under microwave(1 bar). The mixture was concentrated under reduced pressure to give a residue which was purified by preparative HPLC (column: Agela ASB 150*25 mm*5 μm; mobile phase: [water(0.05% HCl)-ACN]; B %: 37%-67%, 9 min), followed by lyophilization to yield 2-methyl-N-[3-[3-(trifluoromethyl)phenyl]-7-quinolyl]pyrazole-3-carboxamide (49.98 mg, 106.50 μmol, 74.2% yield, 100% purity, 2HCl) as a yellow solid. $^1$H NMR (400 MHz, CD$_3$OD) δ ppm 9.47 (d, J=2.3 Hz, 1H), 9.29 (s, 1H), 9.10 (s, 1H), 8.34 (d, J=9.5 Hz, 1H), 8.25 (s, 1H), 8.18 (d, J=8.0 Hz, 1H), 8.07 (d, J=8.8 Hz, 1H), 7.90-7.79 (m, 2H), 7.59 (d, J=2.0 Hz, 1H), 7.14 (d, J=2.0 Hz, 1H), 4.23 (s, 3H); ES-LCMS m/z 397.1 [M+H]$^+$.

Example 61

Synthesis of I-85

I-85

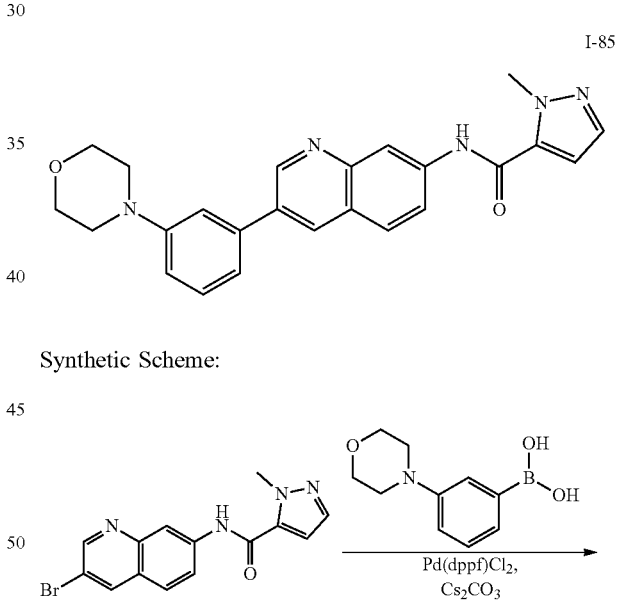

Synthetic Scheme:

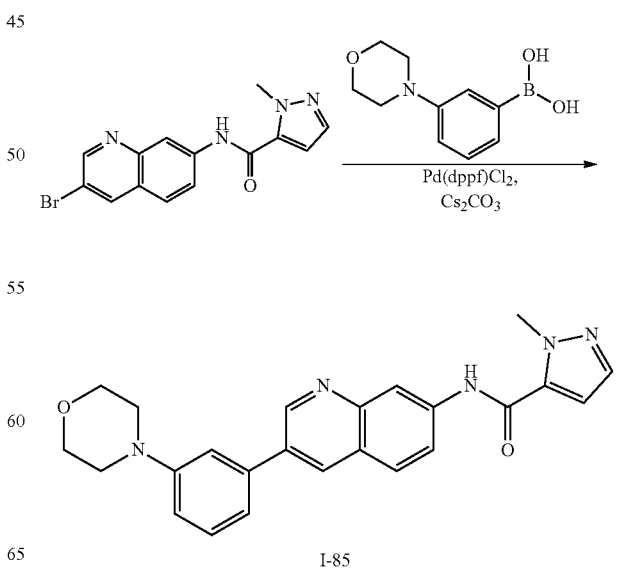

I-85

Step 1: 2-Methyl-N-[3-(3-morpholinophenyl)-7-quinolyl]pyrazole-3-carboxamide (I-85)

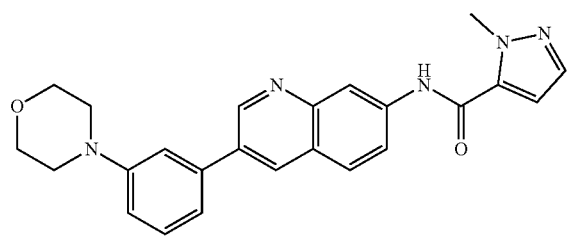 [SMILES: Cn1nccc1C(=O)Nc1ccc2cc(-c3cccc(N4CCOCC4)c3)cnc2c1]

A mixture of N-(3-bromo-7-quinolyl)-2-methyl-pyrazole-3-carboxamide (50 mg, 147.96 mol, 1 eq), (3-morpholinophenyl)boronic acid (30.63 mg, 147.96 mol, 1 eq), Pd(dppf)Cl$_2$ (32.48 mg, 44.39 μmol, 0.3 eq), Cs$_2$CO$_3$ (144.63 mg, 443.88 μmol, 3 eq) in 1,4-dioxane (4 mL) and H$_2$O (1 mL) was degassed and purged with N$_2$ for 3 times. The mixture was stirred at 90° C. for 3 h under N$_2$ atmosphere. The reaction mixture was diluted with water (10 mL) and extracted with EtOAc (20 mL×3). The combined organic layers were dried over Na$_2$SO$_4$, filtered and concentrated under reduced pressure to yield a residue which was purified by preparative HPLC (column: Phenomenex Gemini 150*25 mm*10 um; mobile phase: [water (0.05% HCl)-ACN]; B %: 25%-55%, 9 min), followed by lyophilization to yield 2-methyl-N-[3-(3-morpholinophenyl)-7-quinolyl]pyrazole-3-carboxamide (26.88 mg, 51.41 μmol, 34.8% yield, 100.0% purity, 3HCl) as a yellow solid. $^1$H NMR (400 MHz, CD$_3$OD) δ ppm 9.56 (d, J=1.7 Hz, 1H), 9.47 (s, 1H), 9.21 (s, 1H), 8.42 (d, J=9.3 Hz, 1H), 8.16-8.09 (m, 2H), 7.92 (d, J=7.6 Hz, 1H), 7.80-7.74 (m, 1H), 7.73-7.67 (m, 1H), 7.60 (d, J=2.0 Hz, 1H), 7.17 (d, J=2.2 Hz, 1H), 4.23 (s, 3H), 4.15-4.08 (m, 4H), 3.76-3.66 (m, 4H); ES-LCMS m/z 414.2 [M+H]$^+$.

Example 62

Synthesis of I-86

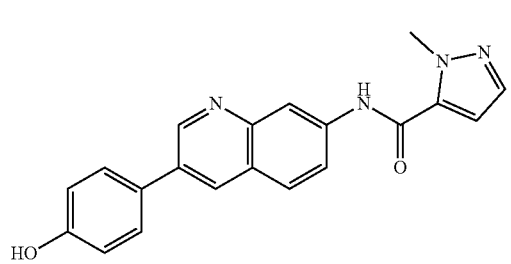 [SMILES: Cn1nccc1C(=O)Nc1ccc2cc(-c3ccc(O)cc3)cnc2c1]

Synthetic Scheme:

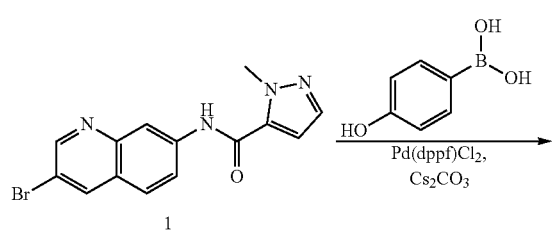

Step 1: N-[3-(4-Hydroxyphenyl)-7-quinolyl]-2-methyl-pyrazole-3-carboxamide (I-86)

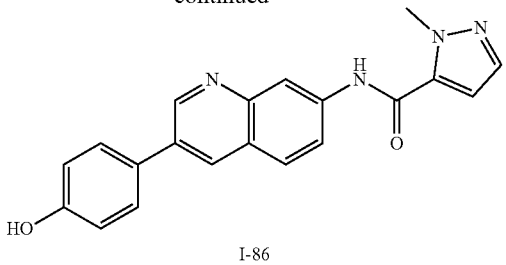

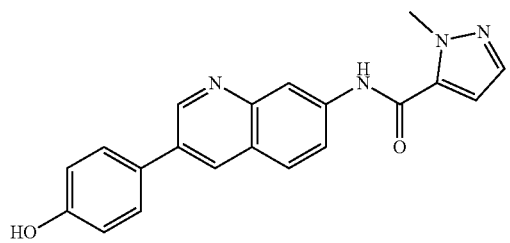

A mixture of N-(3-bromo-7-quinolyl)-2-methyl-pyrazole-3-carboxamide (50 mg, 147.96 μmol, 1 eq), (4-hydroxyphenyl)boronic acid (26.53 mg, 192.35 μmol, 1.3 eq), Cs$_2$CO$_3$ (241.04 mg, 739.81 μmol, 5 eq) and Pd(dppf)Cl$_2$ (10.83 mg, 14.80 μmol, 0.1 eq) in 1,4-dioxane (3 mL) and H$_2$O (1 mL) were taken up into a microwave tube and then purged with N$_2$ for 1 min. The sealed tube was heated at 110° C. for 1 h under microwave (1 bar). The reaction mixture was concentrated to yield a residue which was purified by preparative HPLC (column: Agela ASB 150*25 mm*5 um; mobile phase: [water(0.05% HCl)-ACN]; B %: 20%-50%, 8 min) followed by lyophilization to yield N-[3-(4-hydroxyphenyl)-7-quinolyl]-2-methyl-pyrazole-3-carboxamide (29.81 mg, 71.44 μmol, 48.3% yield, 100.0% purity, 2HCl) as a yellow solid. $^1$H NMR (400 MHz, CD$_3$OD) δ ppm 9.36 (d, J=2.2 Hz, 1H), 9.24 (d, J=1.5 Hz, 1H), 9.11 (d, J=1.5 Hz, 1H), 8.31 (d, J=9.3 Hz, 1H), 8.04 (dd, J=2.0, 9.0 Hz, 1H), 7.78-7.73 (m, 2H), 7.57 (d, J=2.0 Hz, 1H), 7.13 (d, J=2.2 Hz, 1H), 7.02-6.97 (m, 2H), 4.20 (s, 3H); ES-LCMS m/z 345.2[M+H]$^+$.

Example 63

Synthesis of I-87

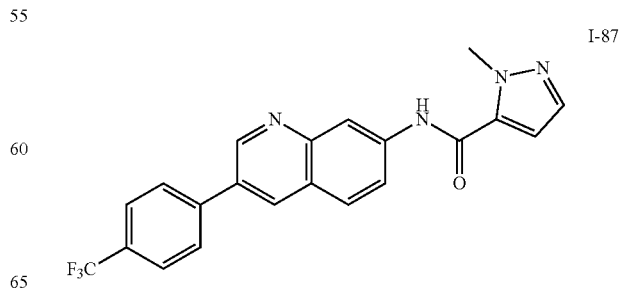

Synthetic Scheme:

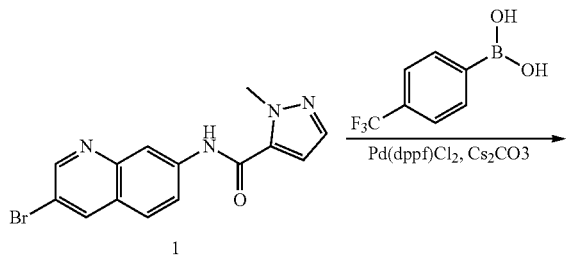

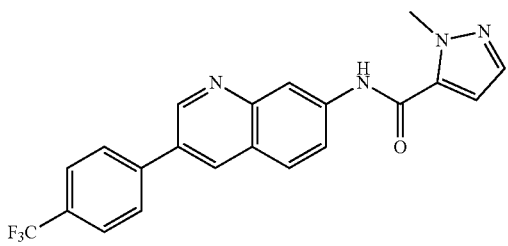 [SMILES: Cn1nccc1C(=O)Nc1ccc2cc(-c3ccc(C(F)(F)F)cc3)cnc2c1]

Step 1: 2-Methyl-N-[3-[4-(trifluoromethyl)phenyl]-7-quinolyl]pyrazole-3-carboxamide (I-87)

A mixture of N-(3-bromo-7-quinolyl)-2-methyl-pyrazole-3-carboxamide (52.63 mg, 150.98 μmol, 1 eq), [4-(trifluoromethyl)phenyl]boronic acid (28.68 mg, 150.98 μmol, 1 eq), Cs$_2$CO$_3$ (147.58 mg, 452.94 μmol, 3 eq) and Pd(dppf)Cl$_2$ (11.05 mg, 15.10 μmol, 0.1 eq) in 1,4-dioxane (3 mL) and water (1 mL) was taken up into a microwave tube and then purged with N$_2$ for 1 min. The sealed tube was heated at 110° C. for 1 h under microwave (1 bar). The reaction mixture was concentrated under reduced pressure to yield a residue which was purified by preparative HPLC (column: Agela ASB 150*25 mm*5 μm; mobile phase: [water (0.05% HCl)-ACN]; B %: 40%-70%, 8 min), followed by lyophilization to yield 2-methyl-N-[3-[4-(trifluoromethyl)phenyl]-7-quinolyl]pyrazole-3-carboxamide (46.24 mg, 98.53 μmol, 65.2% yield, 100% purity, 2HCl) as a yellow solid. $^1$H NMR (400 MHz, CD$_3$OD) δ ppm 9.51 (d, J=2.0 Hz, 1H), 9.39 (s, 1H), 9.18 (s, 1H), 8.38 (d, J=9.0 Hz, 1H), 8.14 (s, 1H), 8.13-8.07 (m, 2H), 7.93 (d, J=8.3 Hz, 2H), 7.59 (d, J=2.2 Hz, 1H), 7.15 (d, J=2.2 Hz, 1H), 4.23 (s, 3H); ES-LCMS m/z 397.2 [M+H]$^+$.

Example 64

Synthesis of I-88

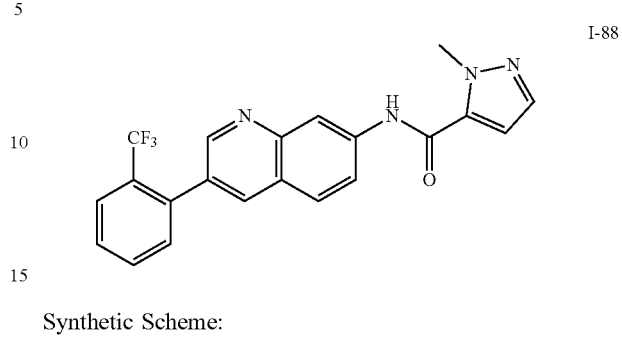

Synthetic Scheme:

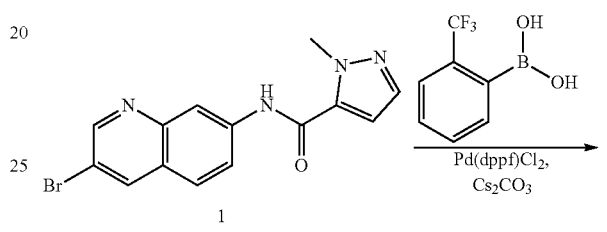

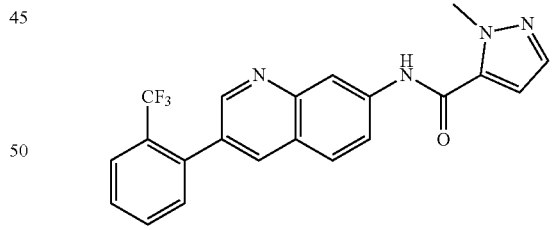

Step 1: 2-Methyl-N-[3-[2-(trifluoromethyl)phenyl]-7-quinolyl]pyrazole-3-carboxamide (I-88)

A mixture of N-(3-bromo-7-quinolyl)-2-methyl-pyrazole-3-carboxamide (50 mg, 143.43 μmol, 1 eq), [2-(trifluoromethyl)phenyl]boronic acid (27.24 mg, 143.43 μmol, 1 eq), Cs$_2$CO$_3$ (140.20 mg, 430.30 μmol, 3 eq) and Pd(dppf)Cl$_2$ (10.50 mg, 14.34 μmol, 0.1 eq) in 1,4-dioxane (3 mL) and water (1 mL) was taken up into a microwave tube and then purged with N$_2$ for 1 min. The sealed tube was heated at 110° C. for 1 h under microwave (1 bar). The mixture was filtered. The filtrate was concentrated under reduced pressure to yield a residue which was purified by preparative HPLC (column: Agela ASB 150*25 mm*5 μm; mobile phase: [water (0.05% HCl)-ACN]; B %: 35%-65%, 8 min), followed by lyophilization to yield 2-methyl-N-[3-[2-(trifluoromethyl)

phenyl]-7-quinolyl]pyrazole-3-carboxamide (32.65 mg, 82.37 µmol, 57.4% yield, 100% purity) as a yellow solid. $^1$H NMR (400 MHz, CD$_3$OD) δ ppm 9.17 (d, J=5.4 Hz, 2H), 9.02 (s, 1H), 8.34 (d, J=9.3 Hz, 1H), 8.11 (dd, J=2.0, 9.0 Hz, 1H), 7.97 (d, J=7.3 Hz, 1H), 7.89-7.81 (m, 1H), 7.81-7.72 (m, 1H), 7.65 (d, J=7.8 Hz, 1H), 7.60 (d, J=2.2 Hz, 1H), 7.15 (d, J=2.2 Hz, 1H), 4.23 (s, 3H); ES-LCMS m/z 397.2 [M+H]$^+$.

Example 65

Additional compounds of the invention are prepared according to methods substantially similar to that described in Example 55. Such compounds include I-89, I-90, I-91, I-92, I-93, I-94, I-95, I-96, I-97, I-98, I-99 and I-100.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula IV-g:

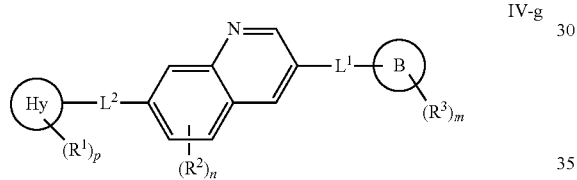

IV-g or a pharmaceutically acceptable salt thereof, wherein:
Hy is a 5-6 membered heteroaryl ring having 1-2 nitrogens;
L$^2$ is

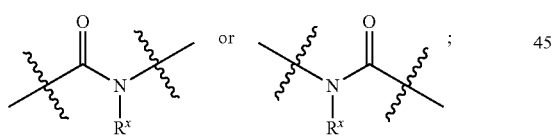

each R$^x$ is independently hydrogen or C$_{1-4}$ alkyl;
Ring B is phenyl, or a 5-6 membered monocyclic heteroaromatic ring having 1-4 heteroatoms independently selected from nitrogen, oxygen, or sulfur;
each R$^1$ is independently hydrogen, deuterium, or optionally substituted C$_{1-6}$ aliphatic;
each R is independently hydrogen, deuterium, or optionally substituted C$_{1-6}$ aliphatic;
L$^1$ is a covalent bond; and
each of R$^2$ and R$^3$ is independently selected from R, halogen, cyano, nitro, and —OR;
each of m and n is independently 1, 2, 3, 4, or 5; and
p is 0, 1, 2, or 3.

2. The compound according to claim 1 wherein the compound is selected from:

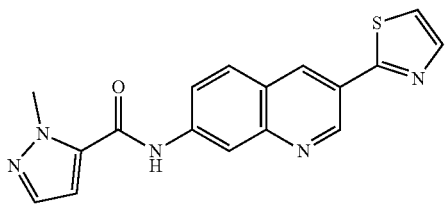
I-44

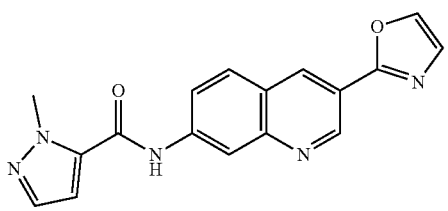
I-45

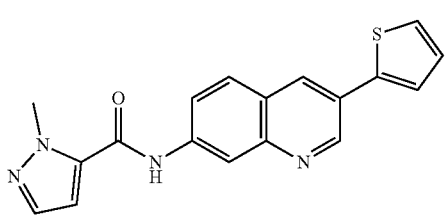
I-46

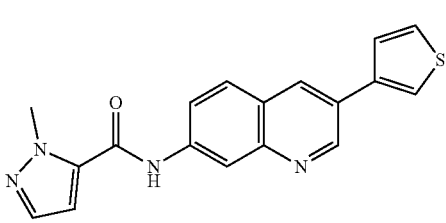
I-48

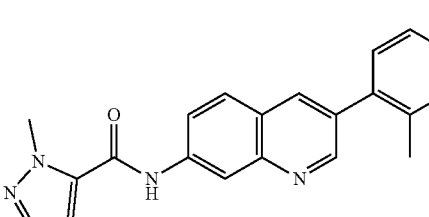
I-51

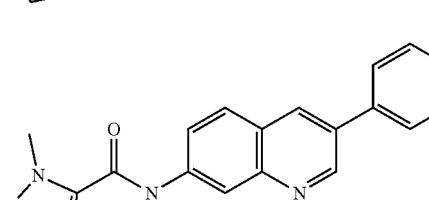
I-70

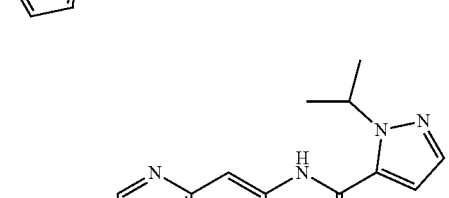
I-76

| I-78 | I-87 |
| I-79 | I-88 |
| I-81 | I-90 |
| I-82 | I-91 |
| I-84 | I-92 |
| I-86 | I-93 |

-continued

I-94

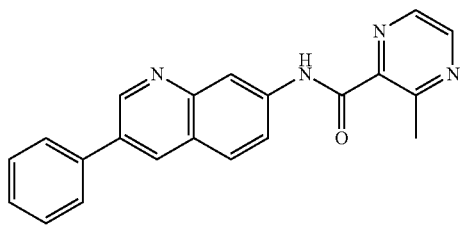

or a pharmaceutically acceptable salt thereof.

3. A composition comprising a compound according to claim 1, or a pharmaceutically acceptable salt thereof, and a pharmaceutically acceptable carrier, adjuvant, or vehicle.

4. The composition according to claim 3, further comprising an additional therapeutic agent.

5. The compound according to claim 1, or a pharmaceutically acceptable salt thereof, wherein Hy is a 5-membered heteroaryl ring having 1-2 nitrogens.

6. The compound according to claim 1, or a pharmaceutically acceptable salt thereof, wherein Hy is pyrazolyl, imidazolyl, pyridinyl, or pyrazinyl.

7. The compound according to claim 1, or a pharmaceutically acceptable salt thereof, wherein $R^1$ is optionally substituted $C_{1-6}$ aliphatic.

8. The compound according to claim 1, or a pharmaceutically acceptable salt thereof, wherein $R^1$ is unsubstituted $C_{1-6}$ aliphatic.

9. The compound according to claim 1, or a pharmaceutically acceptable salt thereof, wherein $R^1$ is —$CH_3$.

10. The compound according to claim 1, or a pharmaceutically acceptable salt thereof, wherein p is 1.

11. The compound according to claim 1, or a pharmaceutically acceptable salt thereof, wherein

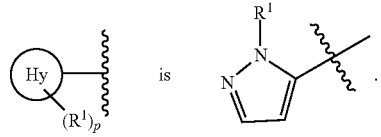 is 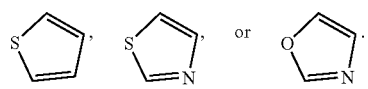.

12. The compound according to claim 1, or a pharmaceutically acceptable salt thereof, wherein $L^2$ is

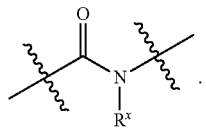.

13. The compound according to claim 1, or a pharmaceutically acceptable salt thereof, wherein $R^x$ is hydrogen.

14. The compound according to claim 1, or a pharmaceutically acceptable salt thereof, wherein

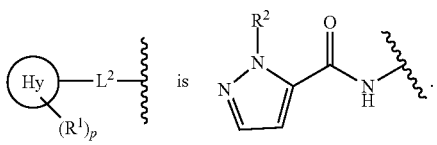 is 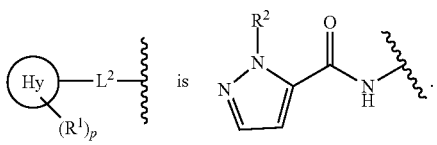.

15. The compound according to claim 1, or a pharmaceutically acceptable salt thereof, wherein $R^2$ is hydrogen.

16. The compound according to claim 1, or a pharmaceutically acceptable salt thereof, wherein $L^1$ is a covalent bond.

17. The compound according to claim 1, or a pharmaceutically acceptable salt thereof, wherein Ring B is phenyl.

18. The compound according to claim 1, or a pharmaceutically acceptable salt thereof, wherein Ring B is a 5-6 membered monocyclic heteroaromatic ring having 1-4 heteroatoms independently selected from nitrogen, oxygen, or sulfur.

19. The compound according to claim 1, or a pharmaceutically acceptable salt thereof, wherein Ring B is 20. The compound according to claim 1, or a pharmaceutically acceptable salt thereof, wherein $R^3$ is hydrogen.

* * * * *